(12) United States Patent
Cameron

(10) Patent No.: US 10,329,324 B2
(45) Date of Patent: *Jun. 25, 2019

(54) INDOLINE COMPOUNDS AS GRANZYME B INHIBITORS

(71) Applicant: viDA Therapeutics Inc., Vancouver (CA)

(72) Inventor: Dale R. Cameron, Richmond (CA)

(73) Assignee: viDA Therapeutics, North Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,596

(22) Filed: Mar. 27, 2017

(65) Prior Publication Data

US 2018/0057528 A1 Mar. 1, 2018

Related U.S. Application Data

(63) Continuation of application No. 14/869,750, filed on Sep. 29, 2015, now Pat. No. 9,605,021, which is a continuation-in-part of application No. PCT/CA2014/050317, filed on Mar. 28, 2014, which is a continuation-in-part of application No. PCT/CA2014/050318, filed on Mar. 28, 2014.

(60) Provisional application No. 61/941,358, filed on Feb. 18, 2014, provisional application No. 61/806,767, filed on Mar. 29, 2013.

(51) Int. Cl.
| | |
|---|---|
| C07K 5/08 | (2006.01) |
| C07K 5/083 | (2006.01) |
| C07K 5/087 | (2006.01) |
| C07K 5/097 | (2006.01) |
| A61K 38/00 | (2006.01) |

(52) U.S. Cl.
CPC ............ C07K 5/0821 (2013.01); C07K 5/081 (2013.01); C07K 5/0804 (2013.01); C07K 5/0808 (2013.01); C07K 5/0812 (2013.01); C07K 5/0827 (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,458,138 B1 | 10/2016 | Cameron | |
| 9,458,192 B1 | 10/2016 | Cameron | |
| 9,458,193 B1 | 10/2016 | Cameron | |
| 2003/0148511 A1 | 8/2003 | Ashton-Rickardt | |
| 2005/0208000 A1 | 9/2005 | Bernstein | |
| 2016/0083422 A1 | 3/2016 | Cameron | |
| 2017/0015705 A1 | 1/2017 | Cameron | |
| 2017/0015706 A1 | 1/2017 | Cameron | |
| 2017/0015707 A1 | 1/2017 | Cameron | |

FOREIGN PATENT DOCUMENTS

| | | |
|---|---|---|
| WO | 03/065987 A2 | 8/2003 |
| WO | 2007/101354 A1 | 9/2007 |
| WO | 2012/076985 A2 | 6/2012 |
| WO | 2014/153666 A1 | 10/2014 |

OTHER PUBLICATIONS

Bloom, B.M., and G.D. Laubach, "The Relationship Between Chemical Structure and Pharmacological Activity" Annual Review of Pharmacology 2:67-108, Apr. 1962.
Buzza, M.S., et al., "Glycobiology and Extracellular Matrices: Extracellular Matrix Remodeling by Human Granzyme B via Cleavage of Vitronectin, Fibronectin, and Laminin," Journal of Biological Chemistry 280(25):23549-23558, Jun. 2005.
International Preliminary Report on Patentability dated Sep. 29, 2015, from International Application No. PCT/CA2014/050317, filed Mar. 28, 2014, 7 pages.
International Search Report and Written Opinion dated Jul. 2, 2014, from International Application No. PCT/CA2014/050317, filed Mar. 28, 2014, 12 pages.
International Preliminary Report on Patentability dated Sep. 29, 2015, from International Application No. PCT/CA2014/050318, filed Mar. 28, 2014, 6 pages.
International Search Report and Written Opinion dated Jul. 3, 2014, from International Application No. PCT/CA2014/050318, filed Mar. 28, 2014, 8 pages.
International Preliminary Report on Patentability dated Feb. 7, 2017, from International Application No. PCT/CA2015/050724, filed Jul. 31, 2015, 8 pages.
International Search Report and Written Opinion dated Nov. 3, 2015, from International Application No. PCT/CA2015/050724, filed Jul. 31, 2015, 13 pages.
International Preliminary Report on Patentability dated Feb. 7, 2017, from International Application No. PCT/CA2015/050725, filed Jul. 31, 2015, 7 pages.
International Search Report and Written Opinion dated Oct. 6, 2015, from International Application No. PCT/CA2015/050725, filed Jul. 31, 2015, 11 pages.
Kam, C.-M., et al., "Granzymes (Lymphocyte Serine Proteases): Characterization With Natural and Synthetic Substrates and Inhibitors," Biochimica et Biophysica Acta (BBA)—Protein Structure and Molecular Enzymology 1477(1-2):307-323, Mar. 2000.
Willoughby, C.A., "Discovery of Potent, Selective Human Granzyme B Inhibitors That Inhibit CTL Mediated Apoptosis," Bioorganic & Medicinal Chemistry Letters 12(16):2197-2200, Aug. 2002.
Cullen, S.P., et al., "Granzymes in Cancer and Immunity," Cell Death and Differentiation 17(4):616-623, Apr. 2010.

*Primary Examiner* — Alicia L Otton
(74) *Attorney, Agent, or Firm* — Christensen O'Connor Johnson Kindness PLLC

(57) ABSTRACT

Granzyme B inhibitor compounds, compositions that include the compounds, and methods for using the compounds. The compounds of the invention have advantageous water solubility and effectively inhibit Granzyme B.

9 Claims, 3 Drawing Sheets

INDOLINE COMPOUNDS AS GRANZYME B INHIBITORS

CROSS-REFERENCE TO RELATED APPLICATIONS

This application is a continuation of U.S. patent application Ser. No. 14/869,750, filed Sep. 29, 2015 (now U.S. Pat. No. 9,605,021), which is a continuation-in-part of International Application No. PCT/CA2014/050317, filed Mar. 28, 2014, which claims the benefit of U.S. Patent Application No. 61/806,767, filed Mar. 29, 2013, and U.S. Patent Application No. 61/941,358, filed Feb. 18, 2014, and is a continuation-in-part of International Application No. PCT/CA2014/050318, filed Mar. 28, 2014, which claims the benefit of U.S. Patent Application No. 61/806,767, filed Mar. 29, 2013, and U.S. Patent Application No. 61/941,358, filed Feb. 18, 2014, each expressly incorporated herein by reference in its entirety.

FIELD OF THE INVENTION

The present invention disclosure relates generally to agents for treating diseases, disorders, and conditions treatable by inhibiting Granzyme B, and more specifically to substituted indoline compounds that are inhibitors of Granzyme B.

BACKGROUND OF THE INVENTION

Granzyme B is a pro-apoptotic serine protease found in the granules of cytotoxic lymphocytes (CTL) and natural killer (NK) cells. Granzyme B is released towards target cells, along with the pore-forming protein, perforin, resulting in its perforin-dependent internalization into the cytoplasm and subsequent induction of apoptosis (see, for e.g., Medema et al., *Eur. J. Immunol.* 27:3492-3498, 1997). However, during aging, inflammation and chronic disease, Granzyme B can also be expressed and secreted by other types of immune (e.g., mast cell, macrophage, neutrophil, and dendritic cells) or non-immune (keratinocyte, chondrocyte) cells and has been shown to possess extracellular matrix remodeling activity (Choy et al., *Arterioscler. Thromb. Vasc. Biol.* 24(12):2245-2250, 2004 and Buzza et al., *J. Biol. Chem.* 280:23549-23558, 2005).

Inhibitors of Granzyme B in humans have been limited to (a) relatively weak, nonspecific inhibitors such as isocoumarins (Odake et al., (1991), *Biochemistry*, 30(8), 2217-2227); (b) biological inhibitors such as serpinB9 (Sun et al., (1996), *J. Biol. Chem.*, 271(44), 27802-27809); (c) covalently coupled inhibitors such as aldehydes (Willoughby et al., (2002), *Bioorg. Med. Chem. Lett.*, 12(16), 2197), halomethyl ketones (Kam et al., (2000), *Biochim. Biophy. Acta*, 1477(1-2), 307-323), and phosphonates (Mahrus and Craik, (2005), *Chem. & Biol.*, 12, 567-77 and Kam et al., (2000)); and (d) tricyclic inhibitors (Willoughby et al., (2002)).

Nonspecific inhibitors (such as isocoumarins) are not sufficiently potent or specific to be effective treatments for Granzyme-B-related diseases, disorders, and conditions. Likewise, the use of biological inhibitors such as serpins is limited by the ability to deliver the inhibitor to the target mammal, the cost of manufacturing the biological agents, and other, off-target activities, such as inhibition of other serine proteases such as human neutrophil elastase (Dahlen et al., (1999), *Biochim. Biophys. Acta*, 1451(2-3), 233-41); Caspase-1 (Annaud et al., (1999), *Biochem. J.*, September 15: 342 Pt3, 655-65; Krieg et al., (2001), *Mol. Endocrinol.*, 15(11), 1971-82; and Young et al., (2000), *J. Exp. Med.*, 191(9), 1535-1544); Caspase-4 and Caspase-8 (Annaud et al., (1999)).

The tricyclic inhibitors (Willoughby et al. (2001)) also suffer from synthetic complexity/high manufacturing cost due to the complex core and accompanying low water solubility.

Despite the advances in development of Granzyme B inhibitors, there exists a need for compounds that inhibit Granzyme B with selectivity, that are relatively simple to manufacture at low cost, that are highly water soluble, and that do not present drug delivery challenges. The present invention seeks to fulfill this need and provides further related advantages.

SUMMARY OF THE INVENTION

The present invention provides Granzyme B inhibitor compounds, compositions that include the compounds, and methods for using the compounds.

In one aspect of the invention, the invention provides Granzyme B inhibitor compounds. In one embodiment, the invention provides the compounds having Formula (I):

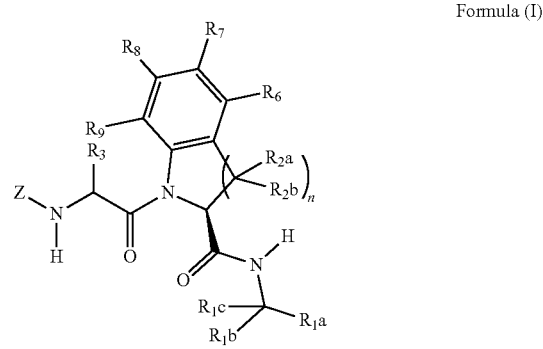

Formula (I)

its stereoisomers and pharmaceutically acceptable salts thereof, wherein:

$R_1a$ is a heteroaryl group selected from
(a) 1,2,3-triazolyl optionally substituted with $C_1$-$C_2$ alkyl,
(b) 1,2,3,4-tetrazolyl, and
(c) 1,2,3-thiadiazolyl;

$R_1b$ and $R_1c$ are independently selected from hydrogen, methyl, and halogen;

$R_2a$ and $R_2b$ are independently selected from hydrogen and methyl, or $R_2a$ and $R_2b$ taken together are oxo (i.e., =O, $R_2a$ and $R_2b$ together with the carbon to which they are attached form a carbonyl group);

n is or 2;

$R_3$ is selected from hydrogen and $C_1$-$C_4$ alkyl optionally substituted with a carboxylic acid or a carboxylate group (—$CO_2H$ or —$CO_2^-$) or an amine group (—$NH_2$);

Z is an acyl group selected from the group

(a)

(b)

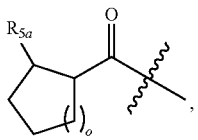

wherein o is 1 or 2, and $R_{5a}$ is $C_4$-acyl substituted with a carboxylic acid;

(c)

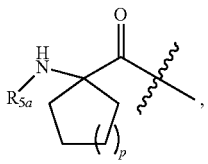

wherein p is 1 or 2, and $R_{5a}$ is $C_4$-acyl substituted with a carboxylic acid; and (d)

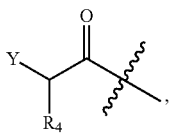

wherein Y is heteroaryl;
wherein
$R_4$ is selected from
(i) $C_1$-$C_2$ alkyl,
(ii) $C_1$-$C_6$ heteroalkyl optionally substituted with $C_1$-$C_6$ alkyl,
(iii) $C_3$-$C_6$ cycloalkyl,
(iv) $C_6$-$C_{10}$ aryl,
(v) heterocyclyl,
(vi) $C_3$-$C_{10}$ heteroaryl,
(vii) aralkyl, and
(viii) heteroalkylaryl;
$R_5$ is —C(=O)—$R_{10}$, wherein $R_{10}$ is selected from
(i) $C_1$-$C_{12}$ alkyl optionally substituted with $C_6$-$C_{10}$ aryl, optionally substituted $C_3$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(v) heterocyclyl,
(vi) $C_3$-$C_{10}$ heteroaryl,
(vii) aralkyl, and
(viii) heteroalkylaryl, and
$R_6$, $R_7$, $R_8$, and $R_9$ are independently selected from
(a) hydrogen,
(b) halogen,
(c) $C_1$-$C_6$ alkyl,
(d) —X$R_{11}$, wherein X is selected from O, C(=O), S, S=O, or S(=O)$_2$,
(e) —C(=O)N($R_{12}$)($R_{13}$),
(f) —N($R_{11}$)($R_{12}$)($R_{13}$),
(g) —N—C(=O)—$R_{11}$, and
(h) —N—C(=O)O—$R_{11}$,
wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl.

In another embodiment, the invention provides compounds having Formula (I), its stereoisomers and pharmaceutically acceptable salts thereof, wherein:
$R_1a$ is a heteroaryl group selected from
(a) 1,2,3-triazolyl optionally substituted with $C_1$-$C_2$ alkyl, and
(b) 1,2,3,4-tetrazolyl;
$R_1b$ and $R_1c$ are independently selected from hydrogen and methyl;
$R_2a$ and $R_2b$ are independently selected from hydrogen and methyl;
n is 1;
$R_3$ is selected from hydrogen and $C_1$-$C_4$ alkyl optionally substituted with a carboxylic acid or a carboxylate group (—$CO_2H$ or —$CO_2^-$) or an amine group (—$NH_2$);
Z is an acyl group selected from the group (a)

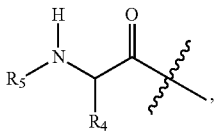

(b)

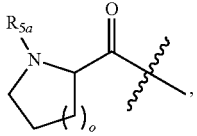

wherein o is 1 or 2, and $R_{5a}$ is $C_4$-acyl substituted with a carboxylic acid;

(c)

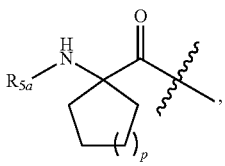

wherein p is 1 or 2, and $R_{5a}$ is $C_4$-acyl substituted with a carboxylic acid; and (d)

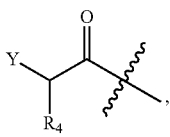

wherein Y is heteroaryl;

$R_4$ is selected from
(i) $C_1$-$C_2$ alkyl,
(ii) $C_3$-$C_6$ cycloalkyl,
(iii) $C_6$-$C_{10}$ aryl, and
(iv) $C_3$-$C_{10}$ heteroaryl;

$R_5$ is —C(═O)—$R_{10}$, wherein $R_{10}$ is selected from
(i) $C_1$-$C_{12}$ alkyl optionally substituted with $C_6$-$C_{10}$ aryl, optionally substituted $C_3$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(v) $C_3$-$C_{10}$ heteroaryl; and $R_6$, $R_7$, $R_8$, and $R_9$ are independently selected from
(a) hydrogen,
(b) halogen,
(c) $C_1$-$C_6$ alkyl,
(d) —X$R_{11}$, wherein X is selected from O and C(═O),
(f) —N($R_{11}$)($R_{12}$)($R_{13}$),
(g) —N—C(═O)—$R_{11}$, and
wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl.

In further embodiments, the invention provides compounds having Formula (I), its stereoisomers and pharmaceutically acceptable salts thereof, wherein:

$R_{1a}$ is tetrazole or triazole; $R_{1b}$ and $R_{1c}$ are H; n is 1; $R_{2a}$ and $R_{2b}$ are H, $R_3$ is H or C1-C4 alkyl substituted with a carboxylic acid or carboxylate group; $R_6$-$R_9$ are H; and Z is

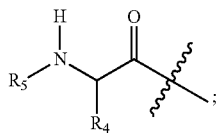

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

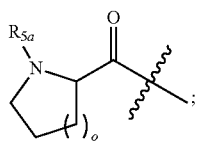

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

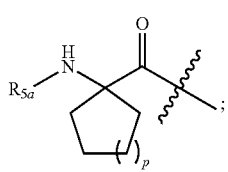

and
$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

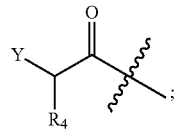

wherein $R_4$, $R_{5a}$, o, p, and Y are as described above.

In another embodiment, the invention provides compounds having Formula (II):

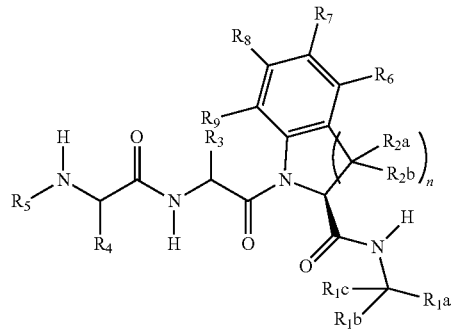

Formula (II)

its stereoisomers and pharmaceutically acceptable salts thereof, wherein:

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H;

$R_4$ is C3-C6 cycloalkyl or C1-C6 alkyl optionally substituted with hydroxyl or C1-C6 alkoxy; and $R_5$ is —C(═O)—$R_{10}$, wherein $R_{10}$ is selected from
(i) $C_1$-$C_{12}$ alkyl optionally substituted with $C_6$-$C_{10}$ aryl, optionally substituted $C_3$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(v) $C_3$-$C_{10}$ heteroaryl.

In a further embodiment, the invention provides compounds having Formula (III):

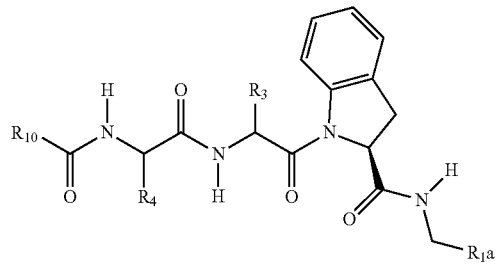

Formula (III)

its stereoisomers and pharmaceutically acceptable salts thereof, wherein:

$R_{1a}$, $R_3$, $R_4$, and $R_{10}$ are as above for Formula (II);

wherein $R_{10}$, when defined as C1-C12 alkyl substituted with a carboxylic acid or carboxylate group, is:

—(CH$_2$)$_n$—CO$_2$H, where n is 2, 3, 4, 5, or 6;

optionally wherein one or more single methylene carbons are substituted with a fluoro, hydroxy, amino, C1-C3 alkyl (e.g., methyl), or C6-C10 aryl group;

optionally wherein one or more single methylene carbons are substituted with two fluoro (e.g., difluoro, perfluoro) or C1-C3 alkyl (e.g., gem-dimethyl) groups;

optionally wherein one or more single methylene carbons are substituted with two alkyl groups that taken together with the carbon to which they are attached form a 3, 4, 5, or 6-membered carbocyclic ring (e.g., spiro groups such as cyclopropyl, cyclobutyl, cyclopentyl, and cyclohexyl); and optionally wherein adjacent carbon atoms from an unsaturated carbon-carbon bond (e.g., alkenyl such as —CH═CH—) or taken form a benzene ring (e.g., 1,2-, 1,3-, and 1,4-phenylene); or wherein $R_{10}$, when defined as C3-C6 cycloalkyl substituted with a carboxylic acid or carboxylate group, is:

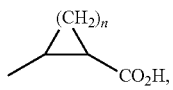

wherein n is 1, 2, 3, or 4; and optionally, for n=3 or 4, wherein adjacent carbon atoms from an unsaturated carbon-carbon bond (e.g., cyclopentenyl or cyclohexenyl).

In another embodiment, the invention provides compounds having Formula (IV):

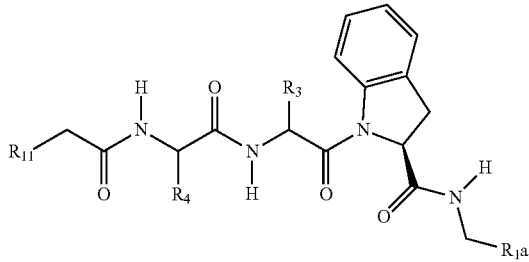

Formula (IV)

its stereoisomers and pharmaceutically acceptable salts thereof, wherein:

$R_{1a}$, $R_3$, and $R_4$ are as above for Formulae (II) and (III); and $R_{11}$ is selected from:

(a) optionally substituted C6-C10 aryl (e.g., unsubstituted phenyl and substituted phenyl such as carboxyphenyl, aminophenyl, alkylaminophenyl, dialkylaminophenyl); and (b) optionally substituted C3-C10 heteroaryl (e.g., optionally substituted pyridyl, optionally substituted thiazolyl, optionally substituted benzothiophenyl, optionally substituted tetrazolyl, and optionally substituted triazolyl (e.g., —NH$_2$ substituted).

In another aspect, the invention provides pharmaceutical compositions comprising a Granzyme B inhibitor compound of the invention and a pharmaceutically acceptable carrier.

In a further aspect of the invention, a method for inhibiting Granzyme B is provided. In one embodiment, the method comprises administering an effective amount of a Granzyme B inhibitor compound of the invention or a pharmaceutical composition of the invention to a subject in need thereof.

In a further aspect of the invention, a method for treating a disease, disorder, or condition treatable by inhibiting Granzyme B is provided. In one embodiment, the method comprises administering a therapeutically effective amount of a Granzyme B inhibitor compound of the invention or a pharmaceutical composition of the invention to a subject in need thereof. Representative routes of administration include topical administration, oral administration, and administration by injection.

In certain embodiments, the invention provides methods for treating cutaneous scleroderma, epidermolysis bullosa, radiation dermatitis, alopecia areata, or discoid lupus erythematosus comprising administering a therapeutically effective amount of a Granzyme B inhibitor compound of the invention or a pharmaceutical composition of the invention to a subject in need thereof. In certain embodiments, the Granzyme B inhibitor compound of the invention or pharmaceutical composition is administered topically.

Cosmetic compositions comprising a Granzyme B inhibitor compound of the invention and a cosmetically acceptable carrier are also provided, as are methods for using the compositions to treat, reduce, and/or inhibit the appearance of ageing in the skin.

DETAILED DESCRIPTION OF THE INVENTION

Figure 1:
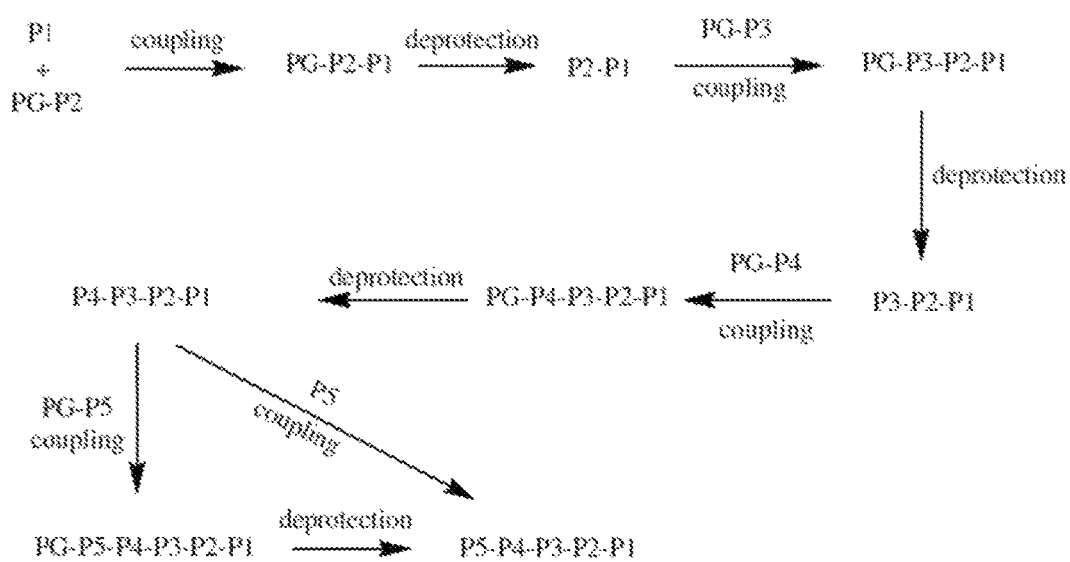
FIG. 1 is a schematic illustration of a representative synthetic pathway for the preparation of representative compounds of the invention P5-P4-P3-P2-P1 starting from P1.

The present invention provides Granzyme B inhibitor compounds, compositions that include the compounds, and methods for using the compounds. The compounds of the invention have advantageous water solubility and effectively inhibit Granzyme B.

In one aspect of the invention, the invention provides Granzyme B inhibitor compounds. In one embodiment, the invention provides the compounds having Formula (I):

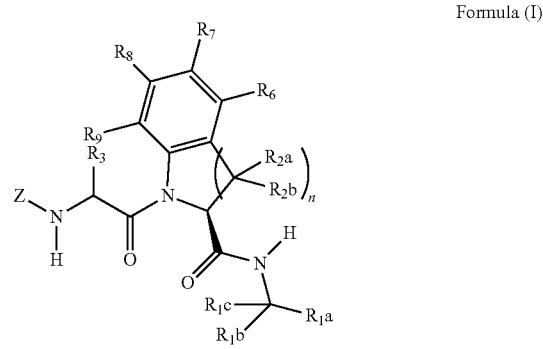

Formula (I)

its stereoisomers and pharmaceutically acceptable salts thereof, wherein:

$R_1a$ is a heteroaryl group selected from
(a) 1,2,3-triazolyl optionally substituted with $C_1$-$C_2$ alkyl,
(b) 1,2,3,4-tetrazolyl, and
(c) 1,2,3-thiadiazolyl;

$R_1b$ and $R_1c$ are independently selected from hydrogen, methyl, and halogen;

$R_2a$ and $R_2b$ are independently selected from hydrogen and methyl, or $R_2a$ and $R_2b$ taken together are oxo (i.e., =O, $R_2a$ and $R_2b$ together with the carbon to which they are attached form a carbonyl group);

n is 1 or 2;

$R_3$ is selected from hydrogen and $C_1$-$C_4$ alkyl optionally substituted with a carboxylic acid or a carboxylate group (—$CO_2H$ or —$CO_2^-$) or an amine group (—$NH_2$);

Z is an acyl group selected from the group

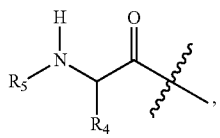
(a)

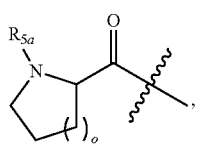
(b)

wherein o is 1 or 2, and $R_{5a}$ is $C_4$-acyl substituted with a carboxylic acid;

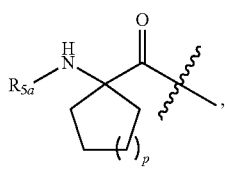
(c)

wherein p is 1 or 2, and $R_{5a}$ is $C_4$-acyl substituted with a carboxylic acid; and

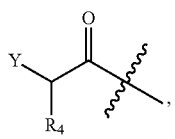
(d)

wherein Y is heteroaryl;
wherein
$R_4$ is selected from
(i) $C_1$-$C_{12}$ alkyl,
(ii) $C_1$-$C_6$ heteroalkyl optionally substituted with $C_1$-$C_6$ alkyl,
(iii) $C_3$-$C_6$ cycloalkyl,
(iv) $C_6$-$C_{10}$ aryl,
(v) heterocyclyl,
(vi) $C_3$-$C_{10}$ heteroaryl,
(vii) aralkyl, and
(viii) heteroalkylaryl;

$R_5$ is —C(=O)—$R_{10}$, wherein $R_{10}$ is selected from
(i) $C_1$-$C_{12}$ alkyl optionally substituted with $C_6$-$C_{10}$ aryl, optionally substituted $C_3$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(v) heterocyclyl,
(vi) $C_3$-$C_{10}$ heteroaryl,
(vii) aralkyl, and
(viii) heteroalkylaryl; and $R_6$, $R_7$, $R_8$, and $R_9$ are independently selected from
(a) hydrogen,
(b) halogen,
(c) $C_1$-$C_6$ alkyl,
(d) —$XR_{11}$, wherein X is selected from O, C(=O), S, S=O, or S(=O)$_2$,
(e) —C(=O)N($R_{12}$)($R_{11}$),
(f) —N($R_{11}$)($R_{12}$)($R_{13}$),
(g) —N—C(=O)—$R_{11}$, and
(h) —N—C(=O)O—$R_{11}$, wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl.

Representative compounds of the above embodiment include Examples A41 and B2.

In another embodiment, the invention provides compounds having Formula (I), its stereoisomers and pharmaceutically acceptable salts thereof, wherein:

$R_1a$ is a heteroaryl group selected from
(a) 1,2,3-triazolyl optionally substituted with $C_1$-$C_2$ alkyl, and
(b) 1,2,3,4-tetrazolyl;

$R_1b$ and $R_1c$ are independently selected from hydrogen and methyl;

$R_2a$ and $R_2b$ are independently selected from hydrogen and methyl;

n is 1;

$R_3$ is selected from hydrogen and $C_1$-$C_4$ alkyl optionally substituted with a carboxylic acid or a carboxylate group (—$CO_2H$ or —$CO_2^-$) or an amine group (—$NH_2$);

Z is an acyl group selected from the group

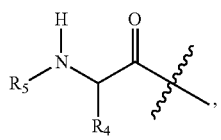
(a)

(b)

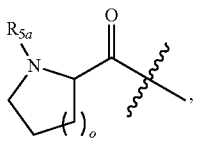

wherein o is 1 or 2, and $R_{5a}$ is $C_4$-acyl substituted with a carboxylic acid;

(c)

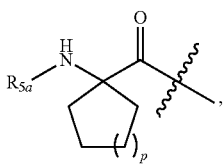

wherein p is 1 or 2, and $R_{5a}$ is $C_4$-acyl substituted with a carboxylic acid; and (d)

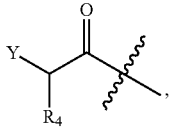

wherein Y is heteroaryl;
$R_4$ is selected from
(i) $C_1$-$C_{12}$ alkyl,
(ii) $C_3$-$C_6$ cycloalkyl,
(iii) $C_6$-$C_{10}$ aryl, and
(iv) $C_3$-$C_{10}$ heteroaryl;
$R_5$ is —C(=O)—$R_{10}$, wherein $R_{10}$ is selected from
(i) $C_1$-$C_{12}$ alkyl optionally substituted with $C_6$-$C_{10}$ aryl, optionally substituted $C_3$-$C_{10}$ heteroaryl, amino, or carboxylic acid,
(ii) $C_1$-$C_{10}$ heteroalkyl optionally substituted with $C_1$-$C_6$ alkyl or carboxylic acid,
(iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid,
(v) $C_3$-$C_{10}$ heteroaryl; and
$R_6$, $R_7$, $R_8$, and $R_9$ are independently selected from
(a) hydrogen,
(b) halogen,
(c) $C_1$-$C_6$ alkyl,
(d) —X$R_{11}$, wherein X is selected from O and C(=O),
(f) —N($R_{11}$)($R_{13}$),
(g) —N—C(=O)—$R_{11}$, and
wherein $R_{11}$, $R_{12}$, and $R_{13}$ are independently selected from the group consisting of hydrogen, $C_1$-$C_6$ alkyl, $C_1$-$C_6$ heteroalkyl, $C_2$-$C_6$ alkenyl, $C_6$-$C_{10}$ aryl, aralkyl, and $C_3$-$C_{10}$ heteroaryl.
Representative compounds of the above embodiment include Examples C25, C26, C28, C29, C36, and C37.
Other representative compounds of the above embodiment include Examples C23, C24, and C38.

Other representative compounds of the above embodiment include Examples B3, B4, I-5, A6, A7, A15, A29 and C47.

In further embodiments, the invention provides compounds having Formula (I), its stereoisomers and pharmaceutically acceptable salts thereof, wherein:

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

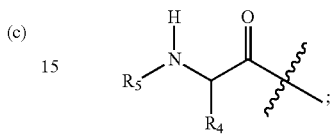

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

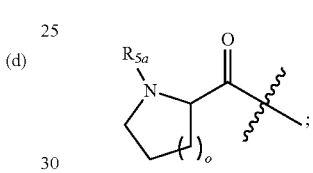

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

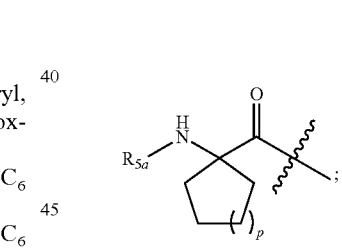

and $R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H; and Z is

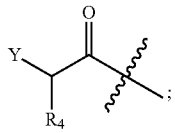

wherein $R_4$, $R_{5a}$, o, p, and Y are as described above.

In another embodiment, the invention provides compounds having Formula (II):

Formula (II)

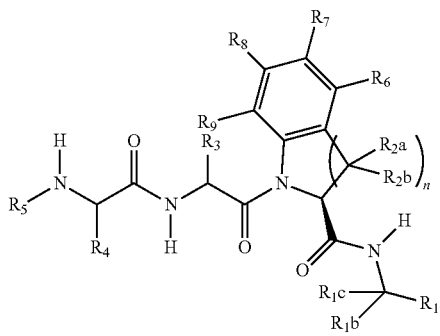

its stereoisomers and pharmaceutically acceptable salts thereof, wherein:

$R_{1a}$ is tetrazole or triazole; $R_{1b}$ and $R_{1c}$ are H; n is 1; $R_{2a}$ and $R_{2b}$ are H; $R_3$ is H or C1-C4 alkyl substituted with a carboxylic acid or carboxylate group; $R_6$-$R_9$ are H;

$R_4$ is C3-C6 cycloalkyl or C1-C6 alkyl optionally substituted with hydroxyl or C1-C6 alkoxy; and $R_5$ is —C(=O)—$R_{10}$, wherein $R_{10}$ is selected from (i) $C_1$-$C_{12}$ alkyl optionally substituted with $C_6$-$C_{10}$ aryl, optionally substituted $C_3$-$C_{10}$ heteroaryl, amino, or carboxylic acid, (ii) $C_1$-$C_{10}$ heteroalkyl optionally substituted with $C_1$-$C_6$ alkyl or carboxylic acid, (iii) $C_3$-$C_6$ cycloalkyl optionally substituted with $C_1$-$C_6$ alkyl, optionally substituted $C_6$-$C_{10}$ aryl, optionally substituted $C_3$-$C_{10}$ heteroaryl, amino, or carboxylic acid, (iv) $C_6$-$C_{10}$ aryl optionally substituted with $C_1$-$C_6$ alkyl, optionally substituted $C_6$-$C_{10}$ aryl, optionally substituted $C_3$-$C_{10}$ heteroaryl, amino, or carboxylic acid, (v) $C_3$-$C_{10}$ heteroaryl.

Representative compounds of the above embodiment include Examples B5, B6, B7, C19, C20, C21, C22, C27, C30, C31, C32, C33, C34, and C35.

In a further embodiment, the invention provides compounds having Formula (III):

Formula (III)

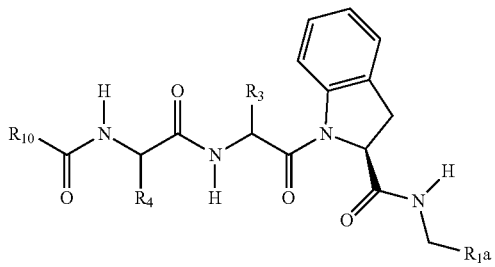

its stereoisomers and pharmaceutically acceptable salts thereof, wherein:

$R_{1a}$, $R_3$, $R_4$, and $R_{10}$ are as above for Formula (II);

wherein $R_{10}$, when defined as C1-C12 alkyl substituted with a carboxylic acid or carboxylate group, is:

—$(CH_2)_n$—$CO_2H$, where n is 2, 3, 4, 5, or 6;

optionally wherein one or more single methylene carbons are substituted with a fluoro, hydroxy, amino, C1-C3 alkyl (e.g., methyl), or C6-C10 aryl group;

optionally wherein one or more single methylene carbons are substituted with two fluoro (e.g., difluoro, perfluoro) or C1-C3 alkyl (e.g., gem-dimethyl) groups;

optionally wherein one or more single methylene carbons are substituted with two alkyl groups that taken together with the carbon to which they are attached form a 3, 4, 5, or 6-membered carbocyclic ring (e.g., spiro groups such as cyclopropyl, cyclobutyl, cyclopentyl, and cyclohexyl); and optionally wherein adjacent carbon atoms from an unsaturated carbon-carbon bond (e.g., alkenyl such as —CH═CH—) or taken form a benzene ring (e.g., 1,2-, 1,3-, and 1,4-phenylene); or wherein $R_{10}$, when defined as C3-C6 cycloalkyl substituted with a carboxylic acid or carboxylate group, is:

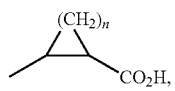

wherein n is 1, 2, 3, or 4; and optionally, for n=3 or 4, wherein adjacent carbon atoms from an unsaturated carbon-carbon bond (e.g., cyclopentenyl or cyclohexenyl).

Representative compounds of the above embodiment include Examples A5, A13, A14, A16, A17-1, A17-2, A18, A19, A20-1, A20-2, A21-1, A21-2, A22-1, A22-2, A23-1, A23-2, A24, A25, A26-1, A26-2, A30-1, A30-2, A31, A32, A33, A36, A37, A38, A39, A40, A43, A44, A45, A46, A48, A51, A52, A53, A54-1, A54-2, A55, A56, A57-1, and A57-2.

In another embodiment, the invention provides compounds having Formula (IV):

Formula (IV)

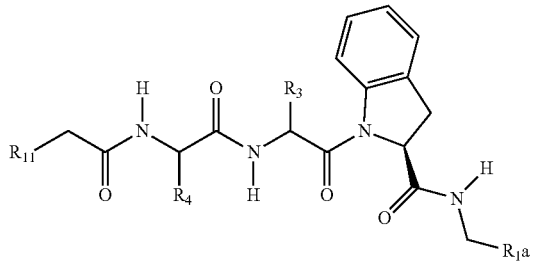

its stereoisomers and pharmaceutically acceptable salts thereof, wherein:

$R_{1a}$, $R_3$, and $R_4$ are as above for Formulae (II) and (III); and $R_{11}$ is selected from:

(a) optionally substituted C6-C10 aryl (e.g., unsubstituted phenyl and substituted phenyl such as carboxyphenyl, aminophenyl, alkylaminophenyl, dialkylaminophenyl); and (b) optionally substituted C3-C10 heteroaryl (e.g., optionally substituted pyridyl, optionally substituted thiazolyl, optionally substituted benzothiophenyl, optionally substituted tetrazolyl, and optionally substituted triazolyl (e.g., —$NH_2$ substituted).

Representative compounds of the above embodiment include Examples A1, A2, A3, A4, A8, A9, A10, A11, A12, A27, A28, A34, A35, A42, A49, A50, B1, C1, C2, C3, C4, C5, C6, C7, C8, C9, C10, C11, C12, C13, C14, C15, C16, C17, C18, and C39.

Each of the inhibitor compounds of the invention contain asymmetric carbon centers and give rise to stereoisomers (i.e., optical isomers such as diastereomers and enantiomers). It will be appreciated that the present invention includes such diastereomers as well as their racemic and resolved enantiomerically pure forms. It will also be appreciated that in certain configurations, the relative stereochemistry of certain groups may be depicted as "cis" or "trans" when absolute stereochemistry is not shown.

Some of the compounds described herein contain olefinic double bonds, and unless specified otherwise, are meant to include both E and Z geometric isomers.

When the compounds of the present invention are basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids.

The invention is described using the following definitions unless otherwise indicated.

As used herein, the term "alkyl" refers to a saturated or unsaturated, branched, straight-chain or cyclic monovalent hydrocarbon group derived by the removal of one hydrogen atom from a single carbon atom of a parent alkane, alkene, or alkyne. Representative alkyl groups include methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, and prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, and but-3-yn-1-yl; and the like. Where a specific level of saturation is intended, the expressions "alkanyl," "alkenyl," and "alkynyl" are used. Alkyl groups include cycloalkyl groups. The term "cycloalkyl" refers to mono-, bi-, and tricyclic alkyl groups having the indicated number of carbon atoms. Representative cycloalkyl groups include cyclopropyl, cyclopentyl, cycloheptyl, adamantyl, cyclododecylmethyl, and 2-ethyl-1-bicyclo[4.4.0]decyl groups. The alkyl group may be unsubstituted or substituted as described below.

"Alkanyl" refers to a saturated branched, straight-chain, or cyclic alkyl group. Representative alkanyl groups include methanyl; ethanyl; propanyls such as propan-1-yl, propan-2-yl(isopropyl), and cyclopropan-1-yl; butanyls such as butan-1-yl, butan-2-yl (sec-butyl), 2-methyl-propan-1-yl (isobutyl), 2-methyl-propan-2-yl(t-butyl), and cyclobutan-1-yl; and the like. The alkanyl group may be substituted or unsubstituted. Representative alkanyl group substituents include —$R_{14}$, —$OR_{14}$, —$SR_{14}$, —$NR_{14}(R_{15})$,
—X, —$CX_3$, —CN, —$NO_2$,
—C(=O)$R_{14}$, —C(=O)O$R_{14}$, —C(=O)N$R_{14}(R_{15})$, —C(=O)S$R_{14}$,
—C(=N$R_{14}$)$R_{14}$, —C(=N$R_{14}$)O$R_{14}$, —C(=N$R_{14}$)N$R_{14}(R_{15})$, —C(=N$R_{14}$)S$R_{14}$,
—C(=S)$R_{14}$, —C(=S)O$R_{14}$, —C(=S)N$R_{14}(R_{15})$, —C(=S)S$R_{14}$,
—N$R_{14}$C(=O)N$R_{14}(R_{15})$, —$N_{14}$(=N$R_{14}$)N$R_{14}(R_{15})$, —N$R_{14}$C(=S)N$R_{14}(R_{15})$,
—S(=O)$_2R_{14}$, —S(=O)$_2$O$R_{14}$, —S(=O)$_2$N$R_{14}(R_{15})$,
—OC(=O)$R_{14}$, —OC(=O)O$R_{14}$, —OC(=O)N$R_{14}(R_{15})$, —OC(=O)S$R_{14}$,
—OS(=O)$_2$O$R_{14}$, —OS(=O)$_2$N$R_{14}(R_{15})$, and
—OP(=O)$_2$(O$R_4$), wherein each X is independently a halogen, and $R_{14}$ and $R_{15}$ are independently hydrogen, C1-C6 alkyl, C6-C14 aryl, arylalkyl, C3-C10 heteroaryl, and heteroarylalkyl, as defined herein.

In certain embodiments, two hydrogen atoms on a single carbon atom can be replaced with =O, =N$R_{12}$, or =S.

"Alkenyl" refers to an unsaturated branched, straight-chain, cyclic alkyl group, or combinations thereof having at least one carbon-carbon double bond derived by the removal of one hydrogen atom from a single carbon atom of a parent alkene. The group may be in either the cis or trans conformation about the double bond(s). Representative alkenyl groups include ethenyl; propenyls such as prop-1-en-1-yl, prop-1-en-2-yl, prop-2-en-1-yl (allyl), prop-2-en-2-yl, and cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, and cyclobuta-1,3-dien-1-yl; and the like. The alkenyl group may be substituted or unsubstituted. Representative alkenyl group substituents include —$R_{14}$,
—X, —$CX_3$, —CN,
—C(=O)$R_{14}$, —C(=O)O$R_{14}$, —C(=O)N$R_{14}(R_{15})$, —C(=O)S$R_{14}$,
—C(=N$R_{14}$)$R_{14}$, —C(=N$R_{14}$)O$R_{14}$, —C(=N$R_{14}$)N$R_{14}(R_{15})$, —C(=N$R_{14}$)S$R_{14}$,
—C(=S)$R_{14}$, —C(=S)O$R_{14}$, —C(=S)N$R_{14}(R_{15})$, —C(=S)S$R_{14}$, wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

"Alkynyl" refers to an unsaturated branched, straight-chain, or cyclic alkyl group having at least one carbon-carbon triple bond derived by the removal of one hydrogen atom from a single carbon atom of a parent alkyne. Representative alkynyl groups include ethynyl; propynyls such as prop-1-yn-1-yl and prop-2-yn-1-yl; butynyls such as but-1-yn-1-yl, but-1-yn-3-yl, and but-3-yn-1-yl; and the like. The alkynyl group may be substituted or unsubstituted. Representative alkynyl group substituents include those as described above for alkenyl groups.

The term "haloalkyl" refers to an alkyl group as defined above having the one or more hydrogen atoms replaced by a halogen atom. Representative haloalkyl groups include halomethyl groups such as chloromethyl, fluoromethyl, and trifluoromethyl groups; and haloethyl groups such as chloroethyl, fluoroethyl, and perfluoroethyl groups. The term "heteroalkyl" refers to an alkyl group having the indicated number of carbon atoms and where one or more of the carbon atoms is replaced with a heteroatom selected from O, N, or S. Where a specific level of saturation is intended, the expressions "heteroalkanyl," "heteroalkenyl," and "heteroalkynyl" are used. Representative heteroalkyl groups include ether, amine, and thioether groups. Heteroalkyl groups include heterocyclyl groups. The term "heterocyclyl" refers to a 5- to 10-membered non-aromatic mono- or bicyclic ring containing 1-4 heteroatoms selected from O, S, and N. Representative heterocyclyl groups include pyrrolidinyl, piperidinyl, piperazinyl, tetrahydrofuranyl, tetrahydropuranyl, and morpholinyl groups. The heteroalkyl group may be substituted or unsubstituted. Representative heteroalkyl substituents include —$R_{14}$, —$OR_{14}$, —$SR_{14}$, —$NR_{14}(R_{15})$,
—X, —$CX_3$, —CN, —$NO_2$,

—C(=O)$R_{14}$, —C(=O)O$R_{14}$, —C(=O)N$R_{14}$($R_{15}$), —C(=O)S$R_{14}$,

—C(=N$R_{14}$)$R_{14}$, —C(=N$R_{14}$)O$R_{14}$, —C(=N$R_{14}$)N$R_{14}$($R_{15}$), —C(=N$R_{14}$)S$R_{14}$,

—C(=S)$R_{14}$, —C(=S)O$R_{14}$, —C(=S)N$R_{14}$($R_{15}$), —C(=S)S$R_{14}$,

—N$R_{14}$C(=O)N$R_{14}$($R_{15}$), —N$R_{14}$(=N$R_{14}$)N$R_{14}$($R_{15}$), —N$R_{14}$C(=S)N$R_{14}$($R_{15}$),

—S(=O)$_2R_{14}$, —S(=O)$_2$O$R_{14}$, —S(=O)$_2$N$R_{14}$($R_{15}$),

—OC(=O)$R_{14}$, —OC(=O)O$R_{14}$, —OC(=O)N$R_{14}$($R_{15}$), —OC(=O)S$R_{14}$,

—OS(=O)$_2$O$R_{14}$, —OS(=O)$_2$N$R_{14}$($R_{15}$), and

—OP(=O)$_2$(O$R_{14}$), wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

In certain embodiments, two hydrogen atoms on a single carbon atom can be replaced with =O, =N$R_{12}$, or =S.

The term "alkoxy" refers to an alkyl group as described herein bonded to an oxygen atom. Representative C1-C3 alkoxy groups include methoxy, ethoxy, propoxy, and isopropoxy groups.

The term "alkylamino" refers an alkyl group as described herein bonded to a nitrogen atom. The term "alkylamino" includes monoalkyl- and dialkylaminos groups. Representative C1-C6 alkylamino groups include methylamino, dimethylamino, ethylamino, methylethylamino, diethylamino, propylamino, and isopropylamino groups.

The term "alkylthio" refers an alkyl group as described herein bonded to a sulfur atom. Representative C1-C6 alkylthio groups include methylthio, propylthio, and isopropylthio groups.

The term "aryl" refers to a monovalent aromatic hydrocarbon group derived by the removal of one hydrogen atom from a single carbon atom of a parent aromatic ring system. Suitable aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, the aryl group is a C5-C14 aryl group. In other embodiments, the aryl group is a C5-C10 aryl group. The number of carbon atoms specified refers to the number of carbon atoms in the aromatic ring system. Representative aryl groups are phenyl, naphthyl, and cyclopentadienyl. The aryl group may be substituted or unsubstituted. Representative aryl group substituents include —$R_{14}$, —O$R_{14}$, —S$R_{14}$, —N$R_{14}$($R_{15}$),
—X, —C$X_3$, —CN, —N$O_2$,
—C(=O)$R_{14}$, —C(=O)O$R_{14}$, —C(=O)N$R_{14}$($R_{15}$), —C(=O)S$R_{14}$,
—C(=N$R_{14}$)$R_{14}$, —C(=N$R_{14}$)O$R_{14}$, —C(=N$R_{14}$)N$R_{14}$($R_{15}$), —C(=N$R_{14}$)S$R_{14}$,
—C(=S)$R_{14}$, —C(=S)O$R_{14}$, —C(=S)N$R_{14}$($R_{15}$), —C(=S)S$R_{14}$,
—N$R_{14}$C(=O)N$R_{14}$($R_{15}$), —N$R_{14}$(=NR)N$R_{14}$($R_{15}$), —N$R_{14}$C(=S)N$R_{14}$($R_{15}$),
—S(=O)$_2R_{14}$, —S(=O)$_2$O$R_{14}$, —S(=O)$_2$N$R_{14}$($R_{15}$),
—OC(=O)$R_{14}$, —OC(=O)O$R_{14}$, —OC(=O)N$R_{14}$($R_{15}$), —OC(=O)S$R_{14}$,
—OS(=O)$_2$O$R_{14}$, —OS(=O)$_2$N$R_{14}$($R_{15}$), and
—OP(=O)$_2$(O$R_{14}$), wherein each X is independently a halogen; and $R_{14}$ and $R_{15}$ are independently hydrogen, C1-C6 alkyl, C6-C14 aryl, arylalkyl, C3-C10 heteroaryl, and heteroarylalkyl, as defined herein.

The term "aralkyl" refers to an alkyl group as defined herein with an aryl group, optionally substituted, as defined herein substituted for one of the alkyl group hydrogen atoms. Suitable aralkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the terms aralkanyl, aralkenyl, and aralkynyl are used. In certain embodiments, the aralkyl group is a C6-C20 aralkyl group, (e.g., the alkanyl, alkenyl, or alkynyl moiety of the aralkyl group is a C1-C6 group and the aryl moiety is a C5-C14 group). In other embodiments, the aralkyl group is a C6-C13 aralkyl group (e.g., the alkanyl, alkenyl, or alkynyl moiety of the aralkyl group is a C1-C3 group and the aryl moiety is a C5-C10 aryl group. In certain embodiments, the aralkyl group is a benzyl group.

The term "heteroaryl" refers to a monovalent heteroaromatic group derived by the removal of one hydrogen atom from a single atom of a parent heteroaromatic ring system, which may be monocyclic or fused ring (i.e., rings that share an adjacent pair of atoms). A "heteroaromatic" group is a 5- to 14-membered aromatic mono- or bicyclic ring containing 1-4 heteroatoms selected from O, S, and N. Representative 5- or 6-membered aromatic monocyclic ring groups include pyridine, pyrimidine, pyridazine, furan, thiophene, thiazole, oxazole, and isooxazole. Representative 9- or 10-membered aromatic bicyclic ring groups include benzofuran, benzothiophene, indole, pyranopyrrole, benzopyran, quionoline, benzocyclohexyl, and naphthyridine. Suitable heteroaryl groups include groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is a 5-14 membered heteroaryl group. In other embodiments, the heteroaryl group is a 5-10 membered heteroaryl group. Preferred heteroaryl groups are those derived from thiophene, pyrrole, benzothiophene, benzofuran, indole, pyridine, quinoline, imidazole, oxazole, and pyrazine. The heteroaryl group may be substituted or unsubstituted. Representative heteroaryl group substituents include those described above for aryl groups.

The term "heteroarylalkyl" refers to an alkyl group as defined herein with a heteroaryl group, optionally substituted, as defined herein substituted for one of the alkyl group hydrogen atoms. Where specific alkyl moieties are intended, the terms heteroarylalkanyl, heteroarylalkenyl, or heteroarylalkynyl are used. In certain embodiments, the heteroarylalkyl group is a 6-20 membered heteroarylalkyl (e.g., the alkanyl, alkenyl or alkynyl moiety of the heteroarylalkyl is a C1-C6 group and the heteroaryl moiety is a 5-14-membered heteroaryl group. In other embodiments, the heteroarylalkyl group is a 6-13 membered heteroarylalkyl (e.g., the alkanyl, alkenyl or alkynyl moiety is C1-C3 group and the heteroaryl moiety is a 5-10-membered heteroaryl group).

The term "acyl" group refers to the —C(=O)—R' group, where R' is selected from optionally substituted alkyl, optionally substituted aryl, and optionally substituted heteroaryl, as defined herein.

The term "halogen" or "halo" refers to fluoro, chloro, bromo, and iodo groups.

The term "substituted" refers to a group in which one or more hydrogen atoms are each independently replaced with the same or different substituent(s).

Representative compounds of the invention and related intermediates were prepared from commercially available starting materials or starting materials prepared by conventional synthetic methodologies. Representative compounds of the invention were prepared according to Methods A to P as described below and illustrated in FIGS. 1-3. The preparations of certain intermediates (I-1 to I-15) useful in the preparation of compounds of the invention are described in the Synthetic Intermediate section below.

Figure 2:
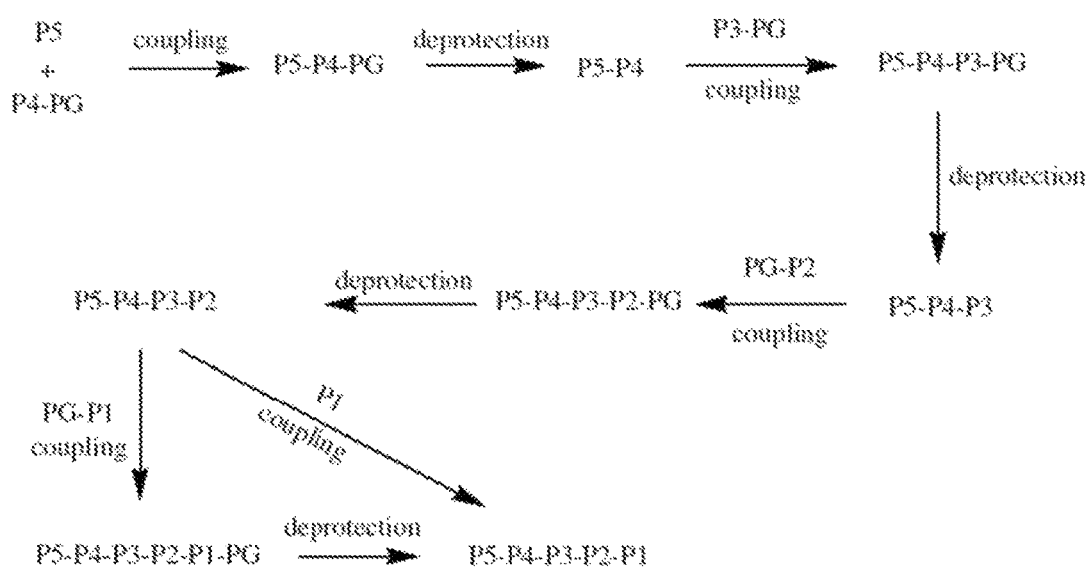
FIG. 2 is a schematic illustration of another representative synthetic pathway for the preparation of representative compounds of the invention P5-P4-P3-P2-P1 starting from P5.
Figure 3:
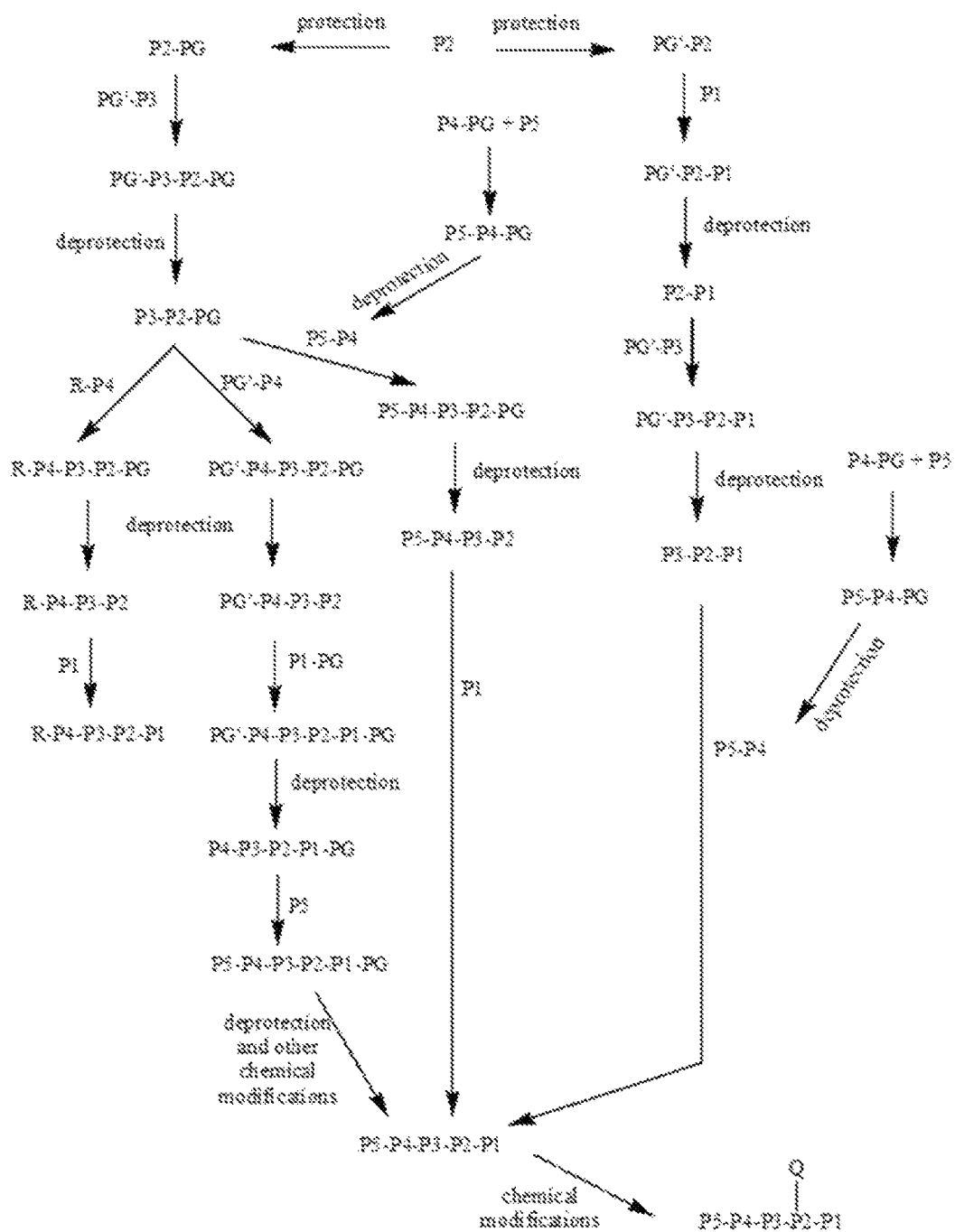
FIG. 3 is a schematic illustration of a further representative synthetic pathway for the preparation of representative compounds of the invention P5-P4-P3-P2-P1 starting from a component other than P1 or P5.

FIGS. 1-3 present schematic illustrations of representative synthetic pathways for the preparation of representative compounds of the invention P5-P4-P3-P2-P1. As used herein. "P5-P4-P3-P2-P1" refers to compounds of the invention prepared from five (5) components: P1, P2, P3, P4, and P5. Protected version of the components useful in the preparation of the compounds of the invention are designated as, for example, "PG-P2," "PG-P2-P1," "PG-3," and "PG-P3-P2-P1," where "PG" is refers to a protecting group that allows for the coupling of, for example, P1 to P2 or P3 to P1-P2, and that is ultimately removed to provide, for example, P1-P2 or P1-P2-P3.

FIG. 1 is a schematic illustration of a representative synthetic pathway for the preparation of representative compounds of the invention P5-P4-P3-P2-P1 starting from P1. In this pathway, compound P5-P4-P3-P2-P1 is prepared in a stepwise manner starting with P1 by sequential coupling steps, separated as appropriate by deprotection steps and other chemical modifications. As shown in FIG. 1. P1 is coupled with PG-P2 to provide PG-P2-P1, which is then deprotected to provide P2-P1 and ready for coupling with the next component, PG-P3. The process is continued with subsequent couplings PG-P4 with P3-P2-P1 and PG-P5 with P4-P3-P2-P1 to ultimately provide P5-P4-P3-P2-P1. Examples A1-A57 were prepared by this pathway.

FIG. 2 is a schematic illustration of another representative synthetic pathway for the preparation of representative compounds of the invention P5-P4-P3-P2-P1 starting from P5. In this pathway, compound P5-P4-P3-P2-P1 is prepared in a stepwise manner starting with P5 by sequential coupling steps, separated as appropriate by deprotection steps and other chemical modifications. As shown in FIG. 2, P5 is coupled with PG-P4 to provide P5-P4-PG, which is then deprotected to provide P5-P4 and ready for coupling with the next component. P3-PG. The process is continued with subsequent couplings PG-P2 with P5-P4-P3 and PG-P1 with P5-P4-P3-P2 to ultimately provide P5-P4-P3-P2-P1. Examples B1-B7 were prepared by this method.

FIG. 3 is a schematic illustration of a further representative synthetic pathway for the preparation of representative compounds of the invention P5-P4-P3-P2-P1 starting from a component other than P1 or P5. In this pathway, compound P5-P4-P3-P2-P1 is prepared in a stepwise manner starting with P2 by sequential coupling steps, separated as appropriate by deprotection steps and other chemical modifications. As shown in FIG. 3, there are multiple pathways to P5-P4-P3-P2-P1. Pathways are shown involving representative Synthetic Intermediates (I-1, I-2, I-3, I-4, I-6, I-7, I-9, I-10, I-11, and I-12). Examples C1-C39 were prepared by this method.

The preparation of representative compounds and their characterization are described in Examples A1 to A57, B1 to B7, and C1 to C39. The structures of representative compounds are set forth in Table 1.

TABLE 1

Representative Compounds.

| Cmpd # | Structure |
|---|---|
| I-5 | 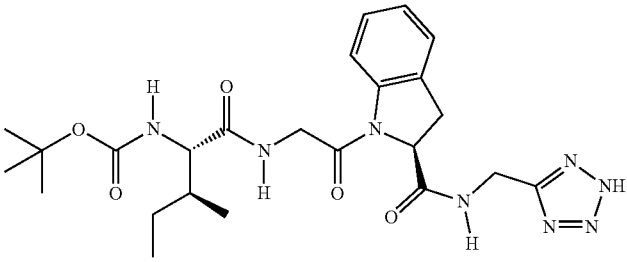 [SMILES: CC[C@H](C)[C@H](NC(=O)OC(C)(C)C)C(=O)NCC(=O)N1c2ccccc2C[C@H]1C(=O)NCc1nn[nH]n1] |
| A1 | 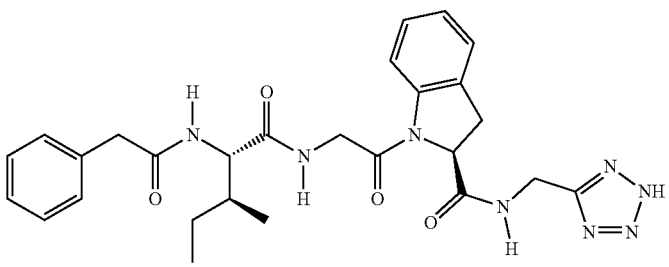 [SMILES: CC[C@H](C)[C@H](NC(=O)Cc1ccccc1)C(=O)NCC(=O)N1c2ccccc2C[C@H]1C(=O)NCc1nn[nH]n1] |

TABLE 1-continued
Representative Compounds.
| Cmpd # | Structure |
|---|---|
| A2 | 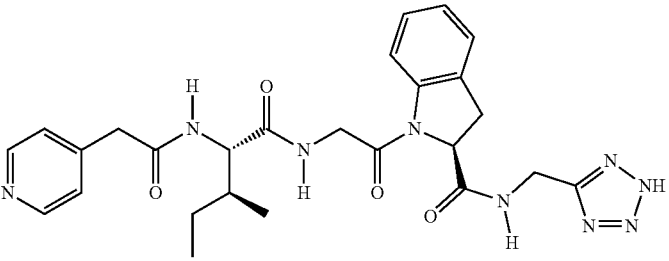 [SMILES: CC[C@H](C)[C@H](NC(=O)Cc1ccncc1)C(=O)NCC(=O)N1c2ccccc2C[C@H]1C(=O)NCc1nn[nH]n1] |
| A3 | 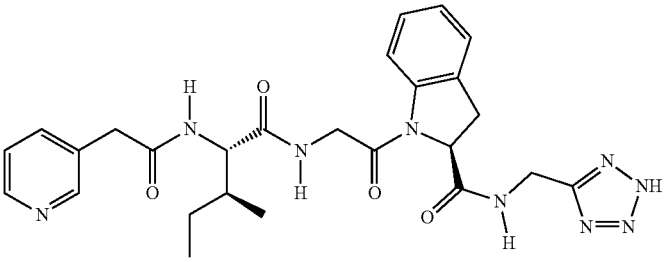 [SMILES: CC[C@H](C)[C@H](NC(=O)Cc1cccnc1)C(=O)NCC(=O)N1c2ccccc2C[C@H]1C(=O)NCc1nn[nH]n1] |
| A4 | 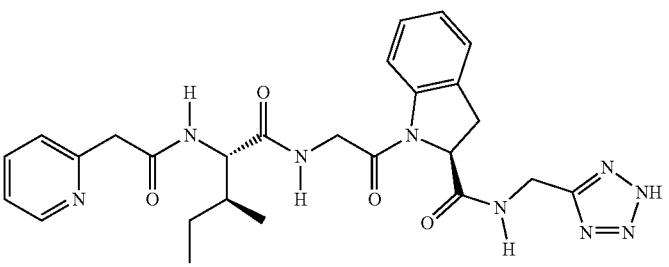 [SMILES: CC[C@H](C)[C@H](NC(=O)Cc1ccccn1)C(=O)NCC(=O)N1c2ccccc2C[C@H]1C(=O)NCc1nn[nH]n1] |
| A5 | 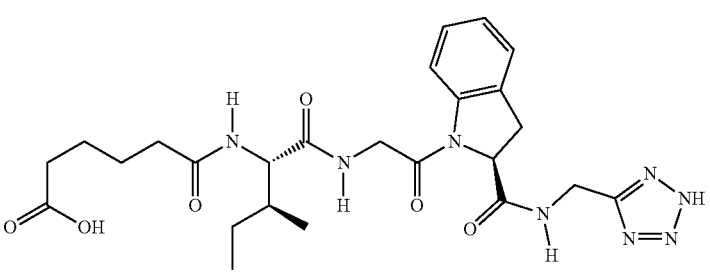 [SMILES: CC[C@H](C)[C@H](NC(=O)CCCCC(=O)O)C(=O)NCC(=O)N1c2ccccc2C[C@H]1C(=O)NCc1nn[nH]n1] |
| A6 | 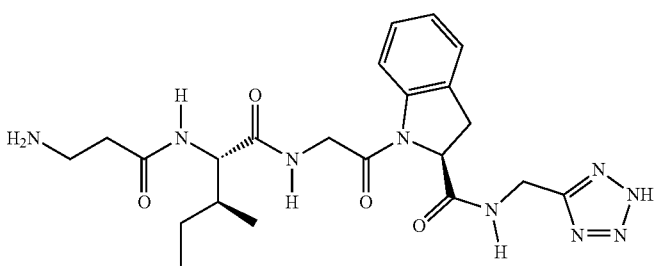 [SMILES: CC[C@H](C)[C@H](NC(=O)CCN)C(=O)NCC(=O)N1c2ccccc2C[C@H]1C(=O)NCc1nn[nH]n1] |

TABLE 1-continued
Representative Compounds.
| Cmpd # | Structure |
|---|---|
| A7 | 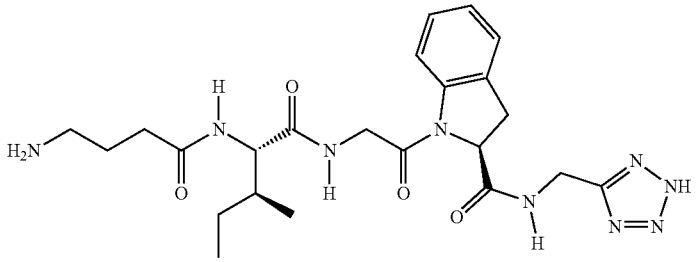 [SMILES: CC[C@H](C)[C@H](NC(=O)CCCN)C(=O)NCC(=O)N1c2ccccc2C[C@H]1C(=O)NCc1nn[nH]n1] |
| A8 | 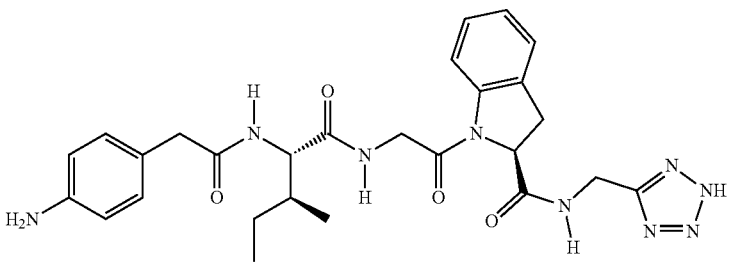 [SMILES: CC[C@H](C)[C@H](NC(=O)Cc1ccc(N)cc1)C(=O)NCC(=O)N1c2ccccc2C[C@H]1C(=O)NCc1nn[nH]n1] |
| A9 | 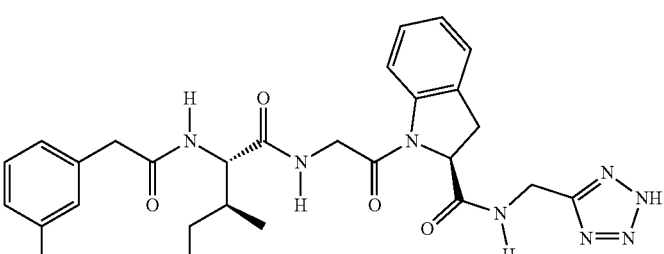 |
| A10 | 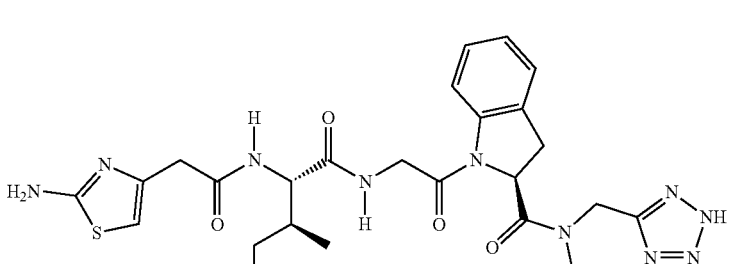 |
| A11 | 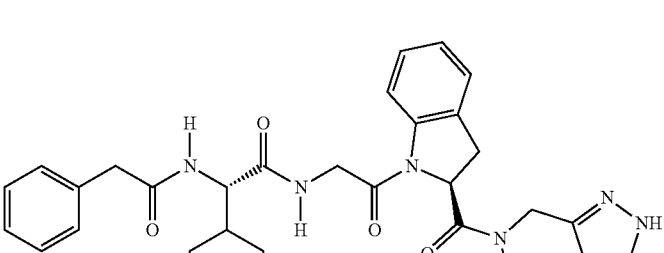 |

TABLE 1-continued

Representative Compounds.

| Cmpd # | Structure |
|---|---|
| A12 | 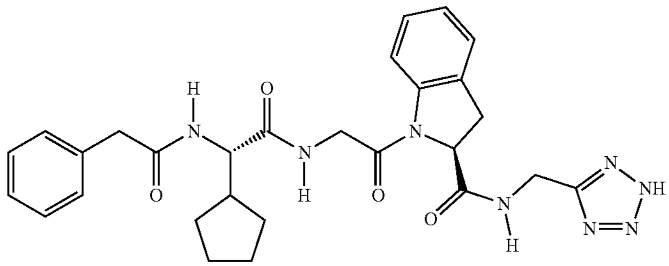 [SMILES: O=C(Cc1ccccc1)N[C@H](C(=O)NCC(=O)N1c2ccccc2C[C@H]1C(=O)NCc1nn[nH]n1)C1CCCC1] |
| A13 | 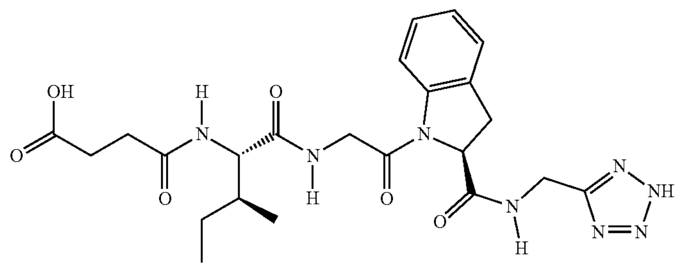 [SMILES: CC[C@H](C)[C@H](NC(=O)CCC(=O)O)C(=O)NCC(=O)N1c2ccccc2C[C@H]1C(=O)NCc1nn[nH]n1] |
| A14 | 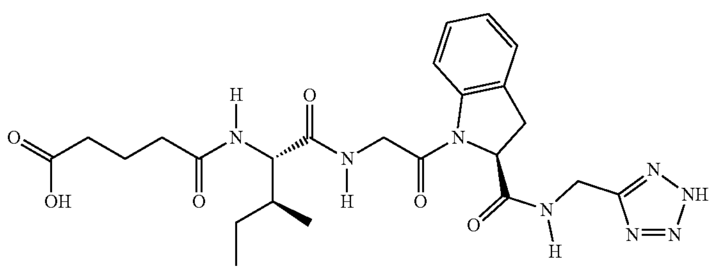 [SMILES: CC[C@H](C)[C@H](NC(=O)CCCC(=O)O)C(=O)NCC(=O)N1c2ccccc2C[C@H]1C(=O)NCc1nn[nH]n1] |
| A15 | 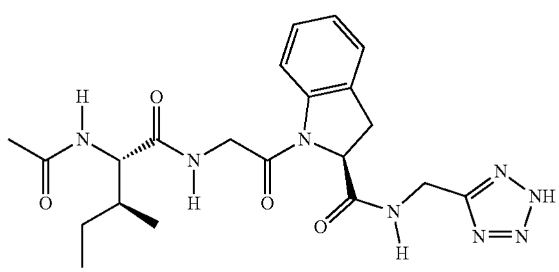 [SMILES: CC[C@H](C)[C@H](NC(C)=O)C(=O)NCC(=O)N1c2ccccc2C[C@H]1C(=O)NCc1nn[nH]n1] |
| A16 | 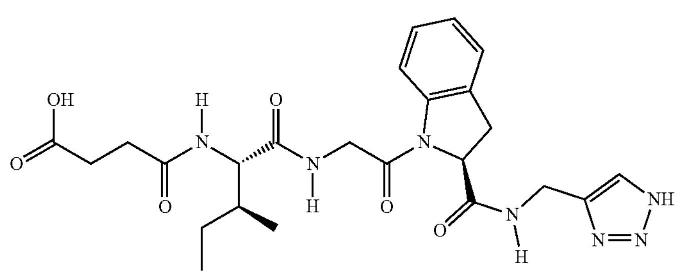 [SMILES: CC[C@H](C)[C@H](NC(=O)CCC(=O)O)C(=O)NCC(=O)N1c2ccccc2C[C@H]1C(=O)NCc1c[nH]nn1] |

TABLE 1-continued
Representative Compounds.
| Cmpd # | Structure |
|---|---|
| A17-1 | 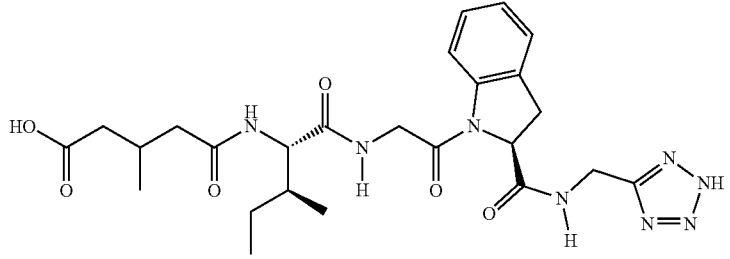<br>diastereomer 1 |
| A17-2 | 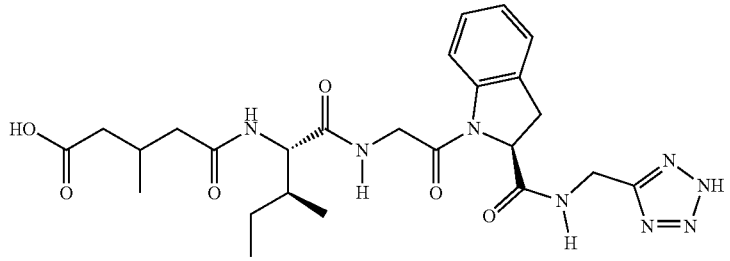<br>diastereomer 2 |
| A18 | 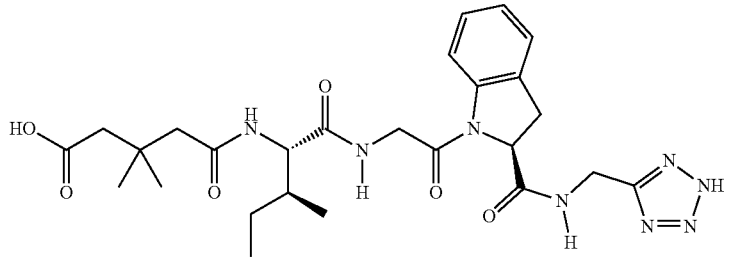 [SMILES: CC[C@H](C)[C@H](NC(=O)CC(C)(C)CC(=O)O)C(=O)NCC(=O)N1c2ccccc2C[C@H]1C(=O)NCc1nn[nH]n1] |
| A19 | 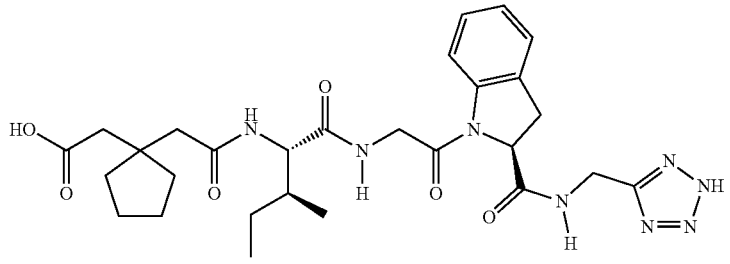 [SMILES: CC[C@H](C)[C@H](NC(=O)CC1(CC(=O)O)CCCC1)C(=O)NCC(=O)N1c2ccccc2C[C@H]1C(=O)NCc1nn[nH]n1] |
| A20-1 | 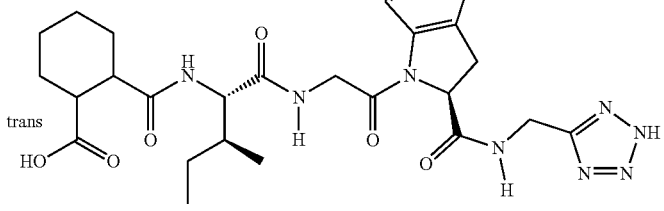<br>diastereomer 1 |

TABLE 1-continued
Representative Compounds.
| Cmpd # | Structure |
|---|---|
| A20-2 | 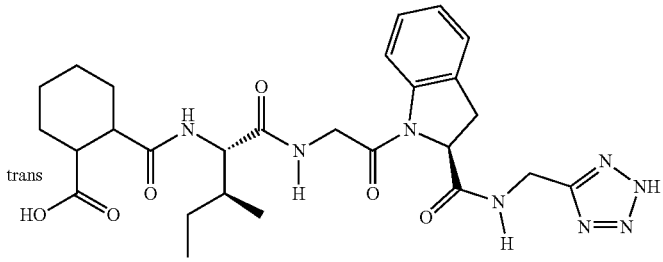<br>diastereomer 2 |
| A21-1 | 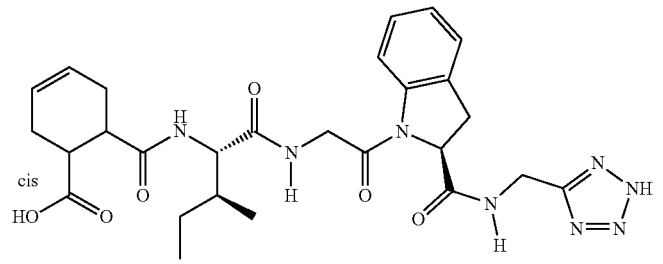<br>diastereomer 1 |
| A21-2 | 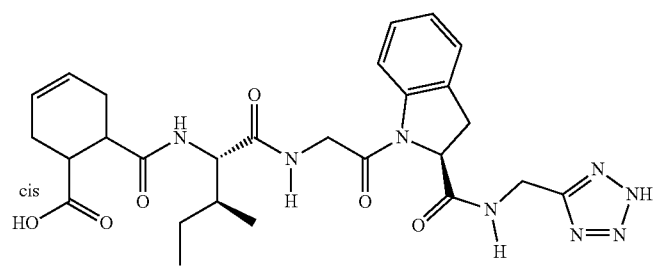<br>diastereomer 2 |
| A22-1 | 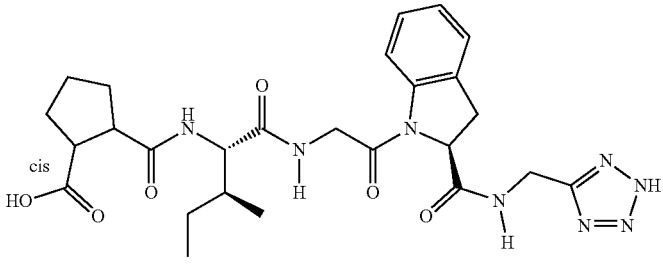<br>diastereomer 1 |
| A22-2 | 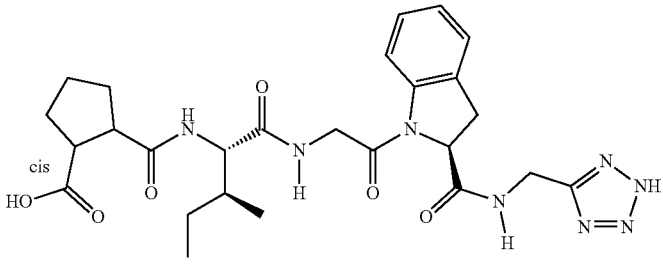<br>diastereomer 2 |

TABLE 1-continued
Representative Compounds.
| Cmpd # | Structure |
|---|---|
| A23-1 | 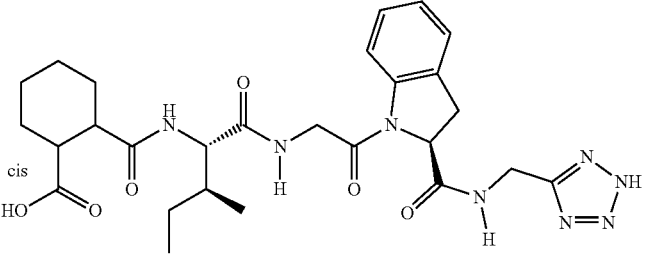<br>diastereomer 1 |
| A23-2 | 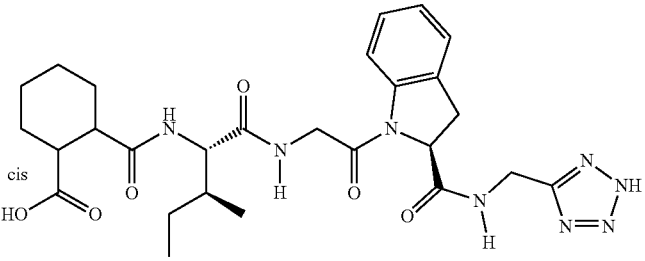<br>diastereomer 2 |
| A24 | 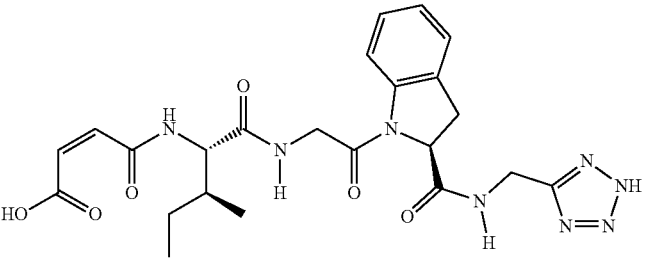 [SMILES: CC[C@H](C)[C@H](NC(=O)/C=C\C(=O)O)C(=O)NCC(=O)N1c2ccccc2C[C@H]1C(=O)NCc1nn[nH]n1] |
| A25 | 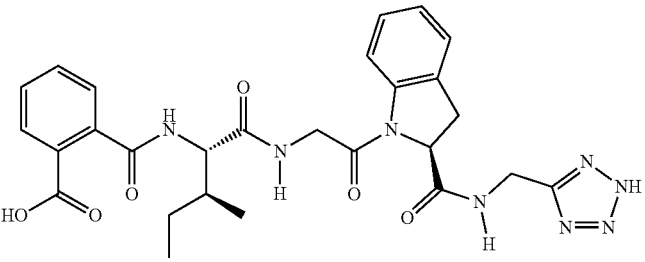 [SMILES: CC[C@H](C)[C@H](NC(=O)c1ccccc1C(=O)O)C(=O)NCC(=O)N1c2ccccc2C[C@H]1C(=O)NCc1nn[nH]n1] |
| A26-1 | 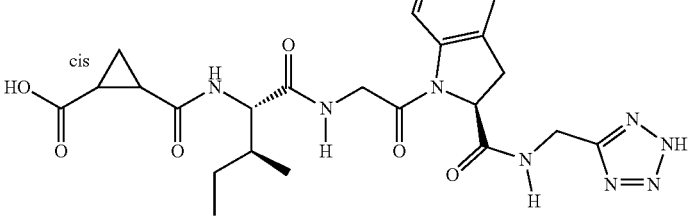<br>diastereomer 1 |

TABLE 1-continued
Representative Compounds.
| Cmpd # | Structure |
|---|---|
| A26-2 | 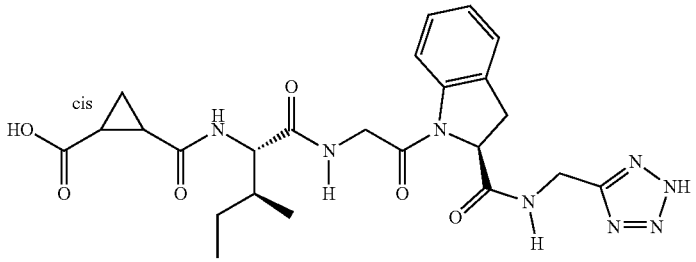<br>diastereomer 2 |
| A27 | 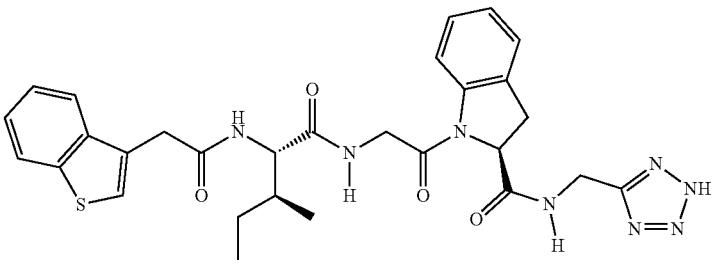 [SMILES: CC[C@H](C)[C@H](NC(=O)Cc1csc2ccccc12)C(=O)NCC(=O)N1c2ccccc2C[C@H]1C(=O)NCc1nn[nH]n1] |
| A28 | 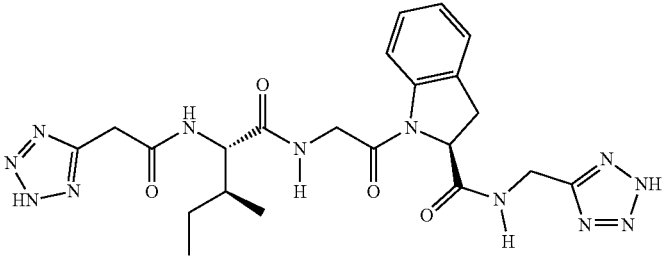 [SMILES: CC[C@H](C)[C@H](NC(=O)Cc1nn[nH]n1)C(=O)NCC(=O)N1c2ccccc2C[C@H]1C(=O)NCc1nn[nH]n1] |
| A29 | 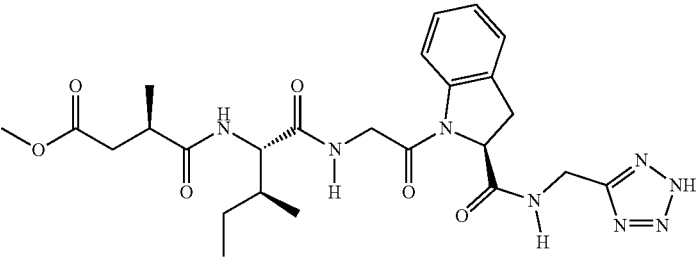 [SMILES: CC[C@H](C)[C@H](NC(=O)[C@H](C)CC(=O)OC)C(=O)NCC(=O)N1c2ccccc2C[C@H]1C(=O)NCc1nn[nH]n1] |
| A30-1 | 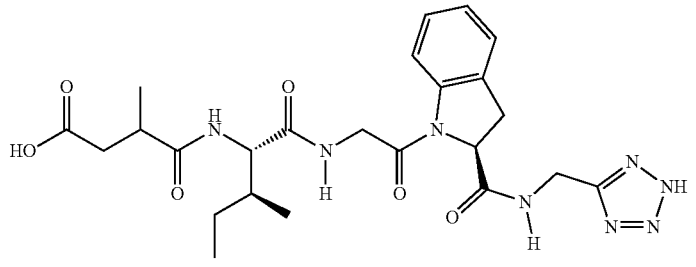<br>diastereomer 1 |

TABLE 1-continued
Representative Compounds.
| Cmpd # | Structure |
|---|---|
| A30-2 | 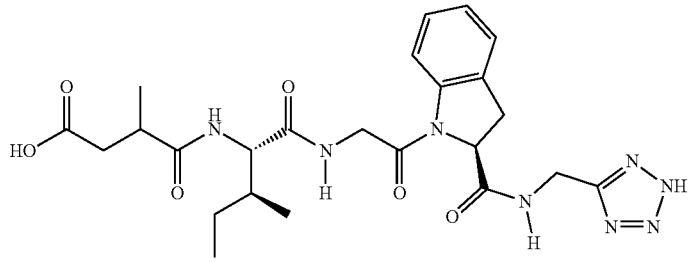<br>diastereomer 2 |
| A31 | 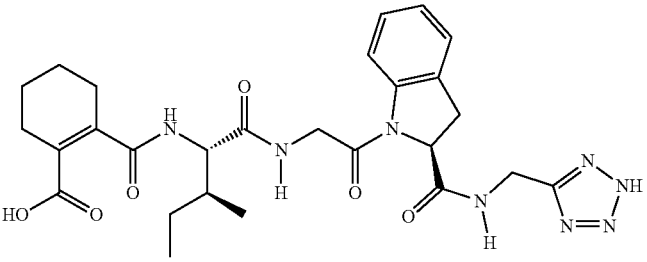 [SMILES: CC[C@H](C)[C@H](NC(=O)C1=C(C(=O)O)CCCC1)C(=O)NCC(=O)N1c2ccccc2C[C@H]1C(=O)NCc1nn[nH]n1] |
| A32 | 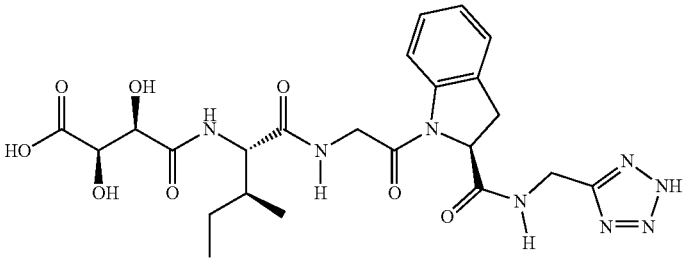 [SMILES: CC[C@H](C)[C@H](NC(=O)[C@H](O)[C@@H](O)C(=O)O)C(=O)NCC(=O)N1c2ccccc2C[C@H]1C(=O)NCc1nn[nH]n1] |
| A33 | 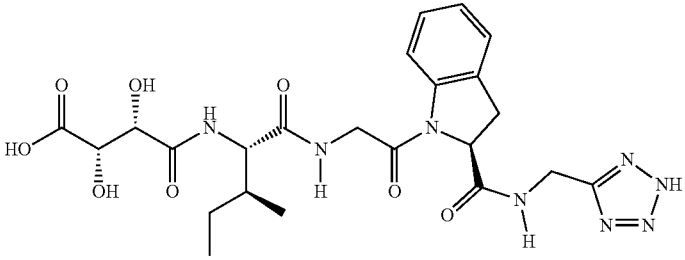 [SMILES: CC[C@H](C)[C@H](NC(=O)[C@@H](O)[C@H](O)C(=O)O)C(=O)NCC(=O)N1c2ccccc2C[C@H]1C(=O)NCc1nn[nH]n1] |
| A34 | 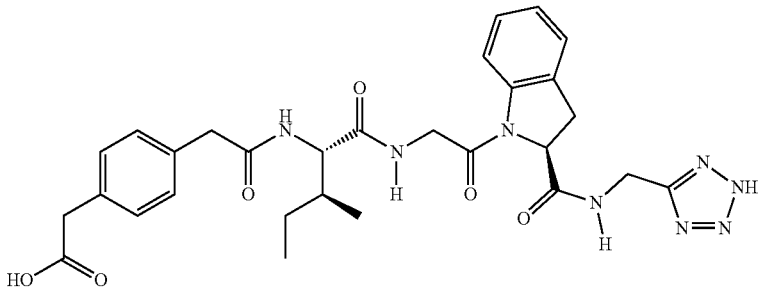 [SMILES: CC[C@H](C)[C@H](NC(=O)Cc1ccc(CC(=O)O)cc1)C(=O)NCC(=O)N1c2ccccc2C[C@H]1C(=O)NCc1nn[nH]n1] |

TABLE 1-continued

Representative Compounds.

| Cmpd # | Structure |
|---|---|
| A35 | 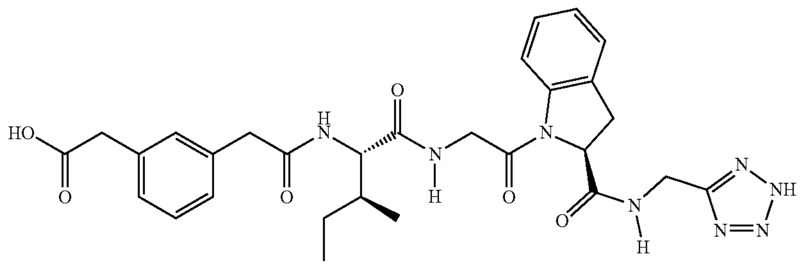 [SMILES: CC[C@H](C)[C@H](NC(=O)Cc1cccc(CC(=O)O)c1)C(=O)NCC(=O)N1c2ccccc2C[C@H]1C(=O)NCc1nn[nH]n1] |
| A36 | 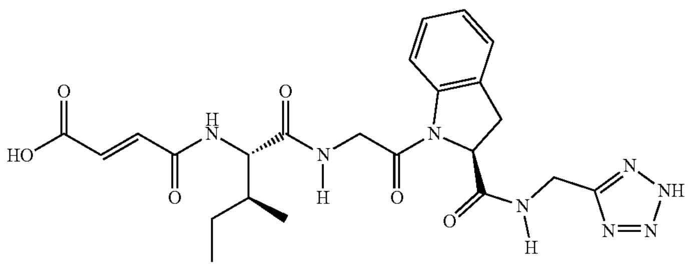 [SMILES: CC[C@H](C)[C@H](NC(=O)/C=C/C(=O)O)C(=O)NCC(=O)N1c2ccccc2C[C@H]1C(=O)NCc1nn[nH]n1] |
| A37 | 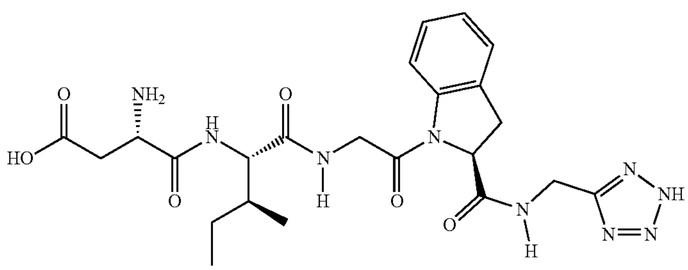 [SMILES: CC[C@H](C)[C@H](NC(=O)[C@@H](N)CC(=O)O)C(=O)NCC(=O)N1c2ccccc2C[C@H]1C(=O)NCc1nn[nH]n1] |
| A38 | 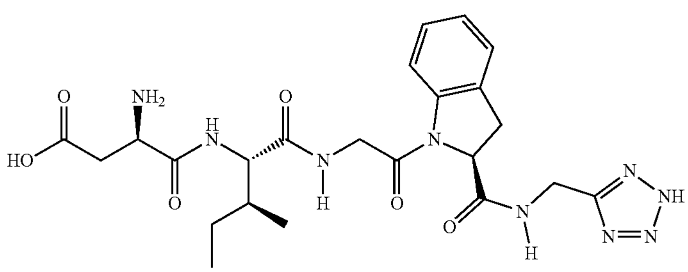 [SMILES: CC[C@H](C)[C@H](NC(=O)[C@H](N)CC(=O)O)C(=O)NCC(=O)N1c2ccccc2C[C@H]1C(=O)NCc1nn[nH]n1] |
| A39 | 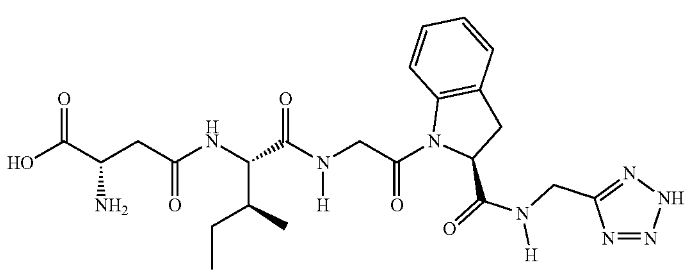 [SMILES: CC[C@H](C)[C@H](NC(=O)C[C@H](N)C(=O)O)C(=O)NCC(=O)N1c2ccccc2C[C@H]1C(=O)NCc1nn[nH]n1] |

TABLE 1-continued

Representative Compounds.

| Cmpd # | Structure |
| --- | --- |
| A40 | 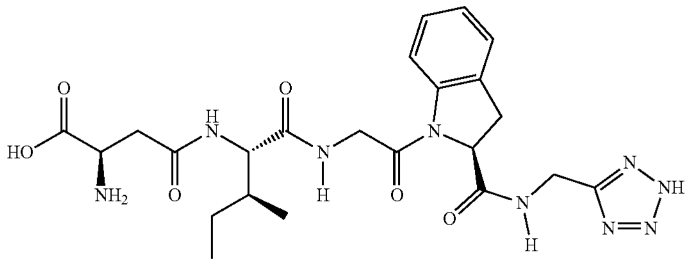 [SMILES: CC[C@H](C)[C@H](NC(=O)C[C@@H](N)C(=O)O)C(=O)NCC(=O)N1c2ccccc2C[C@H]1C(=O)NCc1nn[nH]n1] |
| A41 | 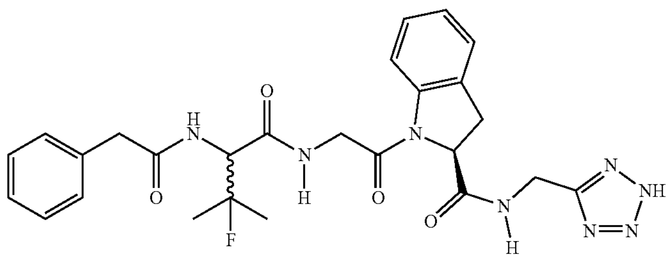 [SMILES: CC(C)(F)C(NC(=O)Cc1ccccc1)C(=O)NCC(=O)N1c2ccccc2C[C@H]1C(=O)NCc1nn[nH]n1] |
| A42 | 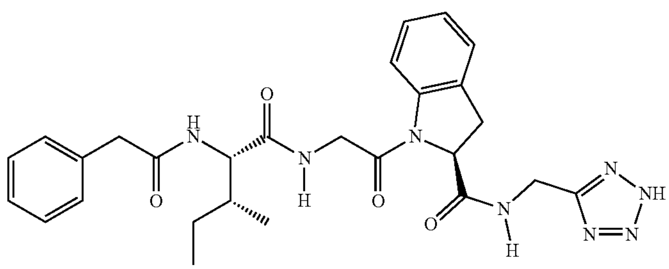 [SMILES: CC[C@@H](C)[C@H](NC(=O)Cc1ccccc1)C(=O)NCC(=O)N1c2ccccc2C[C@H]1C(=O)NCc1nn[nH]n1] |
| A43 | 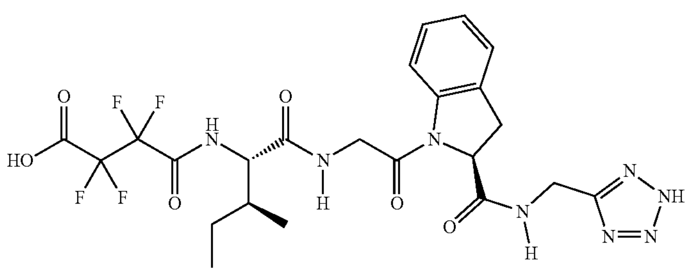 [SMILES: CC[C@H](C)[C@H](NC(=O)C(F)(F)C(F)(F)C(=O)O)C(=O)NCC(=O)N1c2ccccc2C[C@H]1C(=O)NCc1nn[nH]n1] |
| A44 | 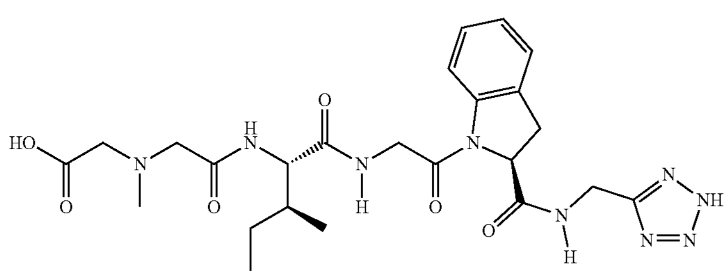 [SMILES: CC[C@H](C)[C@H](NC(=O)CN(C)CC(=O)O)C(=O)NCC(=O)N1c2ccccc2C[C@H]1C(=O)NCc1nn[nH]n1] |

TABLE 1-continued

Representative Compounds.

| Cmpd # | Structure |
|---|---|
| A45 | 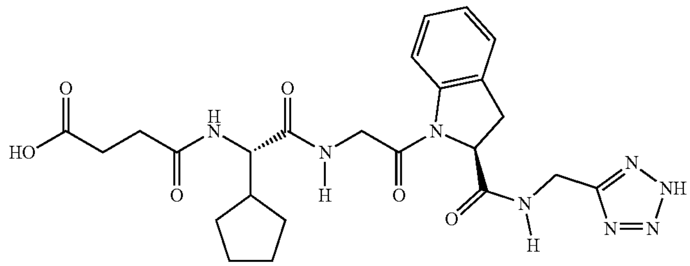 [SMILES: O=C(O)CCC(=O)N[C@H](C(=O)NCC(=O)N1c2ccccc2C[C@H]1C(=O)NCc1nn[nH]n1)C1CCCC1] |
| A46 | 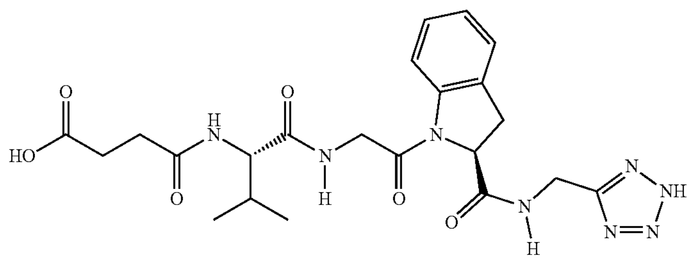 [SMILES: CC(C)[C@H](NC(=O)CCC(=O)O)C(=O)NCC(=O)N1c2ccccc2C[C@H]1C(=O)NCc1nn[nH]n1] |
| A47 | 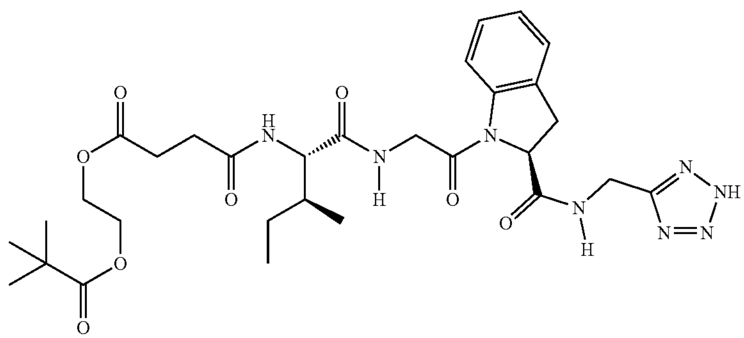 [SMILES: CC[C@H](C)[C@H](NC(=O)CCC(=O)OCCOC(=O)C(C)(C)C)C(=O)NCC(=O)N1c2ccccc2C[C@H]1C(=O)NCc1nn[nH]n1] |
| A48 | 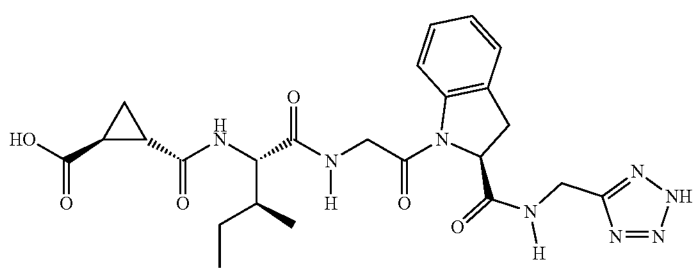 |
| A49 | 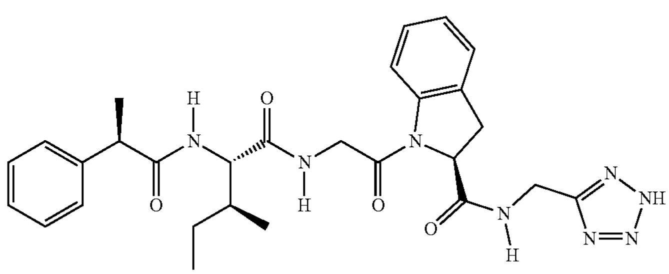 [SMILES: CC[C@H](C)[C@H](NC(=O)[C@H](C)c1ccccc1)C(=O)NCC(=O)N1c2ccccc2C[C@H]1C(=O)NCc1nn[nH]n1] |

TABLE 1-continued
Representative Compounds.
| Cmpd # | Structure |
|---|---|
| A50 | 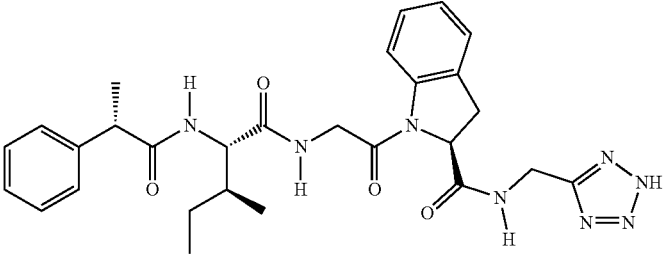 [SMILES: CC[C@H](C)[C@H](NC(=O)[C@@H](C)c1ccccc1)C(=O)NCC(=O)N1c2ccccc2C[C@H]1C(=O)NCc1nn[nH]n1] |
| A51 | 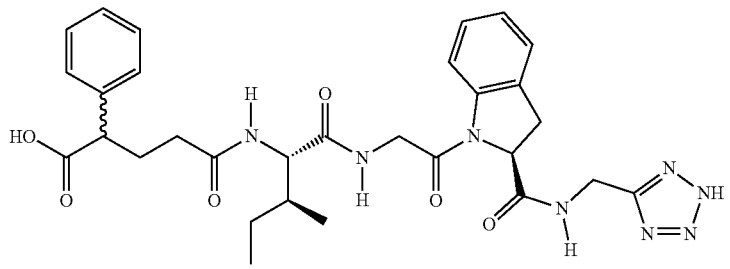 [SMILES: CC[C@H](C)[C@H](NC(=O)CCC(C(=O)O)c1ccccc1)C(=O)NCC(=O)N1c2ccccc2C[C@H]1C(=O)NCc1nn[nH]n1] |
| A52 | 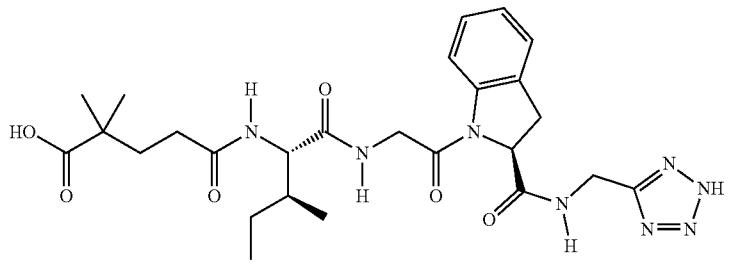 [SMILES: CC[C@H](C)[C@H](NC(=O)CCC(C)(C)C(=O)O)C(=O)NCC(=O)N1c2ccccc2C[C@H]1C(=O)NCc1nn[nH]n1] |
| A53 | 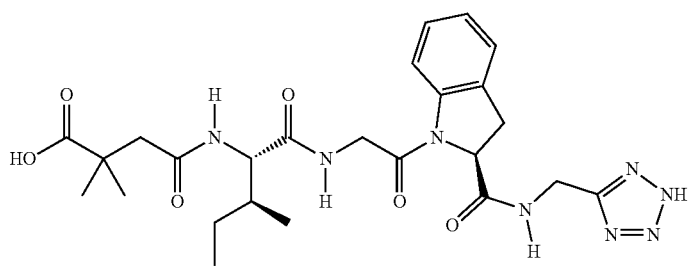 [SMILES: CC[C@H](C)[C@H](NC(=O)CC(C)(C)C(=O)O)C(=O)NCC(=O)N1c2ccccc2C[C@H]1C(=O)NCc1nn[nH]n1] |
| A54-1 | 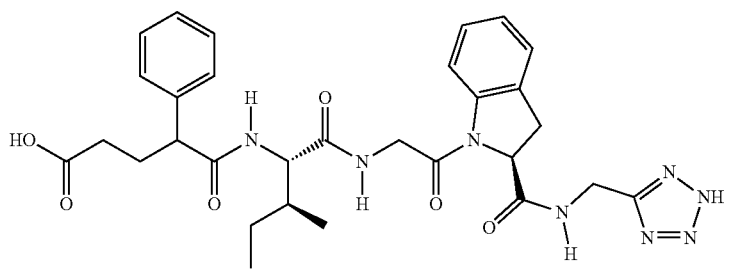<br>diastereomer 1 |

TABLE 1-continued
Representative Compounds.
| Cmpd # | Structure |
|---|---|
| A54-2 | 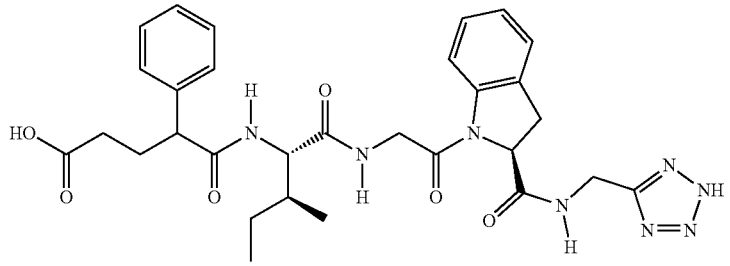 diastereomer 2 |
| A55 | 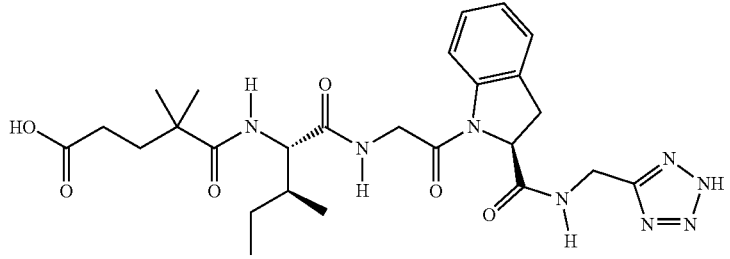 [SMILES: CC[C@H](C)[C@H](NC(=O)C(C)(C)CCC(=O)O)C(=O)NCC(=O)N1c2ccccc2C[C@H]1C(=O)NCc1nn[nH]n1] |
| A56 | 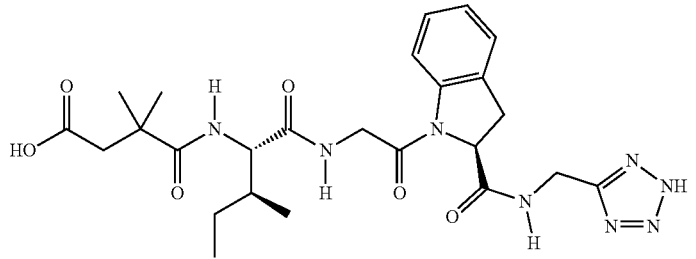 [SMILES: CC[C@H](C)[C@H](NC(=O)C(C)(C)CC(=O)O)C(=O)NCC(=O)N1c2ccccc2C[C@H]1C(=O)NCc1nn[nH]n1] |
| A57-1 | 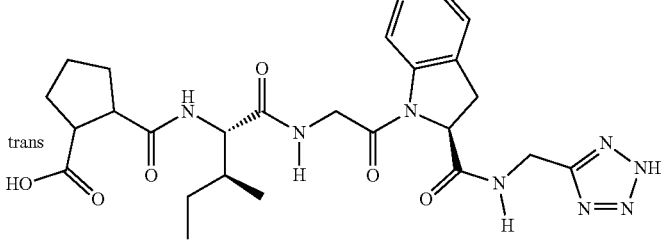 diastereomer 1 |
| A57-2 | 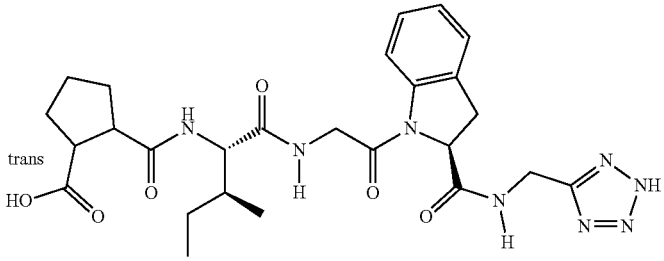 diastereomer 2 |

TABLE 1-continued
Representative Compounds.
| Cmpd # | Structure |
|---|---|
| B1 | 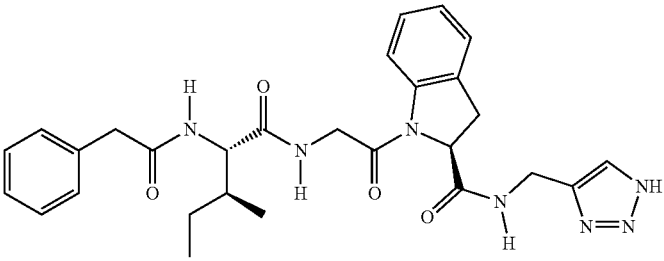 |
| B2 | 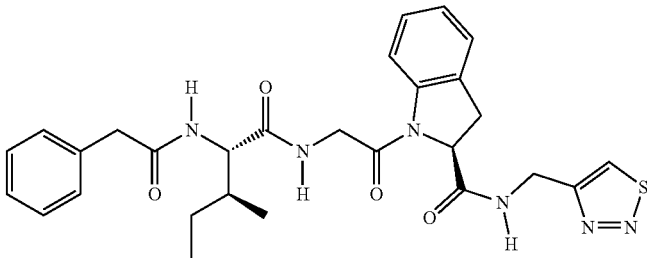 [SMILES: CC[C@H](C)[C@H](NC(=O)Cc1ccccc1)C(=O)NCC(=O)N1c2ccccc2C[C@H]1C(=O)NCc1csnn1] |
| B3 | 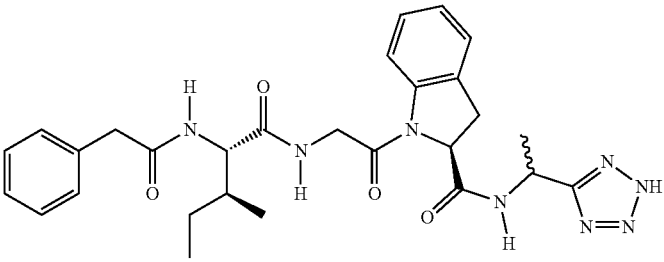 [SMILES: CC[C@H](C)[C@H](NC(=O)Cc1ccccc1)C(=O)NCC(=O)N1c2ccccc2C[C@H]1C(=O)NC(C)c1nn[nH]n1] |
| B4 | 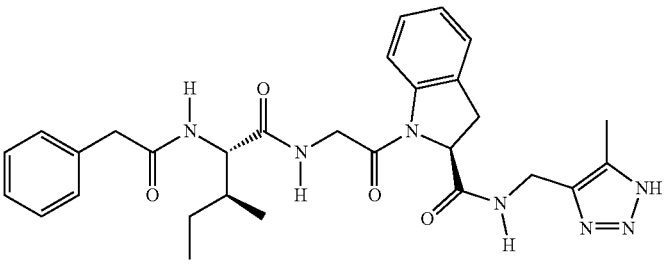 |
| B5 | 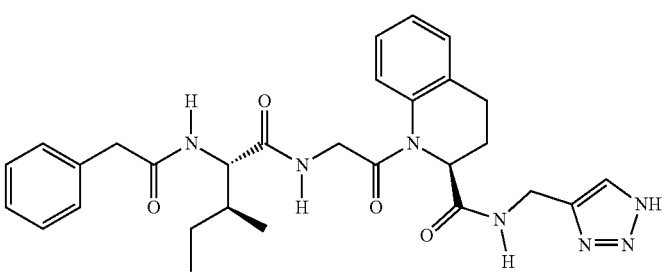 [SMILES: CC[C@H](C)[C@H](NC(=O)Cc1ccccc1)C(=O)NCC(=O)N1c2ccccc2CC[C@H]1C(=O)NCc1c[nH]nn1] |

TABLE 1-continued

Representative Compounds.

| Cmpd # | Structure |
|---|---|
| B6 | 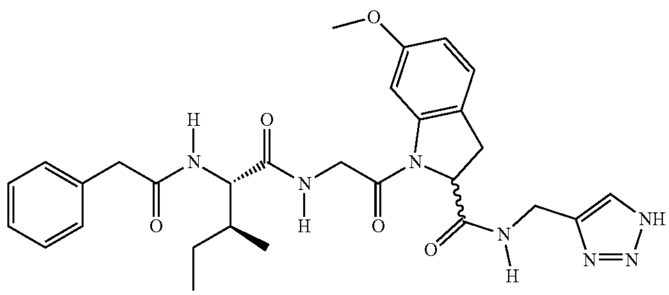 [SMILES: CC[C@H](C)[C@H](NC(=O)Cc1ccccc1)C(=O)NCC(=O)N1c2cc(OC)ccc2CC1C(=O)NCc1c[nH]nn1] |
| B7 | 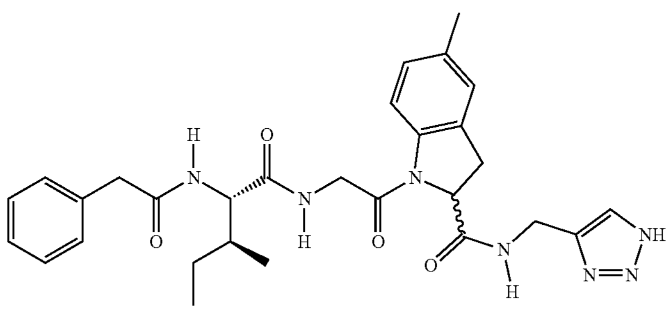 [SMILES: CC[C@H](C)[C@H](NC(=O)Cc1ccccc1)C(=O)NCC(=O)N1c2ccc(C)cc2CC1C(=O)NCc1c[nH]nn1] |
| C1 | 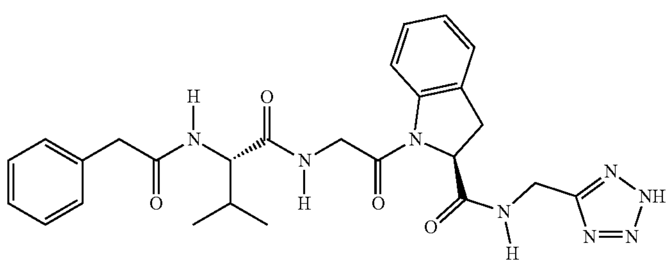 [SMILES: CC(C)[C@H](NC(=O)Cc1ccccc1)C(=O)NCC(=O)N1c2ccccc2C[C@H]1C(=O)NCc1nn[nH]n1] |
| C2 | 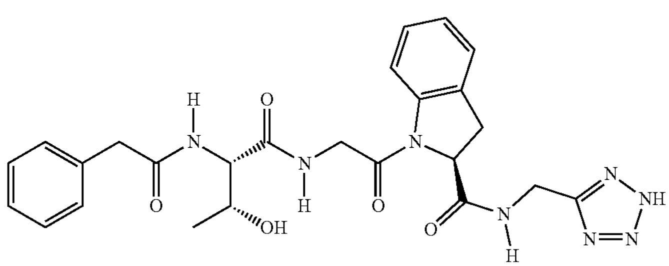 [SMILES: C[C@@H](O)[C@H](NC(=O)Cc1ccccc1)C(=O)NCC(=O)N1c2ccccc2C[C@H]1C(=O)NCc1nn[nH]n1] |
| C3 | 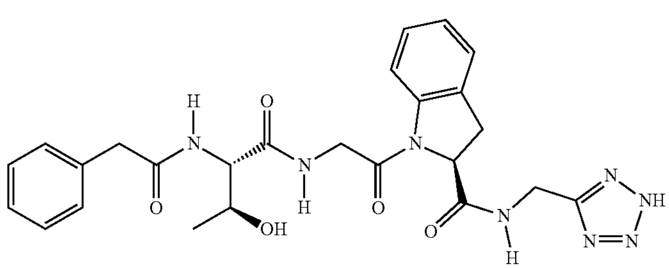 [SMILES: C[C@H](O)[C@H](NC(=O)Cc1ccccc1)C(=O)NCC(=O)N1c2ccccc2C[C@H]1C(=O)NCc1nn[nH]n1] |

TABLE 1-continued
Representative Compounds.
| Cmpd # | Structure |
|---|---|
| C4 | 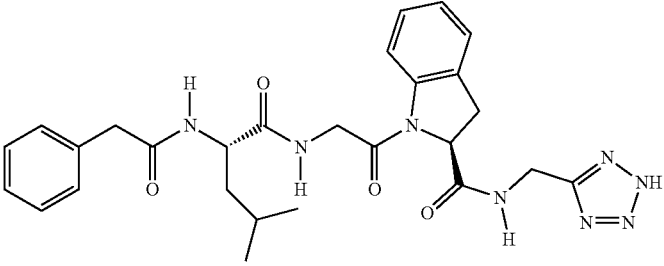 [SMILES: CC(C)C[C@H](NC(=O)Cc1ccccc1)C(=O)NCC(=O)N1c2ccccc2C[C@H]1C(=O)NCc1nn[nH]n1] |
| C5 | 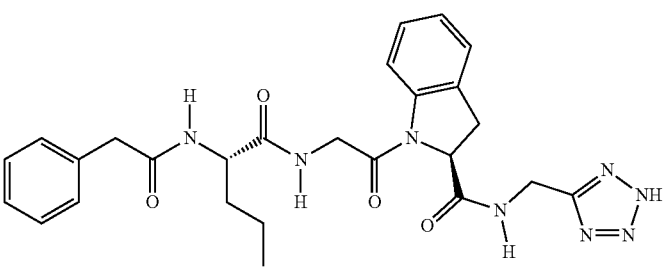 [SMILES: CCC[C@H](NC(=O)Cc1ccccc1)C(=O)NCC(=O)N1c2ccccc2C[C@H]1C(=O)NCc1nn[nH]n1] |
| C6 | 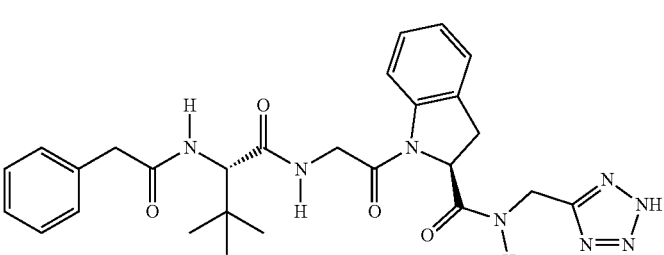 |
| C7 | 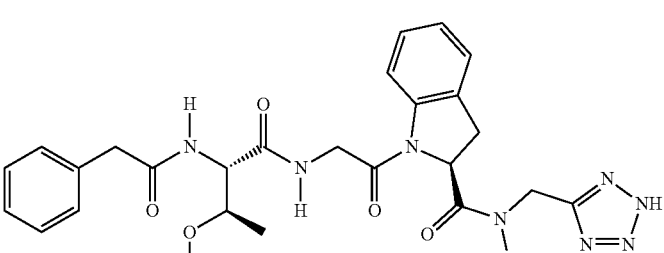 |
| C8 | 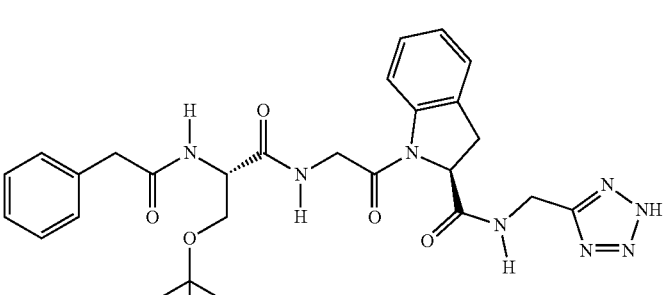 |

TABLE 1-continued
Representative Compounds.
| Cmpd # | Structure |
|---|---|
| C9 | 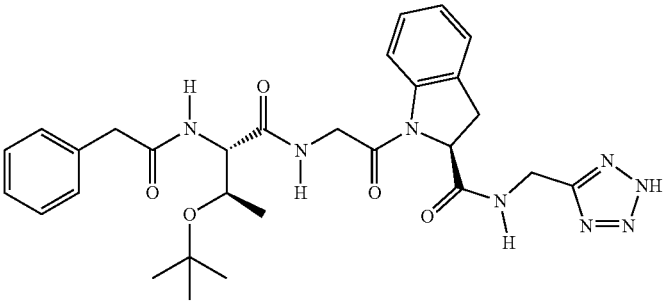 [SMILES: C[C@@H](OC(C)(C)C)[C@H](NC(=O)Cc1ccccc1)C(=O)NCC(=O)N1c2ccccc2C[C@H]1C(=O)NCc1nn[nH]n1] |
| C10 | 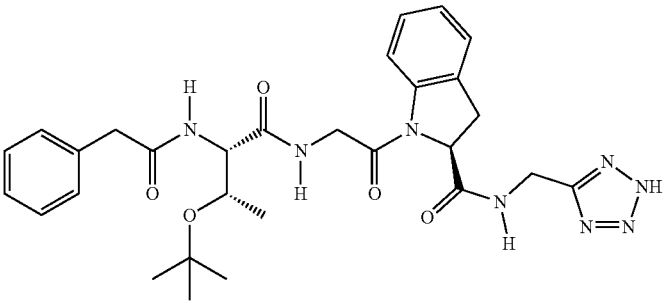 [SMILES: C[C@H](OC(C)(C)C)[C@H](NC(=O)Cc1ccccc1)C(=O)NCC(=O)N1c2ccccc2C[C@H]1C(=O)NCc1nn[nH]n1] |
| C11 | 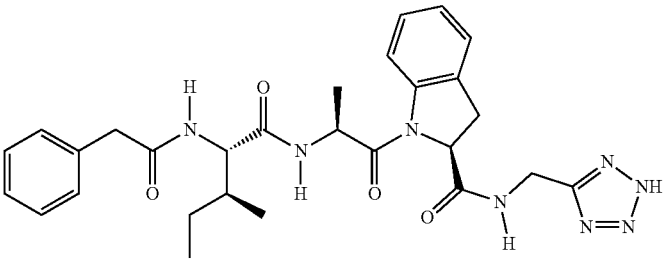 [SMILES: CC[C@H](C)[C@H](NC(=O)Cc1ccccc1)C(=O)N[C@@H](C)C(=O)N1c2ccccc2C[C@H]1C(=O)NCc1nn[nH]n1] |
| C12 | 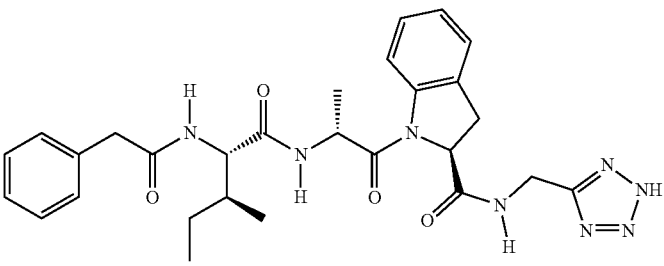 [SMILES: CC[C@H](C)[C@H](NC(=O)Cc1ccccc1)C(=O)N[C@H](C)C(=O)N1c2ccccc2C[C@H]1C(=O)NCc1nn[nH]n1] |
| C13 | 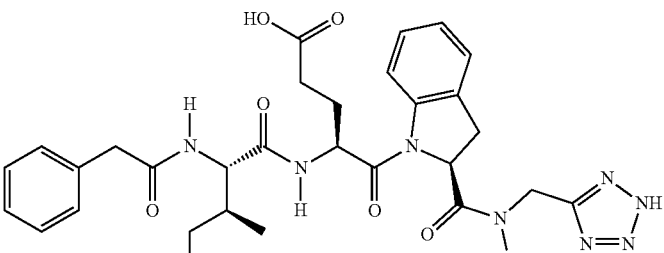 |

TABLE 1-continued

Representative Compounds.

| Cmpd # | Structure |
|---|---|
| C14 | 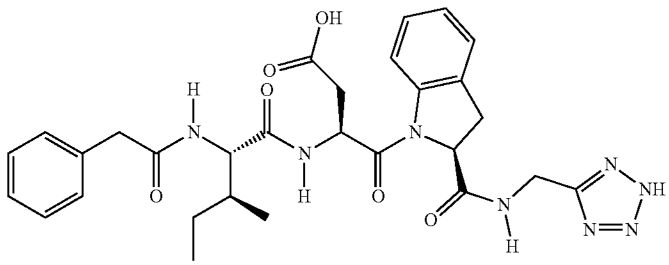 [SMILES: CC[C@H](C)[C@H](NC(=O)Cc1ccccc1)C(=O)N[C@@H](CC(=O)O)C(=O)N1c2ccccc2C[C@H]1C(=O)NCc1nn[nH]n1] |
| C15 | 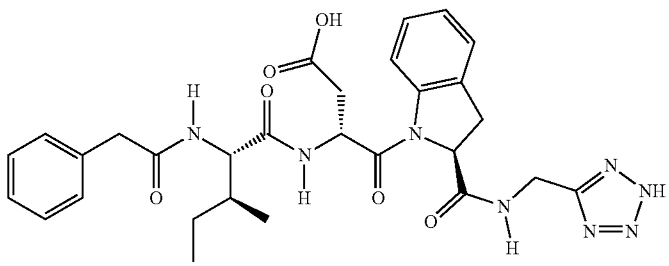 [SMILES: CC[C@H](C)[C@H](NC(=O)Cc1ccccc1)C(=O)N[C@H](CC(=O)O)C(=O)N1c2ccccc2C[C@H]1C(=O)NCc1nn[nH]n1] |
| C16 | 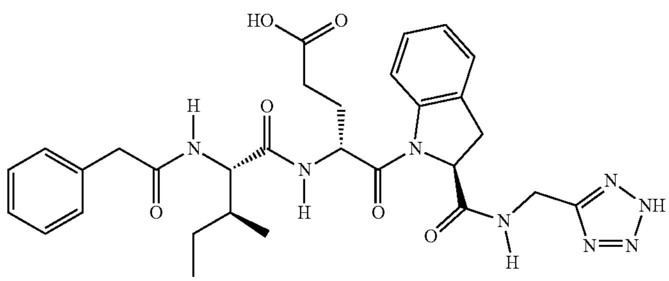 [SMILES: CC[C@H](C)[C@H](NC(=O)Cc1ccccc1)C(=O)N[C@H](CCC(=O)O)C(=O)N1c2ccccc2C[C@H]1C(=O)NCc1nn[nH]n1] |
| C17 | 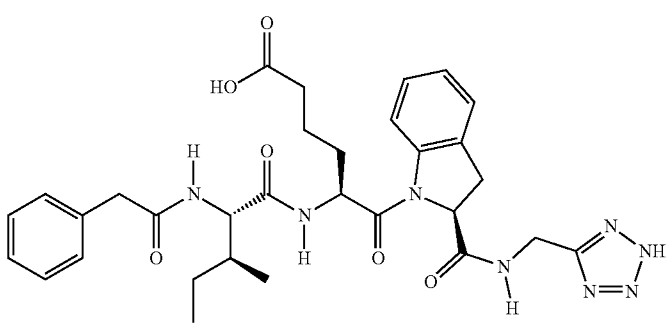 [SMILES: CC[C@H](C)[C@H](NC(=O)Cc1ccccc1)C(=O)N[C@@H](CCCC(=O)O)C(=O)N1c2ccccc2C[C@H]1C(=O)NCc1nn[nH]n1] |
| C18 | 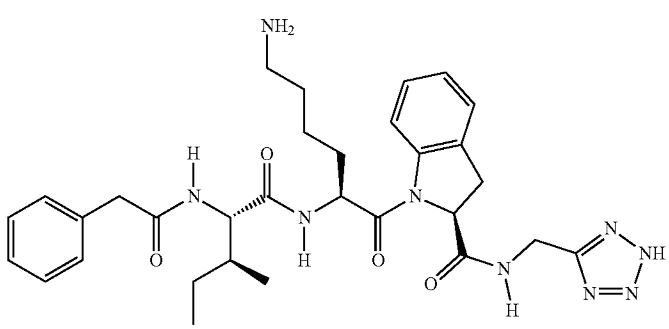 [SMILES: CC[C@H](C)[C@H](NC(=O)Cc1ccccc1)C(=O)N[C@@H](CCCCN)C(=O)N1c2ccccc2C[C@H]1C(=O)NCc1nn[nH]n1] |

TABLE 1-continued

Representative Compounds.

| Cmpd # | Structure |
|---|---|
| C19 | 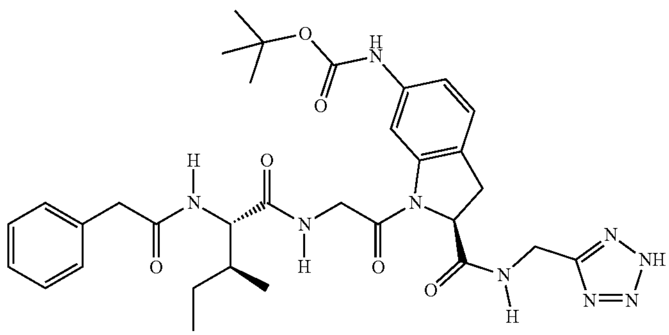 [SMILES: CC[C@H](C)[C@H](NC(=O)Cc1ccccc1)C(=O)NCC(=O)N1c2cc(NC(=O)OC(C)(C)C)ccc2C[C@H]1C(=O)NCc1nn[nH]n1] |
| C20 | 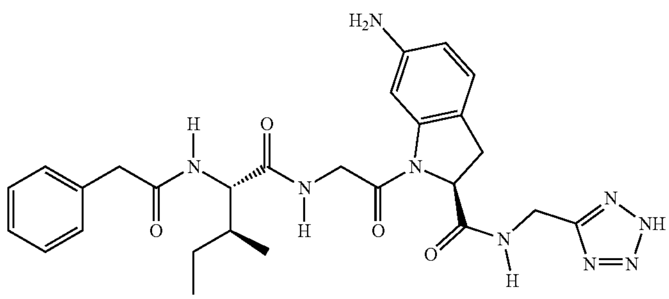 [SMILES: CC[C@H](C)[C@H](NC(=O)Cc1ccccc1)C(=O)NCC(=O)N1c2cc(N)ccc2C[C@H]1C(=O)NCc1nn[nH]n1] |
| C21 | 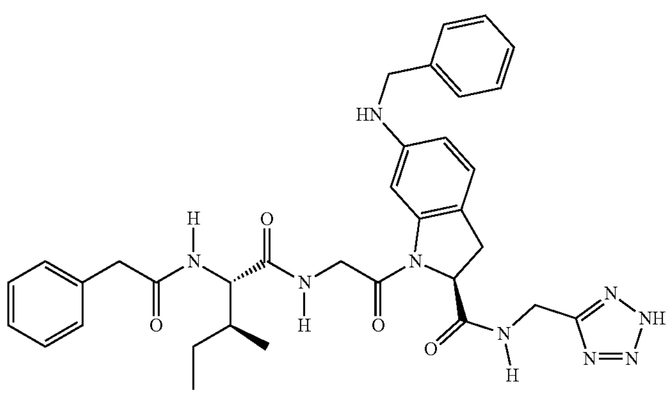 [SMILES: CC[C@H](C)[C@H](NC(=O)Cc1ccccc1)C(=O)NCC(=O)N1c2cc(NCc3ccccc3)ccc2C[C@H]1C(=O)NCc1nn[nH]n1] |
| C22 | 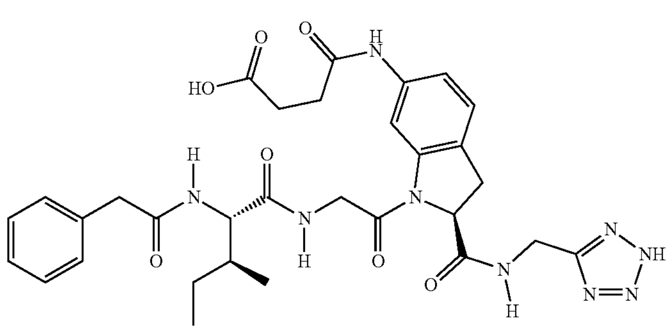 [SMILES: CC[C@H](C)[C@H](NC(=O)Cc1ccccc1)C(=O)NCC(=O)N1c2cc(NC(=O)CCC(=O)O)ccc2C[C@H]1C(=O)NCc1nn[nH]n1] |

TABLE 1-continued
Representative Compounds.
| Cmpd # | Structure |
|---|---|
| C23 | 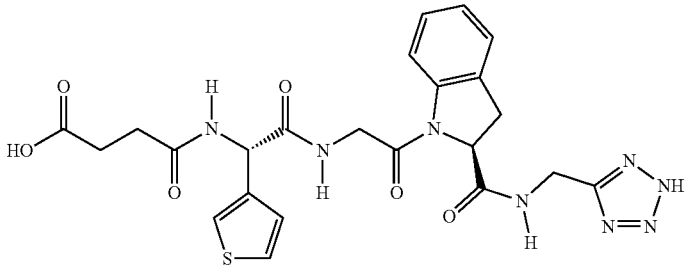 [SMILES: O=C(O)CCC(=O)N[C@H](C(=O)NCC(=O)N1c2ccccc2C[C@H]1C(=O)NCc1nn[nH]n1)c1ccsc1] |
| C24 | 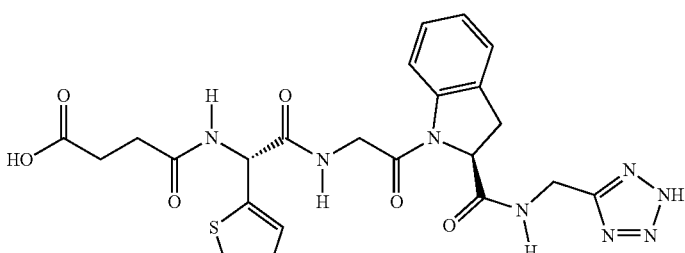 |
| C25 | 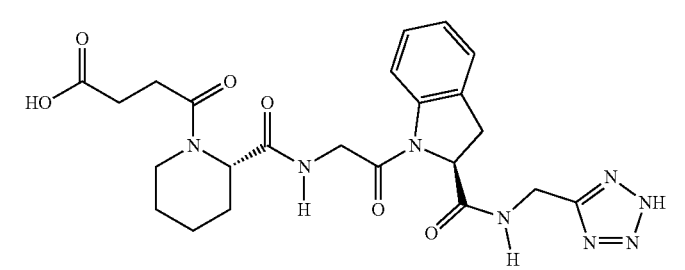 [SMILES: O=C(O)CCC(=O)N1CCCC[C@H]1C(=O)NCC(=O)N1c2ccccc2C[C@H]1C(=O)NCc1nn[nH]n1] |
| C26 | 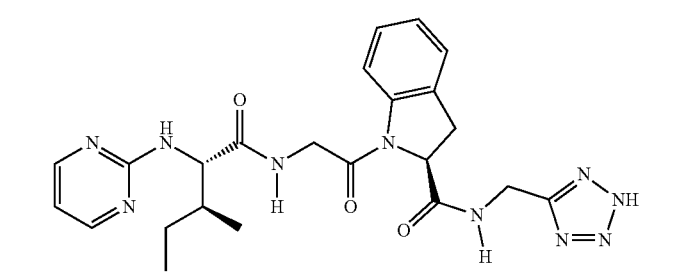 [SMILES: CC[C@H](C)[C@H](Nc1ncccn1)C(=O)NCC(=O)N1c2ccccc2C[C@H]1C(=O)NCc1nn[nH]n1] |
| C27 | 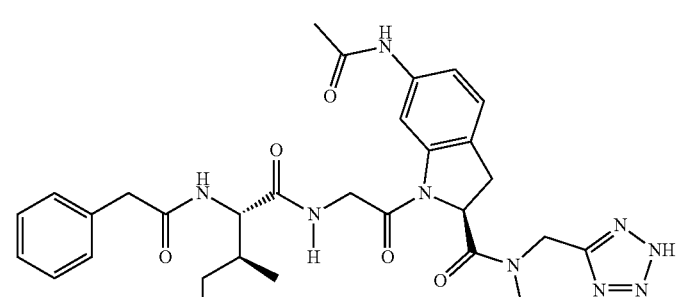 |

TABLE 1-continued

Representative Compounds.

| Cmpd # | Structure |
|---|---|
| C28 | 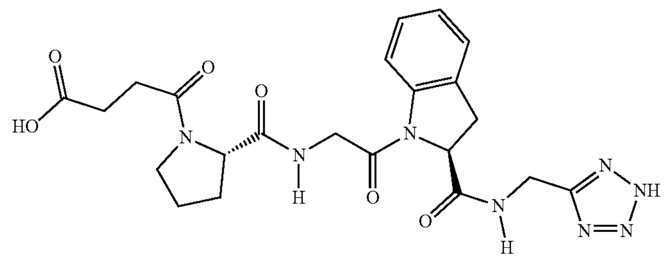 [SMILES: O=C(O)CCC(=O)N1CCC[C@H]1C(=O)NCC(=O)N1c2ccccc2C[C@H]1C(=O)NCc1nn[nH]n1] |
| C29 | 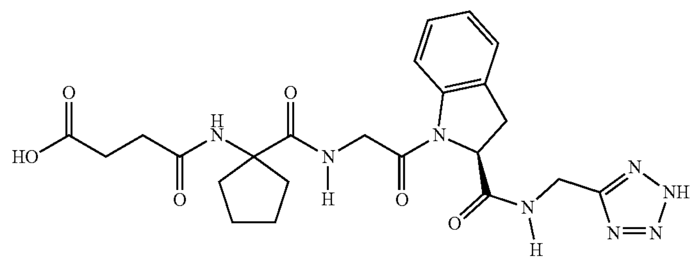 [SMILES: O=C(O)CCC(=O)NC1(C(=O)NCC(=O)N2c3ccccc3C[C@H]2C(=O)NCc2nn[nH]n2)CCCC1] |
| C30 | 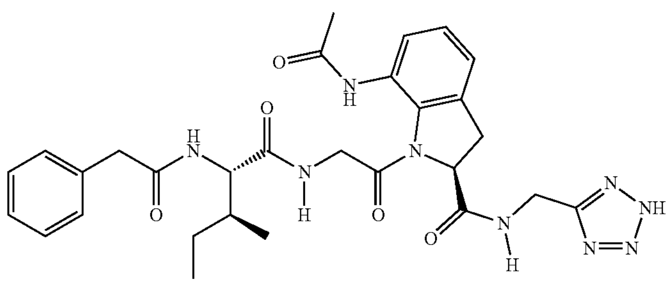 [SMILES: CC[C@H](C)[C@H](NC(=O)Cc1ccccc1)C(=O)NCC(=O)N1c2c(cccc2NC(C)=O)C[C@H]1C(=O)NCc1nn[nH]n1] |
| C31 | 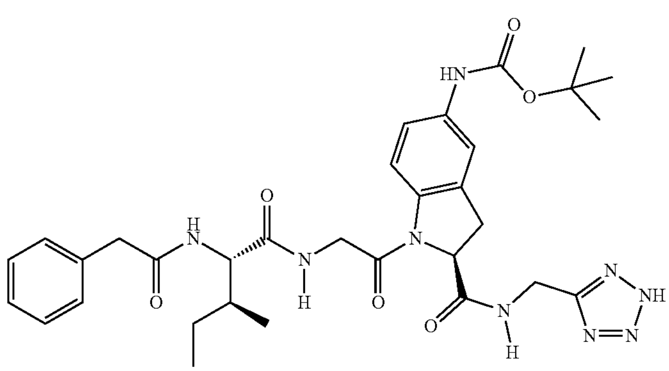 [SMILES: CC[C@H](C)[C@H](NC(=O)Cc1ccccc1)C(=O)NCC(=O)N1c2ccc(NC(=O)OC(C)(C)C)cc2C[C@H]1C(=O)NCc1nn[nH]n1] |
| C32 | 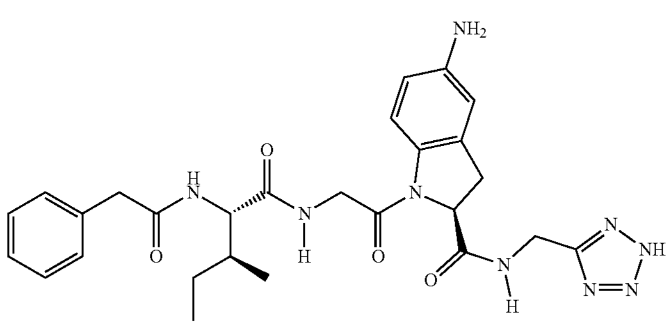 [SMILES: CC[C@H](C)[C@H](NC(=O)Cc1ccccc1)C(=O)NCC(=O)N1c2ccc(N)cc2C[C@H]1C(=O)NCc1nn[nH]n1] |

TABLE 1-continued
Representative Compounds.
| Cmpd # | Structure |
|---|---|
| C33 | 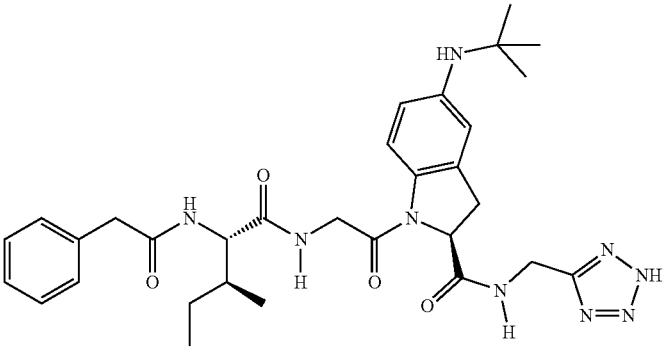 [SMILES: CC[C@H](C)[C@H](NC(=O)Cc1ccccc1)C(=O)NCC(=O)N1c2ccc(NC(C)(C)C)cc2C[C@H]1C(=O)NCc1nn[nH]n1] |
| C34 | 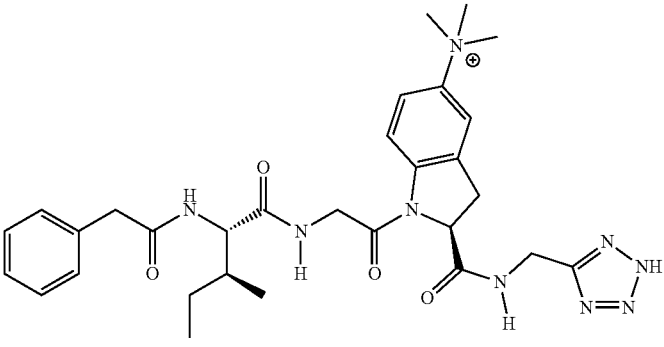 [SMILES: CC[C@H](C)[C@H](NC(=O)Cc1ccccc1)C(=O)NCC(=O)N1c2ccc([N+](C)(C)C)cc2C[C@H]1C(=O)NCc1nn[nH]n1] |
| C35 | 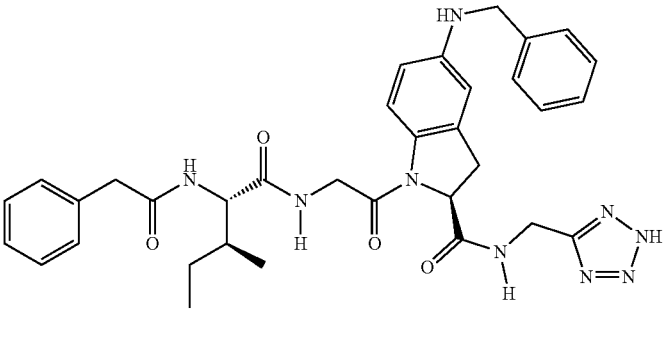 [SMILES: CC[C@H](C)[C@H](NC(=O)Cc1ccccc1)C(=O)NCC(=O)N1c2ccc(NCc3ccccc3)cc2C[C@H]1C(=O)NCc1nn[nH]n1] |
| C36 | 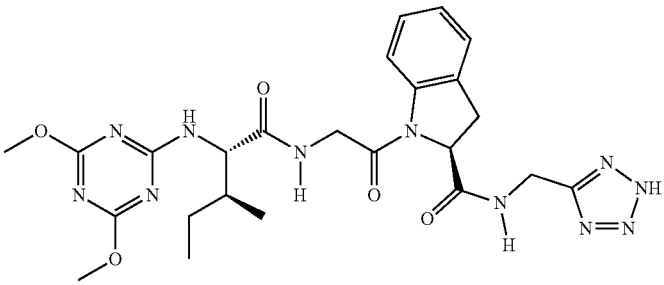 [SMILES: CC[C@H](C)[C@H](Nc1nc(OC)nc(OC)n1)C(=O)NCC(=O)N1c2ccccc2C[C@H]1C(=O)NCc1nn[nH]n1] |

TABLE 1-continued

Representative Compounds.

| Cmpd # | Structure |
| --- | --- |
| C37 | 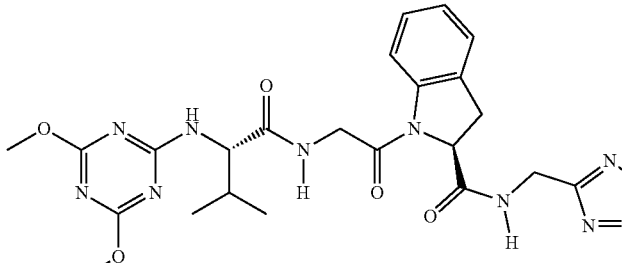 |
| C38 | 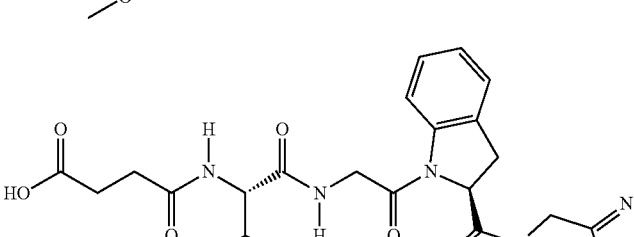 |
| C39 | 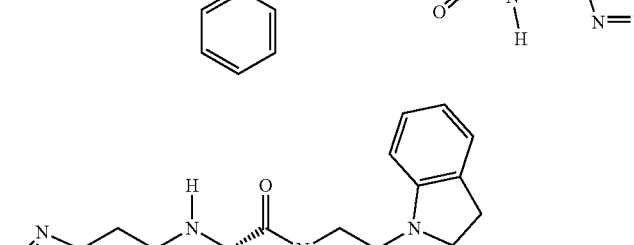 |

A general kinetic enzyme assay useful for determining the inhibitory activity of the compounds of the invention is described in Example D1.

Granzyme B enzymatic inhibition assays are described in Examples D2 and D6. The compounds of the invention identified in Table 1 exhibited Granzyme B inhibitory activity. In certain embodiments, select compounds exhibited $IC_{50}<50,000$ nM. In other embodiments, select compounds exhibited $IC_{50}<10,000$ nM. In further embodiments, select compounds exhibited $IC_{50}<1,000$ nM. In still further embodiments, select compounds exhibited $IC_{50}<100$ nM. In certain embodiments, select compounds exhibited $IC_{50}$ from 10 nM to 100 nM, preferably from 1 nM to 10 nM, more preferably from 0.1 nM to 1 nM, and even more preferably from 0.01 nM to 0.1 nM.

Caspase enzymatic inhibition assays are described in Examples D3 and D7. None of the compounds of the invention tested demonstrated an ability to significantly inhibit any of the caspases evaluated at a concentration of 50 µM. In certain embodiments, the compounds exhibited less than 50% inhibition at 50 µM. In other embodiments, the compounds exhibited greater than 50% inhibition at 50 µM, but less than 10% inhibition at 25 µM. The results demonstrate that select compounds of the invention selectively inhibit Granzyme B without significantly inhibiting caspases.

A method for determining kinetic solubility is described in Example D4. The results demonstrate that select compounds of the invention have significantly greater solubility than Willoughby 20, a representative Granzyme B inhibitor known in the art.

A fibronectin cleavage assay is described in Example D8.

A cell adhesion based on fibronectin cleavage assay is described in Example D9.

Pharmaceutical Compositions

The pharmaceutical compositions of the present invention include an inhibitor compound of the invention (e.g., a compound of Formulae (I), (II), (III), or (IV)) as an active ingredient or a pharmaceutically acceptable salt thereof in combination with a pharmaceutically acceptable carrier, and optionally other therapeutic ingredients.

The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic, manganous, ammonium, potassium, sodium, and zinc salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and trimethamine.

Compositions can include one or more carriers acceptable for the mode of administration of the preparation, be it by topical administration, lavage, epidermal administration, sub-epidermal administration, dermal administration, sub-dermal administration, transdermal administration, subcutaneous administration, systemic administration, injection, inhalation, oral, or any other mode suitable for the selected treatment. Topical administration includes administration to external body surfaces (e.g., skin) as well as to internal body surfaces (e.g., mucus membranes for vaginal or rectal applications by, for example, suppositories). Suitable carriers are those known in the art for use in such modes of administration.

Suitable compositions can be formulated by means known in the art and their mode of administration and dose determined by a person of skill in the art. For parenteral administration, the compound can be dissolved in sterile water or saline or a pharmaceutically acceptable vehicle used for administration of non-water soluble compounds. For enteral administration, the compound can be administered in a tablet, capsule, or dissolved or suspended in liquid form. The tablet or capsule can be enteric coated, or in a formulation for sustained release. Many suitable formulations are known including, polymeric or protein microparticles encapsulating a compound to be released, ointments, pastes, gels, hydrogels, foams, creams, powders, lotions, oils, semi-solids, soaps, medicated soaps, shampoos, medicated shampoos, sprays, films, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20th ed., Williams & Wilkins, (2000). Formulations can contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers can be used to control the release of a compound. Other potentially useful delivery systems for a modulatory compound include ethylene-vinyl acetate copolymer particles, osmotic pumps, implantable infusion systems, and liposomes. Formulations can contain an excipient, for example, lactose, or may be aqueous solutions containing, for example, polyoxyethylene-9-lauryl ether, glycocholate, and deoxycholate, or can be an oily solution for administration in the form of drops, as a gel, or for other semi-solid formulation.

Compounds or pharmaceutical compositions in accordance with this invention or for use in the methods disclosed herein can be administered in combination with one or more other therapeutic agents as appropriate. Compounds or pharmaceutical compositions in accordance with this invention or for use in the methods disclosed herein can be administered by means of a medical device or appliance such as an implant, graft, prosthesis, stents, and wound dressings. Also, implants can be devised that are intended to contain and release such compounds or compositions. An example would be an implant made of a polymeric material adapted to release the compound over a period of time.

One skilled in the art will appreciate that suitable methods of administering a Granzyme B inhibitor directly to the eye are available (i.e., invasive and noninvasive methods). Although more than one route can be used to administer the Granzyme B inhibitor, a particular route can provide a more immediate and more effective reaction than another route. The present use is not dependent on the mode of administering the agent to an animal, preferably a human, to achieve the desired effect, and the described routes of administration are exemplary. As such, any route of administration is appropriate so long as the agent contacts an ocular cell. Thus, the Granzyme B inhibitor can be appropriately formulated and administered in the form of an injection, eye lotion, ointment, and implant.

The Granzyme B inhibitor can be applied, for example, systemically, topically, intracamerally, subconjunctivally, intraocularly, retrobulbarly, periocularly (e.g., subtenon delivery), subretinally, or suprachoroidally. In certain cases, it can be appropriate to administer multiple applications and employ multiple routes to ensure sufficient exposure of ocular cells to the Granzyme B inhibitor (e.g., subretinal and intravitreous). Multiple applications of the Granzyme B inhibitor can also be required to achieve the desired effect.

Depending on the particular case, it may be desirable to non-invasively administer the Granzyme B inhibitor to a patient. For instance, if multiple surgeries have been performed, the patient displays low tolerance to anesthetic, or if other ocular-related disorders exist, topical administration of the Granzyme B inhibitor may be most appropriate. Topical formulations are well known to those of skill in the art. Such formulations are suitable in the context of the use described herein for application to the skin or to the surface of the eye. The use of patches, corneal shields (see, U.S. Pat. No. 5,185,152), and ophthalmic solutions (see, e.g., U.S. Pat. No. 5,710,182) and ointments is within the skill in the art.

The Granzyme B inhibitor also can be present in or on a device that allows controlled or sustained release, such as an ocular sponge, meshwork, mechanical reservoir, or mechanical implant. Implants (see U.S. Pat. Nos. 5,443,505, 4,853,224 and 4,997,652), devices (see U.S. Pat. Nos. 5,554,187, 4,863,457, 5,098,443 and 5,725,493), such as an implantable device (e.g., a mechanical reservoir, an intraocular device or an extraocular device with an intraocular conduit, or an implant or a device comprised of a polymeric composition are particularly useful for ocular administration of the expression vector). The Granzyme B inhibitor also can be administered in the form of sustained-release formulations (see U.S. Pat. No. 5,378,475) comprising, for example, gelatin, chondroitin sulfate, a polyphosphoester, such as bis-2-hydroxyethyl-terephthalate, or a polylactic-glycolic acid.

When used for treating an ocular disease the Granzyme B inhibitor is administered via an ophthalmologic instrument for delivery to a specific region of an eye. Use of a specialized ophthalmologic instrument ensures precise administration while minimizing damage to adjacent ocular tissue. Delivery of the Granzyme B inhibitor to a specific region of the eye also limits exposure of unaffected cells to the Granzyme B inhibitor. A preferred ophthalmologic instrument is a combination of forceps and subretinal needle or sharp bent cannula.

Alternatively, the Granzyme B inhibitor can be administered using invasive procedures, such as, for instance, intravitreal injection or subretinal injection, optionally preceded by a vitrectomy, or periocular (e.g., subtenon) delivery. The pharmaceutical composition of the invention can be injected into different compartments of the eye (e.g., the vitreal cavity or anterior chamber).

While intraocular injection is preferred, injectable compositions can also be administered intramuscularly, intravenously, intraarterially, and intraperitoneally. Pharmaceutically acceptable carriers for injectable compositions are well-known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)).

An "effective amount" of a Granzyme B inhibitor or a pharmaceutical composition of the invention as described herein includes a therapeutically effective amount or a prophylactically effective amount. A "therapeutically effective amount" refers to an amount effective, at dosages and for periods of time necessary, to achieve the desired therapeutic result, such as reduced levels of Granzyme B activity. A therapeutically effective amount of a compound may vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as Granzyme B activity. Typically, a prophylactic dose is used in subjects prior to or at an earlier stage of disease, so that a prophylactically effective amount may be less than a therapeutically effective amount.

It is to be noted that dosage values can vary with the severity of the condition to be alleviated. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by a medical practitioner. The amount of active compound(s) in the composition can vary according to factors such as the disease state, age, sex, and weight of the subject. Dosage regimens can be adjusted to provide the optimum therapeutic response. For example, a single bolus can be administered, several divided doses can be administered over time or the dose can be proportionally reduced or increased as indicated by the exigencies of the therapeutic situation. It may be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index (i.e., the ratio between the $LD_{50}$, the dose lethal to 50% of the population, and the $LD_{100}$, the dose lethal to 100% of the population). In some circumstances however, such as in severe disease conditions, it may be necessary to administer substantial excesses of the composition.

Methods of Use

In a further aspect, the invention provides methods of using the compounds of the invention as Granzyme B inhibitors.

In one embodiment, the invention provides a method for inhibiting Granzyme B in a subject. In the method, an effective amount of a compound of the invention (e.g., a compound of Formulae (I), (II), (III), or (IV)) is administered to a subject in need thereof.

In another embodiment, the invention provides a method for treating a disease, disorder, or condition treatable by inhibiting Granzyme B. In the method, a therapeutically effective amount of a compound of the invention (e.g., a compound of Formulae (I), (II), (III), or (IV)) is administered to a subject in need thereof.

As used herein, the term "disease, disorder, or condition treatable by inhibiting Granzyme B" refers to a disease, disorder, or condition in which Granzyme B is involved in the pathway related to for the disease, disorder, or condition, and that inhibiting Granzyme B results in the treatment or prevention of the disease, disorder, or condition.

Representative methods of treatment using the compounds of the invention include those described for Granzyme B inhibitors in WO 2007/101354 (Methods of Treating, Reducing, and Inhibiting the Appearance of Ageing in the Skin), WO 2009/043170 (Treatment of Dissection, Aneurysm, and Atherosclerosis Using Granzyme B Inhibitors), WO 2012/076985 (Granzyme B Inhibitor Compositions, Methods and Uses for Promoting Wound Healing), each expressly incorporated herein by reference in its entirety. The compounds of the invention are useful for treating, reducing, and inhibiting the appearance of aging of the skin; treating dissection, aneurysm, and atherosclerosis; and promoting wound healing.

Other disease and disorders described as treatable using the Granzyme B inhibitors are disclosed in WO 2003/065987 (Granzyme B Inhibitors), expressly incorporated herein by reference in its entirety. Disease and disorders described as treatable by Granzyme B inhibitors in this reference include autoimmune or chronic inflammatory diseases, such as systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, asthma, scleroderma and Sjogren's syndrome. The Granzyme B inhibitors described in the reference are noted as more particularly useful to treat or prevent diseases or disorders including diseases or disorders resulting from transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis *nodosa*, myocardosis, scleroderma, Wegener's granuloma, Sjogren's syndrome, adiposis, eosinophilic fasciitis, lesions of gingiva, periodontium, alveolar bone, substantia ossea dentis, glomerulonephritis, male pattern alopecia or alopecia *senilis* by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection. To the extent that the diseases and disorders noted in the reference are treatable by the Granzyme B inhibitors described in the reference, the Granzyme B inhibitors of the present invention are also useful in treating and/or ameliorating a symptom associated with these diseases and conditions.

Elevated Granzyme B levels have been identified in cells and tissues from subjects suffering from a variety of diseases and conditions including Rasmussen encephalitis, amyotrophic lateral sclerosis (ALS), chronic inflammation, Stevens-Johnson syndrome (SJS), toxic epidermal necrolysis (TEN), Kawasaki disease, idiopathic pulmonary fibrosis, chronic obstructive pulmonary disease (COPD), coronary artery disease (CAD), transplant vascular disease (TVD), restenosis, acute respiratory distress syndrome (ARDS), chronic obstructive sialadentis (associated with sialolithiasis), vitiligo, allergic contact dermatitis (ACD), atopic dermatitis (AD), *pityriasis rosea* (PR), rheumatoid arthritis (RA), osteoarthritis (OA), vasculitic neuropathy, sensory perineuritis, ischemic stroke, spinal cord injury, myasthenia gravis (MG), lymphocytic gastritis, autoimmune cholangitis (AIC), nodular regenerative hyperplasia (NRH) of the liver, achalasia, esophagitis, eosinophilic fasciitis, cryptorchidism, necrotizing lymphadenitis, Duchenne muscular dystrophy, facioscapulo humeral muscular dystrophy, and Higashi syndrome. Other diseases and conditions in which elevated Granzyme B levels have been identified include those described in WO 2009/043167 (Granzyme A and Granzyme B Diagnostics), expressly incorporated herein by reference in its entirety. The Granzyme B inhibitors of the invention may be useful for treating, alleviating or ameliorating a symptom of, diminishing the extent of, stabilizing, or ameliorating or palliating the diseases and conditions noted above in which elevated Granzyme B levels have been identified. A description of intracellular versus extracellular Granzyme B in immunity and disease is provided in Granville et al., *Laboratory Investigation*, 2009, 1-26, expressly incorporated herein by reference in its entirety. The reference provides a listing of conditions in which the pathogenic role of Granzyme B has been identified.

The compounds of the invention are useful in treating cutaneous scleroderma, epidermolysis bullosa, radiation dermatitis, alopecia areata, and discoid lupus erythematosus.

Cutaneous Scleroderma.

Scleroderma refers to a heterogeneous group of autoimmune fibrosing disorders. Limited cutaneous systemic sclerosis (CREST syndrome or LcSSc) develop sclerosis of the skin distal to their elbows and knees and have facial involvement. Patients with diffuse cutaneous systemic sclerosis (DcSSc) develop proximal, in addition to distal, skin sclerosis. Both groups of patients are also at high risk of developing internal organ involvement. Patients with LcSSc and DcSSc suffer from Raynaud's phenomenon (excessively reduced blood flow in response to cold or emotional stress, causing discoloration of the fingers, toes, and occasionally other areas believed to be the result of vasospasms that decrease blood supply to the respective regions) with high frequencies. Management of progressive skin involvement is dependent on additional comorbidities. In patients with skin involvement only, mycophenolate mofetil (Cellsept, immunomodulator) or methotrexate (T cell modulator) have been recommended.

Epidermolysis Bullosa.

Epidermolysis bullosa acquisita (EBA) is a chronic mucocutaneous autoimmune skin blistering disease. EBA patients can be classified into two major clinical subtypes: noninflammatory (classical or mechanobullous) and inflammatory EBA, which is characterized by cutaneous inflammation. In patients with inflammatory EBA, widespread vesiculobullous eruptions are observed, typically involving the trunk, central body, extremities, and skin folds. Usually the patients suffer from pruritus (rashes). Autoantibodies targeting type VII collagen (COL7) has been implicated in the pathogenesis. Therefore, EBA is a prototypical autoimmune disease with a well-characterized pathogenic relevance of autoantibody binding to the target antigen. EBA is a rare disease with an incidence of 0.2-0.5 new cases per million and per year. The current treatment of EBA relies on general immunosuppressive therapy, which does not lead to remission in all cases.

Radiation Dermatitis.

Radiation Dermatitis (acute skin reaction) ranges from a mild rash to severe ulceration. Approximately 85-90% of patients treated with radiation therapy will experience a moderate-to-severe skin reaction. Acute radiation-induced skin reactions often lead to itching and pain, delays in treatment, and diminished aesthetic appearance—and subsequently to a decrease in quality of life. Skin reactions related to radiation therapy usually manifest within 1-4 weeks of radiation start, persist for the duration of radiation therapy, and may require 2-4 weeks to heal after completion of therapy. The severity of the skin reaction ranges from mild erythema (red rash) and dry desquamation (itchy, peeling skin) to more severe moist desquamation (open wound) and ulceration. Treatments that have been assessed for the management of radiation-induced skin reactions include topical steroid creams, nonsteroidal creams, dressings, and herbal remedies. Only three trials have showed a significant difference: one in favor of a corticosteroid cream, one favoring a nonsteroidal cream, and one for a dressing. However, all three of these trials were small and had limitations, thus there is still an unmet medical need.

Late effects of radiation therapy, typically months to years post exposure, occur at doses greater than a single dose of 20-25 Gy or fractionated doses of 70 Gy or higher. The major underlying histopathological findings at the chronic stage include telangiectasia, dense dermal fibrosis (round fibrosis), sebaceous and sweat gland atrophy, loss of hair follicles, and with higher doses, increased melanin deposition or depigmentation and skin ulcers.

Ramipril was very effective in reducing the late effects of skin injury, whereas its mitigating effects on the acute and sub-acute injury were modest. However, the dose required to mitigate these late effects may be pharmacologically too high to be clinically relevant. More recently, it has been shown that significant mitigation of acute skin injury using an adeno-associated virus encoding the manganese SOD gene, when injected subcutaneously shortly after irradiation. However, difficulties in delivery, application and cost limit the utility of this treatment strategy.

Alopecia Aerata.

Alopecia areata (AA) is a CD8+ T-cell dependent autoimmune disease of the hair follicle (HF) in which the collapse of HF immune privilege (IP) plays a key role. Mast cells (MCs) are crucial immunomodulatory cells implicated in the regulation of T cell-dependent immunity, IP, and hair growth. Many of these infiltrating immune cells express GzmB, suggesting it may be a key mediator in immune cell-mediated follicular attack. The peptide substance P was shown to increase the CD8+ cells expressing GzmB in the intrafollicular dermis, co-relating to a regression of follicles into the catagen stage of follicle growth cessation (Siebenhaar et al., *J Invest Dermatol*, 2007, 127: 1489-1497).

In mice fed a diet with excess vitamin A, AA was accelerated and GzmB expressing cells were found in excess surrounding hair follicles, including in the isthmus (the region of the follicle containing stem cells) (Duncan et al., *J Invest Dermatol* 2013, 133: 334-343). As GzmB is expressed in the immune cell infiltrate within and surrounding growing follicles, it may be a key protease involved in hair loss through autoimmunity, apoptosis and ECM degradation.

No drug is currently approved by the US FDA for the treatment of alopecia areata. A number of treatments have been found to be effective using the American College of Physician's criteria, for example, topical and oral corticosteroids and the sensitizing agents diphenylcyclopropenone and dinitrochlorobenzene. However, there is no cure for alopecia areata, nor is there any universally proven therapy that induces and sustains remission.

Discoid Lupus Erythematosus.

Granzyme B is a serine protease found in cytoplasmic granules of cytotoxic lymphocytes and natural killer cells that plays an important role in inducing apoptotic changes in target cells during granule exocytosis-induced cytotoxicity. When Granzyme B is secreted into the cytoplasm of a target cell through the pore formed by perforin, it triggers cytotoxic-induced cell death (Shah et al., *Cell Immunology* 2011, 269:16-21).

Lupus erythematosus (LE) is a chronic, autoimmune, multisystem disease that displays many diverse symptoms in which localized cutaneous LE (CLE) is on one end of the spectrum and severe systemic LE (SLE) on the other end. CLE is a disfiguring, chronic skin disease, with a significant impact on the patients' everyday life. CLE are further divided into four main subsets: Acute CLE (ACLE), subacute CLE (SCLE) and chronic CLE (CCLE), where classic discoid LE (DLE) is the most common form. There is also a drug-induced form of the disease. The disease often has a chronic and relapsing course that can be induced or aggravated by UV light. CLE patients display well-defined skin lesions, often in sun-exposed areas. Discoid LE is the most common subtype of CLE, 60-80% is localized above the neck and 20-40% is generalized (lesions both above and below the neck). 70-90% of the DLE patients suffer from photosensitivity and sun exposed areas such as the scalp, ears and cheeks, which are most commonly involved areas. The lesions start as erythematosus maculae or papules with a scaly surface and then grow peripherally into larger discoid plaques that heal with atrophic scar and pigmentary changes. DLE often results in scarring and alopecia. Mutilation with tissue loss can be seen when the lesions affect the ears and tip of the nose. CLE can be managed but so far, not cured. Avoidance of trigger factors is of utmost importance, such as, cessation of smoking and avoidance of sun exposure. The treatment is about the same for the different CLE subsets where first-line of treatment is sun-protection and local therapy with corticosteroids or calcineurin inhibitors. Antimalarial are the first choice of systemic treatment.

Strong co-expression of Granzyme B and the skin-homing molecule, cutaneous lymphocyte antigen (CLA) was found in lesional lymphocytes of patients with scarring localized chronic DLE and disseminated chronic DLE, which was enhanced compared with nonscarring subacute CLE and healthy controls (Wenzel et al., *British Journal of Dermatology* 2005, 153: 1011-1015). Wenzel et al. conclude that skin-homing cytotoxic Granzyme B-positive lymphocytes play an important role in the pathophysiology of scarring chronic DLE and that the potentially autoreactive cytotoxic lymphocytes targeting adnexal structures may lead to scarring lesions in chronic DLE.

Correlation between Granzyme B-positive lymphocytes and the presence of CLE was shown by Grassi (Grassi et al., *Clinical and Experimental Dermatology* 2009, 34:910-914). Granzyme B is an apoptosis immunological mediator that, once synthesized and free from activated cytotoxic lymphocytes, enters the target cell and starts apoptotic mechanisms involved at different levels in all apoptotic pathways. In CLE, apoptosis is characterized by the presence of colloid or Civatte bodies, which are evident in the epidermis and papillary dermis of CLE lesions, and since Granzyme B is mainly expressed in CLE lesions, Grassi et al. conclude that Granzyme B could play a role in the induction of apoptotic mechanisms in CLE.

The expression of Granzyme B and perforin was correlated with clinicopathological features in patients with DLE, where both Granzyme B and perforin were expressed in DLE, with absent expression in normal skin (Abdou et al., *Ultrastructural Pathology* 2013, Early Online 1-9). Abdou et al. concluded that cytotoxicity in dermal lymphocytic inflammation was due to expression of both Granzyme B and perforin.

Extracellular Granzymes B is also reported to play a role in DLE by Grassi et al. Further, UV light increases Granzyme B expression in keratinocytes as well as mast cells (Hernandez-Pigeon, *J. Biol. Chem.*, 2007, 282:8157-8164). As Granzymes B is in abundance at the dermal-epidermal junction (DEJ), where many key extracellular matrix substrates are present (for example, laminin, fibronectin, decorin), it follows that Granzymes B may also be damaging the DEJ, as is observed in DLE. Given its expression in adnexal structures, Granzyme B may also be contributing to alopecia, as reduced Granzymes B is associated with reduced hair loss in a murine model of skin aging. Similarly, reduced extracellular Granzyme B activity is associated with improved collagen organization and reduced scarring in the skin and aorta.

In view of the established connection between Granzyme B and DLE, by virtue of their ability to inhibit Granzyme B, the compounds of the invention are useful in methods for treating lupus erythematosus (LE) including severe systemic LE (SLE) and localized cutaneous LE (CLE) (e.g., acute CLE (ACLE), subacute CLE (SCLE), chronic CLE (CCLE) and the most common form classic discoid LE (DLE)). In one embodiment, the invention provides a method for treating DLE comprising administering a therapeutically effective amount of a compound of the invention to a subject suffering from DLE.

Administration.

In the above methods, the administration of the Granzyme B inhibitor can be a systemic administration, a local administration (e.g., administration to the site, an inflamed microenvironment, an inflamed joint, an area of skin, a site of a myocardial infarct, an eye, a neovascularized tumor), or a topical administration to a site (e.g., a site of inflammation or a wound).

The term "subject" or "patient" is intended to include mammalian organisms. Examples of subjects or patients include humans and non-human mammals, e.g., nonhuman primates, dogs, cows, horses, pigs, sheep, goats, cats, mice, rabbits, rats, and transgenic non-human animals. In specific embodiments of the invention, the subject is a human.

The term "administering" includes any method of delivery of a Granzyme B inhibitor or a pharmaceutical composition comprising a Granzyme B inhibitor into a subject's system or to a particular region in or on a subject. In certain embodiments, a moiety is administered topically, intravenously, intramuscularly, subcutaneously, intradermally, intranasally, orally, transcutaneously, intrathecal, intravitreally, intracerebral, or mucosally.

As used herein, the term "applying" refers to administration of a Granzyme B inhibitor that includes spreading, covering (at least in part), or laying on of the inhibitor. For example, a Granzyme B inhibitor may be applied to an area of inflammation on a subject or applied to, for example the eye or an area of inflammation by spreading or covering the surface of the eye with an inhibitor, by injection, oral or nasal administration.

As used herein, the term "contacting" includes contacting a cell or a subject with a Granzyme B inhibitor. Contacting also includes incubating the Granzyme B inhibitor and the cell together in vitro (e.g., adding the inhibitor to cells in culture) as well as administering the inhibitor to a subject such that the inhibitor and cells or tissues of the subject are contacted in vivo.

As used herein, the terms "treating" or "treatment" refer to a beneficial or desired result including, but not limited to, alleviation or amelioration of one or more symptoms, diminishing the extent of a disorder, stabilized (i.e., not worsening) state of a disorder, amelioration or palliation of the disorder, whether detectable or undetectable. "Treatment" can also mean prolonging survival as compared to expected survival in the absence of treatment.

Cosmetic Compositions and Related Methods

In further aspects, the invention provides cosmetic compositions that include one or more granzyme B inhibitors of the invention and methods for using the compositions to treat, reduce, and/or inhibit the appearance of ageing of the skin.

This aspect of the invention is based, in part, on the observation that granzyme B expression is induced in keratinocytes and immune cells, such as mast cells in the skin during aging. When released by these cells, granzyme B cleaves extracellular matrix proteins such as decorin which can result in collagen disorganization. This invention is also based in part on the observation that granzyme B cleaves decorin, in addition to other extracellular matrix proteins, in the interstitial space surrounding cells.

Skin is comprised of three main layers: the epidermis, the dermis and subcutaneous layers. Each of these three layers has individual compositions. The functions and structures of these layers are known to a person of skill in the art. The epidermis is the outermost layer of skin and includes both living and dead cell layers. The dermis is the middle layer of skin and is comprised of arrangements of collagen fibers, which surround many specialized cells and structures. Hair follicles are found within the dermis, and produce the hair shaft which grows out through layers of the dermis and epidermis to become visible as hair. The lowermost layer of the skin is the subcutaneous layer, often called the subdermis. The subcutaneous layer is comprised largely of fat and connective tissue and houses larger blood vessels and nerves. Collagen may be found in all layers of the skin, but is most prominently in the dermis layer.

A youthful appearance is achieved by not having at least one of the characteristic signs of age. This is often achieved by being young. Nevertheless, there are circumstances in which being young does not confer a youthful appearance as a disease or disorder or other non-time related event has conferred the characteristics associated with age. A youthful appearance is often characterized by the condition of the skin and the following skin qualities are typically associated with, but not limited to, a youthful appearance: small pore size, healthy skin tone, radiance, clarity, tautness, firmness, plumpness, suppleness, elasticity, softness, healthy skin texture, healthy skin contours, such as few or no wrinkles, shallow wrinkle depth, few or no fine lines, healthy skin luster and brightness, moisturized skin, healthy skin thickness and resilient skin. If a skin of a subject comprises any one or more of these characteristics then a youthful appearance is achieved.

The appearance of ageing can occur for a variety of reasons, but typically happens at a normal rate associated with the passage of time. A rate of appearance of ageing will be different for different subjects, depending on a variety of factors including age, gender, diet and lifestyle. An appearance of ageing is often characterized by the condition of the skin. Characteristics associated with an appearance of ageing in the skin include, but are not limited to, skin fragility, skin atrophy, skin wrinkles, fine lines, skin discoloration, skin sagging, skin fatigue, skin stress, skin inelasticity, skin fragility, skin softening, skin flakiness, skin dryness, enlarged pore size, skin thinning, reduced rate of skin cell turnover, deep and deepening of skin wrinkles. The rate of appearance of ageing can be measured by measuring the rate at which any one or more of the above characteristics appear.

An appearance of ageing may be inhibited, reduced, or treated by reducing or maintaining a state of any one or more of these skin characteristics.

In many circumstances a reduction in the appearance of ageing of skin occurs when the rate of collagen cleavage exceeds the rate of collagen formation. In many other circumstances, a youthful appearance of skin is maintained when the rate of collagen formation is equal to the rate of collagen cleavage. In many other circumstances, a reduction in a rate of appearance of ageing of skin is achieved when the rate of decorin cleavage and collagen disorganization and cleavage is slowed such that the rate of collagen fibrillogenesis exceeds the rate of collagen cleavage and the ratio of the rate of collagen fibrillogenesis to the rate of collagen cleavage is greater after application of granzyme B inhibitor compound compared to the ratio before application of the compound. In many other circumstances, an extracellular protein, other than decorin, is also cleaved by granzyme B, and the beneficial effects of inhibiting granzyme B can be enhanced beyond what is realized by inhibiting decorin cleavage alone.

In one aspect, the invention provides a cosmetic composition. The composition comprises a cosmetically acceptable carrier and one or more compounds of the invention (e.g., a compound of Formulae (I), (II), (III), or (IV), or stereoisomers, tautomers, and cosmetically acceptable salts thereof, as described herein).

As used herein, the term "cosmetically acceptable salt" refers to a salt prepared from a cosmetically acceptable base, such as an inorganic base and an organic base, or a salt prepared from a cosmetically acceptable acid. Representative salts derived from inorganic bases include aluminum, ammonium, calcium, copper, ferric, ferrous, lithium, magnesium, manganic, manganous, ammonium, potassium, sodium, and zinc salts. Representative salts derived from cosmetically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and trimethamine.

The cosmetic compositions can be formulated by means known in the art and their mode of administration and the amount of granzyme B inhibitor compound as described herein can be determined by a person of skill in the art. Compositions for use in the methods described herein can comprise one of more of a granzyme B inhibitor compound or a cosmetically acceptable salt thereof as an active ingredient, in combination with a cosmetically acceptable carrier.

The cosmetic compositions can include diluents, excipients, solubilizing agents, emulsifying agents, and salts known to be useful for cosmetic compositions. Examples of suitable agents include thickeners, buffers, preservatives, surface active agents, neutral or cationic lipids, lipid complexes, liposomes, and penetration enhancers. In certain embodiments, the cosmetic compositions further include other cosmetic ingredients known in the art.

In certain embodiments, the cosmetic composition can include one or more penetration enhancers. Numerous types of penetration enhancers are known, such as fatty acids, bile salts, chelating agents, surfactants and non-surfactants (Lee et al., Critical Reviews in Therapeutic Drug Carrier Systems 8:91-192, 1991; Muranishi, Critical Reviews in Therapeutic Drug Carrier Systems 7:1-33, 1990). Fatty acids and their derivatives which act as penetration enhancers include, for example, cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, nervonic acid, dicaprate, tricaprate, recinleate, monoolein (also known as 1-monooleoyl-rac-glycerol), dilaurin, arachidonic acid, glyceryll-monocaprate, 1-dodecylazacycloheptan-2-one, acylcarnitines, acylcholines, mono- and di-glycerides and physiologically acceptable salts thereof (e.g., oleate, laurate, caprate, myristate, palmitate, stearate, linoleate) (Lee et al., Critical Reviews in Therapeutic Drug Carrier Systems page 92, 1991; Muranishi, Critical Reviews in Therapeutic Drug Carrier Systems 7:1, 1990; El-Hariri et al., *J. Pharm. Pharmacol.* 44:651-654, 1992).

In certain embodiments, the cosmetic composition further includes other cosmetic ingredients known in the art to be useful for cosmetic, skincare, and/or dermatological applications (e.g., anti-wrinkle active ingredients including flavone glycosides such as alpha-glycosylrutin; coenzyme Q10 vitamin E and derivatives; as well as sunblock ingredients, moisturizers, and perfumes).

The cosmetic compositions of the invention can be administered for "cosmetic" or "skincare" (e.g., dermatologic) applications, either alone or as an "additive" in combination with other suitable agents or ingredients. As used herein, "cosmetic" and "skincare" applications includes, for example, preventive and/or restorative applications in connection with dermatological changes in the skin, such as, for example, during pre-mature skin aging; dryness; roughness; formation of dryness wrinkles; itching; reduced re-fatting (e.g., after washing); visible vascular dilations (e.g., telangiectases, cuperosis); flaccidity; formation of wrinkles and lines; local hyperpigmentation; hypopigmentation; incorrect pigmentation (e.g., age spots); increased susceptibility to mechanical stress (e.g., cracking); skin-sagging (e.g., lack of firmness) and the appearance of dry or rough skin surface features.

The cosmetic compositions of the invention can be formulated for topical administration. Such compositions can be administered topically in any of a variety of forms. Such compositions are suitable in the context of the use described herein for application to the skin or to the surface of the eye. The use of patches, corneal shields (see, U.S. Pat. No. 5,185,152), and ophthalmic solutions (see, for example, U.S. Pat. No. 5,710,182) and ointments is within the skill in the art.

Compositions for topical administration include dermal patches, ointments, lotions, serums, creams, gels, hydrogels, pastes, foams, oils, semi-solids, shampoos, soaps, drops, sprays, films, liquids, and powders. Examples of such compositions include those in which a cosmetically effective amount of a compound of the invention is encapsulated in a vehicle selected from macro-capsules, micro-capsules, nano-capsules, liposomes, chylomicrons and microsponges. Another example of such a composition includes absorption of a compound of the invention on or to a material selected from powdered organic polymers, talcs, bentonites, and other mineral supports. A third example of such a composition or formulation includes a mixture of a cosmetically effective amount of a compound of the invention with other ingredients selected from extracted lipids, vegetable extracts, liposoluble active principles, hydrosoluble active principles, anhydrous gels, emulsifying polymers, tensioactive polymers, synthetic lipids, gelifying polymers, tissue extracts, marine extracts, vitamin A, vitamin C, vitamin D, vitamin E, solar filter compositions, and antioxidants. Other examples of suitable composition ingredients can be found in US2005/0249720.

In the cosmetic compositions, the compounds of the invention can be incorporated into any gelanic form, such as oil/water emulsions and water/oil emulsions, milks, lotions, gelifying and thickening tensioactive and emulsifying polymers, pomades, lotions, capillaries, shampoos, soaps, powders, sticks and pencils, sprays, and body oils.

Regardless of the compound or formulation described herein, application/administration to a subject as a colloidal dispersion system can be used as a delivery vehicle to enhance the in vivo stability of the compound and/or to target the granzyme B inhibitor compound to a particular skin layer, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:inhibitor complexes of uncharacterized structure. An example of a colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 6:698-708, 1995). Sustained-release dosage forms of the compounds described herein can also be used.

The amount of the granzyme B inhibitor compound administered or applied to a subject is not critical, except that it should be an amount sufficient to effect improvement of the condition for which the composition is administered/applied. Application can be dependent on a number of factors, including severity and responsiveness of the condition to be treated, and with the course of treatment lasting from several days to several months, or until improvement of a condition is effected or a diminution of a symptom is achieved.

A "cosmetically effective amount" of a granzyme B inhibitor compound includes a cosmetically effective amount or a prophylactically effective amount. A "cosmetically effective amount" refers to an amount effective, at dosages and for periods of time necessary, to achieve the desired cosmetic result, such as improved skin elasticity, skin durability, skin firming, skin texture, decrease the appearance or decrease rate of appearance of aging, and the like. A cosmetically effective amount of a compound may vary according to factors such as the skin state, age, sex, and weight of the subject, and the ability of the compound to elicit a desired response in the subject. Dosage regimens can be adjusted to provide the optimum cosmetic response. A cosmetically effective amount is also one in which any toxic or detrimental effects of the compound are outweighed by the cosmetically beneficial effects. A "prophylactically effective amount" refers to an amount effective, at dosages and for periods of time necessary, to achieve the desired prophylactic result, such as improved skin elasticity, skin durability, skin firming, skin texture, a decrease appearance or a decrease in the rate of appearance of aging, and the like. Typically, a prophylactic dose is used in subjects prior to or at an earlier stage of skin deterioration, so that a prophylactically effective amount may be less than a cosmetically effective amount.

The amount of granzyme B inhibitor administered/applied may vary with the severity of the appearance, or rate of appearance, of age of the skin. For any particular subject, specific dosage regimens may be adjusted over time according to the individual need and the judgment of the person applying or supervising the applying of the compositions. Dosage ranges set forth herein are exemplary only and do not limit the dosage ranges that may be selected. The amount of granzyme B inhibitor compound(s) in the composition or formulation can vary according to factors such as the skin state, age, sex, and weight of the subject. Dosage regimens can be adjusted to provide the optimum response. For example, a single application can be administered/applied, several divided doses can be administered/applied over time or the amount of the composition administered/applied can be proportionally reduced or increased as indicated by the exigencies of the situation. It can be advantageous to formulate the granzyme B inhibitor compounds in a composition into a dosage unit form for ease of administration and uniformity of application.

By way of example, a granzyme B inhibitor compound of the cosmetic composition can be administered/applied to achieve from about 0.01 micrograms per milliliter (g/mL) to about 10 milligrams per milliliter, from about 0.1 μg/mL to about 500 μg/mL, from about 0.1 μg/mL to about 1500 μg/mL, from about 1 μg/mL to about 2000 μg/mL, and from about 0.1 μg/mL to about 5000 μg/mL, including any range within these ranges, final concentrations at a target site.

Appropriate dosage values can depend on the characteristics of the site to which the composition is to be applied/administered and on the form of the granzyme B inhibitor compound used. Guidance as to particular dosages and methods of delivery is provided in the literature and generally available to practitioners in the art. Those skilled in the art will employ different formulations for different uses and the granzyme B inhibitor compound used. Persons of ordinary skill in the art can easily estimate repetition rates for dosing based on measured residence times and concentrations of the granzyme B inhibitor compound in, for example, a bodily fluid or a tissue. Following successful treatment, it can be desirable to have the subject undergo maintenance therapy to prevent the recurrence of the condition, wherein a selected compound is administered/applied in maintenance doses applied, for example, once or more daily, to once every few days. In certain embodiments, granzyme B inhibitor compounds are administered/applied in an amount to achieve ex vivo concentrations from about 1 micromolar to about 10 millimolar, from about 10 micromolar to about 5000 micromolar, or from about 30 micromolar to about 3000 micromolar, and from about 25 micromolar to about 3000 micromolar final concentration over a site of interest, and including, about 25 micromolar, or about 1600 micromolar, or about 3000 micromolar final concentration over the site, and still more typically between about 1 micromolar to about 1000 micromolar.

Compounds or compositions of granzyme B inhibitors can be administered/applied by means of a device or appliance such as an implant, graft, prosthesis, garment of clothing, stent, and the like. Also, implants can be devised which are intended to contain and release such compounds or compositions. An example would be an implant made of a polymeric material adapted to release the compound over a period of time. Such implants can be placed into a garment to be worn by a subject, for example a glove, shirt, mask or hat.

The cosmetic compositions of the invention can be used to inhibit or reduce the appearance of ageing. Ageing is a natural phenomenon that cannot be reversed per se, but the appearance of ageing, such as skin deterioration including, but not limited to, skin inelasticity, skin fragility, skin softening, skin flakiness, skin dryness, enlarged pore size, skin thinning, reduced rate of skin cell turnover, skin wrinkling, deepening of skin wrinkles, skin sagging, fine lines, and skin discoloration may be inhibited or reduced.

The cosmetic compositions can be used to increase or decrease a rate of increasing or a rate of decreasing occurrences of a particular skin characteristic. In other words, the composition, when applied to the skin or a portion of the skin of a subject delays the onset of an appearance of aging. For example, in a population of subjects where half of the population applies a granzyme B inhibitor to their skin and another half of the population does not apply a granzyme B inhibitor to their skin, the half which applied a granzyme B inhibitor would not appear as aged as the half which did not apply the granzyme B inhibitor after a period of time had elapsed. The half of the population which applied a granzyme B inhibitor to the skin would also have maintained a youthful appearance.

The rate at which a particular subject experiences a change in the rate of appearance of a particular skin characteristic, i.e., an increasing or decreasing rate of the appearance of a particular skin characteristic, will depend on a variety of factors, including, but not limited to age, weight, sex and lifestyle of the subject. As such, rates are not necessarily constant, but a normal rate of increase or of decrease of an appearance of a characteristic, defined as being the new occurrence of a particular characteristic over a predetermined period of time under a set of conditions that do not include the presence of a granzyme B inhibitor applied by a method or use of this invention, is increased or decreased by applying a granzyme B inhibitor in accordance with a method or use of this invention. Methods of measuring skin characteristics, rates of increasing appearance of skin characteristics and rates of decreasing appearance of skin characteristics are known to a person of skill in the art, see for example, *Measuring the Skin* by Agache et al., Springer (2004).

Surprisingly, granzyme B inhibitors can also be used to increase the density of hair follicles of a skin of a subject and may be used to reduce the occurrences of cutaneous xanthomas of a skin of a subject. Actively growing hair follicles contain melanocytes that transfer pigment to matrix keratinocytes, imparting color to hair. Additionally, sebum, produced in sebaceous glands, is often secreted via hair follicles. Increased density of hair follicles results in increased pigment production and increased sebum secretion resulting in improved hair appearance (e.g., hair that is less grey in color or not grey at all) as well as healthier hair and skin. Granzyme B inhibitors also cause hair follicles to appear deeper in the skin which provide stronger hair that is less susceptible to mechanical damage. Additionally, a characteristic sign of ageing is the reduction in hair follicle density. It is known in the art that age and follicular miniaturization are weak predictors of total hair count (see Chapman et al., *Brit. J. Dermatol.* 152:646-649, 2005). Consequently, the characteristic sign of age associated with hair follicle density is not predictive of hair density.

The cosmetic composition may be applied to a portion of the skin of a subject or to the whole of the skin of the subject. For example, the composition may be applied to the skin, only on the face, only on the scalp, on the whole head or to each part of the body.

INCORPORATION BY REFERENCE

Each reference cited is incorporated herein by reference in its entirety.

Abbreviations

As used herein, the following abbreviations have the indicated meanings.
$^1$H NMR: proton nuclear magnetic resonance
$^{19}$F NMR: fluorine-19 nuclear magnetic resonance
% Inh: Percent inhibition
Ac-IEPD-AMC: acetyl-isoleucyl-glutamyl-prolyl-aspartyl-(7-amino-4-methylcoumarin) substrate
ACN: acetonitrile
BHET: bis-2-hydroxyethyl-terephthalate
Boc: tert-butoxycarbonyl
CHAPS: 3-[(3-cholamidopropyl)dimethylammonio]-1-propanesulfonate
DCM: dichloromethane
DIPEA: diisopropylethylamine
DMAP: 4-dimethylaminopyridine
DMF: dimethylformamide
DMSO: dimethylsulfoxide
DMSO-d6: dimethylsulfoxide-d6
DTT: dithiothreitol
EDC: 1-(3-dimethylaminopropyl)-3-ethylcarbodiimide hydrochloride
EDTA: 2-({2-[Bis(carboxymethyl)amino]ethyl}(carboxymethyl)amino)acetic acid
ESI: Electrospray ionization
EtOAc: ethyl acetate
eq.: equivalent(s)
GzmB: Granzyme B
HATU: 2-(7-aza-1H-benzotriazole-1-yl)-1,1,1,1-tetramethyluronium hexafluorophosphate
HCl: hydrochloric acid
HEPES: 4-(2-hydroxyethyl)-1-piperazineethanesulfonic acid
hGzmB: human Granzyme B
HPLC: high performance liquid chromatography
HOBt: 1-hydroxy-benzotriazol
$IC_{50}$: inhibitory concentration that provides 50% inhibition
LC/MS: liquid chromatography/mass spectrometry
MeOH: methanol
mGzmB: murine Granzyme B
MS: mass spectrometry
m/z: mass to charge ratio.
Oxyma: ethyl 2-cyano-2-(hydroxyimino)acetate
PBS: phosphate buffered saline (pH 7.4)
RPM: revolution per minute
RT: room temperature
THF: tetrahydrofuran
TFA: trifluoroacetic acid General Methods A-P Representative compounds of the invention were prepared according to Methods A to P as described below and illustrated in FIGS. 1-3.

The Willoughby 20 compound was synthesized by published procedures (see Willoughby et al., *Bioorg. Med. Chem. Lett.* 12 (2002) 2197-2200 and WO 03/065987). It will be appreciated that in the following general methods and preparation of synthetic intermediates, reagent levels and relative amounts or reagents/intermediates can be changed to suit particular compounds to be synthesized, up or down by up to 50% without significant change in expected results.

Method A: General Method for Deprotection Followed by Coupling Reaction Using EDC/HOBt/DIPEA.

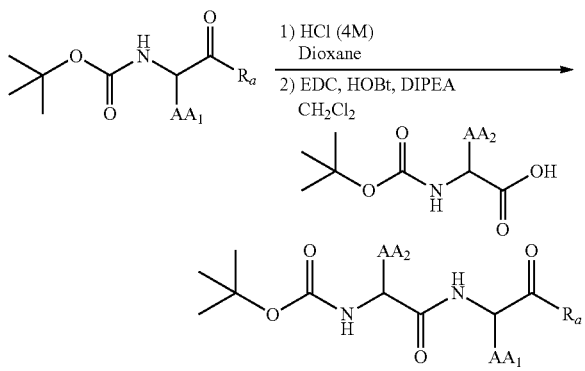

HCl Solution in dioxane (4M, 5 ml) was added to respective carbamate compound (0.125 mmol) and stirred for 2 hrs at RT. The reaction mixture was concentrated to dryness under vacuum and swapped with MeOH (5 ml) three times. Resulting residue was dried well under vacuum and subjected to next reaction as it is. The residue obtained above, respective acid moiety (0.125 mmol), EDC (0.19 mmol), HOBt (0.16 mmol) and DIPEA (0.5 mmol) were stirred in anhydrous DCM (5 ml) for 16 hrs. The reaction mixture was concentrated under vacuum to give the crude product which was purified on a C18 column using 10-50 MeOH in water to yield product as an off-white solid (35-55%).

Method B: General Method for Deprotection Followed by Reaction with Anhydride.

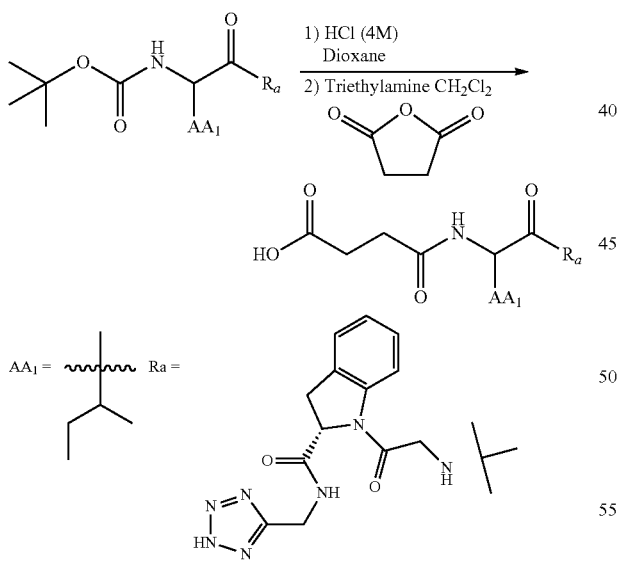

HCl Solution in dioxane (4M, 5 ml) was added to a representative Boc-protected compound (0.125 mmol) and stirred for 2 hrs at RT. The reaction mixture was concentrated to dryness under vacuum and washed with MeOH (5 ml) three times. Resulting residue was dried well under vacuum and subjected to next reaction as it is. The residue obtained above, the respective anhydride moiety (0.125 mmol), and triethylamine (0.5 mmol) were added to anhydrous DCM (5 mL) and stirred for 16 hrs. The mixture was concentrated under vacuum to give the crude product which was purified on a C18 column using 10-50% MeOH in water to yield product as an off-white solid (40-60%).

Method C: General Method of Coupling Reaction Using HATU/DIPEA.

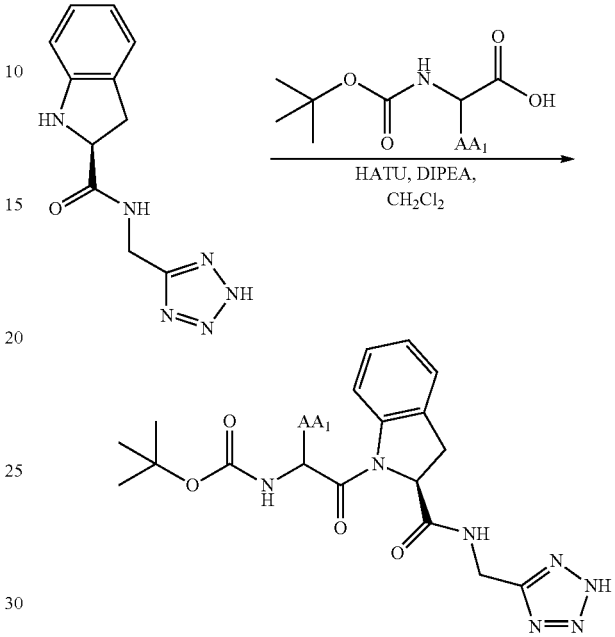

The respective acid moiety (0.125 mmol), HATU (0.17 mmol), DIPEA (0.5 mmol) and respective amine moiety (0.125 mmol) were stirred in anhydrous DCM (5 ml) for 16 hrs. The reaction mixture was concentrated under vacuum to give the crude product which was purified on a C18 column using 10-50% MeOH in water (or similar ratio as needed) to yield product as an off-white solid (35-55%).

Method D: General Method of Hydrolysis Using LiOH.

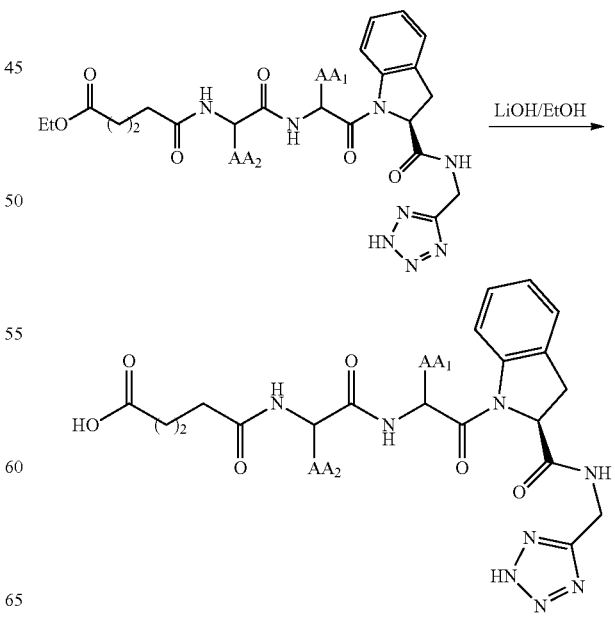

To the stirring solution of the ester compound (0.08 mmol) in ethanol (1 ml) was added solution of lithium hydroxide monohydrate (0.4 mmol) in water (0.5 ml). After stirring the reaction mixture for 5 hrs at RT, the mixture was acidified using citric acid (saturated solution) and concentrated under vacuum to give the crude product which was purified on a C18 column using 10-40%/o MeOH in water to yield product as an off-white solid (50-65%).

Method E: General Method for Boc Deprotection.

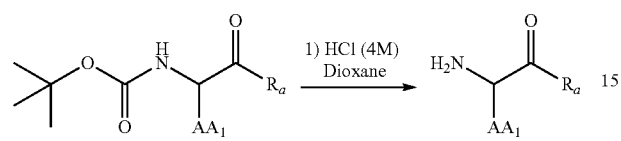

HCl Solution in dioxane (4M, 0.5 ml) was added to the respective carbamate compound (0.06 mmol) and stirred for 3 hrs at RT. The reaction mixture was concentrated under vacuum to give the crude product which was purified on a C18 column using 10-40% MeOH in water to yield product as an off-white solid (50-60%).

Method F: General Method for Methanesulfonyl (Mesyl) Chloride Mediated Amino Acid Coupling.

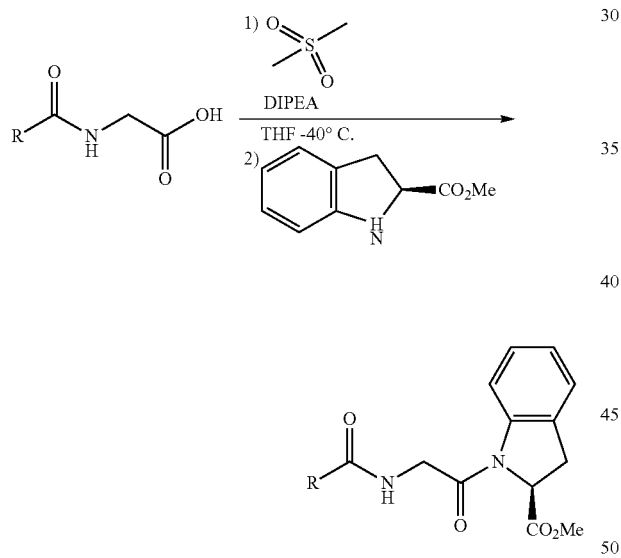

A solution of an appropriate acid (1.0 mmol) in THF (10 mL) was cooled to −40° C. To this solution was added DIPEA (1.7 mmol) followed by CH$_3$SO$_2$Cl (1.3 mmol). The reaction mixture was allowed to stir for 20 minutes before addition of an appropriate amine (such as (S)-methyl indoline-2-carboxylate) (1.1 mmol). After stirring for further 10 min at the same temperature the ice bath was removed and reaction mixture was allowed to warm up to room temperature. The reaction mixture was diluted with EtOAc and then washed with saturated aqueous solution of NaHCO$_3$. The aqueous layer was then extracted with EtOAc (2×20 mL). Combined organic layer was washed with brine and dried over anhydrous Na$_2$SO$_4$, filtered and concentrated in vacuo. Flash chromatography (MeOH:DCM 2-5%) afforded final compound.

Method G: EDC/Oxyma Amino Acid Coupling.

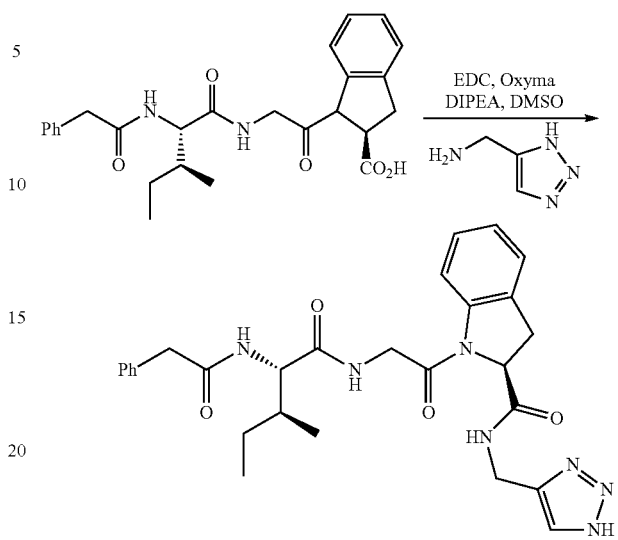

To a mixture of an appropriate acid (0.05 mmol) in DMSO (0.5 mL) DIPEA (0.23 mmol), an appropriate acid (0.075 mmol), EDC (0.1 mmol), and oxyma (0.1 mmol) were added at RT. After stirring for 16 h the reaction mixture was purified by preparative HPLC (column: Ascentis C18, 25 cm×21.2 mm, 10 μm, gradient 0%→100% methanol/water with 0.1% TFA, 10 mL/min or similar) to furnish 11 mg of powder.

Method H: General Method of Acid Chloride Synthesis Followed by Amide Formation.

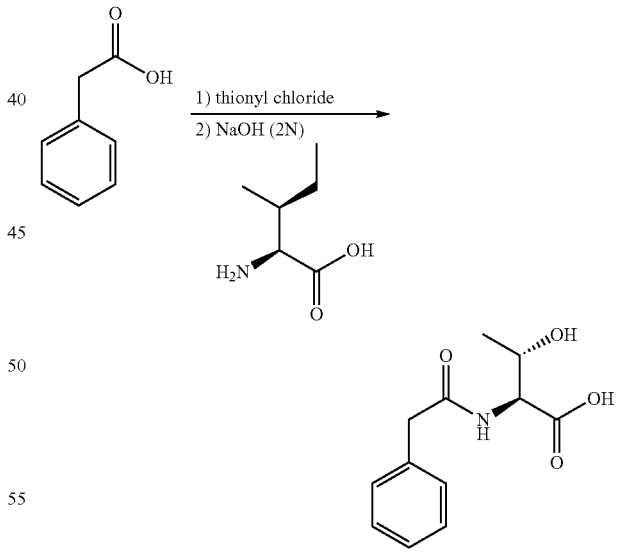

Acid compound (1.5 mmol) and thionyl chloride (90 mmol) were stirred together for 1 hr. at room temperature. Thionyl chloride was removed by distillation under vacuum. The acid chloride was added to the stirring solution of L-isoleucine (1.35 mmol) in NaOH (2N, 1.8 ml) at 0° C. The resulting reaction mixture was warmed to RT and stirred overnight. The reaction mixture was diluted with water (2 ml) and washed with diethyl ether (3 ml). Separated aqueous layer was acidified to pH 2 by adding mixture of 1:1

HCl-water. The precipitated solid was filtered and washed with water to get the product as a white to off-white solid (45-75%).

Method I: General Method for Deprotection Followed by Reaction with Anhydride).

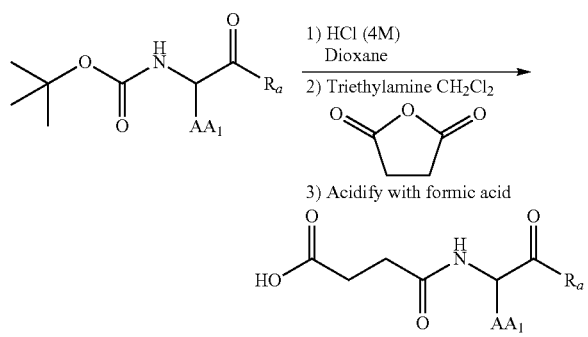

This method is an improved procedure for the method B. HCl Solution in dioxane (4M, 5 ml) was added to a representative Boc-protected compound (0.125 mmol) and stirred for 2 hrs at RT. The reaction mixture was concentrated to dryness under vacuum and swapped with MeOH (5 ml) three times. The resulting residue was dried well under vacuum and subjected to next reaction as it was. The residue obtained above, the respective anhydride moiety (0.19 mmol, 1.5 eq.), and triethylamine (0.5 mmol, 4 eq.) were added to anhydrous DCM (5 mL) and stirred for 16 hrs. The mixture was acidified with formic acid and then concentrated under vacuum to give the crude product which was purified on a C18 column using 25-65% MeOH in water to yield product as an off-white solid (30-80%).

Method J: General Method for Deprotection Followed by Reaction with a Di-Acid.

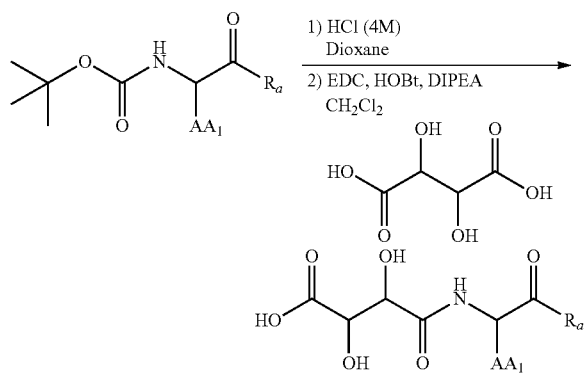

HCl Solution in dioxane (4M, 5 ml) was added to a representative Boc-protected compound (0.125 mmol) and stirred for 2 hrs at RT. The reaction mixture was concentrated to dryness under vacuum and swapped with MeOH (5 ml) three times. Resulting residue was dried well under vacuum and subjected to next reaction as it was. The residue obtained above, the respective di-acid moiety (0.62 mmol, 5 eq.), EDC (0.19 mmol), HOBt (0.15 mmol) and DIPEA (1.6 mmol, 13 eq.) were added to anhydrous DCM (5 mL) and stirred for 4 hrs. The mixture was acidified with formic acid and then concentrated under vacuum to give the crude product which was purified on a C18 column using 25-65% MeOH in water to yield product as an off-white solid (30-80%).

Method K: General Method for Boc Protection.

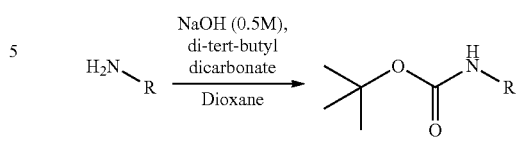

To respective amine compound (6.1 mmol) in dioxane (6 ml) and NaOH solution (0.5M, 12 ml) was added slowly solution of di-tert-butyl dicarbonate (6.7 mmol) in dioxane (6 ml) at 0° C. The reaction mixture was warmed to RT and stirred overnight. The reaction mixture was then washed with hexanes (10 ml). The separated water layer was acidified using saturated solution of citric acid and extracted with ethyl acetate (3×15 ml). The organic layer was washed with brine, separated, dried over sodium sulfate and concentrated to give Boc protected amine compound as off-white solid (65-90%).

Method L: General Method of Hydrolysis Followed by Coupling Reaction Using EDC/HOBt/DIPEA.

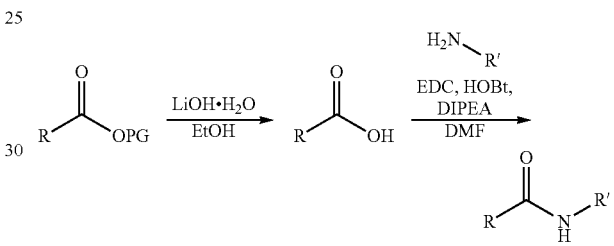

To the stirring solution of the ester compound (0.11 mmol) in ethanol (4 ml) was added solution of lithium hydroxide monohydrate (0.23 mmol) in water (2 ml). After stirring the reaction mixture for 5 hrs at RT, the mixture was acidified using sat. citric acid solution and concentrated under vacuum to remove ethanol. The aqueous residue obtained was extracted with EtOAc (2×15 ml). Combined organic layer was dried over anhydrous $Na_2SO_4$, filtered and concentrated in vacuo. Resulting residue was dried well under vacuum and subjected to next reaction as it was. The residue obtained above, the respective amine moiety (0.11 mmol), EDC (0.17 mmol), HOBT (0.15 mmol) and DIPEA (0.46 mmol) were stirred in DMF (4 ml) for 16 hrs. The mixture was concentrated under vacuum to give the crude product which was purified on a C18 column using 10-50% MeOH in water to yield product as an off-white solid (50-60%).

Method M: General Method for EDC/HOBt/DIPEA Coupling of an Intermediate Existing as an HCl Salt and a Free Carboxylic Acid.

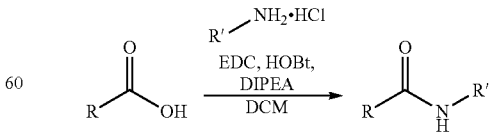

To an intermediate collected as an HCl salt (0.125 mmol) were added the carboxylic acid (0.125 mmol), EDC (0.19 mmol), HOBt (0.16 mmol), and anhydrous DCM (5 ml). The flask was purged with $N_2$, sonicated for 20 s and DIPEA (0.5 mmol) was added. The reaction was stirred at room temperature for 6 hrs then concentrated under reduced pressure. The residue was purified on a C18 column using 10-80% MeOH in water to yield the product as an off-white solid (40-90%).

Method N: General Method for Anhydride Ring Opening by an Intermediate Existing as an HCl Salt.

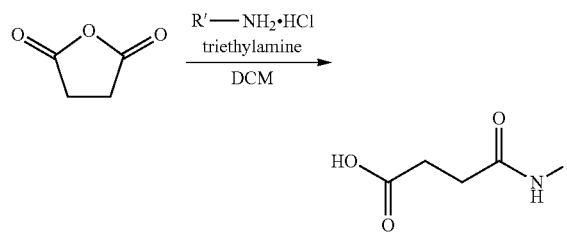

To an intermediate collected as an HCl salt (0.11 mmol) were added the respective anhydride (0.13 mmol), and anhydrous DCM (6 mL). The flask was purged with $N_2$, sonicated for 20 s and triethylamine (0.44 mmol) was added. The reaction was stirred at room temperature for 5.5 hrs. The reaction was acidified to approximately pH 5 using citric acid (aqueous, saturated solution), and then concentrated under reduced pressure. The residue was purified on a C18 column using 10-75% MeOH in water to yield the product as an off-white solid (40-67%).

Method O: General Method for Coupling (2H-Tetrazol-5-Yl)Methylamine and a Free Carboxylic Acid.

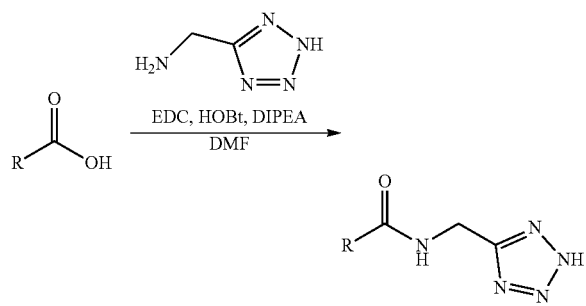

To the carboxylic acid (0.18 mmol), were added the (2H-tetrazol-5-yl)methylamine (0.22 mmol), EDC (0.275 mmol), HOBt (0.22 mmol), and anhydrous DMF (15 ml). The flask was purged with $N_2$, sonicated for 20 s and DIPEA (0.73 mmol) was added. The reaction was stirred at room temperature for 16 hrs. Analysis of the reaction by LC/MS showed approximately 75% conversion of the acid. An additional one half of the portion of the amine, EDC, HOBt, and DIPEA were added and the reaction was heated at 45° C. for another 6 hrs then concentrated under reduced pressure. The residue was purified on a C18 column using 10-70% MeOH in water to yield the product as an off-white solid (40-95%).

Method P: General Method for (a) Preparation of Unsymmetric Anhydride Ring Opening Products with Proximal Substitution (Via Anhydride Ring Opening with MeOH) Followed by (b) Coupling to an Amine (Ex. I-15) and c) Subsequent Hydrolysis.

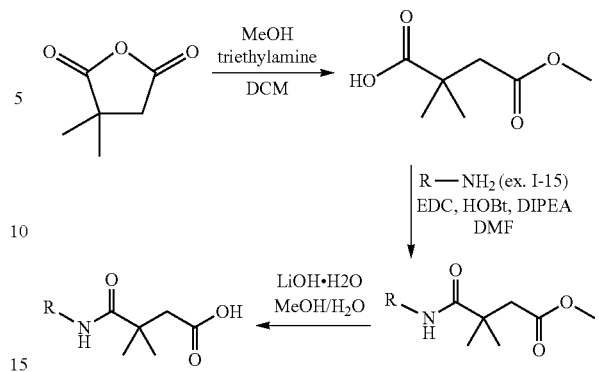

To the respective anhydride (2.8 mmol) were added methanol (5.6 mmol), anhydrous DCM (28 mL) and triethylamine (11 mmol). The reaction was stirred at RT for 4 hrs then diluted with diethyl ether (30 mL) and HCl (1M, aqueous, 30 mL) and transferred to a separatory funnel. The organic layer was collected, washed with a NaCl solution (saturated, aqueous) and then dried over anhydrous $Na_2SO_4$. After filtration and concentration under reduced pressure, the crude ring-opened product was collected as a colourless oil and as a mixture of isomers. The ring-opened product mixture was used in the subsequent step without further purification. To the crude ring-opened product (0.11 mmol) were added the amine (ex. I-15) (0.11 mmol) EDC (0.17 mmol), HOBt (0.13 mmol) and anhydrous DCM (6 mL). The flask was purged with $N_2$, sonicated for 20 s and triethylamine (0.44 mmol) was added. The reaction was stirred at RT for 3 hrs. The reaction mixture was concentrated under reduced pressure and the residue was purified on a C18 column using 10-70% MeOH in water to yield the methyl ester product as an off-white solid and as a mixture of isomers (49-65%). To the mixture of isomers (0.12 mmol) were added LiOH $H_2O$ (0.23 mmol), methanol (3 mL), and $H_2O$ (4.5 mL). The reaction was stirred at room temperature in air for 10 h. The reaction was acidified to approximately pH 5 using citric acid (aqueous, saturated), and then concentrated under reduced pressure. The residue was purified on a C18 column using 10-75° % MeOH in water to yield the product as an off-white solid (17-54%).

The following examples are provided for the purpose of illustrating, not limiting, the invention.

EXAMPLES

Synthetic Intermediates

The following is a description of synthetic intermediates (I-1 to I-15) useful for making representative compounds of the invention.

Intermediate I-1

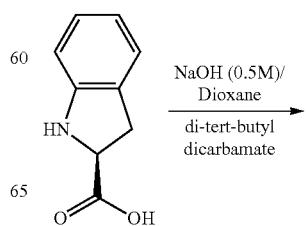

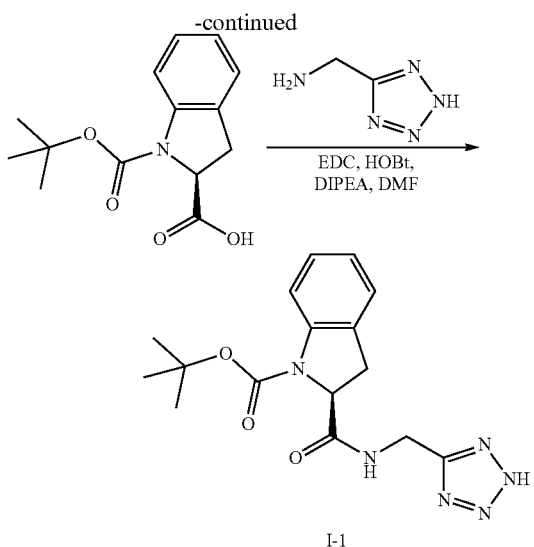

tert-Butyl (2S)-2-[(2H-1,2,3,4-tetrazol-5-ylmethyl)carbamoyl]-2,3-dihydro-1H-indole-1-carboxylate
(I-1)

To (2S)-2,3-dihydro-1H-indole-2-carboxylic acid (1 g, 6.13 mmol) in dioxane (6 ml) and NaOH solution (0.5M, 12 ml) was added slowly di-tert-butyl dicarbonate (1.47 g, 6.74 mmol) in dioxane (6 ml) at 0° C. The reaction mixture was warmed to RT and stirred overnight. The reaction mixture was then washed with hexanes (10 ml). The separated water layer was acidified using saturated solution of citric acid and extracted with ethyl acetate (3×15 ml). The organic layer was washed with brine, separated, dried over sodium sulfate and concentrated to give (2S)-1-[(tert-butoxy)carbonyl]-2,3-dihydro-1H-indole-2-carboxylic acid, as light orange colored solid (1.45 g, 90%), used further as described. $^1$H NMR (400 MHz, DMSO-d6) δ 1.41 (9H, s), 2.99-3.04 (1H, d, J=20 Hz), 3.48-3.55 (1H, dd, J=12, 16 Hz), 4.74-4.78 (1H, dd, J=4, 12 Hz), 6.91-6.95 (1H, t, J=8 Hz), 7.14-7.18 (2H, m), 7.72-7.74 (1H, d, J=8 Hz), 12.85 (1H, bs), MS (LC/MS) m/z observed 285.89, expected 286.11 [M+Na].

(2S)-1-[(tert-Butoxy)carbonyl]-2,3-dihydro-1H-indole-2-carboxylic acid (3 g, 11.40 mmol), 2H-1,2,3,4-tetrazol-5-ylmethanamine (1.16 g, 11.40 mmol), EDC (2.4 g, 12.53 mmol), HOBt (1.54 g, 11.40 mmol) and DIPEA (15.9 ml, 91.15 mmol) were stirred in anhydrous DMF (60 ml) for 16 hrs. The reaction mixture was concentrated under vacuum and re-dissolved in ethyl acetate (180 ml) and washed with citric acid (aqueous, saturated solution), water and brine. The organic layer was separated, dried over sodium sulfate and concentrated to give the crude product as an orange-red oil. The crude compound recrystallized in diethyl ether (80 ml) to yield tert-butyl (2S)-2-[(2H-1,2,3,4-tetrazol-5-ylmethyl)carbamoyl]-2,3-dihydro-1H-indole-1-carboxylate (I-1) as an off-white solid (2.8 g, 71%). $^1$H NMR (400 MHz, DMSO-d6) δ 1.32 (9H, s), 2.94-2.99 (1H, dd, J=4, 15 Hz), 3.41-3.48 (1H, dd, J=12, 20 Hz), 4.50-4.64 (2H, dq, J=4, 20 Hz), 4.73-4.77 (1H, dd, J=4, 12 Hz), 6.89-6.83 (1H, t, J=8 Hz), 7.12-7.16 (2H, t, J=8 Hz), 7.71 (1H, bs), 7.86 (1H, bs), MS (LC/MS) m/z observed 344.73, expected 345.17 [M+H].

Intermediate I-2

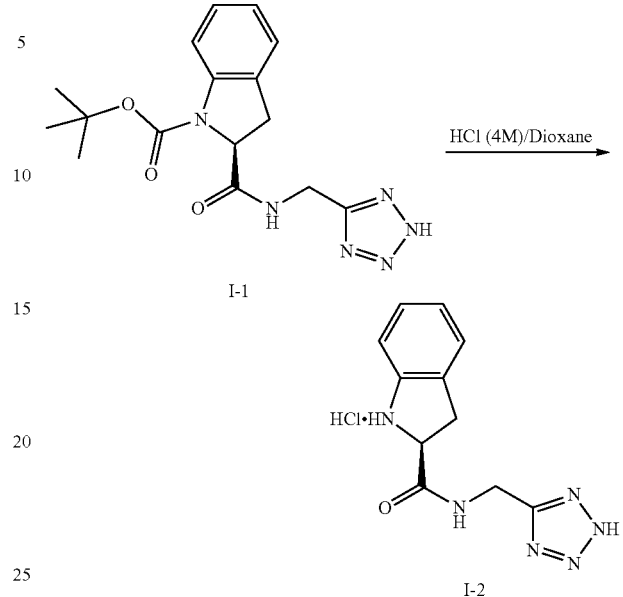

(2S)—N-(2H-1,2,3,4-Tetrazol-5-ylmethyl)-2,3-dihydro-1H-indole-2-carboxamide Hydrochloride
(I-2)

HCl Solution in dioxane (4M, 28 ml) was added to I-1 (1.4 g, 4.07 mmol) and stirred for 2 hrs at RT. Precipitated solid was filtered under nitrogen and washed with diethyl ether (2×15 ml) to yield (2S)—N-(2H-1,2,3,4-tetrazol-5-ylmethyl)-2,3-dihydro-1H-indole-2-carboxamide hydrochloride (I-2) as a light pink colored solid (1.1 g, 96%), $^1$H NMR (400 MHz, DMSO-d6) δ 2.93-2.99 (1H, dd, J=8, 16 Hz), 3.26-3.33 (1H, dd, J=12, 16 Hz), 4.24-4.29 (1H, t, J=8 Hz), 5.56-5.58 (2H, dd, J=1.6, 8 Hz), 5.89 (1H, bs), 6.55-6.59 (2H, t, J=8 Hz), 6.91-6.95 (1H, t, J=8 Hz), 6.99-7.01 (1H, d, J=8 Hz), 8.59-8.62 (1H, t, J=8 Hz), MS (LC/MS) m/z observed 244.97, expected 245.12[M+H].

Intermediate I-3

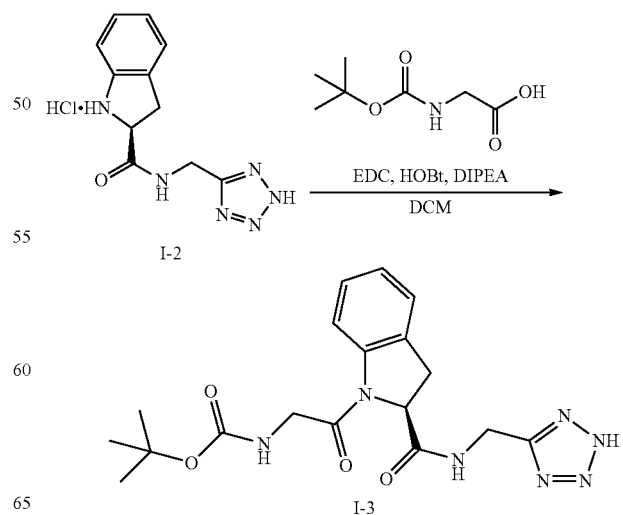

tert-Butyl N-{(2-oxo-2-[(2S)-2-[(2H-1,2,3,4-tetrazol-5-ylmethyl)carbamoyl]-2,3-dihydro-1H-indol-1-yl]ethyl}carbamate (I-3)

I-2 (0.5 g, 1.78 mmol), N-Boc-glycine (0.37 g, 2.14 mmol), EDC (2.4 g, 12.5 mmol), HOBt (0.75 g, 3.92 mmol) and DIPEA (1.24 ml, 7.125 mmol) were stirred in anhydrous DCM (20 ml) for 16 hrs. The reaction mixture was diluted using DCM (15 ml) and washed with citric acid (aqueous, saturated solution), followed by water and then brine. The organic layer was separated, dried over sodium sulfate and concentrated to give the crude product as a yellow-orange colored oil. The crude compound was purified on a C18 column using 10-50% MeOH in water to yield tert-butyl N-{2-oxo-2-[(2S)-2-[(2H-1,2,3,4-tetrazol-5-ylmethyl)carbamoyl]-2,3-dihydro-1H-indol-yl]ethyl}carbamate (I-3) as an off-white solid (0.4 g, 56%), $^1$H NMR (400 MHz, DMSO-d6) δ 1.39 (9H, s), 3.08-3.12 (2H, d, J=16 Hz), 3.56-3.63 (1H, dd, J=12, 20 Hz), 3.92-3.97 (1H, dd, J=4, 16 Hz), 4.56-4.62 (2H, m), 5.09-5.12 (1H, d, J=12 Hz), 6.96-7.00 (2H, t, J=8 Hz), 7.13-7.17 (1H, t, J=8 Hz), 7.19-7.21 (1H, d, J=8 Hz), 8.00-8.02 (1H, d, J=8 Hz), 9.06 (1H, s), MS (LC/MS) m/z observed 401.82, expected 402.19 [M+H], and observed 424.04, expected 424.17 [M+Na].

Intermediate I-4

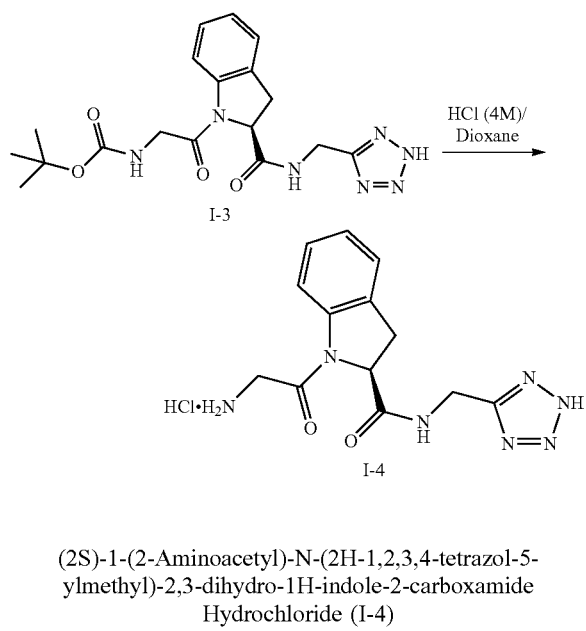

(2S)-1-(2-Aminoacetyl)-N-(2H-1,2,3,4-tetrazol-5-ylmethyl)-2,3-dihydro-1H-indole-2-carboxamide Hydrochloride (I-4)

HCl Solution in dioxane (4M, 5 ml) was added to I-3 (0.24 g, 0.6 mmol) and stirred for 2 hrs at RT. The precipitated solid was filtered under nitrogen and washed with diethyl ether (2×5 ml) and dried to yield (2S)-1-(2-aminoacetyl)-N-(2H-1,2,3,4-tetrazol-5-ylmethyl)-2,3-dihydro-1H-indole-2-carboxamide hydrochloride (I-4) as an off-white solid (0.11 g, 54%), $^1$H NMR (400 MHz, DMSO-d6) δ 2.20-2.24 (2H, d, J=16 Hz), 3.46-3.50 (1H, d, J=16 Hz), 3.56-3.65 (1H, m), 4.05-4.09 (1H, d, J=16 Hz), 5.09-5.12 (1H, d, 12 Hz), 4.60-4.61 (2H, d, J=4 Hz), 5.19-5.22 (1H, d, J=12 Hz), 7.04-7.08 (1H, t, J=8 Hz), 7.19-7.23 (1H, t, J=8 Hz), 7.25-7.27 (1H, d, J=8 Hz), 8.03-8.05 (1H, d, J=8 Hz), 8.30 (2H, bs), 9.30 (2H, s), MS (LC/MS) m/z observed 301.98, expected 302.14 [M+H].

Intermediate I-5

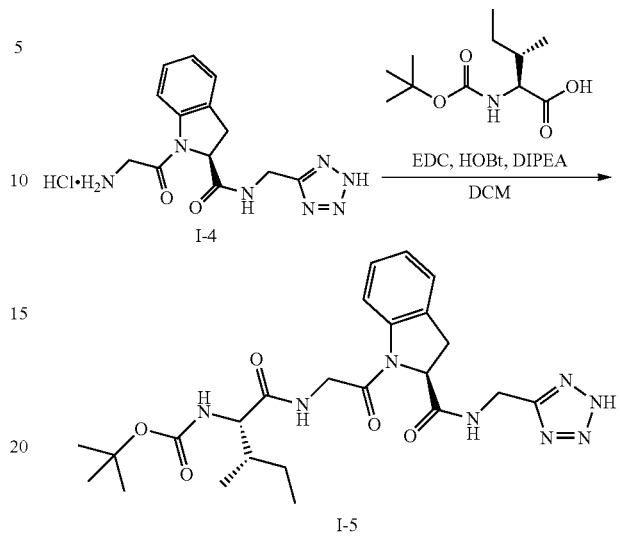

tert-Butyl N-[(1S,2S)-2-methyl-1-({2-oxo-2-[(2S)-2-[(2H-1,2,3,4-tetrazol-5-ylmethyl)carbamoyl]-2,3-dihydro-1H-indol-1-yl]ethyl}carbamoyl)butyl]carbamate (I-5)

I-4 (0.15 g, 0.44 mmol), N-Boc-Isoleucine (0.10 g, 0.44 mmol), EDC (0.13 g, 0.67 mmol), HOBt (0.078 g, 0.58 mmol) and DIPEA (0.31 ml, 1.78 mmol) were stirred in anhydrous DCM (15 ml) for 16 hrs. The reaction mixture was diluted using DCM (15 ml) and washed consecutively with citric acid (aqueous, saturated solution), water and brine. The organic layer was separated, dried over sodium sulfate and concentrated to give the crude product as a yellow-orange colored oil. The crude compound was purified on a C18 column using 10-50° % MeOH in water to yield tert-butyl N-[(1S,2S)-2-methyl-1-({2-oxo-2-[(2S)-2-[(2H-1,2,3,4-tetrazol-5-ylmethyl)carbamoyl]-2,3-dihydro-1H-indol-1-yl]ethyl}carbamoyl)butyl]carbamate (I-5) as an off-white solid (0.14 g, 60%). $^1$H NMR (400 MHz, DMSO-d6) δ 0.80-0.84 (3H, t, J=8 Hz), 0.85-0.87 (3H, d, J=8 Hz), 1.39 (9H, s), 1.40-1.46 (1H, m), 1.69-1.75 (1H, m), 3.02-3.12 (2H, m), 3.52-3.66 (3H, m), 3.89-3.93 (1H, t, J=8 Hz), 4.12-4.16 (1H, d, J=16 Hz), 4.33-4.38 (1H, dd, J=4, 16 Hz), 4.50-4.55 (1H, dd, J=4, 16 Hz), 5.13-5.16 (1H, d, J=12 Hz), 6.73-6.75 (1H, d, J=8 Hz), 6.98-7.02 (1H, t, J=8 Hz), 7.15-7.22 (2H, m), 8.04-8.06 (1H, d, J=8 Hz), 8.10) 1H, s), 8.73 (1H, s), MS (LC/MS) m/z observed 514.86, expected 515.27[M+H].

Intermediate I-6

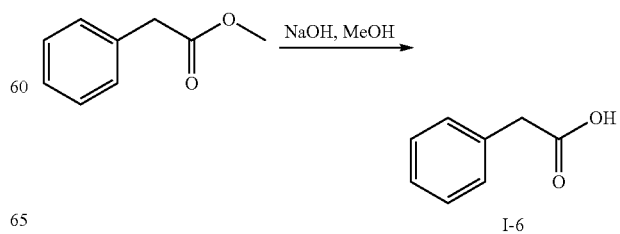

2-Phenylacetic Acid (I-6)

A solution of methyl 2-phenylacetate (10 g, 64 mmol) in methanol (60 ml) was treated with solution of sodium hydroxide (5.1 g, 127 mmol) in water (40 ml) at 70° C. for 3 hrs. The resulting mixture was concentrated under vacuum to remove the methanol. The residue was diluted with water (40 ml) and washed with diethyl ether (40 ml). The separated water layer was acidified to pH 2 using a mixture of water and HCl (1:1) and extracted with DCM (3×80 ml). Combined organic extracts were washed with brine, 80 ml, separated, dried over sodium sulfate and concentrated to give 2-phenylacetic acid (I-6) as a white solid (9 g, 96%) used without further characterization. $^1$H NMR (400 MHz, CDCl$_3$) δ 3.64 (2H, s), 7.27-7.35 (5H, m), 11.5 (1H, bs).

Intermediate I-7

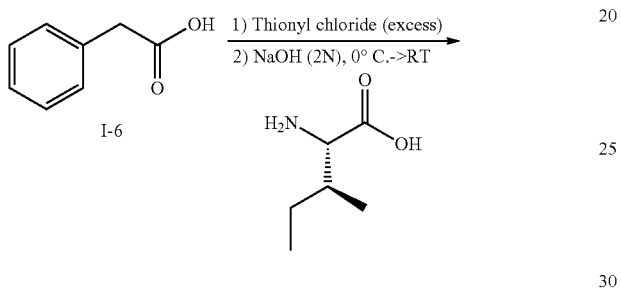

(2S,3S)-3-Methyl-2-(2-phenylacetamido)pentanoic Acid (I-7)

I-6 (2.0 g, 14.7 mmol) and thionyl chloride (6.6 ml, 90.3 mmol) were stirred together for 1 hr at RT. Thionyl chloride was removed by distillation under vacuum. The acid chloride was added to the stirring solution of L-isoleucine (1.75 g, 13.37 mmol) in NaOH (2N, 17 ml) at 0° C. The resulting mixture was warmed to RT and stirred overnight. The mixture was washed with diethyl ether (20 ml) and acidified to pH 4-5 by adding citric acid (aqueous, saturated solution). The precipitated solid was filtered, washed with diethyl ether and dried to yield (2S,3S)-3-methyl-2-(2-phenylacetamido)pentanoic acid (I-7) as a white solid (1.6 g, 44%). $^1$H NMR (400 MHz, DMSO-d6) δ 0.78-0.82 (6H, t, J=8 Hz), 1.12-1.18 (1H, m), 1.34-1.40 (1H, m), 1.72-1.78 (1H, m), 3.41-3.53 (2H, q, J=16 Hz), 4.13-4.16 (1H, dd, J=4.12 Hz), 7.15-7.19 (1H, m), 7.22-7.28 (1H, m), 8.19-8.21 (1H, d, J=8 Hz), 12.54 (1H, s), MS (LC/MS) m/z observed 250.02, expected 250.14 [M+H].

Intermediate I-8

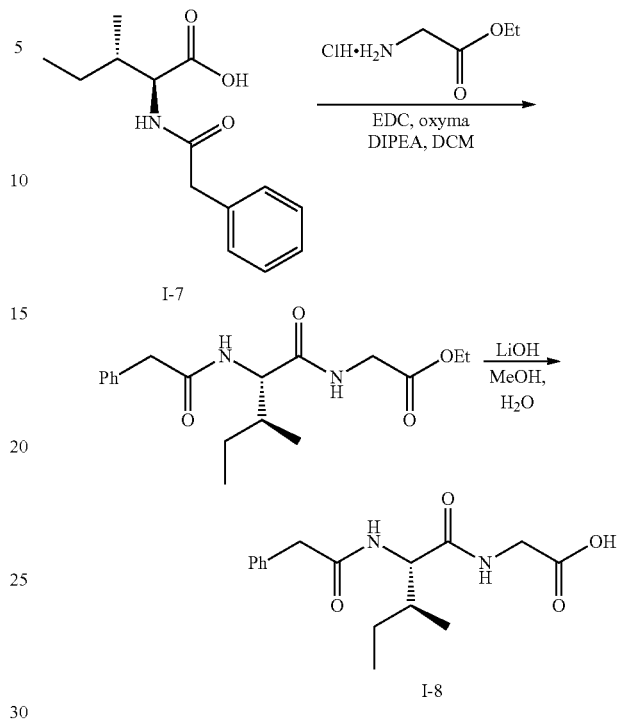

2-[(2S,3S)-3-Methyl-2-(2-phenylacetamido)pentanamido]acetic Acid (I-8)

To a suspension of I-7 (24 g, 96.3 mmol) in DCM (400 mL) was added DIPEA (87 mL, 500 mmol) at 0° C. The reaction mixture was allowed to stir for 10 min, upon which a homogeneous mixture was obtained. To this was added glycine ethyl ester hydrochloride (15.1 g, 108 mmol). After stirring a further 5 min at the same temperature, EDC (24.5 g, 116 mmol) and oxyma (18.8 g 116 mmol) were added. The reaction mixture was then allowed to stir overnight (approximately 15 hr) while allowed to slowly warm to RT. Another batch of glycine ethyl ester hydrochloride (2.1 g) was added and the reaction mixture was allowed to stir a further 4 hr at ambient temperature. Reaction mixture was transferred to a separatory funnel and washed with NaHCO$_3$ (300 mL, aqueous, saturated), followed by HCl (3M, 50 mL), and brine (200 mL). The organic layer was then dried over anhydrous sodium sulfate, filtered and concentrated in vacuo. Ethyl 2-[(2S,3S)-3-methyl-2-(2-phenylacetamido)pentanamido]acetate was obtained from flash column chromatography (MeOH:DCM 1-5%) followed by recrystallization from acetonitrile (16 g, colourless crystals) and used further as described. $^1$H NMR (300 MHz, CD$_3$OD) δ 7.32-7.21 (m, 5H), 4.34 (m, 1H), 4.17 (q, 2H), 4.03-3.96 (m, 1H), 3.89-3.81 (m, 1H), 3.68-3.52 (m, 2H), 1.98-1.89 (m, 1H), 1.62-1.35 (m, 1H), 1.26 (t, 3H), 1.21-1.09 (m, 1H), 0.96-0.86 (m, 6H), MS (ESI) m/z observed 357.29, expected 357.18 [M+Na].

Intermediate I-8 was obtained from hydrolysis of ethyl 2-[(2S,3S)-3-methyl-2-(2-phenylacetamido)pentanamido]acetate (8.1 g, 24 mmol) using Method D (6 g, white powder). $^1$H NMR (300 MHz, CD$_3$OD) δ 12.40 (br s, 1H), 7.31-7.16 (m, 5H), 4.23-4.18 (m, 1H), 3.76-3.70 (m, 2H), 3.57-3.40 (m, 2H), 1.83-1.68 (m, 1H), 1.48-1.35 (m, 1H), 1.13-0.99 (m, 1H), 0.83-0.75 (m, 6H), MS (ESI) m/z observed 305.20, expected 305.15 [M–H].

Intermediate I-9

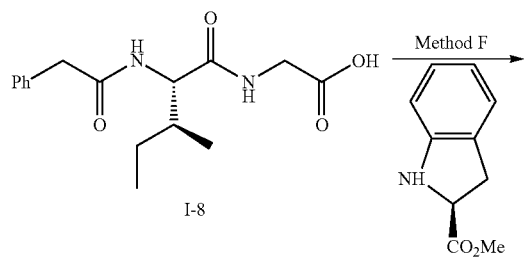

(2S)-1-{2-[(2S,3S)-3-Methyl-2-(2-phenylacetamido)pentanamido]acetyl}-2,3-dihydro-1H-indole-2-carboxylic Acid (I-9)

Intermediate I-9 was obtained from I-8 (170 mg, 0.37 mmol) using Method F followed by Method D (120 mg, white powder) and used further as is. $^1$H NMR (300 MHz, DMSO-d6) δ 8.37-8.18 (m, 1H), 8.06 (d, 1H), 7.28-7.08 (m, 7H), 6.95-6.90 (m, 1H), 4.57-4.53 (m, 1H), 4.44-4.24 (m, 1H), 4.13-3.89 (m, 2H), 3.59-3.18 (m, 4H), 1.92-1.71 (m, 1H), 1.47-1.22 (m, 1H), 1.13-0.99 (m, 1H), 0.84-0.75 (m, 6H).

Intermediate I-10

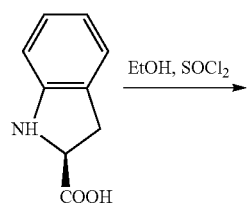

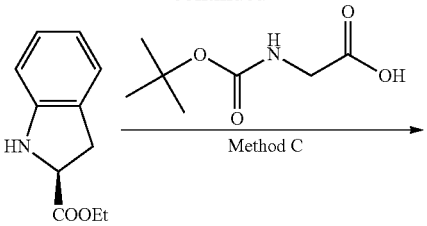

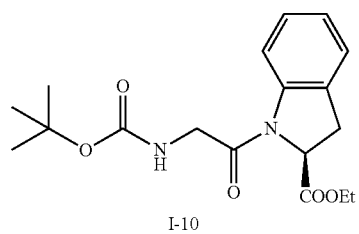

Ethyl (2S)-1-{2-[(tert-butoxy)carbonyl]amino)acetyl}-2,3-dihydro-1H-indole-2-carboxylate (I-10)

(2S)-2,3-dihydro-1H-indole-2-carboxylic acid (500 mg, 306 mmol) was suspended in EtOH (5 mL) at 0° C. and thionyl chloride (0.45 mL, 6.13 mmol, 2 eq.) was added. The resulting clear mixture was allowed to come to RT and stirred for 16 hours. The reaction mixture was then concentrated to dryness and swapped with EtOH (2×10 mL). The solid obtained was dried well under reduced pressure to give ethyl (2S)-2,3-dihydro-1H-indole-2-carboxylate hydrochloride as a light brown solid (0.58 g, quantitative). $^1$H NMR (400 MHz, DMSO-d6) δ 1.18 (3H, s), 3.10-3.18 (1H, m), 3.30-3.40 (1H, m), 4.05-4.17 (2H, m), 4.55 (1H, bs), 6.80 (2H, bs), 7.02-7.08 (2H, m), 7.7 (2H, bs). Compound was used further as described.

I-10 was prepared from ethyl (2S)-2,3-dihydro-1H-indole-2-carboxylate hydrochloride and 2-((tert-butoxycarbonyl)amino)acetic acid using method C however the purification was performed on normal phase using 0% to 50% ethyl acetate in hexanes as the eluent. $^1$H NMR (400 MHz, DMSO-d6) δ1.18 (3H, t, J=6 Hz), 1.38 (9H, s), 3.19 (1H, d, J=16 Hz), 3.48-3.62 (2H, m), 3.95-4.20 (3H, m), 5.35 (1H, d, J=1 Hz), 7.00 (2H, t, J=8 Hz), 7.15-7.25 (2H, m), 8.01 (1H, d, J=8 Hz), MS (LC/MS) m/z 370.95 [M+Na]

Intermediate I-11

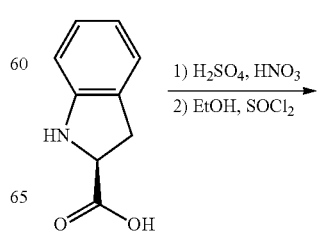

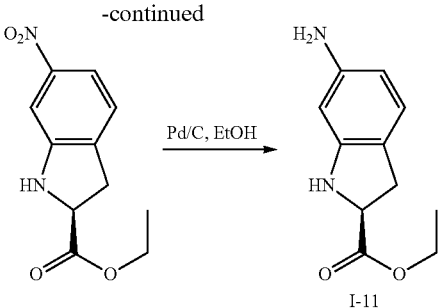

Ethyl (2S)-6-amino-2,3-dihydro-1H-indole-2-carboxylate (I-11)

(2S)-2,3-Dihydro-1H-indole-2-carboxylic acid (5 g, 30.640 mmol) was dissolved in sulfuric acid (concentrated, 40 ml) at 0° C. The resulting reaction mixture was chilled to −20° C. and nitric acid (concentrated, 1.4 ml, 33.1 mmol) was then added dropwise. The reaction mixture was stirred at −20° C. for 1 hr and then allowed to warm to RT and stirred for 2 hrs. The reaction mixture was diluted with cold water (100 ml), neutralized to pH 4 using NaOH solution (10N) and extracted with EtOAc (3×200 ml). The combined organic layers were dried over sodium sulphate and concentrated to give an orange solid. This solid was dissolved in ethanol (200 mL) and treated with thionyl chloride (4.45 ml, 61.3 mmol) at 0° C. and stirred overnight at RT. The reaction mixture was concentrated and purified by column chromatography on silica gel using 0% to 50% ethyl acetate in hexanes as the eluent to give ethyl (2S)-6-nitro-2,3-dihydro-1H-indole-2-carboxylate, as a yellow solid (1.61 g, 22%). $^1$H NMR (400 MHz, CDCl$_3$) δ 1.30-1.34 (3H, t, J=8 Hz), 3.30-3.57 (2H, m), 4.21-4.27 (2H, q, J=8 Hz), 4.47-4.52 (1H, q, J=8 Hz), 4.70 (1H, bs), 7.16-7.18 (1H, d, J=8 Hz), 7.47-7.48 (1H, d, J=4 Hz), 7.62-7.65 (1H, dd, J=8, 4 Hz), MS (LC/MS) m/z observed 237.00, expected 237.08 [M+H].

Ethyl (2S)-6-nitro-2,3-dihydro-1H-indole-2-carboxylate (2 g, 8.474 mmol) and 10% Pd on activated carbon (0.4 g, 20% wt./wt.) in ethanol (60 ml) was stirred under hydrogen (balloon) for 3 hrs. The reaction mixture was filtered through a bed of CELITE® and washed with ethanol (4×30 ml). Collected filtrate was concentrated and dried well under vacuum to yield I-11 as pale yellow oil (1.4 g, 80%). $^1$H NMR (400 MHz, CDCl$_3$) δ 1.14-1.18 (3H, t, J=8 Hz), 2.94-3.01 (3H, m), 3.30 (1H, s), 4.57-4.61 (1H, t, J=8 Hz), 7.45-7.48 (1H, q, J=4 Hz), 8.03 (1H, s), 8.06-8.09 (1H, m), 8.41-8.42 (1H, d, J=4 Hz), 8.96-8.97 (1H, d, J=4 Hz), MS (LC/MS) m/z observed 207.09, expected 207.11 [M+H].

Intermediate I-12

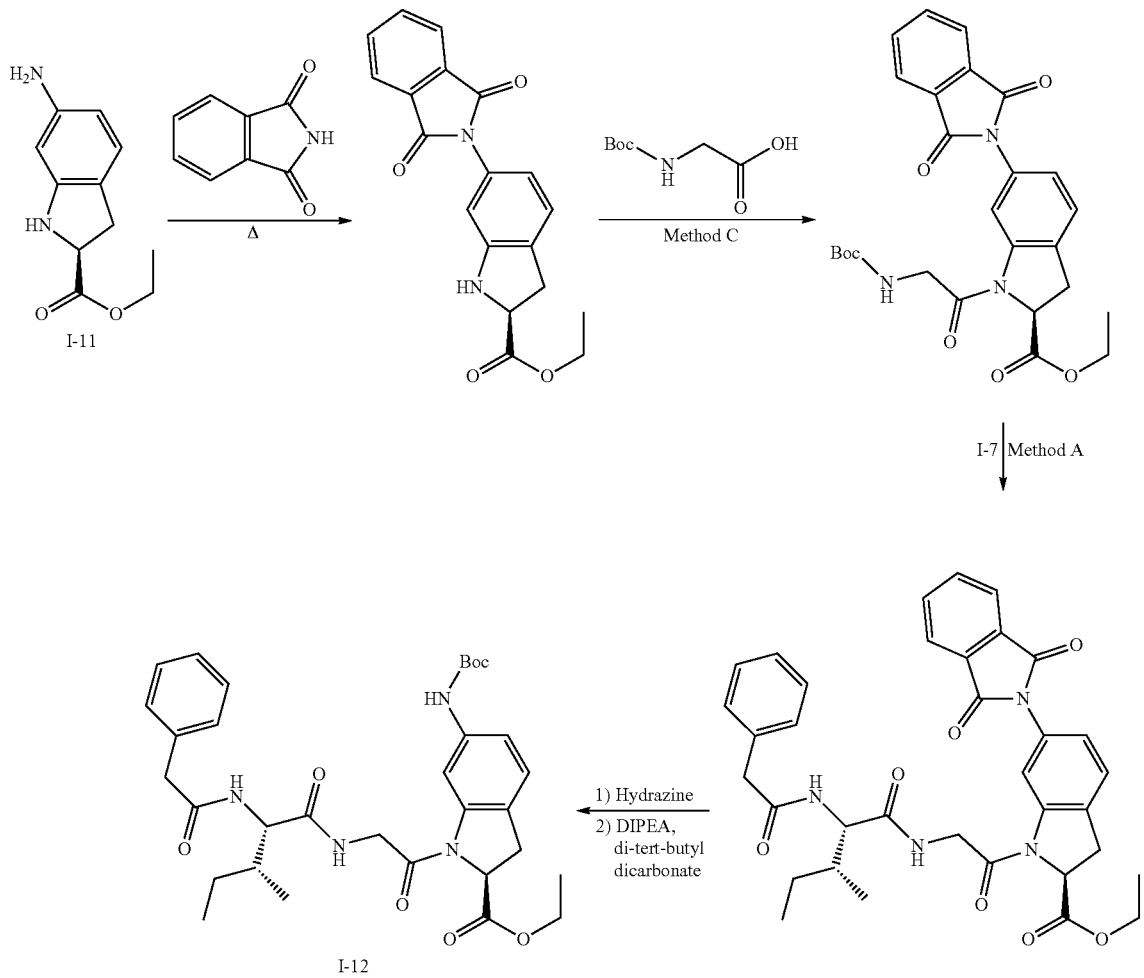

(S)-Ethyl 6-((tert-butoxycarbonyl)amino)-1-(2-((2S, 3S)-3-methyl-2-(2-phenylacetamido)pentanamido) acetyl)indoline-2-carboxylate (I-12)

I-11 (0.6 g, 2.91 mmol) and isoindoline-1,3-dione (0.43 g, 2.91 mmol) in toluene was heated at 90° C. for 4 hrs. Resulting reaction mixture was concentrated and purified by column chromatography on silica gel using 0% to 30% ethyl acetate in hexanes as the eluent to give (S)-6-(1,3-dioxo-1, 3-dihydro-isoindolin-2-yl)-2,3-dihydro-1H-indole-2-carboxylic acid ethyl ester, as an off-white solid (0.7 g, 72%). $^1$H NMR (400 MHz, CDCl$_3$) δ 1.29-1.33 (3H, t, J=8 Hz), 3.38-3.44 (2H, m), 4.20-4.26 (2H, m), 4.42-4.46 (1H, dd, J=12.8 Hz), 4.56 (1H, bs), 6.72 (1H, s), 6.75-6.78 (1H, dd, J=12.4 Hz), 7.17-7.19 (1H, d, J=12 Hz), 7.76-7.78 (2H, m), 7.92-7.95 (2H, m), MS (LC/MS) m/z observed 337.07, expected 337.11 [M+H].

(S)-1-(2-tert-Butoxycarbonylamino-acetyl)-6-(1,3-dioxo-1,3-dihydro-isoindol-2-yl)-2,3-dihydro-1H-indole-2-carboxylic acid ethyl ester was prepared from (S)-6-(1,3-dioxo-1,3-dihydro-isoindolin-2-yl)-2,3-dihydro-1H-indole-2-carboxylic acid ethyl ester and Boc-glycine using method C and purified by column chromatography on silica gel using 0% to 50% ethyl acetate in hexanes as the eluent to give (S)-1-(2-tert-Butoxycarbonylamino-acetyl)-6-(1,3-dioxo-1, 3-dihydro-isoindol-2-yl)-2,3-dihydro-1H-indole-2-carboxylic acid ethyl ester, as an off-white solid (42%). MS (LC/MS) m/z observed 493.87, expected 494.19[M+H]. Compound was confirmed using LC/MS and moved to next step as it was.

(S)-1-(2-tert-Butoxycarbonylamino-acetyl)-6-(1,3-dioxo-1,3-dihydro-isoindol-2-yl)-2,3-dihydro-1H-indole-2-carboxylic acid ethyl ester and I-7 were combined using method A to produce (S)-6-(1,3-dioxo-1,3-dihydro-isoindol-2-yl)-1-[2-(3-methyl-2-phenylacetylamino-pentanoylamino)-acetyl]-2,3-dihydro-1H-indole-2-carboxylic acid ethyl ester. MS (LC/MS) m/z observed 625.09, expected 625.26 [M+H]. Compound was confirmed using LC/MS and moved to next step as it was.

(S)-6-(1,3-Dioxo-1,3-dihydro-isoindol-2-yl)-1-[2-(3-methyl-2-phenylacetylamino-pentanoylamino)-acetyl]-2,3-dihydro-1H-indole-2-carboxylic acid ethyl ester (0.3 g, 0.48 mmol) was dissolved in 1:4 mixture of DMF:dioxane (10 ml) and hydrazine monohydrate (0.026 ml, 0.53 mmol) was added. The reaction mixture was heated at 50° C. for 2 hr., concentrated and dried well under vacuum to give a yellow solid. This solid was dissolved in 1:5 mixture of water:dioxane (12 mL, v/v) and treated with DIPEA (0.67 ml, 3.85 mmol) and di-tert-butyl dicarbonate (0.42 g, 1.92 mmol) and stirred overnight at RT. The reaction mixture was concentrated and purified by column chromatography on silica gel using 0% to 50% ethyl acetate in hexanes as the eluent to give I-12, as a pale yellow solid (0.16 g, 56%). MS (LC/MS) m/z observed 595.09, expected 595.31 [M+H] used further as needed.

Intermediates I-13 and I-14

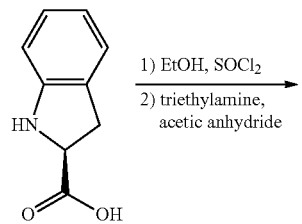

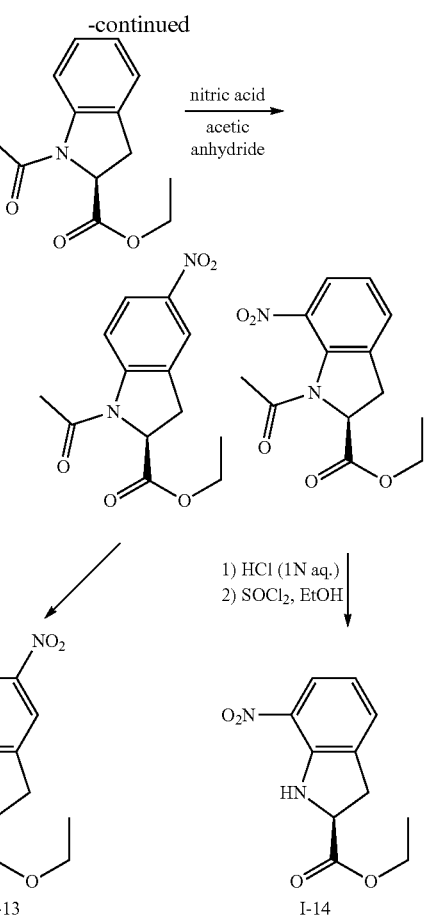

(S)-Ethyl 5-nitroindoline-2-carboxylate (I-12) and (S)-ethyl 7-nitroindoline-2-carboxylate (I-13)

(S)-2,3-Dihydro-H-indole-2-carboxylic acid (20 g, 0.123 mol) was suspended in absolute ethanol (200 mL) and the suspension was cooled to 0° C. SOCl$_2$ (18 mL, 0.25 mol) was then added dropwise to the reaction mixture and it was allowed to warm to RT and was stirred for 16 hrs. The solvent was then evaporated and the residue was swapped twice with ethanol (100 mL) to get a brown solid. This solid was dissolved triethylamine (34.2 mL, 0.245 mol) and acetic anhydride (170 mL) and the mixture was stirred at RT for 2 hrs. Then it was diluted with EtOAc (500 mL) and washed with NaHCO$_3$ (2×200 mL, aqueous, saturated solution) and citric acid (2×200 mL, aqueous, saturated solution). The combined organic layers were dried over sodium sulphate and concentrated to give a brown solid. This solid was dissolved in acetic anhydride (200 mL) and a solution of nitric acid (11.1 mL) in acetic anhydride (161 mL) was added dropwise at 0° C. The reaction mixture was left at 0° C. for 15 min then warm to RT and stirred for 3 hrs. Cold water (250 mL) was added to the reaction mixture and the product was extracted with EtOAC (3×450 mL). The combined organic layers were dried over sodium sulphate and concentrated. The two isomers obtained were separated by normal phase column chromatography using 10% to 30% ethyl acetate in hexanes as the eluent to give first, (S)-1-acetyl-5-nitro-2,3-dihydro-1H-indole-2-carboxylic acid ethyl ester as a yellow solid (18.49 g, 54%) and second, (S)-1-acetyl-7-nitro-2,3-dihydro-1H-indole-2-carboxylic acid ethyl ester as an orange oil (8.21 g, 24%).

(S)-1-Acetyl-5-nitro-2,3-dihydro-1H-indole-2-carboxylic acid ethyl ester: $^1$H NMR (400 MHz, CDCl$_3$) δ 1.30 (3H, t, J=7.0 Hz), 2.22 (3H, bs), 3.34 (1H, m), 3.65 (1H, m), 4.19-4.34 (2H, m), 5.02 (1H, bs), 8.03 (1H, s), 8.17 (1H, dd, J=2, 9 Hz), 8.34 (1H, bs), MS (LC/MS) m/z observed 279.01, expected 279.10 [M+H].

(S)-1-Acetyl-7-nitro-2,3-dihydro-1H-indole-2-carboxylic acid ethyl ester: $^1$H NMR (400 MHz, CDCl$_3$) δ 1.28 (3H, t, J=7.0 Hz), 2.28 (3H, bs), 3.41 (1H, d, J=16 Hz), 3.62 (1H, dd, J=10, 17 Hz), 4.19-4.30 (2H, m), 5.05 (1H, dd, J=2, 10 Hz), 7.16 (1H, t, J=8 Hz), 7.42 (1H, dd, J=2, 9 Hz), 7.67 (1H, d, J=8 Hz), MS (LC/MS) m/z observed 279.01, expected 279.10 [M+H].

I-13: (S)-1-Acetyl-5-nitro-2,3-dihydro-1H-indole-2-carboxylic acid ethyl ester (18.49 g) was refluxed in a aqueous HCl solution (1N, 500 mL) for 2 hrs until the compound dissolved completely. Then, the reaction mixture was concentrated to dryness and the residue was dissolved in ethanol (500 mL). SOCl$_2$ (60 mL) was then added dropwise and the reaction was left at RT for 16 hrs. The solvent was then evaporated and the product was purified by normal phase column chromatography using 5% to 20% ethyl acetate in hexanes as the eluent to give intermediate I-13 as a yellow solid (10.81 g, 69%). $^1$H NMR (400 MHz, CDCl$_3$) δ 1.32 (3H, t, J=7.0 Hz), 3.35-3.52 (2H, m), 4.22-4.30 (2H, q, J=7 Hz), 4.57 (1H, dd, J=5, 10 Hz), 5.01 (1H, bs,), 6.63 (1H, d, J=9 Hz), 7.98 (1H, bs), 8.05 (1H, dd, J=2, 9 Hz), MS (LC/MS) m/z observed 237.03, expected 237.09 [M+H].

I-14: (S)-1-Acetyl-7-nitro-2,3-dihydro-1H-indole-2-carboxylic acid ethyl ester (1.6 g) was refluxed in a HCl solution (1N, aqueous, 80 mL) for 2 hrs until the compound dissolved completely. Then, the reaction mixture was concentrated to dryness and the residue was dissolved in ethanol (60 mL). SOCl$_2$ (10 mL) was then added dropwise and the reaction was left at RT for 16 hrs. The solvent was then evaporated and the product was purified by normal phase column chromatography using 5% to 20% ethyl acetate in hexanes as the eluent to give intermediate I-14 as a yellow solid (0.97 g, 71%). $^1$H NMR (400 MHz, CDCl$_3$) δ 1.31 (3H, t, J=7.0 Hz), 3.37-3.53 (2H, m), 4.19-4.30 (2H, q, J=7 Hz), 4.69 (1H, dd, J=4, 10 Hz), 6.66 (1H, dd, J=7, 8 Hz), 7.03 (1H, bs), 7.24 (1H, d, J=7 Hz), 7.83 (1H, d, J=8 Hz), MS (LC/MS) m/z observed 237.03, expected 237.09 [M+H].

Intermediate I-15

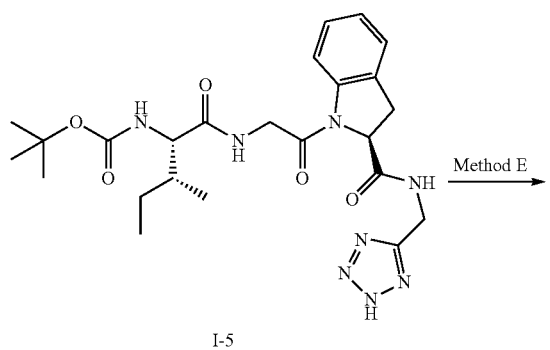

I-5

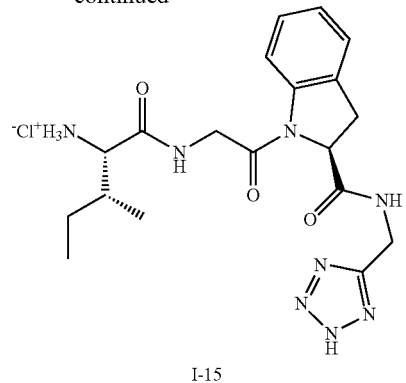

I-15

(1S,2S)-2-Methyl-1-(2-oxo-2-{(2S)-2-[(2H-1,2,3,4-tetrazol-5-ylmethyl)-carbamoyl]-2,3-dihydro-indol-1-yl}-ethylcarbamoyl)-butyl-ammonium; Chloride (I-15)

I-15 was collected as a faint pink solid from deprotection of I-5 using method E. MS (LC/MS) m/z observed 415.09, expected 415.22 [M−Cl]. The compound was confirmed using LC/MS and moved to next step as it was.

Representative Granzyme B Inhibitor Compounds

The following is a description of representative Granzyme B inhibitor compounds of the invention.

Examples A1-A57 were prepared by the representative synthetic pathway illustrated schematically in FIG. 1.

Example A1

(2S)-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Title compound A1 was prepared from I-5 and I-6 using method A: $^1$H NMR (400 MHz, DMSO-d6) δ0.76-0.80 (3H, t, J=8 Hz), 0.82-0.84 (3H, d, J=8 Hz), 1.04-1.11 (1H, m), 1.39-1.45 (1H, m), 1.70-1.76 (1H, m), 3.10-3.14 (2H, d, J=16 Hz), 3.42-3.45 (1H, d, J=8 Hz), 3.53-3.56 (1H, d, J=8 Hz), 3.62-3.65 (1H, m), 3.66-3.69 (1H, m), 4.14-4.16 (1H, t, J=4 Hz), 4.24-4.28 (1H, t, J=8 Hz), 4.47-4.51 (1H, d, J=16 Hz), 4.59-4.63 (1H, d, J=16 Hz), 5.14-5.16 (1H, d, J=16 Hz), 6.97-7.01 (1H, t, J=8 Hz), 7.15-7.30 (7H, m), 8.08-8.11 (1H, d, J=12 Hz), 8.24 (1H, bs), 8.99 (1H, bs), MS (LC/MS) m/z observed 533.05, expected 533.26 [M+H] and observed 555.17, expected 555.24 [M+Na].

Example A2

(2S)-1-{2-[(2S,3S)-3-Methyl-2-[2-(Pyridin-4-Yl)Acetamido]Pentanamido]Acetyl}-N-(2H-1,2,3,4-Tetrazol-5-Ylmethyl)-2,3-Dihydro-1H-Indole-2-Carboxamide Title compound A2 was prepared from I-5 and 4-pyridineacetic acid using method A: $^1$H NMR (400 MHz, DMSO-d6) δ 0.76-0.80 (3H, t, J=8 Hz), 0.82-0.84 (3H, d, J=8 Hz), 1.04-1.11 (1H, m), 1.38-1.46 (1H, m), 1.71-1.77 (1H, m), 3.07-3.11 (2H, t, J=8 Hz), 3.48-3.61 (2H, m), 4.11-4.15 (1H, d, J=16 Hz), 4.25-4.29 (1H, t, J=8 Hz), 4.39-4.43 (1H, d, J=16 Hz), 4.52-56 (1H, d, J=16 Hz), 5.12-5.15 (1H, d, J=12 Hz), 6.95-6.99 (1H, t, J=8 Hz), 7.13-7.22 (2H, m), 7.25-7.26 (2H, d, J=4 Hz), 7.25-7.28 (1H, d, J=8 Hz), 7.30 (1H, bs), 8.44-8.45 (2H, d, J=4 Hz), 8.81 (1H, bs), MS (LC/MS) m/z observed 534.11, expected 534.26 [M+H].

Example A3

(2S)-1-{2-[(2S,3S)-3-Methyl-2-[2-(Pyridin-3-Yl) Acetamido]Pentanamido]Acetyl}-N-(2H-1,2,3,4-Tetrazol-5-Ylmethyl)-2,3-Dihydro-1H-Indole-2-Carboxamide Title compound A3 was prepared from I-5 and 3-pyridineacetic acid using method A: $^1$H NMR (400 MHz, DMSO-d6) δ 0.76-0.80 (3H, t, J=8 Hz), 0.82-0.84 (3H, d, J=8 Hz), 1.04-1.12 (1H, m), 1.37-1.46 (1H, m), 1.72-1.77 (1H, m), 3.06-3.12 (2H, m), 3.47-3.62 (2H, m), 4.12-4.16 (1H, d, J=16 Hz), 4.24-4.28 (1H, t, J=8 Hz), 4.39-4.43 (1H, d, J=16 Hz), 4.53-4.57 (1H, d, J=16 Hz), 5.13-5.15 (1H, d, J=8 Hz), 6.97-7.01 (1H, t, J=8 Hz), 7.14-7.18 (1H, t, J=8 Hz), 7.19-7.21 (1H, d, J=8 Hz), 7.28-7.31 (1H, q, J=8 Hz), 7.65-7.67 (1H, d, J=8 Hz), 8.02-8.04 (1H, d, J=8 Hz), 8.23-8.26 (1H, d, J=12 Hz), 8.29 (1H, bs), 8.40-8.41 (1H, d, J=4 Hz), 8.44 (1H, s), 8.82 (1H, bs), MS (LC/MS) m/z observed 534.15, expected 534.26 [M+H].

Example A4

(2S)-1-{2-[(2S,3S)-3-Methyl-2-[2-(Pyridin-2-Yl) Acetamido]Pentanamido]Acetyl}-N-(2H-1,2,3,4-Tetrazol-5-Ylmethyl)-2,3-Dihydro-1H-Indole-2-Carboxamide Title compound A4 was prepared from I-5 and 2-pyridineacetic acid using method A: $^1$H NMR (400 MHz, DMSO-d6) δ 0.77-0.81 (3H, t, J=8 Hz), 0.83-0.85 (3H, d, J=8 Hz), 1.06-1.13 (1H, m), 1.42-1.47 (1H, m), 1.74-1.81 (1H, m), 3.06-3.12 (2H, m), 3.53-3.62 (2H, m), 4.15-4.19 (1H, d, J=16 Hz), 4.24-4.28 (1H, t, J=8 Hz), 4.25-4.29 (1H, q, J=12 Hz), 4.44-4.47 (1H, d, J=8 Hz), 4.59-4.63 (1H, d, J=16 Hz), 5.11-5.14 (1H, d, J=12 Hz), 6.94-6.98 (1H, t, J=8 Hz), 7.12-7.22 (3H, m), 7.68-7.72 (1H, td, J=4, 8 Hz), 8.01-8.03 (1H, d, J=8 Hz), 8.18-8.20 (1H, d, J=8 Hz), 8.34 (1H, bs), 8.43-8.45 (1H, d, J=8 Hz), 8.87 (1H, bs), MS (LC/MS) m/z observed 534.12, expected 534.26 [M+H].

Example A5

5-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Pentanoic Acid The starting compound (5-{[(1S,2S)-2-methyl-1-({2-oxo-2-[(2S)-2-[(2H-1,2,3,4-tetrazol-5-ylmethyl)carbamoyl]-2,3-dihydro-1H-indol-1-yl]ethyl}carbamoyl)butyl]carbamoyl}pentanoic acid, ethyl ester) was prepared from I-5 and adipic acid, monoethyl ester using method A: MS (LC/MS) m/z observed 571.02, expected 571.29 [M+H], Compound was confirmed using LCMS and moved to next step as it was.

Title compound A5 was prepared from 5-{[(1S,2S)-2-methyl-1-({2-oxo-2-[(2S)-2-[(2H-1,2,3,4-tetrazol-5-ylmethyl)carbamoyl]-2,3-dihydro-1H-indol-1-yl]ethyl}carbamoyl)butyl]carbamoyl}pentanoic acid, ethyl ester using method D: $^1$H NMR (400 MHz, DMSO-d6) δ 0.78-0.82 (3H, t, J=8 Hz), 0.84-0.86 (3H, d, J=8 Hz), 1.06-1.13 (1H, m), 1.41-1.50 (5H, m), 1.68-1.75 (1H, m), 2.08-2.20 (4H, m), 3.10-3.14 (1H, d, J=16 Hz), 3.50-3.62 (2H, m), 4.11-4.13 (1H, d, J=8 Hz), 4.22-4.26 (1H, m), 4.52-4.56 (1H, d, J=16 Hz), 4.62-4.66 (1H, d, J=16 Hz), 5.14-5.17 (1H, d, J=12 Hz), 6.97-7.01 (1H, t, J=8 Hz), 7.13-7.17 (1H, t, J=8 Hz), 7.20-7.22 (1H, d, J=8 Hz), 7.82-7.85 (1H, q, J=8 Hz), 8.00-8.02 (1H, d, J=8 Hz), 8.13 (1H, bs), 8.22-8.25 (1H, t, J=6 Hz) 9.09 (1H, bs), MS (LC/MS) m/z observed 542.99, expected 543.27 [M+H] and observed 565.09, expected 565.25 [M+Na]

Example A6

(2S)-1-{2-[(2S,3S)-2-(3-Aminopropanamido)-3-Methylpentanamido]Acetyl}-N-(2H-1,2,3,4-Tetrazol-5-Ylmethyl)-2,3-Dihydro-1H-Indole-2-Carboxamide (2S)-1-{2-[(2S,3S)-2-(3-(tert-Butoxylcarbonyl)aminopropanamido)-3-methylpentanamido]acetyl}-N-(2H-1,2,3,4-tetrazol-5-ylmethyl)-2,3-dihydro-1H-indole-2-carboxamide was prepared from I-5 and 3-((tert-butoxycarbonyl)amino)propanoic acid using method A: $^1$H NMR (400 MHz, DMSO-d6) δ 0.78-0.82 (3H, t, J=8 Hz), 0.84-0.86 (3H, d, J=8 Hz), 1.05-1.12 (1H, m), 1.35 (9H, s), 1.39-1.46 (1H, m), 1.70-1.75 (1H, m), 2.23-2.34 (2H, m), 3.06-3.12 (3H, m), 3.53-3.59 (2H, m), 4.10-4.14 (1H, d, J=16 Hz), 4.22-4.26 (1H, t, J=8 Hz), 4.37-4.42 (1H, dd, J=4, 16 Hz), 4.52-4.57 (1H, dd, J=8, 16 Hz), 5.12-5.14 (1H, d, J=8 Hz), 6.96-7.00 (1H, t, J=8 Hz), 7.12-7.16 (1H, t, J=8 Hz), 7.18-7.20 (1H, d, J=8 Hz), 7.87-7.89 (1H, d, J=8 Hz), 8.01-8.03 (1H, d, J=8 Hz), 8.16 (1H, bs), 8.80 (1H, bs), MS (LC/MS) m/z observed 585.98, expected 586.31 [M+H] and observed 608.16, expected 608.29 [M+Na]. The compound was used further as described.

Title compound A6 was prepared from (2S)-1-{2-[(2S,3S)-2-(3-(tert-butoxylcarbonyl)aminopropanamido)-3-methylpentanamido]acetyl}-N-(2H-1,2,3,4-tetrazol-5-ylmethyl)-2,3-dihydro-1H-indole-2-carboxamide using method E: $^1$H NMR (400 MHz, DMSO-d6) δ 0.80-0.84 (3H, t, J=8 Hz), 0.87-0.89 (3H, d, J=8 Hz), 1.07-1.15 (1H, m), 1.43-1.52 (1H, m), 1.72-1.78 (1H, m), 2.52-2.60 (2H, m), 2.97-3.09 (3H, m), 3.51-3.64 (2H, m), 4.09-4.12 (1H, d, J=12 Hz), 4.19-4.23 (1H, t, J=8 Hz), 4.33-4.41 (2H, m), 5.10-5.13 (1H, d, J=12 Hz), 6.96-7.00 (1H, t, J=8 Hz), 7.12-7.16 (1H, t, J=8 Hz), 7.18-7.20 (1H, d, J=8 Hz), 7.72 (2H, bs), 8.01-8.03 (1H, d, J=8 Hz), 8.22 (1H, s), 8.24 (1H, bs), 8.59 (1H, bs), MS (LC/MS) m/z observed 486.14, expected 486.26 [M+H].

Example A7

(2S)-1-{2-[(2S,3S)-2-(4-Aminobutanamido-3-Methylpentanamido]Acetyl}-N-(2H-1,2,3,4-Tetrazol-5-Ylmethyl)-2,3-Dihydro-1H-Indole-2-Carboxamide Hydrochloride (2S)-1-{2-[(2S,3S)-2-(4-(tert-Butoxycarbonyl)aminobutanamido)-3-methylpentanamido]acetyl}-N-(2H-1,2,3,4-tetrazol-5-ylmethyl)-2,3-dihydro-1H-indole-2-carboxamide was prepared from I-5 and 4-((tert-butoxycarbonyl)amino) butanoic acid using method A: MS (LC/MS) m/z observed 599.97, expected 600.32 [M+H], observed 622.15, expected 622.31 [M+Na]. Compound was confirmed using LC/MS and moved to next step as it was.

Title compound A7 was prepared from (2S)-1-{2-[(2S,3S)-2-(4-(tert-butoxycarbonyl)aminobutanamido)-3-methylpentanamido]acetyl}-N-(2H-1,2,3,4-tetrazol-5-ylmethyl)-2,3-dihydro-1H-indole-2-carboxamide using method E: $^1$H NMR (400 MHz, DMSO-d6) δ 0.80-0.84 (3H, t, J=8 Hz), 0.88-0.90 (3H, d, J=8 Hz), 1.08-1.16 (1H, m), 1.47-1.53 (1H, m), 1.72-1.84 (3H, m), 1.18-1.34 (2H, m), 2.75-2.79 (2H, t, J=6 Hz), 3.03-3.07 (1H, d, J=8 Hz), 3.51-3.64 (2H, m), 4.07-4.11 (1H, m), 4.12-4.16 (1H, t, J=12 Hz), 4.30-4.35 (1H, dd, J=6,16 Hz), 4.41-4.46 (1H, dd, J=6, 16 Hz), 5.08-5.11 (1H, d, J=12 Hz), 6.96-7.00 (1H, t, J=8 Hz), 7.12-7.16 (1H, t, J=8 Hz), 7.18-7.20 (1H, d, J=8 Hz), 7.92 (3H, bs), 8.00-8.02 (1H, d, J=8 Hz), 8.13-8.16 (1H, t, J=6 Hz), 8.60 (1H, bs), MS (LC/MS) m/z observed 500.13, expected 500.27 [M+H].

Example A8

(2S)-1-{2-[(2S,3S)-2-[2-(4-Aminophenyl)Acetamido]-3-Methylpentanamido]Acetyl}-N-(2H-1,2,3,4-Tetrazol-5-Ylmethyl)-2,3-Dihydro-1H-Indole-2-Carboxamide Hydrochloride (2S)-1-{2-[(2S,3S)-2-[2-(4-(tert-Butoxycarbonyl)aminophenyl)acetamido]-3-methylpentanamido]acetyl}-N-(2H-1,2,3,4-tetrazol-5-ylmethyl)-2,3-dihydro-1H-indole-2-carboxamide was prepared from I-5 and 2-(4-((tert-butoxycarbonyl)amino)phenyl)acetic acid using method A: MS (LC/MS) m/z observed 648.03, expected 648.31 [M+H]. Compound was confirmed using LC/MS and moved to next step as it was.

Title compound A8 was prepared from (2S)-1-{2-[(2S,3S)-2-[2-(4-(tert-butoxycarbonyl)aminophenyl)acetamido]-3-methylpentanamido]acetyl}-N-(2H-1,2,3,4-tetrazol-5-ylmethyl)-2,3-dihydro-1H-indole-2-carboxamide using method E: $^1$H NMR (400 MHz, DMSO-d6) δ 0.75-0.79 (3H, t, J=8 Hz), 0.81-0.83 (3H, d, J=8 Hz), 1.01-1.06 (1H, m), 1.32-1.43 (1H, m), 1.62-1.74 (1H, m), 3.09-3.13 (2H, d, J=16 Hz), 3.19-3.26 (2H, m), 3.55-3.62 (2H, m), 4.10-4.15 (1H, dd, J=4, 16 Hz), 4.21-4.25 (1H, t, J=8 Hz), 4.51-4.55 (1H, d, J=16 Hz), 4.62-4.66 (1H, d, J=16 Hz), 5.13-5.15 (1H, d, J=8 Hz), 6.44-6.46 (2H, d, J=8 Hz), 6.88-6.90 (2H, d, J=8 Hz), 6.96-7.00 (1H, t, J=8 Hz), 7.14-7.18 (1H, t, J=8 Hz), 7.19-7.21 (1H, d, J=8 Hz), 7.79-7.81 (1H, d, J=8 Hz), 8.01-8.03 (1H, d, J=8 Hz), 8.20 (1H, bs), 9.06 (1H, bs), MS (LC/MS) m/z observed 548.06, expected 548.62 [M+H] and observed 570.17, expected 570.26 [M+Na].

Example A9

(2S)-1-{2-[(2S,3S)-2-[2-(3-Aminophenyl)Acetamido]-3-Methylpentanamido]Acetyl}-N-(2H-1,2,3,4-Tetrazol-5-Ylmethyl)-2,3-Dihydro-1H-Indole-2-Carboxamide Hydrochloride (2S)-1-{2-[(2S,3S)-2-[2-(3-(tert-Butoxylcarbonyl)aminophenyl)acetamido]-3-methylpentanamido]acetyl}-N-(2H-1,2,3,4-tetrazol-5-ylmethyl)-2,3-dihydro-1H-indole-2-carboxamide was prepared from I-5 and 2-(3-((tert-butoxycarbonyl)amino)phenyl)acetic acid using method A: MS (LC/MS) m/z observed 647.96, expected 648.33 [M+H]. Compound was confirmed using LC/MS and moved to next step as it was.

Title compound A9 was prepared from (2S)-1-{2-[(2S,3S)-2-[2-(3-(tert-butoxylcarbonyl)aminophenyl)acetamido]-3-methylpentanamido]acetyl}-N-(2H-1,2,3,4-tetrazol-5-ylmethyl)-2,3-dihydro-1H-indole-2-carboxamide using method E: $^1$H NMR (400 MHz, DMSO-d6) δ 0.76-0.80 (3H, t, J=8 Hz), 0.82-0.84 (3H, d, J=8 Hz), 1.03-1.11 (1H, m), 1.39-1.46 (1H, m), 1.68-1.74 (1H, m), 3.08-3.12 (2H, d, J=16 Hz), 3.17-3.25 (2H, m), 3.54-3.61 (2H, m), 4.10-4.15 (1H, dd, J=4, 16 Hz), 4.22-4.27 (1H, m), 4.42-4.48 (1H, m), 4.51-4.56 (1H, d, m), 5.12-5.14 (1H, d, J=8 Hz), 6.36-6.40 (2H, t, J=8 Hz), 6.43 (1H, s), 6.86-6.90 (1H, t, J=8 Hz), 6.96-7.00 (1H, t, J=8 Hz), 7.13-7.17 (1H, t, J=8 Hz), 7.19-7.21 (1H, d, J=8 Hz), 7.92-7.96 (1H, t, J=8 Hz), 8.01-8.03 (1H, d, J=8 Hz), 8.23 (1H, bs), 8.36 (1H, bs), 8.88 (1H, bs), MS (LC/MS) m/z observed, 548.03, expected 548.27 [M+H].

Example A10

(2S)-1-{2-[(2S,3S)-2-[2-(2-Amino-1,3-Thiazol-4-Yl)Acetamido]-3-Methylpentanamido]Acetyl}-N-(2H-1,2,3,4-Tetrazol-5-Ylmethyl)-2,3-Dihydro-1H-Indole-2-Carboxamide Hydrochloride Thionyl chloride (0.460 mL, 6.321 mmol, 2 eq) was added to a stirred mixture of 2-(2-aminothiazol-4-yl)acetic acid (500 mg, 3.2 mmol) and ethanol (5 mL) at 0° C. The resulting clear reaction mixture was stirred at RT for 16 hr and then concentrated under vacuum to dryness and then swapped with ethanol twice. Ethyl 2-(2-aminothiazol-4-yl)acetate was obtained as a brown oil in a quantitative yield (588 mg). $^1$H NMR (400 MHz, DMSO-d6) δ 1.17 (3H, bs), 3.72 (2H, bs), 4.08 (2H, bs), 6.68 (1H, bs), 9.43 (2H, bs). The compound was used further as described.

Ethyl 2-(2-aminothiazol-4-yl)acetate (250 mg, 1.123 mmol) was treated with triethylamine (0.630 mL, 4.494 mmol, 4 eq.), N,N-dimethylaminopyridine (30 mg, 0.225 mmol, 0.2 eq.) and di-tert-butyl dicarbonate (300 mg, 1.348 mmol, 1.2 eq.) in dichloromethane (10 mL) for 4 hr. The reaction mixture was diluted with dichloromethane (10 mL) and sequentially washed with water (1×10 mL), saturated citric acid solution (1×10 mL) and brine (1×10 mL). The organic layer was dried over sodium sulfate, filtered and concentrated to give a brown residue that was purified by column chromatography using a gradient hexanes/ethyl acetate (0% ethyl acetate to 50% ethyl acetate). Ethyl 2-(2-((tert-butoxycarbonyl)amino)thiazol-4-yl)acetate was obtained as a yellow oil (130 mg, 34%). $^1$H NMR (400 MHz, CDCl$_3$) δ 1.22 (3H, t, J=7 Hz), 1.55 (9H, s), 3.72 (2H, s), 4.11 (2H, q, J=7 Hz), 6.75 (1H, s), 9.55 (1H, bs).

Ethyl 2-(2-((tert-butoxycarbonyl)amino)thiazol-4-yl)acetate (100 mg, 0.350 mmol) was dissolved in ethanol (2 mL) and water (1 mL) and treated with lithium hydroxide (44 mg, 1.05 mmol, 3 eq.) at RT for 2 hrs. The reaction mixture was acidified by adding a saturated solution of citric acid to pH 5 and then concentrated to remove all ethanol. The residue was then extracted with ethyl acetate (2×15 mL) and the combined organic layers were dried over sodium sulfate, filtered and concentrated to give 2-(2-((tert-butoxycarbonyl)amino)thiazol-4-yl)acetic acid as a yellow oil (80 mg, 89%). MS (LC/MS) m/z observed 258.74, expected 259.08 [M+H]. Compound was confirmed using LC/MS and moved to next step as is.

(2S)-1-{2-[(2S,3S)-2-[2-(2-(tert-Butoxycarbonyl)amino-1,3-thiazol-4-yl)acetamido]-3-methylpentanamido]acetyl}-N-(2H-1,2,3,4-tetrazol-5-ylmethyl)-2,3-dihydro-1H-indole-2-carboxamide was prepared from 2-(2-((tert-butoxycarbonyl)amino)thiazol-4-yl)acetic acid and I-5 using method A: MS (LC/MS) m/z observed 654.97, expected 655.28 [M+H]. The compound was confirmed using LC/MS and moved to next step as it was.

Title compound A10 was prepared from (2S)-1-{2-[(2S,3S)-2-[2-(2-(tert-butoxycarbonyl)amino-1,3-thiazol-4-yl)acetamido]-3-methylpentanamido]acetyl}-N-(2H-1,2,3,4-tetrazol-5-ylmethyl)-2,3-dihydro-1H-indole-2-carboxamide using method E: $^1$H NMR (400 MHz, DMSO-d6) δ 0.77-0.92 (6H, m), 1.05-1.15 (1H, m), 1.40-1.52 (1H, m), 1.72-1.82 (1H, m), 3.00-3.65 (5H, m), 4.17 (1H, d, J=15 Hz), 4.30 (1H, t, J=7 Hz), 4.51-4.72 (2H, m), 5.20 (1H, d, J=10 Hz), 6.27 (1H, s), 6.85 (2H, m), 7.02 (1H, t, J=7 Hz), 7.10-7.30 (2H, m), 7.88 (1H, d, J=9 Hz), 8.10 (1H, d, J=8 Hz), 8.25-8.35 (1H, m), 9.10 (1H, bs), MS (LC/MS) m/z observed 555.08, expected 555.23 [M+H].

Example A11

(2S)-1-{2-[(2S)-2-Cyclohexyl-2-(2-Phenylacetamido)Acetamido]Acetyl}-N-(2H-1,2,3,4-Tetrazol-5-Ylmethyl)-2,3-Dihydro-1H-Indole-2-Carboxamide tert-Butyl ((S)-2-((2-((S)-2-(((2H-tetrazol-5-yl)methyl)carbamoyl)indolin-1-yl)-2-oxoethyl)amino)-1-cyclohexyl-2-oxoethyl)carbamate was prepared from I-3 and (S)-2-((tert-butoxycarbonyl)amino)-2-cyclohexylacetic acid using method A: MS (LC/MS) m/z observed 540.84, expected 541.29 [M+H], Compound was confirmed using LC/MS and moved to next step as it was.

Title compound A11 was prepared from tert-butyl ((S)-2-((2-((S)-2-(((2H-tetrazol-5-yl)methyl)carbamoyl)indolin-1-yl)-2-oxoethyl)amino)-1-cyclohexyl-2-oxoethyl)carbamate and I-6 using method A: $^1$H NMR (400 MHz, DMSO-d6) δ 0.93-1.00- (2H, m), 1.05-1.14 (3H, m), 1.55-1.67 (6H, m), 3.05-3.11 (2H, q, J=8 Hz), 3.52 (1H, s), 3.55-3.59 (2H, m), 4.11-4.15 (1H, d, J=16 Hz), 4.23-4.27 (1H, t, J=8 Hz), 4.37-4.41 (1H, d, J=16 Hz), 4.52-4.56 (1H, d, J=16 Hz), 5.12-5.14 (1H, d, J=8 Hz), 6.96-7.00 (1H, t, J=8 Hz), 7.14-7.21 (3H, m), 7.24-7.29 (4H, m), 8.02-8.04 (1H, d, J=8 Hz), 8.06-8.08 (1H, d, J=8 Hz), 8.27 (1H, bs), 8.78 (1H, bs), MS (LC/MS) m/z observed 559.01, expected 559.28 [M+H] and observed 581.13, expected 581.26 [M+Na].

Example A12

(2S)-1-{2-[(2S)-2-Cyclopentyl-2-(2-Phenylacetamido)Acetamido]Acetyl}-N-(2H-1,2,3,4-Tetrazol-5-Ylmethyl)-2,3-Dihydro-1H-Indole-2-Carboxamide tert-Butyl ((S)-2-((2-((S)-2-(((2H-tetrazol-5-yl)methyl)carbamoyl)indolin-1-yl)-2-oxoethyl)amino)-1-cyclopentyl-2-oxoethyl)carbamate was prepared from I-3 and (S)-2-((tert-butoxycarbonyl)amino)-2-cyclopentylacetic acid using method A: MS (LC/MS) m/z observed 526.81, expected 527.27 [M+H]. Compound was confirmed using LC/MS and moved to next step as it was.

Title compound A12 was prepared from tert-butyl ((S)-2-((2-((S)-2-(((2H-tetrazol-5-yl)methyl)carbamoyl)indolin-1-yl)-2-oxoethyl)amino)-1-cyclopentyl-2-oxoethyl)carbamate and I-6 using method A: $^1$H NMR (400 MHz, DMSO-d6) δ 1.36-1.44 (4H, m), 1.47-1.64 (4H, m), 2.12-2.18 (1H, m), 3.03-3.09 (2H, q, J=8 Hz), 3.39-3.43 (1H, d, J=16 Hz), 3.48-3.58 (2H, m), 4.09-4.17 (1H, t, J=16 Hz), 4.25-4.29 (1H, t, J=8 Hz), 4.35-4.43 (1H, t, J=16 Hz), 4.47-4.55 (1H, t, J=16 Hz), 5.09-5.13 (1H, T, J=8 Hz), 6.96-7.00 (1H, t, 0.18 Hz), 7.13-7.20 (3H, m), 7.23-7.28 (4H, m), 8.02-8.04 (1H, d, J=8 Hz), 8.18-8.21 (1H, d, J=12 Hz), 8.26 (1H, bs), 8.73 (1H, bs), MS (LC/MS) m/z observed 544.99, expected 545.26 [M+H].

Example A13

3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A13 was prepared from I-5 and succinic anhydride using method B: $^1$H NMR (400 MHz, DMSO-d6) δ 0.79-0.83 (3H, t, J=8 Hz), 0.85-0.87 (3H, d, J=8 Hz), 1.10-1.16 (1H, m), 1.23-1.25 (4H, d, J=8 Hz), 1.43-1.52 (1H, m), 1.73-1.82 (1H, m), 3.05-3.09 (2H, d, J=16 Hz), 3.55-3.63 (2H, m), 4.13-4.22 (2H, m), 4.46-4.50 (2H, d, J=16 Hz), 5.11-5.13 (1H, d, J=8 Hz), 6.97-7.01 (1H, t, J=8 Hz), 7.15-7.19 (1H, d, J=16 Hz), 7.94-7.96 (1H, d, J=8 Hz), 8.02 (1H, s), 8.15 (1H, bs), 8.86 (1H, bs), MS (LC/MS) m/z observed 515.07, expected 515.24 [M+H] and observed 537.11, expected 537.22 [M+Na].

Example A14

4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Butanoic Acid Title compound A14 was prepared from I-5 and glutaric anhydride using method B: $^1$H NMR (400 MHz, DMSO-d6) δ 0.78-0.82 (3H, t, J=8 Hz), 0.84-0.86 (3H, d, J=8 Hz), 1.06-1.13 (1H, m), 1.40-1.47 (1H, m), 1.66-1.75 (3H, m), 2.13-2.19 (4H, q, J=8 Hz), 3.03-3.07 (1H, d, J=16 Hz), 3.51-3.61 (2H, m), 4.09-4.11 (1H, d, J=8 Hz), 4.21-4.25 (1H, t, J=8 Hz), 4.28-4.32 (1H, d, J=12 Hz), 4.42-4.45 (1H, d, J=12 Hz), 5.10-5.12 (1H, d, J=8 Hz), 6.95-6.99 (1H, t, J=8 Hz), 7.12-7.16 (1H, t, J=8 Hz), 7.18-7.20 (1H, d, J=8 Hz), 7.85-7.87 (1H, d, J=8 Hz), 8.02-8.04 (1H, d, J=8 Hz), 8.19 (1H, bs), 8.58 (1H, bs), MS (LC/MS) m/z observed 528.97, expected 529.24 [M+H] and observed 551.11, expected 551.23 [M+Na].

Example A15

(2S)-1-{2-[(2S,3S)-2-Acetamido-3-Methylpentanamido]Acetyl}-N-(2H-1,2,3,4-Tetrazol-5-Ylmethyl)-2,3-Dihydro-1H-Indole-2-Carboxamide To I-5 (0.12 mmol) was added HCl (4M) solution in dioxane (4 ml) and the reaction mixture was stirred for 2 hr at RT, then concentrated to dryness under vacuum and swapped with MeOH (5 ml) three times. The resulting residue was dried well under vacuum and treated with a mixture of acetic anhydride/pyridine (1:1, 1.5 mL) for 15 minutes at RT. Then the reaction mixture was concentrated and the residue was submitted to reverse phase C18 column using 10-50% MeOH in water to yield the title compound A15 as an off-white solid (5 mg): $^1$H NMR (400 MHz, DMSO-d6) δ 0.77-0.92 (6H, m), 1.05-1.15 (1H, m), 1.40-1.50 (1H, m), 1.68-1.77 (1H, m), 1.87 (3H, s), 3.08-3.15 (1H, m), 3.51-3.65 (2H, m), 4.10-4.18 (1H, m), 4.24 (1H, t, J=9 Hz), 4.48-4.68 (2H, m), 5.15 (1H, d, J=10 Hz), 6.95 (1H, t, 0.17 Hz), 7.15-7.27 (2H, m), 7.90 (1H, d, J=7 Hz), 8.10

(1H, d, J=8 Hz), 8.18-8.33 (1H, m), 9.05 (1H, bs), MS (LC/MS) m/z observed 456.99, expected 457.23 [M+H].

Example A16

3-{[(1S,2S)-2-Methyl-1-({2-Oxo-2-[(2S)-2-[(1H-1,2,3-Triazol-4-Ylmethyl)Carbamoyl]-2,3-Dihydro-1H-Indol-1-Yl]Ethyl}Carbamoyl)Butyl]Carbamoyl}Propanoic Acid (S)-tert-Butyl 2-(((2H-1,2,3-triazol-4-yl)methyl)carbamoyl)indoline-1-carboxylate was prepared from (S)-1-(tert-butoxycarbonyl)indoline-2-carboxylic acid, and (2H-1,2,3-triazol-4-yl)methyl-amine following the same procedure for the preparation of I-1. MS (LC/MS) m/z observed 365.99, expected 366.15 [M+Na]. Compound was confirmed using LC/MS and moved to next step as it was.

(S)-tert-Butyl (2-(2-(((2H-1,2,3-triazol-4-yl)methyl)carbamoyl)indolin-1-yl)-2-oxoethyl)carbamate was prepared from (S)-tert-butyl 2-(((2H-1,2,3-triazol-4-yl)methyl)carbamoyl)indoline-1-carboxylate following the same procedure for the preparation of I-2 followed by the same procedure for the preparation of I-3. MS (LC/MS) m/z observed 400.83, expected 401.19 [M+H]. Compound was confirmed using LC/MS and moved to next step as it was.

Title compound A16 was prepared from (S)-tert-butyl (2-(2-(((2H-1,2,3-triazol-4-yl)methyl)carbamoyl)indolin-1-yl)-2-oxoethyl)carbamate and (2S,3S)-2-((tert-butoxycarbonyl)amino)-3-methylpentanoic acid using method A followed reaction with succinic anhydride using method B: $^1$H NMR (400 MHz, DMSO-d6) δ 0.79-0.83 (3H, t, J=8 Hz), 0.85-0.87 (3H, d, J=8 Hz), 1.15-1.20 (1H, m), 1.40-1.50 (1H, m), 1.68-1.80 (1H, m), 2.31-2.45 (4H, m), 3.01-3.10 (1H, m), 3.50-3.63 (2H, m), 4.05-4.15 (1H, m), 4.25 (1H, t, J=7 Hz), 4.30-4.45 (2H, m), 5.11 (1H, d, J=9 Hz), 6.98 (1H, t, J=8 Hz), 7.10-7.25 (2H, m), 7.90 (1H, d, J=9 Hz), 8.02 (1H, d, J=8 Hz), 8.13 (1H, bs), 8.86 (1H, bs), 12.02 (1H, bs), MS (LC/MS) m/z observed 514.02, expected 514.24 [M+H].

Example A17

3-Methyl-4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Butanoic Acid Title compound A17 was prepared from I-5 and 3-methylglutaric anhydride using method I and was separated by chromatography, into two diastereomers, A17-1 and A17-2, each characterized as below:
A17-1:
$^1$H NMR (400 MHz, DMSO-d6) δ 0.82 (3H, t, J=7.4 Hz), 0.84-0.90 (6H, m), 1.12 (1H, m), 1.45 (1H, m), 1.75 (1H, m), 2.05 (1H, m), 2.15-2.30 (4H, m), 3.10 (1H, m), 3.55-3.65 (2H, m), 4.15 (1H, dd, J=4, 18 Hz), 4.28 (1H, t, J=15 Hz), 4.55 (1H, dd, J=4, 16 Hz), 4.65 (1H, dd, J=6, 16 Hz), 5.16 (1H, d, J=11 Hz), 7.00 (1H, t, J=8 Hz), 7.16 (1H, t, J=8 Hz), 7.22 (1H, d, J=8 Hz), 7.87 (1H, d, J=9 Hz), 8.03 (1H, d, J=8 Hz), 8.17 (1H, bs), 9.08 (1H, bs), MS (LC/MS) m/z observed 543.10, expected 543.27 [M+H].
A17-2
$^1$H NMR (400 MHz, DMSO-d6) δ 0.82 (3H, t, J=7.4 Hz), 0.84-0.90 (6H, m), 1.12 (1H, m), 1.45 (1H, m), 1.75 (1H, m), 2.05 (1H, m), 2.08-2.15 (2H, m), 2.20-2.30 (2H, m), 3.10 (1H, m), 3.55-3.65 (2H, m), 4.13 (1H, d, J=17 Hz), 4.28 (1H, t, J=19 Hz), 4.53 (1H, dd, J=4, 16 Hz), 4.65 (1H, dd, J=6, 16 Hz), 5.15 (1H, d, J=11 Hz), 7.00 (1H, t, J=8 Hz), 7.16 (1H, t, J=8 Hz), 7.22 (1H, d, J=8 Hz), 7.87 (1H, d, J=9 Hz), 8.03 (1H, d, J=8 Hz), 8.17 (1H, bs), 9.08 (1H, bs), MS (LC/MS) m/z observed 543.07, expected 543.27 [M+H].

Example A18

3,3-Dimethyl-4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Butanoic Acid Title compound A18 was prepared from I-5 and 3,3-dimethylglutaric anhydride using method I without acidification with formic acid. The product was obtained as a triethylammonium salt: $^1$H NMR (400 MHz, DMSO-d6) δ 0.82 (3H, t, J=7.4 Hz), 0.87 (3H, d, J=7 Hz), 1.02 (6H, s), 1.05-1.10 (10H, m), 1.45 (1H, m), 1.75 (1H, m), 2-22-2-29 (4H, m), 2.77-2.90 (6H, m), 3.05 (1H, d, J=17 Hz), 3.55-3.65 (2H, m), 4.13 (1H, d, J=16 Hz), 4.26-4.33 (2H, m), 4.53 (1H, m), 5.15 (1H, d, J=11 Hz), 6.98 (1H, t, J=8 Hz), 7.12-7.24 (2H, m), 7.97 (1H, d, J=9 Hz), 8.03 (1H, d, J=8 Hz), 8.21 (1H, bs), 8.62 (1H, bs), MS (LC/MS) m/z observed 557.14, expected 557.28 [M+H]

Example A19

2-[1-({[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Methyl)Cyclopentyl]Acetic Acid Title compound A19 was prepared from I-5 and 3,3-tetramethyleneglutaric anhydride using method I without acidification with formic acid. The product was obtained as a triethylammonium salt: $^1$H NMR (400 MHz, DMSO-d6) δ 0.82 (3H, t, J=7.4 Hz), 0.87 (3H, d, J=7 Hz), 1.07-1.13 (10H, m), 1.40-1.62 (9H, m), 1.75 (1H, m), 2-31-2-38 (3H, m), 2.45 (1H, d, J=15 Hz), 2.86-2.93 (6H, m), 3.05 (1H, d, J=17 Hz), 3.55-3.65 (2H, m), 4.13 (1H, d, J=16 Hz), 4.26-4.33 (2H, m), 4.49 (1H, dd, J=6, 15 Hz), 5.15 (1H, d, J=11 Hz), 6.98 (1H, t, J=8 Hz), 7.12-7.24 (2H, m), 7.97 (1H, d, J=9 Hz), 8.03 (1H, d, J=8 Hz), 8.23 (1H, bs), 8.65 (1H, bs), MS (LC/MS) m/z observed 583.11, expected 583.30 [M+H]

Example A20

2-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Trans-Cyclohexane-1-Carboxylic Acid Title compound A20 was prepared from I-5 and trans-1,2-cyclohexanedicarboxylic anhydride using method I without acidification with formic acid and was separated by chromatography, into two diastereomers, A20-1 and A20-2, each characterized below as triethylammonium salts:
A20-1:
$^1$H NMR (400 MHz, DMSO-d6) δ 0.79 (3H, t, J=7.4 Hz), 0.85 (3H, d, J=7 Hz), 1.06-1.26 (14H, m), 1.46 (1H, m), 1.65-1.77 (3H, m), 1.85 (1H, m), 1.95 (1H, m), 2.40-2.45 (2H, m), 2.85-2.99 (3H, m), 3.05 (1H, d, J=17 Hz), 3.32-3.47 (3H, m), 3.52-3.65 (2H, m), 4.08-4.24 (2H, m), 4.34 (1H, m), 4.47 (1H, m), 5.13 (1H, d, J=11 Hz), 6.98 (1H, t, J=8 Hz), 7.12-7.24 (2H, m), 7.75 (1H, d, J=9 Hz), 8.00-8-10 (2H, m), 8.65 (1H, bs), MS (LC/MS) m/z observed 569.11, expected 569.28 [M+H].

A20-2:

¹H NMR (400 MHz, DMSO-d6) δ 0.80 (3H, t, J=7.4 Hz), 0.85 (3H, d, J=7 Hz), 1.10-1-30 (14H, m), 1.50 (1H, m), 1.68-1.77 (3H, m), 1.91 (1H, m), 2.11 (1H, m), 2.43 (1H, m), 2.65 (1H, t, J=10.7 Hz), 2.90-3.06 (4H, m), 3.32-3.50 (3H, m), 3.60 (1H, d, J=11, 17 Hz), 3.85 (1H, dd, J=5, 17 Hz), 4.08 (1H, dd, J=5, 9 Hz), 4.22 (1H, dd, J=6, 17 Hz), 4.35 (1H, dd, J=6, 17 Hz), 4.47 (1H, dd, J=6, 15 Hz), 5.07 (1H, d, J=11 Hz), 6.97 (1H, t, J=8 Hz), 7.11-7.21 (2H, m), 7.95-8-06 (3H, m), 8.85 (1H, bs), MS (LC/MS) m/z observed 569.12, expected 569.28 [M+H].

Example A21

6-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Cis-Cyclohex-3-Ene-1-Carboxylic Acid Title compound A21 was prepared from I-5 and cis-1,2,3,6-tetrahydrophthalic anhydride using method I and was separated by chromatography, into two diastereomers, A21-1 and A21-2, each characterized as below:

A21-1:
¹H NMR (400 MHz, DMSO-d6) δ 0.81 (3H, t, J=7.4 Hz), 0.86 (3H, d, J=7 Hz), 1.10 (1H, m), 1.48 (1H, m), 1.75 (1H, m), 2.15-2.25 (2H, m), 2.33 (1H, m), 2.43 (1H, m), 2.82-2.95 (2H, m), 3.11 (1H, m), 3.54-3.66 (2H, m), 4.11 (1H, d, J=17 Hz), 4.23 (1H, t, J=8 Hz), 4.54 (1H, dd, J=6, 17 Hz), 4.65 (1H, dd, J=6, 15 Hz), 5.16 (1H, d, J=11 Hz), 5.60 (m, 2H), 7.00 (1H, t, J=8 Hz), 7.11-7.26 (2H, m), 7.65 (1H, d, J=9 Hz), 8.02 (1H, d, J=9 Hz), 8.16 (1H, m), 9.07 (1H, bs), MS (LC/MS) m/z observed 567.11, expected 567.27 [M+H].

A21-2:
¹H NMR (400 MHz, DMSO-d6) δ 0.81 (3H, t, J=7.4 Hz), 0.86 (3H, d, J=7 Hz), 1.11 (1H, m), 1.45 (1H, m), 1.81 (1H, m), 2.22 (1H, m), 2.30-2.36 (2H, m), 2.46 (1H, m), 2.82 (1H, m), 2.94 (1H, m), 3.11 (1H, d, J=17 Hz), 3.54-3.66 (2H, m), 4.12-4.25 (2H, m), 4.50-4.65 (2H, m), 5.15 (1H, d, J=11 Hz), 5.62 (m, 2H), 7.00 (1H, t, J=8 Hz), 7.11-7.26 (2H, m), 7.71 (1H, d, J=9 Hz), 8.02 (1H, d, J=9 Hz), 8.16 (1H, bs), 9.05 (1H, bs), MS (LC/MS) m/z observed 567.11, expected 567.27 [M+H].

Example A22

2-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Cis-Cyclopentane-1-Carboxylic Acid Title compound A22 was prepared from I-5 and cis-1,2-cyclopentanedicarboxylic anhydride using method I and was separated by chromatography, into two diastereomers. A22-1 and A22-2, each characterized as below:

A22-1:
¹H NMR (400 MHz, DMSO-d6) δ 0.81 (3H, t, J=7.4 Hz), 0.86 (3H, d, J=7 Hz), 1.11 (1H, m), 1.44-1.55 (2H, m), 1.66-1.85 (5H, m), 1.95 (1H, m), 2.82 (1H, m), 3.05 (1H, m), 3.11 (1H, m), 3.54-3.66 (2H, m), 4.10-4.23 (2H, m), 4.45-4.70 (2H, m), 5.16 (1H, d, J=11 Hz), 7.00 (1H, t, J=8 Hz), 7.14-7.26 (2H, m), 7.71 (1H, d, J=9 Hz), 7.99-8.10 (2H, m), 9.08 (1H, bs), MS (LC/MS) m/z observed 555.10, expected 555.27 [M+H].

A22-2:
¹H NMR (400 MHz, DMSO-d6) δ 0.81 (3H, t, J=7.4 Hz), 0.85 (3H, d, J=7 Hz), 1.14 (1H, m), 1.43 (1H, m), 1.52 (1H, m), 1.66-1.87 (5H, m), 1.96 (1H, m), 2.82 (1H, m), 3.08 (1H, m), 3.14 (1H, m), 3.56-3.69 (2H, m), 4.15-4.27 (2H, m), 4.52-4.68 (2H, m), 5.16 (1H, d, J=11 Hz), 7.00 (1H, t, J=8 Hz), 7.14-7.26 (2H, m), 7.77 (1H, d, J=9 Hz), 8.00-8.08 (2H, m), 9.08 (1H, bs), MS (LC/MS) m/z observed 555.09, expected 555.27 [M+H].

Example A23

2-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Cis-Cyclohexane-1-Carboxylic Acid Title compound A23 was prepared from I-5 and cis-1,2-cyclohexanedicarboxylic anhydride using method I and was separated by chromatography, into two diastereomers, A23-1 and A23-2, each characterized as below:

A23-1:
¹H NMR (400 MHz, DMSO-d6) δ 0.79 (3H, t, J=7.4 Hz), 0.83 (3H, d, J=7 Hz), 1.08 (1H, m), 1.20-1.32 (2H, m), 1.34-1.57 (4H, m), 1.63 (1H, m), 1.73 (1H, m), 1.87 (1H, m), 1.99 (1H, m), 2.55 (1H, m), 2.77 (1H, m), 3.10 (1H, m), 3.54-3.65 (2H, m), 4.10-4.23 (2H, m), 4.48-4.67 (2H, m), 5.14 (1H, d, J=11 Hz), 6.99 (1H, t, J=8 Hz), 7.12-7.24 (2H, m), 7.56 (1H, d, J=9 Hz), 7.97-8.08 (2H, m), 9.07 (1H, bs), MS (LC/MS) m/z observed 569.08, expected 569.28 [M+H].

A23-2:
¹H NMR (400 MHz, DMSO-d6) δ 0.78 (3H, t, J=7.4 Hz), 0.84 (3H, d, J=7 Hz), 1.11 (1H, m), 1.20-1.48 (4H, m), 1.50-1.69 (3H, m), 1.77 (1H, m), 1.90 (1H, m), 2.03 (1H, m), 2.53 (1H, m), 2.82 (1H, m), 3.10 (1H, m), 3.54-3.65 (2H, m), 4.12-4.23 (2H, m), 4.46-4.64 (2H, m), 5.13 (1H, d, J=11 Hz), 6.97 (1H, t, 0.18 Hz), 7.12-7.24 (2H, m), 7.62 (1H, d, J=9 Hz), 8.00 (1H, d, J=8 Hz), 8.11 (1H, bs), 9.03 (1H, bs), MS (LC/MS) m/z observed 569.06, expected 569.28 [M+H].

Example A24

(2Z)-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Prop-2-Enoic Acid Title compound A24 was prepared from I-5 and maleic anhydride using method I without acidification with formic acid: ¹H NMR (400 MHz, DMSO-d6) δ 0.82 (3H, t, J=7.4 Hz), 0.88 (3H, d, J=7 Hz), 1.08 (1H, m), 1.12 (9H, t, J=7 Hz), 1.47 (1H, m), 1.82 (1H, m), 2.96 (6H, q, J=7 Hz), 3.05 (1H, d, J=17 Hz), 3.50-3.65 (2H, m), 4.13 (1H, d, J=16 Hz), 4.26 (1H, t, J=7 Hz), 4.38 (1H, m), 4.50 (1H, dd, J=6, 15 Hz), 5.13 (1H, d, J=11 Hz), 6.11-6.15 (2H, m), 6.98 (1H, t, J=8 Hz), 7.12-7.24 (2H, m), 8.04 (1H, d, J=8 Hz), 8.37 (1H, bs), 8.85 (1H, bs), MS (LC/MS) m/z observed 513.08, expected 513.22 [M+H]

Example A25

2-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Benzoic Acid Title compound A25 was prepared from I-7 and phthalic anhydride using method I without acidification with formic acid: ¹H NMR (400 MHz, DMSO-d6) δ 0.82 (3H, t, J=7.4 Hz), 0.93 (3H, d, J=7 Hz), 1.10 (9H, t, J=7 Hz), 1.25 (1H, m), 1.55 (1H, m), 1.97 (1H, m), 2.90 (6H, q, J=7 Hz), 3.00 (1H, d, J=17 Hz), 3.56 (1H, m), 3.73 (1H, m), 4.16 (1H, dd, J=6, 16 Hz), 4.25 (1H, dd, J=6, 8 Hz), 4.47-4.51 (2H, m), 5.18 (1H, d, J=11 Hz), 6.98 (1H, t, J=8 Hz), 7.12-7.20 (2H, m), 7.28 (1H, d, J=8 Hz), 7.42-7.50 (2H, m), 7.88 (1H, d, J=9 Hz), 8.03 (1H, d, J=8 Hz), 8.62 (1H, d, J=8 Hz), 8.71 (1H, bs), 9.21 (1H, bs), MS (LC/MS) m/z observed 563.10, expected 563.24 [M+H]

Example A26

2-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Cis-Cyclopropane-1-Carboxylic Acid Title compound A26 was prepared from I-5 and cis-3-oxabicyclo[3.1.0]hexane-2,4-dione using method I and was separated by chromatography, into two diastereomers, A26-1 and A26-2, each characterized as below:
A26-1:
$^1$H NMR (400 MHz, DMSO-d6) δ 0.81 (3H, t, J=7.4 Hz), 0.87 (3H, d, J=7 Hz), 1.04-1.14 (2H, m), 1.31 (1H, m), 1.47 (1H, m), 1.75 (1H, m), 1.92 (1H, m), 2.13 (1H, m), 3.11 (1H, m), 3.55-3.66 (2H, m), 4.15 (1H, dd, J=6, 16 Hz), 4.25 (1H, dd, J=7, 9 Hz), 4.54 (1H, m), 4.65 (1H, m), 5.17 (1H, d, J=11 Hz), 7.01 (1H, t, J=8 Hz), 7.14-7.26 (2H, m), 8.03 (1H, d, J=8 Hz), 8.18-8.30 (2H, m), 9.10 (1H, bs), MS (LC/MS) m/z observed 527.07, expected 527.24 [M+H].
A26-2:
$^1$H NMR (400 MHz, DMSO-d6) δ δ 0.81 (3H, t, J=7.4 Hz), 0.87 (3H, d, J=7 Hz), 1.06-1.17 (2H, m), 1.31 (1H, m), 1.47 (1H, m), 1.76 (1H, m), 1.91 (1H, m), 2.13 (1H, m), 3.11 (1H, m), 3.55-3.66 (2H, m), 4.16 (1H, dd, J=6, 16 Hz), 4.29 (1H, dd, J=7, 9 Hz), 4.54 (1H, m), 4.65 (1H, m), 5.17 (1H, d, J=11 Hz), 7.01 (1H, t, J=8 Hz), 7.14-7.26 (2H, m), 8.03 (1H, d, J=8 Hz), 8.18-8.30 (2H, m), 9.10 (1H, bs), MS (LC/MS) m/z observed 527.06, expected 527.24 [M+H].

Example A27

(2S)-1-{2-[(2S,3S)-2-[2-(1-Benzothiophen-3-Yl)Acetamido]-3-Methylpentanamido]Acetyl}-N-(2H-1,2,3,4-Tetrazol-5-Ylmethyl)-2,3-Dihydro-1H-Indole-2-Carboxamide Title compound A27 was prepared from I-5 and 2-(benzo[b]thiophen-3-yl)acetic acid using method A except a 2:1 ratio DCM/DMF as solvent, was used for the coupling reaction: $^1$H NMR (400 MHz, DMSO-d6) δ 0.80 (3H, t, J=7.4 Hz), 0.86 (3H, d, J=7 Hz), 1.10 (1H, m), 1.47 (1H, m), 1.76 (1H, m), 3.11 (1H, m), 3.55-3.66 (2H, m), 3.73 (1H, d, J=5 Hz), 3.83 (1H, d, J=5 Hz), 4.15 (1H, dd, J=6, 16 Hz), 4.30 (1H, dd, J=7, 9 Hz), 4.54 (1H, m), 4.65 (1H, m), 5.17 (1H, d, J=11 Hz), 7.01 (1H, t, J=8 Hz), 7.14-7.26 (2H, m), 7.32-7.40 (2H, m), 7.52 (1H, s), 7.86 (1H, m), 7.95 (1H, m), 8.04 (1H, d, J=8 Hz), 8.23-8.32 (2H, m), 9.08 (1H, bs), MS (LC/MS) m/z observed 589.05, expected 589.23[M+H]

Example A28

(2S)-1-{2-[(2S,3S)-3-Methyl-2-[2-(2H-1,2,3,4-Tetrazol-5-Yl)Acetamido]Pentanamido]Acetyl}-N-(2H-1,2,3,4-Tetrazol-5-Ylmethyl)-2,3-Dihydro-1H-Indole-2-Carboxamide Title compound A28 was prepared from I-5 and 2-(2H-tetrazol-5-yl)acetic acid using method A but with DMF as solvent for the coupling reaction: $^1$H NMR (400 MHz, DMSO-d6) δ 0.82 (3H, t, J=7.4 Hz), 0.88 (3H, d, J=7 Hz), 1.12 (1H, m), 1.50 (1H, m), 1.77 (1H, m), 3.12 (1H, m), 3.56-3.67 (2H, m), 3.95-4.05 (2H, m), 4.16 (1H, dd, J=6, 16 Hz), 4.31 (1H, t, J=8 Hz), 4.56 (1H, m), 4.65 (1H, m), 5.17 (1H, d, J=11 Hz), 7.01 (1H, t, J=8 Hz), 7.14-7.26 (2H, m), 8.04 (1H, d, J=8 Hz), 8.34 (1H, bs), 8.43 (1H, d, J=9 Hz), 9.08 (1H, bs), MS (LC/MS) m/z observed 525.08, expected 525.24 [M+H]

Example A29

Methyl (3R)-3-Methyl-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoate Title compound A29 was prepared from I-5 and (R)-4-methoxy-2-methyl-4-oxobutanoic acid using method E, followed by method C: $^1$H NMR (400 MHz, DMSO-d6) δ 0.83 (3H, t, J=7.4 Hz), 0.89 (3H, d, J=7 Hz), 1.05 (3H, d, J=7 Hz), 1.14 (1H, m), 1.47 (1H, m), 1.77 (1H, m), 2.33 (1H, dd, J=6, 16 Hz), 2.57 (1H, dd, J=8, 16 Hz), 2.87 (1H, m), 3.12 (1H, m), 3.56 (3H, s), 3.58-3.67 (2H, m), 4.16 (1H, m), 4.25 (1H, t, J=8 Hz), 4.56 (1H, m), 4.66 (1H, m), 5.17 (1H, d, J=11 Hz), 7.01 (1H, t, J=8 Hz), 7.14-7.26 (2H, m), 7.91 (1H, d, J=9 Hz), 8.02-8.12 (2H, m), 9.10 (1H, bs), MS (LC/MS) m/z observed 543.13, expected 543.27 [M+H]

Example A30

3-Methyl-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A30 was prepared from A29 using method D with 3 eq. of LiOH.H$_2$O and was separated by chromatography, into two diastereomers, A30-1 and A30-2, each characterized as below:
A30-1:
$^1$H NMR (400 MHz, DMSO-d6) δ 0.79 (3H, t, J=7.4 Hz), 0.85 (3H, d, J=7 Hz), 1.01 (3H, d, J=7 Hz), 1.10 (1H, m), 1.45 (1H, m), 1.74 (1H, m), 2.17 (1H, dd, J=6, 16 Hz), 2.43 (1H, m), 2.79 (1H, m), 3.08 (1H, m), 3.54-3.64 (2H, m), 4.12 (1H, m), 4.22 (1H, t, J=8 Hz), 4.50 (1H, m), 4.62 (1H, m), 5.14 (1H, d, J=11 Hz), 6.98 (1H, t, J=8 Hz), 7.11-7.23 (2H, m), 7.82 (1H, d, J=9 Hz), 7.98-8.08 (2H, m), 9.01 (1H, bs), MS (LC/MS) m/z observed 529.08, expected 529.25 [M+H].
A310-2:
$^1$H NMR (400 MHz, DMSO-d6) δ 0.79 (3H, t, J=7.4 Hz), 0.85 (3H, d, J=7 Hz), 1.03 (3H, d, J=7 Hz), 1.10 (1H, m), 1.44 (1H, m), 1.72 (1H, m), 2.22 (1H, dd, J=7, 15 Hz), 2.51 (1H, m), 2.68 (1H, m), 3.08 (1H, m), 3.54-3.64 (2H, m), 4.11 (1H, m), 4.22 (1H, t, J=8 Hz), 4.48 (1H, m), 4.60 (1H, m), 5.14 (1H, d, J=11 Hz), 6.98 (1H, t, J=8 Hz), 7.11-7.23 (2H, m), 7.82 (1H, d, J=9 Hz), 8.02 (1H, m), 8.15 (1H, bs), 8.96 (1H, bs), MS (LC/MS) m/z observed 529.10, expected 529.25 [M+H]

Example A31

2-[3-({[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Methyl)Phenyl]Acetic Acid Title compound A31 was prepared from I-5 and 1-cyclohexene-1,2-dicarboxylic anhydride using method I without acidification with formic acid: ¹H NMR (400 MHz, DMSO-d6) δ 0.78 (3H, t, J=7.4 Hz), 0.84 (3H, d, J=7 Hz), 1.08 (1H, m), 1.13 (9H, t, J=7 Hz), 1.17-1.25 (2H, m), 1.43-1.63 (3H, m), 1.99 (1H, m), 2.17-2.25 (3H, m), 2.28 (1H, m), 2.97-3.05 (7H, m), 3.54-3.65 (2H, m), 4.07-4.18 (2H, m), 4.38-4.50 (2H, m), 5.12 (1H, d, J=11 Hz), 6.95 (1H, t, J=8 Hz), 7.12-7.20 (2H, m), 7.97 (1H, d, J=8 Hz), 8.07 (1H, d, J=8 Hz), 8.45 (1H, bs), 9.05 (1H, bs), MS (LC/MS) m/z observed 566.96, expected 567.27 [M+H]

Example A32

(2R,3R)-2,3-Dihydroxy-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A32 was prepared from I-5 and L-(+)-tartaric acid using method J in DMF: ¹H NMR (400 MHz, DMSO-d6) δ 0.83 (3H, t, J=7.4 Hz), 0.87 (3H, d, J=7 Hz), 1.08 (1H, m), 1.48 (1H, m), 1.80 (1H, m), 3.11 (1H, m), 3.56-3.68 (2H, m), 4.17 (1H, m), 4.26 (1H, s), 4.30-4.37 (2H, m), 4.55 (1H, m), 4.66 (1H, m), 5.16 (1H, d, J=11 Hz), 7.00 (1H, t, J=8 Hz), 7.15-7.24 (2H, m), 7.57 (1H, d, J=9 Hz), 8.07 (1H, d, J=8 Hz), 8.33 (1H, bs), 9.10 (1H, bs), MS (LC/MS) m/z observed 547.06, expected 547.23 [M+H]

Example A33

(2S,3S)-2,3-Dihydroxy-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A33 was prepared from I-5 and D-(−)-tartaric acid using method J in DMF: ¹H NMR (400 MHz, DMSO-d6) δ 0.83 (3H, t, J=7.4 Hz), 0.87 (3H, d, J=7 Hz), 1.06 (1H, m), 1.51 (1H, m), 1.73 (1H, m), 3.11 (1H, m), 3.55-3.67 (2H, m), 4.17 (1H, m), 4.22 (1H, s), 4.31 (1H, s), 4.37 (1H, dd, J=7, 9 Hz), 4.55 (1H, m), 4.63 (1H, m), 5.16 (1H, d, J=1 Hz), 7.00 (1H, t, J=8 Hz), 7.15-7.24 (2H, m), 7.44 (1H, d, J=9 Hz), 8.02 (1H, d, J=8 Hz), 8.47 (1H, bs), 9.10 (1H, bs), MS (LC/MS) m/z observed 546.92, expected 547.23 [M+H]

Example A34

2-[4-({[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Methyl)Phenyl]Acetic Acid Title compound A34 was prepared from I-7 and 1,4-phenylenediacetic acid using method J: ¹H NMR (400 MHz, DMSO-d6) δ 0.80 (3H, t, J=7.4 Hz), 0.86 (3H, d, J=7 Hz), 1.10 (1H, m), 1.44 (1H, m), 1.75 (1H, m), 3.11 (1H, m), 3.43 (2H, d, J=14 Hz), 3.53 (2H, d, J=14 Hz), 3.56-3.65 (2H, m), 4.15 (1H, m), 4.27 (1H, t, J=8 Hz), 4.54 (1H, m), 4.65 (1H, m), 5.17 (1H, d, J=11 Hz), 7.01 (1H, t, J=8 Hz), 7.14-7.24 (6H, m), 8.04 (1H, d, J=8 Hz), 8.10 (1H, d, J=9 Hz), 8.25 (1H, bs), 9.08 (1H, bs), MS (LC/MS) m/z observed 591.15, expected 591.27 [M+H]

Example A35

2-[3-({[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Methyl)Phenyl]Acetic Acid Title compound A35 was prepared from I-7 and 1,3-phenylenediacetic acid using method J: ¹H NMR (400 MHz, DMSO-d6) δ 0.80 (3H, t, J=7.4 Hz), 0.86 (3H, d, J=7 Hz), 1.10 (1H, m), 1.44 (1H, m), 1.75 (1H, m), 3.11 (1H, m), 3.43 (2H, d, J=14 Hz), 3.55 (2H, d, J=14 Hz), 3.57-3.66 (2H, m), 4.15 (1H, m), 4.27 (1H, t, J=8 Hz), 4.55 (1H, m), 4.65 (1H, m), 5.17 (1H, d, J=11 Hz), 7.01 (1H, t, J=8 Hz), 7.08-7.24 (6H, m), 8.04 (1H, d, J=8 Hz), 8.12 (1H, d, J=9 Hz), 8.25 (1H, bs), 9.08 (1H, bs), MS (LC/MS) m/z observed 590.98, expected 591.27 [M+H]

Example A36

(2E)-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Prop-2-Enoic Acid Title compound A36 was prepared from I-5 and fumaric acid using method J: ¹H NMR (400 MHz, DMSO-d6) δ 0.83 (3H, t, J=7.4 Hz), 0.90 (3H, d, J=7 Hz), 1.13 (1H, m), 1.46 (1H, m), 1.78 (1H, m), 3.11 (1H, m), 3.57-3.66 (2H, m), 4.15 (1H, m), 4.37 (1H, t, J=8 Hz), 4.55 (1H, m), 4.65 (1H, m), 5.17 (1H, d, J=11 Hz), 6.52 (1H, d, J=15 Hz), 7.01 (1H, t, J=8 Hz), 7.12-7.24 (3H, m), 8.04 (1H, d, J=8 Hz), 8.35 (1H, bs), 8.60 (1H, d, J=9 Hz), 9.08 (1H, bs), MS (LC/MS) m/z observed 513.46, expected 513.22 [M+H]

Example A37

(3S)-3-Amino-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid The intermediate compound ((S)-tert-Butyl 4-(((2S,3S)-1-((2-(2-(((2H-tetrazol-5-yl)methyl)carbamoyl)indolin-1-yl)-2-oxoethyl)amino)-3-methyl-1-oxopentan-2-yl)amino)-3-(S)-((tert-butoxycarbonyl)amino)-4-oxobutanoate) was prepared from I-5 and Boc-L-aspartic acid-β-tert-butyl ester using method A. MS (LC/MS) m/z observed 685.99, expected 686.36 [M+H]. Compound was confirmed using LC/MS and moved to next step as it was.

(S)-tert-Butyl 4-(((2S,3S)-1-((2-(2-(((2H-tetrazol-5-yl)methyl)carbamoyl)indolin-1-yl)-2-oxoethyl)amino)-3-methyl-1-oxopentan-2-yl)amino)-3-(S)-((tert-butoxycarbonyl)amino)-4-oxobutanoate (30 mg) was dissolved in a 1:1 mixture TFA/DCM (4 mL) and left under stirring at RT for 2 h. The solvents were evaporated and the product was purified on a C18 column using 10-30% MeOH in water to give title compound A37 as an off-white solid: ¹H NMR (400 MHz, DMSO-d6) δ 0.83 (3H, t, J=7.4 Hz), 0.90 (3H, d, J=7 Hz), 1.15 (1H, m), 1.55 (1H, m), 1.82 (1H, m), 2.68-2.84 (2H, m), 3.17 (1H, d, J=16 Hz), 3.57-3.67 (2H, m), 4.07-4.18 (3H, m), 4.44 (1H, m), 4.56 (1H, m), 5.08 (1H, d, J=11 Hz), 6.99 (1H, t, J=8 Hz), 7.12-7.24 (2H, m), 8.04 (1H, d, J=8 Hz), 8.32 (1H, bs), 8.45 (1H, m), 9.08 (1H, bs), MS (LC/MS) m/z observed 530.17, expected 530.25 [M+H]

Example A38

(3R)-3-Amino-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid (S)-tert-Butyl 4-(((2S,3S)-1-((2-(2-(((2H-tetrazol-5-yl)methyl)carbamoyl)indolin-1-yl)-2-oxoethyl)amino)-3-methyl-1-oxopentan-2-yl)amino)-3-(R)-((tert-butoxycarbonyl)amino)-4-oxobutanoate was prepared from I-7 and Boc-D-aspartic acid-1-tert-butyl ester dicyclohexylammonium salt using method A. MS (LC/MS) m/z observed 686.07, expected 686.36 [M+H]. Compound was confirmed using LC/MS and moved to next step as it was.

(S)-tert-Butyl 4-(((2S,3S)-1-((2-(2-(((2H-tetrazol-5-yl)methyl)carbamoyl)indolin-1-yl)-2-oxoethyl)amino)-3-methyl-1-oxopentan-2-yl)amino)-3-(R)-((tert-butoxycarbonyl)amino)-4-oxobutanoate (30 mg) was dissolved in a 1:1 mixture trifluoroacetic acid/DCM (4 mL) and left under stirring at RT for 2 h. The solvents were evaporated and the product was purified on a C18 column using 10-30% MeOH in water to give title compound A38 as an off-white solid: $^1$H NMR (400 MHz, DMSO-d6) δ 0.83 (3H, t, J=7.4 Hz), 0.90 (3H, d, J=7 Hz), 1.13 (1H, m), 1.46 (1H, m), 1.78 (1H, m), 2.55-2.72 (2H, m), 3.08 (1H, d, J=16 Hz), 3.52-3.65 (2H, m), 4.05 (1H, m), 4.18 (1H, m), 4.27 (1H, m), 4.44-4.49 (2H, m), 5.14 (1H, d, J=11 Hz), 7.00 (1H, t, J=8 Hz), 7.12-7.24 (2H, m), 8.03 (1H, d, J=8 Hz), 8.35 (1H, bs), 8.52 (1H, m), 8.87 (1H, bs), MS (LC/MS) m/z observed 530.16, expected 530.25 [M+H]

Example A39

(2S)-2-Amino-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid (S)-tert-Butyl 4-((1-((2-(2-(S)-(((2H-tetrazol-5-yl)methyl)carbamoyl)indolin-1-yl)-2-oxoethyl)amino)-3-(S)-methyl-1-oxopentan-2-yl)amino)-2-(S)-((tert-butoxycarbonyl)amino)-4-oxobutanoate was prepared from I-5 and Boc-L-aspartic acid-α-tert-butyl ester using method A. MS (LC/MS) m/z observed 686.09, expected 686.36 [M+H]. Compound was confirmed using LC/MS and moved to next step as it was.

(S)-tert-Butyl 4-((1-((2-(2-(S)-(((2H-tetrazol-5-yl)methyl)carbamoyl)indolin-1-yl)-2-oxoethyl)amino)-3-(S)-methyl-1-oxopentan-2-yl)amino)-2-(S)-((tert-butoxycarbonyl)amino)-4-oxobutanoate (30 mg) was dissolved in a 1:1 mixture trifluoroacetic acid/DCM (4 mL) and left under stirring at RT for 2 h. The solvents were evaporated and the product was purified on a C18 column using 10-30% MeOH in water to give title compound A39 as an off-white solid: $^1$H NMR (400 MHz, DMSO-d6) δ 0.83 (3H, t, J=7.4 Hz), 0.88 (3H, d, J=7 Hz), 1.20 (1H, m), 1.51 (1H, m), 1.86 (1H, m), 2.37 (1H, d, J=15 Hz), 2.88 (1H, dd, J=10, 14 Hz), 3.01 (1H, d, J=16 Hz), 3.52-3.63 (2H, m), 3.86 (1H, m), 4.10-4.20 (2H, m), 4.49 (1H, m), 4.61 (1H, m), 5.11 (1H, d, J=11 Hz), 6.98 (1H, t, J=8 Hz), 7.12-7.23 (2H, m), 8.03 (1H, d, J=8 Hz), 8.35 (1H, d, J=8 Hz), 8.52 (1H, m), 9.30 (1H, bs), MS (LC/MS) m/z observed 530.10, expected 530.25 [M+H]

Example A40

(2R)-2-Amino-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid (S)-tert-Butyl 4-((1-((2-(2-(S)-(((2H-tetrazol-5-yl)methyl)carbamoyl)indolin-1-yl)-2-oxoethyl)amino)-3-(S)-methyl-1-oxopentan-2-yl)amino)-2-(R)-((tert-butoxycarbonyl)amino)-4-oxobutanoate was prepared from I-5 and Boc-D-aspartic acid-α-tert-butyl ester using method A. MS (LC/MS) m/z observed 686.05, expected 686.36 [M+H]. Compound was confirmed using LC/MS and moved to next step as it was.

(S)-tert-Butyl 4-((1-((2-(2-(S)-(((2H-tetrazol-5-yl)methyl)carbamoyl)indolin-1-yl)-2-oxoethyl)amino)-3-(S)-methyl-1-oxopentan-2-yl)amino)-2-(R)-((tert-butoxycarbonyl)amino)-4-oxobutanoate (30 mg) was dissolved in a 1:1 mixture trifluoroacetic acid/DCM (4 mL) and left under stirring at RT for 2 h. The solvents were evaporated and the product was purified on a C18 column using 10-30% MeOH in water to give title compound A40 as an off-white solid: $^1$H NMR (400 MHz, DMSO-d6) δ 0.82 (3H, t, J=7.4 Hz), 0.86 (3H, d, J=7 Hz), 1.20 (1H, m), 1.50 (1H, m), 1.81 (1H, m), 2.50 (1H, m), 2.97-3.11 (2H, m), 3.55 (1H, m), 3.70 (1H, m), 3.82 (1H, m), 4.03 (1H, t, J=8 Hz), 4.18 (1H, dd, J=7, 16 Hz), 4.49 (1H, dd, J=5, 6 Hz), 4.66 (1H, dd, J=6, 17 Hz), 5.08 (1H, d, J=11 Hz), 6.98 (1H, t, J=8 Hz), 7.12-7.23 (2H, m), 8.03 (1H, d, J=8 Hz), 8.35 (1H, m), 8.48 (1H, d, J=8 Hz), 9.34 (1H, bs), MS (LC/MS) m/z observed 530.13, expected 530.25 [M+H]

Example A41

(2S)-1-{2-[3-Fluoro-3-Methyl-2-(2-Phenylacetamido)Butanamido]Acetyl}-N-(2H-1,2,3,4-Tetrazol-5-Ylmethyl)-2,3-Dihydro-1H-Indole-2-Carboxamide 3-Fluoro-3-methyl-2-(2-phenylacetamido)butanoic acid was prepared from I-6 and 3-fluoro-DL-valine using method H: $^1$H NMR (400 MHz, DMSO-d6) δ 1.33 (3H, d, J=219 Hz), 1.39 (3H, d, J=19 Hz), 3.52 (1H, d, J=14 Hz), 3.59 (1H, d, J=14 Hz), 4.41, 4.46 (1H, 2xd, J=19 Hz), 7.20 (1H, m), 7.22-7.29 (3H, m), 8.50 (1H, d, J=9 Hz), 12.90 (1H, bs), MS (LC/MS) m/z observed 254.02, expected 254.12 [M+H]. Compound was used further as described.

Title compound A41 was prepared from I-4 and 3-fluoro-3-methyl-2-(2-phenylacetamido)butanoic acid using method C (as a mixture of diastereomers): MS (LC/MS) m/z observed 537.09, expected 537.24 [M+H].

Example A42

(2S)-1-{2-[(2S,3R)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide (2S,3R)-3-Methyl-2-(2-phenylacetamido)pentanoic acid was prepared from I-6 and allo-isoleucine using method H: $^1$H NMR (400 MHz, DMSO-d6) δ 0.75-0.90 (6H, m), 1.10 (1H, m), 1.25 (1H, m), 1.85 (1H, m), 3.47 (1H, d, J=14 Hz), 3.56 (1H, d, J=14 Hz), 4.35 (1H, m), 7.20 (1H, m), 7.24-7.30 (3H, m), 8.15 (1H, d, J=9 Hz), 12.57 (1H, bs), MS (LC/MS) m/z observed 250.04, expected 250.14 [M+H]. Compound was used further as described.

Title compound A42 was prepared from I-3 and (2S,3R)-3-methyl-2-(2-phenylacetamido)pentanoic acid using method A: $^1$H NMR (400 MHz, MeOH-d4) δ 0.87-0.97 (6H, m), 1.18 (1H, m), 1.45 (1H, m), 1.99 (1H, m), 3.21 (1H, d, J=8 Hz), 3.23 (1H, d, J=8 Hz), 3.55-3.67 (2H, m), 3.69-3.76 (2H, m), 4.51 (1H, d, J=5 Hz), 4.58-4.74 (2H, m), 5.16 (1H, d, J=11 Hz), 7.05 (1H, t, J=8 Hz), 7.15-7.35 (7H, m), 8.13 (1H, bs), MS (LC/MS) m/z observed 533.12, expected 533.26 [M+H].

Example A43

2,2,3,3-Tetrafluoro-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A43 was prepared from I-5 and 2,2,3,3-tetrafluorosuccinic acid using method J in DMF: $^1$H NMR (400 MHz, DMSO-d6) δ 0.80-0.84 (3H, t, J=8 Hz), 0.88-0.90 (3H, d, J=8 Hz), 1.08-1.15 (1H, m), 1.45-1.51 (1H, m), 1.83-1.91 (1H, m), 2.92-3.12 (2H, m), 3.56-3.64 (2H, m), 3.13-3.17 (1H, d, J=16 Hz), 4.27-4.31 (1H, t, J=8 Hz), 4.42-4.46 (1H, d, J=8 Hz), 4.58-4.62 (1H, d, J=16 Hz), 5.13-5.15 (1H, d, J=8 Hz), 6.98-7.02 (1H, t, J=8 Hz), 7.15-7.22 (2H, m), 8.03-8.05 (1H, d, J=8 Hz), 8.39 (1H, s), 8.97 (1H, bs), 9.90 (1H, bs) $^{19}$F NMR (376 MHz, DMSO-d6) δ −114.28, −115.00, −115.62, −116.35, −116.56, −117.28, −118.35, −119.06, MS (LC/MS) m/z observed 587.01, expected 587.19 [M+H].

Example A44

2-[Methyl({[(1S,2S)-2-Methy-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Methyl)Amino]Acetic Acid Title compound A44 was prepared from I-5 and 4-methylmorpholine-2,6-dione using method I: $^1$H NMR (400 MHz, DMSO-d6) δ 0.82-0.86 (3H, t, J=8 Hz), 0.88-0.90 (3H, d, J=8 Hz), 1.04-1.11 (1H, m), 1.47-1.53 (1H, m), 1.77-1.84 (1H, m), 2.73 (1H, s), 2.89 (1H, s), 2.98-3.04 (4H, q, J=8 Hz), 3.53-3.67 (2H, m), 4.13-4.17 (1H, d, J=16 Hz), 4.30-4.34 (1H, t, J=8 Hz), 4.36-4.40 (1H, dd, J=12, 4 Hz), 4.48-4.52 (1H, dd, J=12, 4 Hz), 5.10-5.13 (1H, d, J=12 Hz), 6.97-7.01 (1H, t, J=8 Hz), 7.14-7.18 (1H, t, J=8 Hz), 7.20-7.22 (1H, d, J=8 Hz), 7.95 (1H, s), 7.98-8.04 (1H, m), 8.42 (1H, bs), 8.79 (1H, bs), MS (LC/MS) m/z observed 544.17, expected 544.26 [M+H].

Example A45

3-{[(S)-Cyclopentyl({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Methyl]Carbamoyl}Propanoic Acid tert-Butyl ((S)-2-((2-((S)-2-(((2H-tetrazol-5-yl)methyl)carbamoyl)indolin-1-yl)-2-oxoethyl)amino)-1-cyclopentyl-2-oxoethyl)carbamate was prepared from I-3 and (S)-2-((tert-butoxycarbonyl)amino)-2-cyclopentylacetic acid using general method A. MS (LC/MS) m/z observed 527.03, expected 527.27 [M+H]. Compound was confirmed using LC/MS and moved to next step as is.

Title compound A45 was prepared from tert-butyl ((S)-2-((2-((S)-2-(((2H-tetrazol-5-yl)methyl)carbamoyl)indolin-1-yl)-2-oxoethyl)amino)-1-cyclopentyl-2-oxoethyl)carbamate and succinic anhydride using method I: $^1$H NMR (400 MHz, DMSO-d6) δ 1.26-1.34 (2H, m), 1.41-1.48 (2H, m), 1.51-1.67 (4H, m), 2.14-2.20 (1H, m), 2.37-2.44 (3H, m), 3.54-3.67 (3H, m), 4.16-4.26 (3H, m), 4.34-4.38 (1H, d, J=16 Hz), 4.44-4.48 (1H, d, J=16 Hz), 5.09-5.11 (1H, d, J=8 Hz), 6.96-7.00 (1H, t, J=8 Hz), 7.13-7.17 (1H, t, J=8 Hz), 7.19-7.21 (1H, d, J=8 Hz), 8.02-8.09 (2H, dd, J=20, 8 Hz), 8.16 (1H, bs), 8.72 (1H, bs), MS (LC/MS) m/z observed 527.10, expected 527.23 [M+H].

Example A46

3-{[(1S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Propyl]Carbamoyl}Propanoic Acid tert-Butyl ((S)-1-((2-((S)-2-(((2H-tetrazol-5-yl)methyl)carbamoyl)indolin-1-yl)-2-oxoethyl)amino)-3-methyl-1-oxobutan-2-yl)carbamate was prepared from I-3 and (S)-2-((tert-butoxycarbonyl)amino)-3-methylbutanoic acid using general method A. MS (LC/MS) m/z observed 500.98, expected 501.25 [M+H]. Compound was confirmed using LC/MS and moved to next step as is.

Title compound A46 was prepared from tert-butyl ((S)-1-((2-((S)-2-(((2H-tetrazol-5-yl)methyl)carbamoyl)indolin-1-yl)-2-oxoethyl)amino)-3-methyl-1-oxobutan-2-yl)carbamate and succinic anhydride using method I: $^1$H NMR (400 MHz, DMSO-d6) δ 0.90-0.96 (6H, m), 2.01-2.08 (1H, m), 2.44-2.50 (2H, m), 3.15-3.22 (2H, m), 3.57-3.66 (2H, m), 4.18-4.22 (1H, d, J=16 Hz), 4.26-4.30 (1H, t, J=8 Hz), 4.57-4.61 (1H, d, J=16 Hz), 4.64-4.68 (1H, d, J=16 Hz), 5.20-5.23 (1H, d, J=12 Hz), 7.03-7.07 (1H, t, J=8 Hz), 7.18-7.22 (1H, t, J=8 Hz), 7.26-7.28 (1H, d, J=8 Hz), 7.91-7.95 (1H, dd, J=16, 4 Hz), 8.06-8.08 (1H, d, J=8 Hz), 8.21 (1H, bs), 8.27-8.31 (1H, t, J=8 Hz), 9.14 (1H, bs), MS (LC/MS) m/z observed 501.07, expected 501.21 [M+H] and observed 523.19, expected 523.21 [M+Na].

Example A47

2-[(2,2-Dimethylpropanoyl)Oxy]Ethyl 3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoate Triethylamine (4.13 mL, 29.63 mmol) was added to ethylene glycol (22.5 mL). Pivaloyl chloride (3.1 mL, 25.19 mL) was then added slowly to this mixture and it was left at RT for 2 hrs. The reaction mixture was diluted with water (25 mL) and the product was extracted with DCM (4×20 mL). The combined organic layers were dried over sodium sulphate and concentrated. The product was purified on normal phase using 0% to 40% ethyl acetate in hexanes as the eluent to give a 2-hydroxyethyl pivalate as a colorless oil (3.99 g, 97%). $^1$H NMR (400 MHz, CDCl$_3$) δ 1.22-1.25 (9H, s), 2.02 (1H, bs), 3.80-3.85 (2H, m), 4.19-4.23 (2H, m).

Title compound A47 (75 mg, 0.146 mmol), 2-hydroxyethyl pivalate (32 mg, 0.219 mmol), EDC (42 mg, 0.219 mmol), DMAP (3.6 mg, 0.0292 mmol) were dissolved in DMF (5 mL). DIPEA (59 μL, 0.584 mmol) was then added and the reaction was heated to 50 for 6 hrs. The reaction mixture was concentrated and the product was purified on a C18 column using 10-65% MeOH in water to yield A47 as an off-white solid (35 mg, 37%). $^1$H NMR (400 MHz, DMSO-d6) δ 0.81 (3H, t, J=7.4 Hz), 0.87 (3H, d, J=7 Hz), 1.06-1.16 (10H, m), 1.45 (1H, m), 1.75 (1H, m), 2.35-2.48 (4H, m), 3.11 (1H, m), 3.55-3.65 (2H, m), 4.11-4.28 (6H, m), 4.52 (1H, m), 4.65 (1H, m), 5.13 (1H, d, J=11 Hz), 7.01 (1H, t, J=8 Hz), 7.14-7.26 (2H, m), 7.92 (1H, d, J=9 Hz), 8.03 (1H, d, J=8 Hz), 8.18 (1H, bs), 9.08 (1H, bs), MS (LC/MS) m/z observed 643.15, expected 643.32 [M+H].

Example A48

(1S,2S)-2-{[(1S,2S)-2-Methy-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Cyclopropane-1-Carboxylic Acid To the stirring mixture of (1S,2S)-diethyl cyclopropane-1,2-dicarboxylate (0.5 gm, 2.69 mmol) in 1:1 mixture of water:THF (2.7 ml) was added ammonium hydroxide (28%, 3.8 ml). The resulting reaction mixture was sealed in a flask and stirred at RT for 16 hrs. The reaction mixture was concentrated to dryness under vacuum. The resulting residue of (1S,2S)-cyclopropane-1,2-dicarboxylic acid, was dried well under vacuum and subjected to next reaction as it is.

Title compound A48 was prepared from I-5 and (1S,2S)-cyclopropane-1,2-dicarboxylic acid using method J. MS (LC/MS) m/z observed 525.99, expected 527.55 [M+H]. Compound was confirmed using LCMS.

Example A49

(2S)-1-{2-[(2S,3S)-3-Methyl-2-[(2R)-2-Phenylpropanamido]Pentanamido]Acetyl}-N-(2H-1,2,3,4-Tetrazol-5-Ylmethyl)-2,3-Dihydro-1H-Indole-2-Carboxamide Title compound A49 (7 mg, 0.01 mmol, 10%) was collected as an off white solid from intermediate I-15 (60 mg, 0.13 mmol) using general method M via reaction with (R)-2-phenyl-propionic acid. $^1$H NMR (400 MHz, DMSO-d6) δ 9.00 (1H, bs), 8.23 (1H, bs), 8.04 (1H, d, J=7 Hz), 7.96 (1H, d, J=9 Hz), 7.35 (2H, d, J=7 Hz), 7.28 (2H, t, J=7 Hz), 7.25-7.15 (3H, m), 7.01 (1H, t, J=7 Hz), 5.17 (1H, d, J=9 Hz), 4.64 (1H, d, J=16 Hz), 4.50 (1H, d, J=16 Hz), 4.23 (1H, t, J=8 Hz), 4.10 (1H, dd, J=10, 5 Hz), 3.81 (1H, q, J=7 Hz), 3.70-3.55 (2H, m), 3.16 (1H, d, J=5 Hz), 1.68 (1H, m), 1.31 (3H, d, J=7 Hz), 1.25 (1H, m), 0.97 (1H, m), 0.72 (3H, d, J=7 Hz), 0.66 (3H, t, J=7 Hz), MS (LC/MS) m/z observed 547.09, expected 547.28 [M+H].

Example A50

(2S)-1-{2-[(2S,3S)-3-Methyl-2-[(2S)-2-Phenylpropanamido]Pentanamido]Acetyl}-N-(2H-1,2,3,4-Tetrazol-5-Ylmethyl)-2,3-Dihydro-1H-Indole-2-Carboxamide Title compound A50 (10 mg, 0.01 mmol, 15%) was collected as an off white solid from intermediate I-15 (60 mg, 0.13 mmol) using general method M via reaction with (S)-2-phenyl-propionic acid. $^1$H NMR (400 MHz, DMSO-d6) δ 9.06 (1H, bs), 8.15 (1H, bs), 8.00 (2H, d, J=9 Hz), 7.32 (2H, d, J=7 Hz), 7.27 (2H, t, J=7 Hz), 7.23-7.13 (3H, m), 7.00 (1H, t, J=7 Hz), 5.13 (1H, d, J=10 Hz), 4.64 (1H, dd, J=16, 5 Hz), 4.53 (1H, dd, J=16, 5 Hz), 4.30 (1H, t, J=8 Hz), 4.10 (1H, dd, J=16, 5 Hz), 3.81 (1H, q, J=7 Hz), 3.67-3.50 (2H, m), 3.13 (1H, d, J=16 Hz), 1.77 (1H, m), 1.47 (1H, m), 1.33 (3H, d, J=7 Hz), 1.18 (1H, m), 0.88 (3H, d, J=7 Hz), 0.84 (3H, t, J=7 Hz), MS (LC/MS) m/z observed 547.05, expected 547.28 [M+H].

Example A51

4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-2-Phenylbutanoic Acid Title compound A51 (20 mg, 0.035 mmol, 49%) was collected as an off white solid from intermediate I-15 (30 mg, 0.07 mmol) using general method N via reaction with 3-phenyl-dihydro-pyran-2,6-dione, as an inseparable mixture of diastereomers. $^1$H NMR (400 MHz, DMSO-d6) δ 9.06 (1H, bs), 8.14 (1H, bs), 8.03 (1H, bs), 7.87 (1H, t, J=7 Hz), 7.40-7.10 (7H, m), 7.01 (1H, t, J=7 Hz), 5.16 (1H, m), 4.65 (1H, d, J=16 Hz), 4.53 (1H, d, J=16 Hz), 4.25 (1H, t, J=7 Hz), 4.14 (1H, m), 3.60 (2H, m), 3.50 (1H, t, J=7 Hz), 3.13 (1H, d, J=12 Hz), 2.25-2.00 (3H, m), 1.86 (1H, m), 1.73 (1H, m), 1.43 (1H, m), 1.10 (1H, m), 0.86 (3H, d, J=6 Hz), 0.82 (3H, t, J=6 Hz), (MS (LC/MS) m/z observed 605.06, expected 605.28 [M+H].

Example A52

2,2-Dimethyl-4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Butanoic Acid Title compound A52 (24 mg, 0.04 mmol, 40%) was collected as an off white solid from intermediate I-15 (50 mg, 0.11 mmol) using general method N via reaction with 3,3-dimethyl-dihydro-pyran-2,6-dione. $^1$H NMR (400 MHz, DMSO-d6) δ 9.05 (1H, bs), 8.15 (1H, bs), 8.03 (1H, d, J=8 Hz), 7.89 (1H, d, J=9 Hz), 7.22 (1H, d, J=7 Hz), 7.17 (1H, t, J=7 Hz), 7.01 (1H, t, J=8 Hz), 5.17 (1H, d, J=10 Hz), 4.65 (1H, dd, J=16, 6 Hz), 4.53 (1H, dd, J=16, 4 Hz), 4.24 (1H, t, J=8 Hz), 4.15 (1H, dd, J=16, 4 Hz), 3.60 (2H, m), 3.14 (1H, d, J=16 Hz), 2.14 (2H, m), 1.80-1.62 (3H, m), 1.45 (1H, m), 1.20-1.10 (7H, m), 0.86 (3H, d, J=7 Hz), 0.81 (3H, t, J=8 Hz), MS (LC/MS) m/z observed 557.16, expected 557.28 [M+H].

Example A53

2,2-Dimethyl-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A53 (22 mg, 0.04 mmol, 62%) was collected as an off white solid from intermediate I-15 (30 mg, 0.07 mmol) using general method N via reaction with 3,3-dimethyl-dihydro-furan-2,5-dione. $^1$H NMR (400 MHz, DMSO-d6) δ 9.09 (1H, bs), 8.17 (1H, bs), 8.02 (1H, d, J=9 Hz), 7.81 (1H, d, J=9 Hz), 7.22 (1H, d, J=7 Hz), 7.17 (1H, t, 0.18 Hz), 7.01 (1H, t, J=8 Hz), 5.17 (1H, d, J=12 Hz), 4.66 (1H, dd, J=16, 5 Hz), 4.55 (1H, dd, J=16, 4 Hz), 4.26 (1H, t, J=8 Hz), 4.14 (1H, dd, J=16, 5 Hz), 3.60 (2H, m), 3.14 (1H, d, J=16 Hz), 2.46 (1H, d, J=11 Hz), 2.41 (1H, d, J=11 Hz), 1.74 (1H, m), 1.45 (1H, m) 1.19 (1H, m), 1.12 (3H, s), 1.11 (3H, s), 0.86 (3H, d, J=6 Hz), 0.81 (3H, t, J=7 Hz), MS (LC/MS) m/z observed 543.04, expected 543.27 [M+H].

Example A54

4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-4-Phenylbutanoic Acid Title compound A54 (25 mg, 0.08 mmol, 37%) was prepared from I-15 (100 mg, 0.22 mmol) and 3-phenyl-dihydro-pyran-2,6-dione using method P, where the hydrolysis step was stopped after 8 h. A54 was separated by chromatography, into two diastereomers, A54-1 (eluted at 63% MeOH in water) and A54-2 (eluted at 65%0 MeOH in water), each characterized as below:

A54-1:

$^1$H NMR (400 MHz, DMSO-d6) δ 8.70 (1H, bs), 8.22-8.10 (2H, bs), 8.01 (1H, d, J=8 Hz), 7.37-7.10 (7H, m), 6.99 (1H, t, J=8 Hz), 5.08 (1H, d, J=9 Hz), 4.51 (1H, d, J=14 Hz), 4.40-4.20 (2H, m), 4.06 (1H, d, J=13 Hz), 3.66 (1H, m), 3.51 (1H, m), 3.38 (1H, m), 3.06 (1H, d, J=18 Hz), 2.20-2.05 (3H, m), 1.83 (1H, m), 1.77 (1H, m), 1.45 (1H, m), 1.12 (1H, m), 0.89 (3H, d, J=7 Hz), 0.84 (3H, t, J=7 Hz), MS (LC/MS) m/z observed 605.09, expected 605.28 [M+H].

A54-2:

$^1$H NMR (400 MHz, DMSO-d6) δ 9.07 (1H, bs), 8.20 (1H, bs), 8.10-8.00 (2H, m), 7.40-7.10 (7H, m), 7.01 (1H, t, J=7 Hz), 5.17 (1H, d, J=10 Hz), 4.65 (1H, dd, J=16, 5 Hz), 4.54 (1H, dd, J=16, 4 Hz), 4.28-4.12 (2H, m), 3.68 (1H, t, J=6 Hz), 3.61 (1H, m), 3.39 (1H, m), 3.14 (1H, d, J=16 Hz), 2.25-2.00 (3H, m), 1.84 (1H, m), 1.70 (1H, m), 1.23 (1H, m), 0.89 (1H, m), 0.70 (3H, d, J=6 Hz), 0.82 (3H, t, J=7 Hz), MS (LC/MS) m/z observed 605.13, expected 605.28 [M+H].

Example A55

4,4-Dimethyl-4-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Butanoic Acid Title compound A55 (9 mg, 0.03 mmol, 30%) was prepared from I-15 (51 mg, 0.11 mmol) and 3,3-dimethyl-dihydro-pyran-2,6-dione using method P, where the hydrolysis step was stopped after 20 h. $^1$H NMR (400 MHz, DMSO-d6) δ 9.06 (1H, bs), 8.15 (1H, bs), 8.05 (1H, d, J=8 Hz), 7.30-7.15 (3H, m) 7.02 (1H, t, J=8 Hz), 5.17 (1H, d, J=10 Hz), 4.64 (1H, dd, J=16, 5 Hz), 4.54 (1H, dd, J=16, 5 Hz), 4.24 (1H, t, J=8 Hz), 4.19 (1H, m), 3.61 (2H, m), 3.39 (1H, m), 3.14 (1H, d, J=16 Hz), 2.12 (2H, m), 1.86 (1H, m), 1.75 (1H, m), 1.48 (1H, m), 1.20-1.05 (7H, m), 0.89 (3H, d, J=7 Hz), 0.83 (3H, t, J=7 Hz), MS (LC/MS) m/z observed 557.10, expected 557.28 [M+H]

Example A56

3,3-Dimethyl-3-{[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}Propanoic Acid Title compound A56 (11 mg, 0.02 mmol, 11%) was prepared as an off-white solid, from I-15 (80 mg, 0.18 mmol) and 3,3-dimethyl-dihydro-furan-2,5-dione using method P, where the hydrolysis step was stopped after 7 h. $^1$H NMR (400 MHz, DMSO-d6) δ 9.04 (1H, bs), 8.17 (1H, bs), 8.02 (1H, d, J=8 Hz), 7.82 (1H, d, J=9 Hz), 7.22 (1H, d, J=7 Hz), 7.17 (1H, t, J=8 Hz), 7.01 (1H, t, J=8 Hz), 5.17 (1H, d, J=10 Hz), 4.63 (1H, dd, J=16, 5 Hz), 4.53 (1H, dd, J=16, 4 Hz), 4.25 (1H, t, J=8 Hz), 4.14 (1H, dd, J=16, 4 Hz), 3.62 (2H, m), 3.14 (1H, d, J=16 Hz), 2.48 (1H, d, J=16 Hz), 2.42 (1H, d, J=16 Hz), 1.76 (1H, m), 1.45 (1H, m), 1.25-1.05 (7H, m), 0.86 (3H, d, J=6 Hz), 0.82 (3H, t, J=7 Hz), MS (LC/MS) m/z observed 543.10, expected 543.27 [M+H]

Example A57

2-{[[(1S,2S)-2-Methyl-1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Butyl]Carbamoyl}-Trans-Cyclopentane-1-Carboxylic Acid Title compound A57 was prepared from I-15 (71 mg, 0.16 mmol) and cis-cyclopentane-1,2-dicarboxylic acid using method J without HCl treatment and was further separated by chromatography, into two diastereomers, A57-1 (9.9 mg, 0.04 mmol, 23%) and A57-2 (6.7 mg, 0.02 mmol, 15%), each characterized as below: A57-1:

$^1$H NMR (400 MHz, DMSO-d6) δ 8.90 (1H, bs), 8.15 (1H, bs), 8.03 (1H, d, J=8 Hz), 7.80 (1H, d, J=9 Hz), 7.22 (1H, d, J=7 Hz), 7.17 (1H, t, J=8 Hz), 7.00 (1H, t, J=7 Hz), 5.15 (1H, d, J=9 Hz), 4.57 (1H, d, J=12 Hz), 4.45 (1H, d, J=12 Hz), 4.27 (1H, t, J=8 Hz), 4.16 (1H, dd, J=9, 5 Hz), 3.69 (1H, dd, J=8, 4 Hz), 3.64 (1H, m), 3.11 (1H, d, J=14 Hz), 3.06-2.85 (2H, m), 2.10-1.82 (2H, m), 1.80-1.66 (2H, m), 1.66-1.52 (3H, m), 1.46 (1H, m), 1.09 (1H, m), 0.86 (3H, d, J=6 Hz), 0.81 (3H, t, J=7 Hz), MS (LC/MS) m/z observed 554.94, expected 555.27 [M+H].

A57-2:

$^1$H NMR (400 MHz, DMSO-d6) δ 8.81 (1H, bs), 8.13 (1H, bs), 8.10-7.95 (2H, m), 7.21 (1H, d, J=7 Hz), 7.16 (1H, t, J=8 Hz), 6.99 (1H, t, J=8 Hz), 5.15 (1H, d, J=10 Hz), 4.49 (1H, dd, J=17, 6 Hz), 4.45 (1H, d, J=17, 6 Hz), 4.25 (1H, t, J=8 Hz), 4.17 (1H, dd, J=14, 5 Hz), 3.69 (1H, dd, J=13, 4 Hz), 3.58 (1H, dd, J=15, 8 Hz), 3.05 (1H, d, J=16 Hz), 2.97 (2H, m), 2.00-1.85 (2H, m), 1.85-153 (5H, m), 1.13 (1H, m), 0.87 (3H, d, J=6 Hz), 0.82 (3H, t, J=7 Hz), MS (LC/MS) m/z observed 554.98, expected 555.27 [M+H].

Examples B1-B7 were prepared by the representative synthetic pathway illustrated schematically in FIG. 2.

Example B1

(2S)-1-{2-[(2S,3S)-3-Methyl-2-(2-Phenylacetamido)Pentanamido]Acetyl}-N-(1H-1,2,3-Triazol-4-Ylmethyl)-2,3-Dihydro-1H-Indole-2-Carboxamide Title compound B1 was prepared from I-9 and (1H-[1,2,3]triazol-4-yl)methanamine using method G followed by purification by preparative HPLC (Column: ASCENTIS™ C18, 25 cm×21.2 mm, 10 m, gradient 0%-100% Methanol/water with 0.1% TFA, 10 mL/min) (11 mg, cream-coloured powder). $^1$H NMR (300 MHz, DMSO-d6) δ 8.91-8.83 (m, 1H), 8.29-8.02 (m, 2H), 7.74-7.64 (m, 1H), 7.30-7.15 (m, 7H), 7.03-6.97 (m, 1H), 5.15-5.04 (m, 1H), 4.44-4.07 (m, 4H), 3.63-3.02 (m, 5H), 1.90-1.68 (m, 1H), 1.50-1.21 (m, 1H), 1.16-1.01 (m, 1H), 0.85-0.76 (m, 6H). MS (ESI) m/z observed 532.33 observed, expected 532.27 [M+H].

Example B2

(2S)-1-{2-[(2S,3S)-3-Methyl-2-(2-Phenylacetamido)Pentanamido]Acetyl}-N-(1,2,3-Thiadiazol-4-Ylmethyl)-2,3-Dihydro-1H-Indole-2-Carboxamide Title compound B2 was prepared from I-9 and ([1,2,3]thiadiazol-4-yl)methanamine using method G. $^1$H NMR, (300 MHz, DMSO-d6) δ 9.15-8.96 (m, 1H), 8.26-7.98 (m, 2H), 7.31-7.15 (m, 8H), 7.04-6.94 (m, 1H), 5.19-5.10 (m, 1H), 4.87-4.68 (m, 2H), 4.31-4.22 (m, 1H), 4.18-4.01 (m, 1H), 3.66-3.43 (m, 4H), 3.12-3.02 (m, 1H), 1.82-1.66 (m, 1H), 1.51-1.37 (m, 1H), 1.18-1.03 (m, 1H), 0.89-0.76 (m, 6H). MS (ESI) m/z observed 583.20, expected 583.19 [M+Cl] and observed 549.20, expected 549.23 [M+H] and observed 571.20, expected 571.21 [M+Na].

Example B3

(2S)-1-{2-[(2S,3S)-3-Methyl-2-(2-Phenylacetamido)Pentanamido]Acetyl}-N-[1-(1H-1,2,3-Triazol-4-Yl)Ethyl]-2,3-Dihydro-1H-Indole-2-Carboxamide Title compound B3 was prepared from I-9 and 1-(2H-tetrazol-5-yl)ethanamine using method G as a mixture of diastereomers. ¹H NMR, (300 MHz, CD₃OD) δ 7.35-7.21 (m, 8H), 7.09-7.03 (m, 1H), 5.39-5.32 (m, 1H), 5.17-5.09 (m, 1H), 4.38-4.32 (m, 2H), 3.62-3.58 (m, 3H), 3.26-3.14 (m, 2H), 1.95-1.84 (m, 1H), 1.68-1.61 (m, 3H), 1.59-1.47 (m, 1H), 1.22-1.09 (m, 1H), 0.98-0.86 (m, 6H). MS (ESI) m/z observed 545.48, expected 545.26 [M−H].

Example B4

(2S)—N-[(4-Methyl-1H-1,2,3-Triazol-5-Yl)Methyl]-1-{2-[(2S,3S)-3-Methyl-2-(2-Phenylacetamido)Pentanamido]Acetyl}-2,3-Dihydro-1H-Indole-2-Carboxamide Title compound B4 was prepared from I-9 and (4-methyl-1H-[1,2,3]triazol-5-yl)methanamine using method C. ¹H NMR, (300 MHz, DMSO-d6) δ 8.76 (br s, 1H), 8.20 (br s, 1H), 8.11-8.00 (m, 1H), 7.31-7.15 (m, 8H), 7.03-6.97 (m, 1H), 4.43-4.24 (m, 3H), 4.19-4.05 (m, 1H), 3.61-3.34 (m, 5H), 3.04-2.98 (m, 1H), 2.17 (s, 3H), 1.89-1.69 (m, 1H), 1.48-1.19 (m, 2H), 0.85-0.77 (m, 6H). MS (ESI) m/z observed 544.52, expected 544.27 [M−H].

Example B5

(2S)-1-{2-[(2S,3S)-3-Methyl-2-(2-Phenylacetamido)Pentanamido]Acetyl}-N-(1H-1,2,3-Triazol-4-Ylmethyl)-1,2,3,4-Tetrahydroquinoline-2-Carboxamide Title compound B5 was prepared from I-8 and 1,2,3,4-tetrahydroquinoline-2-carboxylic acid using method F followed by addition of 1-(1H-[1,2,3]triazol-4-yl)methanamine using method C, as a mixture of diastereomers. ¹H NMR, (300 MHz, acetone-d6) δ 7.83 (br s, 1H), 7.61-7.17 (m, 9H), 5.18 (t, 1H), 4.45-4.33 (m, 4H), 3.85-3.76 (m, 1H), 3.67-3.55 (m, 2H), 2.79-2.69 (m, 1H), 2.62-2.45 (m, 2H), 1.96-1.78 (m, 2H), 1.53-1.40 (m, 1H), 1.15-1.04 (m, 1H), 0.88-0.78 (m, 6H). MS (ESI) m/z observed 546.60, expected 546.28 [M−H].

Example B6

6-Methoxy-1-{2-[(2S,3S)-3-Methyl-2-(2-Phenylacetamido)Pentanamido]Acetyl}-N-(1H-1,2,3-Triazol-5-Ylmethyl)-2,3-Dihydro-1H-Indole-2-Carboxamide Title compound B6 was prepared from I-8 and 5-methoxy-indoline-2-carboxylic acid methyl ester using method F followed by ester hydrolysis using method D and finally addition of 1-(1H-[1,2,3]triazol-4-yl)methanamine using method C. ¹H NMR (300 MHz, DMSO-d6) δ 8.87-8.78 (m, 1H), 8.26-7.98 (m, 2H), 7.74-7.64 (m, 1H), 7.30-7.24 (m, 5H), 7.24-7.16 (m, 1H), 7.12-7.06 (m, 1H), 6.63-6.56 (m, 1H), 5.15-5.06 (m, 1H), 4.44-4.24 (m, 3H), 3.72 (s, 3H), 3.62-3.43 (m, 4H), 3.16 (s, 1H), 3.01-2.92 (m, 1H), 1.90-1.70 (m, 1H), 1.49-1.26 (m, 1H), 1.15-1.02 (m, 1H), 0.85-0.77 (m, 6H). MS (ESI) m/z observed 560.59, expected 560.26 [M+H].

Example B7

5-Methyl-1-{2-[(2S,3S)-3-Methyl-2-(2-Phenylacetamido)Pentanamido]Acetyl}-N-(1H-1,2,3-Triazol-4-Ylmethyl)-2,3-Dihydro-1H-Indole-2-Carboxamide Title compound B7 was prepared from I-8 and 6-methoxy-indoline-2-carboxylic acid ethyl ester using method C followed by ester hydrolysis using method D and finally addition of 1-(1H-[1,2,3]triazol-4-yl)methanamine using method C as a mixture of diastereomers. ¹H NMR, (300 MHz, CD₃OD) δ 8.86-8.62 (m, 1H), 8.32-7.93 (m, 2H), 7.68 (m, 1H), 7.37-6.95 (m, 8H), 5.18-5.02 (m, 2H), 4.55-4.44 (m, 3H), 4.38-4.29 (m, 1H), 3.70-3.54 (m, 3H), 3.22-3.05 (m, 1H), 2.30 (s, 3H), 2.03-1.84 (m, 1H), 1.60-1.49 (m, 1H), 1.25-1.10 (m, 1H), 0.96-0.86 (m, 6H). MS (ESI) m/z observed 544.53, expected 544.27 [M−H].

Examples C1-C39 were prepared by the representative synthetic pathway illustrated schematically in FIG. 3.

Example C1

(2S)-1-{2-[(2S)-3-Methyl-2-(2-Phenylacetamido)Butanamido]Acetyl}-N-(2H-1,2,3,4-Tetrazol-5-Ylmethyl)-2,3-Dihydro-1H-Indole-2-Carboxamide I-6 (0.5 g, 3.67 mmol) and thionyl chloride (1.6 ml, 22 mmol) were stirred together for 1 hr at room temperature. Thionyl chloride was removed by distillation under vacuum. The acid chloride was added to the stirring solution of L-valine (0.39 g, 3.305 mmol) in NaOH (2N, 4.2 ml) at 0° C. The resulting reaction mixture was warmed to RT and stirred overnight. The mixture was washed with diethyl ether (5 ml) and acidified to pH 4-5 by adding citric acid (aqueous, saturated solution). The precipitated solid was filtered, washed with diethyl ether and dried to yield (S)-3-methyl-2-(2-phenylacetamido)butanoic acid as a white solid (0.64 g, 74%). ¹H NMR (400 MHz, DMSO-d6) δ 0.82-0.84 (3H, d, J=8 Hz), 0.85-0.87 (3H, d, J=8 Hz), 1.99-2.06 (1H, m), 3.44-3.55 (2H, q, J=12 Hz), 4.10-4.14 (1H, dd, J=8.12 Hz), 7.16-7.21 (1H, m), 7.24-7.29 (4H, m), 7.19-7.21 (1H, d, J=8 Hz), 12.55 (1H, s), MS (LC/MS) m/z observed 236.04, expected 236.13 [M+H]. The compound was used further as described.

Title compound C1 was prepared from I-3 and (S)-3-methyl-2-(2-phenylacetamido)butanoic acid using method A: ¹H NMR (400 MHz, DMSO-d6) δ 0.81-0.85 (6H, m), 1.94-2.01 (1H, m), 3.04-3.10 (2H, m), 3.42-3.45 (1H, d, J=12 Hz), 3.53-3.58 (3H, m), 4.11-4.15 (1H, d, J=16 Hz), 4.22-4.26 (1H, q, J=12 Hz), 4.37-4.43 (1H, t, J=12 Hz), 4.47-4.54 (1H, m), 5.12-5.14 (1H, d, J=8 Hz), 6.96-7.00 (1H, t, J=8 Hz), 7.13-7.21 (3H, m), 7.25-7.26 (4H, d, J=4 Hz), 8.02-8.03 (1H, d, J=4 Hz), 8.05-8.13 (1H, m), 8.26 (1H, bs), 8.77 (1H, bs), MS (LC/MS) m/z observed 519.01, expected 519.25 [M+H] and observed 541.11, expected 541.23 [M+Na].

Example C2

(2S)-1-{2-[(2S,3R)-3-Hydroxy-2-(2-Phenylacetamido)Butanamido]Acetyl}-N-(2H-1,2,3,4-Tetrazol-5-Ylmethyl)-2,3-Dihydro-1H-Indole-2-Carboxamide I-6 (0.5 g, 3.67 mmol) and thionyl chloride (1.6 ml, 22 mmol) were stirred together for 1 hr at room temperature. Thionyl chloride was removed by distillation under vacuum. The acid chloride was added to the stirring solution of L-threonine (0.39 g, 3.305 mmol) in NaOH (2N, 4.2 ml) at 0° C. The resulting reaction mixture was warmed to RT and stirred overnight. The reaction mixture was washed with diethyl ether (5 ml) and acidified to pH 4-5 by adding citric acid (aqueous, saturated solution). The precipitated solid was filtered, washed with diethyl ether and dried to yield (2S,3R)-3-hydroxy-2-(2-phenylacetamido)butanoic acid as a white solid (0.71 g, 82%). ¹H NMR (400 MHz, DMSO-d6)

δ 0.99-1.01 (3H, d, J=8 Hz), 3.49-3.60 (2H, q, J=12 Hz), 4.08-4.13 (1H, m), 4.17-4.20 (1H, dd, J=4, 8 Hz), 4.89 (1H, bs), 7.16-7.31 (5H, m), 7.97-7.99 (1H, d, J=8 Hz), 12.42 (1H, bs), MS (LC/MS) m/z observed 238.00, expected 238.11 [M+H]. The compound was used further as described.

Title compound C2 was prepared from I-3 and (2S,3R)-3-hydroxy-2-(2-phenylacetamido)butanoic acid using method A: $^1$H NMR (400 MHz, DMSO-d6) δ 1.00-1.02 (3H, d, J=8 Hz), 1.66-1.74 (1H, m), 3.06-3.12 (2H, m), 3.49-3.53 (1H, t, J=8 Hz), 3.55-3.62 (2H, m), 3.98-4.02 (1H, t, J=8 Hz), 4.14-4.18 (1H, d, J=16 Hz), 4.24-4.27 (1H, dd, J=4, 8 Hz), 4.44-4.49 (1H, m), 4.54-4.62 (1H, m), 5.12-5.18 (1H, m), 6.96-7.02 (1H, m), 7.16-7.22 (3H, m), 7.26-7.28 (4H, q, J=4 Hz), 7.99-8.03 (1H, t, J=8 Hz), 8.08 (1H, bs), 8.99 (1H, bs), MS (LC/MS) m/z observed 521.04, expected 521.23 [M+H] and observed 543.11, expected 543.21 [M+Na].

Example C3

(2S)-1-{2-[(2S,3S)-3-Hydroxy-2-(2-Phenylacetamido)Butanamido]Acetyl}-N-(2H-1,2,3,4-Tetrazol-5-Ylmethyl)-2,3-Dihydro-1H-Indole-2-Carboxamide (2S,3S)-3-Hydroxy-2-(2-phenylacetamido)butanoic acid was prepared from I-6 and (2S,3S)-2-amino-4-hydroxybutanoic acid using method H: $^1$H NMR (400 MHz, DMSO-d6) δ 1.05 (3H, d, J=6.4 Hz), 3.55 (2H, s), 3.85 (1H, m), 4.17 (1H, dd, J=4.0, 8.4 Hz), 4.89 (1H, bs), 7.13-7.30 (5H, m), 8.19 (1H, d, J=8.4 Hz), 12.35 (1H, bs), MS (LC/MS) m/z observed 237.86, expected 238.11 [M+H]. Compound was used further as described.

Title compound C3 was prepared from (2S,3S)-3-hydroxy-2-(2-phenylacetamido)butanoic acid and I-4 using method A: $^1$H NMR (400 MHz, DMSO-d6) δ 0.97-1.07 (3H, m), 2.93-3.15 (2H, m), 3.45-3.70 (3H, m), 3.82-3.88 (1H, m), 4.11-4.20 (1H, m), 4.22-4.30 (1H, m), 4.32-4.42 (1H, m), 4.45-4.55 (1H, m), 5.15 (1H, d, J=9.5 Hz), 6.97 (1H, t, J=7.4 Hz), 7.13-7.30 (7H, m), 7.92-8.28 (3H, m), 8.75 (1H, bs), MS (LC/MS) m/z observed 521.00, expected 521.23 [M+H].

Example C4

(2S)-1-{2-[(2S)-4-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide (S)-4-Methyl-2-(2-phenylacetamido)pentanoic acid was prepared from I-6 and (S)-2-amino-4-methylpentanoic acid using method H: $^1$H NMR (400 MHz, DMSO-d6) δ 0.85 (3H, d, J=6.4 Hz), 1.05 (3H, d, J=6, 4 Hz), 1.45-1.53 (2H, m), 1.56-1.66 (1H, m), 3.40-3.50 (2H, m), 4.15-4.25 (1H, m), 7.13-7.30 (5H, m), 8.30 (1H, d, J=8.1 Hz), 12.50 (1H, bs), MS (LC/MS) m/z observed 249.98, expected 250.14 [M+H]. Compound was used further as described.

Title compound C4 was prepared from (S)-4-methyl-2-(2-phenylacetamido)pentanoic acid and I-3 using method A: $^1$H NMR (400 MHz, DMSO-d6) δ 0.77 (3H, d, J=6, 4 Hz), 0.88 (3H, d, J=6.4 Hz), 1.45-1.53 (2H, m), 1.55-1.66 (1H, m), 2.95-3.12 (2H, m), 3.40-3.65 (3H, m), 4.07-4.15 (1H, m), 4.31-4.43 (2H, m), 4.45-4.55 (1H, m), 5.12 (1H, m), 7.01 (1H, t, J=7 Hz), 7.15-7.33 (7H, m), 7.97-8.10 (1H, d, J=8 Hz), 8.20-8.38 (2H, m), 8.72 (1H, bs), MS (LC/MS) m/z observed 533.00, expected 533.26 [M+H].

Example C5

(2S)-1-{2-[(2S)-2-(2-Phenylacetamido)Pentanamido]Acetyl}-N-(2H-1,2,3,4-Tetrazol-5-Ylmethyl)-2,3-Dihydro-1H-Indole-2-Carboxamide (S)-2-(2-Phenylacetamido)pentanoic acid was prepared from I-6 and (S)-2-aminopentanoic acid using method H: $^1$H NMR (400 MHz, DMSO-d6) δ 0.85 (3H, d, J=7 Hz), 1.25-1.35 (2H, m), 1.52-1.70 (2H, m), 3.42-3.50 (2H, m), 4.13-4.20 (1H, m), 7.15-7.32 (5H, m), 8.30 (1H, d, J=8 Hz), 12.50 (1H, bs), MS (LC/MS) m/z observed 235.97, expected 236.13 [M+H]. The compound was used further as described.

Title compound C5 was prepared from (S)-2-(2-phenylacetamido)pentanoic acid and I-3 using method A: $^1$H NMR (400 MHz, DMSO-d6) δ 0.83 (3H, d, J=6.4 Hz), 1.25-1.35 (2H, m), 1.45-1.57 (1H, m), 1.61-1.73 (1H, m), 2.95-3.12 (2H, m), 3.42-3.65 (3H, m), 4.07-4.18 (1H, m), 4.31-4.43 (2H, m), 4.45-4.55 (1H, m), 5.12 (1H, m), 7.01 (1H, t, J=7 Hz), 7.15-7.33 (7H, m), 7.97-8.10 (1H, d, J=8 Hz), 8.20-8.38 (2H, m), 8.75 (1H, bs), MS (LC/MS) m/z observed 518.99, expected 519.25 [M+H].

Example C6

(2S)-1-{2-[(2S)-3,3-Dimethyl-2-(2-Phenylacetamido)Butanamido]Acetyl}-N-(2H-1,2,3,4-Tetrazol-5-Ylmethyl)-2,3-Dihydro-1H-Indole-2-Carboxamide (S)-3,3-Dimethyl-2-(2-phenylacetamido)butanoic acid was prepared from I-6 and (S)-2-amino-3,3-dimethylbutanoic acid using method H: $^1$H NMR (400 MHz, DMSO-d6) δ 0.93 (9H, s), 3.47 (1H, d, J=14 Hz), 3.57 (1H, d, J=14 Hz), 4.10 (1H, d, J=9 Hz), 7.10-7.22 (1H, m), 7.24-7.32 (4H, m), 8.15 (1H, d, J=9 Hz), 12.58 (1H, bs), MS (LC/MS) m/z observed 249.96, expected 250.14 [M+H]. The compound was used further as described.

Title compound C6 was prepared from (S)-3,3-dimethyl-2-(2-phenylacetamido)butanoic acid and I-3 using method A: $^1$H NMR (400 MHz, DMSO-d6) δ 0.91 (9H, s), 2.95-3.12 (2H, m), 3.40-3.70 (3H, m), 4.07-4.18 (1H, m), 4.28-4.40 (2H, m), 4.45-4.55 (1H, m), 5.12 (1H, m), 6.99 (1H, t, J=7 Hz), 7.12-7.31 (7H, m), 7.95-8.07 (1H, m), 8.30-8.50 (2H, m), 8.73 (1H, bs), MS (LC/MS) m/z observed 533.03, expected 533.26 [M+H].

Example C7

(2S)-1-{2-[(2S,3R)-3-Methoxy-2-(2-Phenylacetamido)Butanamido]Acetyl}-N-(2H-1,2,3,4-Tetrazol-5-Ylmethyl)-2,3-Dihydro-1H-Indole-2-Carboxamide (2S,3R)-3-Methoxy-2-(2-phenylacetamido)butanoic acid was prepared from I-6 and (2S,3R)-2-amino-3-methoxybutanoic acid using method H: $^1$H NMR (400 MHz, DMSO-d6) δ 1.01 (3H, d, J=6 Hz), 3.34 (3H, s), 3.51 (1H, d, J=14 Hz), 3.61 (1H, d, J=14 Hz), 3.81-3.85 (1H, m), 4.35 (1H, dd, J=3 Hz, 9 Hz), 7.16-7.22 (1H, m), 7.24-7.32 (4H, m), 8.17 (1H, d, J=9 Hz), 12.61 (1H, bs), MS (LC/MS) m/z observed 252.01, expected 252.12 [M+H]. The compound was used further as described.

Title compound C7 was prepared from (2S,3R)-3-methoxy-2-(2-phenylacetamido)butanoic acid and I-4 using method C: $^1$H NMR (400 MHz, DMSO-d6) δ 1.04 (3H, m), 3.10-3.16 (2H, m), 3.24 (3H, s), 3.45-3.75 (4H, m), 4.11-4.25 (1H, m), 4.37-4.42 (1H, m), 4.50-4.70 (2H, m), 5.15

(1H, d, J=9.5 Hz), 6.97 (1H, t, J=7.4 Hz), 7.13-7.30 (7H, m), 7.97-8.18 (3H, m), 9.12 (1H, bs), MS (LC/MS) m/z observed 535.04, expected 535.24 [M+H].

Example C8

(2S)-1-{2-[(2S)-3-(Tert-Butoxy)-2-(2-Phenylacetamido)Propanamido]Acetyl}-N-(2H-1,2,3,4-Tetrazol-5-Ylmethyl)-2,3-Dihydro-1H-Indole-2-Carboxamide (S)-3-(tert-Butoxy)-2-(2-phenylacetamido)propanoic acid was prepared from I-6 and (S)-2-amino-3-(tert-butoxy)propanoic acid using method H: $^1$H NMR (400 MHz, DMSO-d6) δ 1.06 (9H, s), 3.48 (1H, m), 3.49-3.57 (2H, m), 3.63 (1H, dd, J=5 Hz, 9 Hz), 4.36 (1H, m), 7.16-7.22 (1H, m), 7.24-7.32 (4H, m), 8.15 (1H, d, J=9 Hz), 12.61 (1H, bs), MS (LC/MS) m/z observed 279.86, expected 280.16 [M+H]. The compound was used further as described.

Title compound C8 was prepared from (S)-3-(tert-butoxy)-2-(2-phenylacetamido)propanoic acid and I-3 using method A: $^1$H NMR (400 MHz, DMSO-d6) δ 1.08 (9H, ms), 2.93-3.15 (2H, m), 3.43-3.70 (5H, m), 4.11-4.20 (1H, m), 4.30-4.55 (3H, m), 5.15 (1H, m), 6.97 (1H, t, J=7, 4 Hz), 7.13-7.33 (7H, m), 7.95-8.25 (3H, m), 8.75 (1H, bs), MS (LC/MS) m/z observed 563.00, expected 563.27 [M+H].

Example C9

(2S)-1-{2-[(2S,3R)-3-(Tert-Butoxy)-2-(2-Phenylacetamido)Butanamido]Acetyl}-N-(2H-1,2,3,4-Tetrazol-5-Ylmethyl)-2,3-Dihydro-1H-Indole-2-Carboxamide (2S,3R)-3-(tert-Butoxy)-2-(2-phenylacetamido)butanoic acid was prepared from I-6 and (2S,3R)-2-amino-3-(tert-butoxy)butanoic acid using method H: $^1$H NMR (400 MHz, DMSO-d6) δ 1.06 (3H, d, J=6 Hz), 1.09 (9H, s), 3.48 (1H, d, J=14 Hz), 3.56 (1H, d, J=14 Hz), 3.93 (1H, m), 4.33 (1H, dd, J=5 Hz, 9 Hz), 7.16-7.22 (1H, m), 7.24-7.32 (4H, m), 8.18 (1H, d, J=9 Hz), 12.61 (1H, bs), MS (LC/MS) m/z observed 293.85, expected 294.17 [M+H]. The compound was used further as described.

Title compound C9 was prepared from (2S,3R)-3-(tert-butoxy)-2-(2-phenylacetamido)butanoic acid and I-4 using method C: $^1$H NMR (400 MHz, DMSO-d6) δ 1.02 (3H, m), 1.13 (9H, s), 3.10-3.16 (2H, m), 3.50-3.70 (3H, m), 3.88-3.95 (1H, m), 4.11-4.25 (1H, m), 4.30-4.37 (1H, m), 4.47-4.67 (2H, m), 5.15 (1H, d, J=9.5 Hz), 6.97 (1H, t, J=7.4 Hz), 7.13-7.30 (7H, m), 7.85 (1H, d, J=8 Hz), 8.00-8.10 (2H, m), 9.12 (1H, bs), MS (LC/MS) m/z observed 577.11, expected 577.29 [M+H].

Example C10

(2S)-1-{2-[(2S,3S)-3-(Tert-Butoxy)-2-(2-Phenylacetamido)Butanamido]Acetyl}-N-(2H-1,2,3,4-Tetrazol-5-Ylmethyl)-2,3-Dihydro-1H-Indole-2-Carboxamide (2S,3S)-3-(tert-Butoxy)-2-(2-phenylacetamido)butanoic acid was prepared from I-6 and (2S,3S)-2-amino-3-(tert-butoxy)butanoic acid using method H: $^1$H NMR (400 MHz, DMSO-d6) δ 1.03 (3H, d, J=6 Hz), 1.09 (9H, s), 3.52 (1H, d, J=14 Hz), 3.62 (1H, d, J=14 Hz), 4.10 (1H, m), 4.27 (1H, dd, J=3 Hz, 9 Hz), 7.16-7.22 (1H, m), 7.24-7.32 (4H, m), 7.83 (1H, d, J=9 Hz), 12.53 (1H, bs), MS (LC/MS) m, observed 293.92, expected 294.17 [M+H]. The compound was used further as described.

Title compound C10 was prepared from (2S,3S)-3-(tert-butoxy)-2-(2-phenylacetamido)butanoic acid and I-4 using method C: MS (LC/MS) m/z observed 577.04, expected 577.29 [M+H].

Example C11

(2S)-1-[(2S)-2-[(2S,3S)-3-Methyl-2-(2-Phenylacetamido)Pentanamido]Propanoyl]-N-(2H-1,2,3,4-Tetrazol-5-Ylmethyl)-2,3-Dihydro-1H-Indole-2-Carboxamide tert-Butyl ((S)-1-((S)-2-(((2H-tetrazol-5-yl)methyl)carbamoyl)indolin-1-yl)-1-oxopropan-2-yl)carbamate was prepared from I-2 and (S)-2-((tert-butoxycarbonyl)amino)propanoic acid using method C: MS (LC/MS) m/z observed 415.76, expected 416.20 [M+H], and observed 438.01, expected 438.19 [M+Na], Compound was confirmed using LC/MS and moved to next step as it was.

Title compound C11 was prepared from tert-butyl ((S)-1-((S)-2-(((2H-tetrazol-5-yl)methyl)carbamoyl)indolin-1-yl)-1-oxopropan-2-yl)carbamate and (2S,3S)-3-methyl-2-(2-phenylacetamido)pentanoic acid using method A: $^1$H NMR (400 MHz, CD$_3$OD) δ 0.80-0.88 (6H, m), 1.06-1.13 (1H, m), 1.26-1.28 (3H, d, J=8 Hz), 1.42-1.48 (1H, m), 1.75-1.83 (1H, m), 3.20-3.32 (2H, m), 3.48-3.64 (2H, m), 4.20-4.22 (1H, d, J=8 Hz), 4.37-4.41 (1H, d, J=16 Hz), 4.54-4.58 (1H, d, J=16 Hz), 4.66-4.70 (1H, d, J=16 Hz), 5.49-5.51 (1H, d, J=8 Hz), 7.02-7.05 (1H, t, J=6 Hz), 7.15-7.27 (7H, m), 8.10-8.12 (1H, d, J=8 Hz), MS (LC/MS) m/z observed 546.97, expected 547.28 [M+H].

Example C12

(2S)-1-[(2R)-2-[(2S,3S)-3-Methyl-2-(2-Phenylacetamido)Pentanamido]Propanoyl]-N-(2H-1,2,3,4-Tetrazol-5-Ylmethyl)-2,3-Dihydro-1H-Indole-2-Carboxamide tert-Butyl ((R)-1-((S)-2-(((2H-tetrazol-5-yl)methyl)carbamoyl)indolin-1-yl)-1-oxopropan-2-yl)carbamate was prepared from I-2 and (R)-2-((tert-butoxycarbonyl)amino)propanoic acid using method C: MS (LC/MS) m/z observed 415.79, expected 416.20 [M+H], and observed 438.03, expected 438.19 [M+Na], Compound was confirmed using LC/MS and moved to next step as it was.

Title compound C12 was prepared from tert-butyl ((R)-1-((S)-2-(((2H-tetrazol-5-yl)methyl)carbamoyl)indolin-1-yl)-1-oxopropan-2-yl)carbamate and (2S,3S)-3-methyl-2-(2-phenylacetamido)pentanoic acid using method A: $^1$H NMR (400 MHz, CD$_3$OD) δ 0.83-0.91 (61H, m), 1.10-1.13 (1H, m), 1.34-1.36 (3H, d, J=8 Hz), 1.48-1.56 (1H, m), 1.82-1.91 (1H, m), 3.18-3.28 (2H, m), 3.48-3.64 (2H, m), 4.20-4.22 (1H, d, J=8 Hz), 4.36-4.40 (1H, d, J=16 Hz), 4.54-4.58 (1H, d, J=16 Hz), 4.68-4.72 (1H, d, J=16 Hz), 5.50-5.52 (1H, d, J=8 Hz), 7.02-7.06 (1H, t, J=8 Hz), 7.20-7.34 (7H, m), 8.11-8.13 (1H, d, J=8 Hz), MS (LC/MS) m/z observed, 546.99, expected 547.28 [M+H].

Example C13

(4S)-4-[(2S,3S)-3-Methyl-2-(2-Phenylacetamido)Pentanamido]-5-Oxo-5-[(2S)-2-[(2H-1,2,3,4-Tetrazol-5-Ylmethyl)Carbamoyl]-2,3-Dihydro-1H-Indol-1-Yl]Pentanoic Acid (S)-tert-Butyl 5-((S)-2-(((2H-tetrazol-5-yl)methyl)carbamoyl)indolin-1-yl)-4-((tert-butoxycarbonyl)amino)-5- oxopentanoate was prepared from I-2 and (S)-5-(tert-butoxy)-2-((tert-butoxycarbonyl)amino)-5-oxopentanoic acid using method C: MS (LC/MS) m/z observed 529.83, expected 530.27 [M+H]. Compound was confirmed using LC/MS and moved to next step as it was.

(S)-Ethyl 5-((S)-2-(((2H-tetrazol-5-yl)methyl)carbamoyl) indolin-1-yl)-4-((2S,3S)-3-methyl-2-(2-phenylacetamido) pentanamido)-5-oxopentanoate was prepared from (S)-tert-butyl 5-((S)-2-(((2H-tetrazol-5-yl)methyl)carbamoyl) indolin-1-yl)-4-((tert-butoxycarbonyl)amino)-5-oxopentanoate and I-7 using method F: MS (LC/MS) m/z observed 633.02, expected 633.32 [M+H]. Compound was confirmed using LC/MS and moved to next step as it was.

Title compound C13 was prepared from (S)-ethyl 5-((S)-2-(((2H-tetrazol-5-yl)methyl)carbamoyl)indolin-1-yl)-4-((2S,3S)-3-methyl-2-(2-phenylacetamido)pentanamido)-5-oxopentanoate using method D: $^1$H NMR (400 MHz, DMSO-d6) δ 0.74-0.81 (6H, m), 1.01-1.05 (1H, m), 1.20-1.27 (1H, m), 1.70-1.81 (2H, m), 2.25-2.31 (1H, m), 3.11-3.19 (1H, t, J=16 Hz), 3.36-3.61 (4H, m), 4.19-4.25 (1H, m), 4.32-4.38 (1H, m), 4.42-4.48 (1H, dd, J=8, 16 Hz), 4.54-4.60 (1H, dd, J=8, 16 Hz), 4.62-4.68 (1H, dd, J=8, 16 Hz), 5.17-5.20 (1H, d, J=12 Hz) 6.99-7.03 (1H, t, J=8 Hz), 7.15-7.26 (6H, m), 7.99-8.07 (2H, m), 8.81 (1H, bs), 8.98 (1H, bs), MS (LC/MS) m/z observed 604.97, expected 605.28 [M+H].

Example C14

(3S)-3-[(2S,3S)-3-Methyl-2-(2-Phenylacetamido) Pentanamido]-4-Ox-4-[((2)-2-[(2H-1,2,3,4-Tetrazol-5-Ylmethyl)Carbamoyl]-2,3-Dihydro-1H-Indol-1-Yl]Butanoic Acid (S)-tert-Butyl 4-((S)-2-(((2H-tetrazol-5-yl)methyl)carbamoyl)indolin-1-yl)-3-((tert-butoxycarbonyl)amino)-4-oxobutanoate was prepared from I-2 and (S)-4-(tert-butoxy)-2-((tert-butoxycarbonyl)amino)-4-oxobutanoic acid using method C: MS (LC/MS) m/z observed 515.74, expected 516.26 [M+H]. Compound was confirmed using LC/MS and moved to next step as it was.

(S)-Ethyl 4-((S)-2-(((2H-tetrazol-5-yl)methyl)carbamoyl) indolin-1-yl)-3-((2S,3S)-3-methyl-2-(2-phenylacetamido) pentanamido)-4-oxobutanoate was prepared from (S)-tert-butyl 4-((S)-2-(((2H-tetrazol-5-yl)methyl)carbamoyl) indolin-1-yl)-3-((tert-butoxycarbonyl)amino)-4-oxobutanoate and I-7 using method F: MS (LC/MS) m/z observed 618.93, expected 619.30 [M+H]. Compound was confirmed using LC/MS and moved to next step as it was.

Title compound C14 was prepared from (S)-ethyl 4-((S)-2-(((2H-tetrazol-5-yl)methyl)carbamoyl)indolin-1-yl)-3-((2S,3S)-3-methyl-2-(2-phenylacetamido)pentanamido)-4-oxobutanoate using method D: $^1$H NMR (400 MHz, DMSO-d6) δ 0.68-0.78 (6H, m), 0.95-1.04 (1H, m), 1.22-1.29 (1H, m), 1.66-1.73 (1H, m), 2.55-2.64 (2H, m), 3.15-3.19 (1H, d, J=16 Hz), 3.38-3.42 (1H, d, J=16 Hz), 3.48-3.56 (2H, t, J=16 Hz), 4.29-4.31 (1H, t, J=16 Hz), 4.39-4.44 (1H, dd, J=4, 16 Hz), 4.57-4.66 (2H, dt, J=4, 16 Hz), 5.61-5.63 (1H, d, J=8 Hz), 7.00-7.04 (1H, t, J=8 Hz), 7.14-7.25 (6H, m), 7.96-7.98 (1H, d, J=8 Hz), 8.04-8.06 (1H, d, J=8 Hz), 8.75 (1H, bs), 9.07 (1H, bs), MS (LC/MS) m/z observed 590.97, expected 591.27 [M+H] and observed 613.05, expected 613.25 [M+Na].

Example C15

(3R)-3-[(2S,3S)-3-Methyl-2-(2-Phenylacetamido) Pentanamido]-4-Oxo-4-[(2S)-2-[(2H-1,2,3,4-Tetrazol-5-Ylmethyl)Carbamoyl]-2,3-Dihydro-1H-Indol-1-Yl]Butanoic Acid (R)-tert-Butyl 4-((S)-2-(((2H-tetrazol-5-yl)methyl)carbamoyl)indolin-1-yl)-3-((tert-butoxycarbonyl)amino)-4-oxobutanoate was prepared from I-2 and (R)-4-(tert-butoxy)-2-((tert-butoxycarbonyl)amino)-4-oxobutanoic acid using method C: MS (LC/MS) m/z observed 515.77, expected 516.26 [M+H]. Compound was confirmed using LC/MS and moved to next step as it was.

(R)-Ethyl 4-((S)-2-(((2H-tetrazol-5-yl)methyl)carbamoyl)indolin-1-yl)-3-((2S,3S)-3-methyl-2-(2-phenylacetamido)pentanamido)-4-oxobutanoate was prepared from (R)-tert-butyl 4-((S)-2-(((2H-tetrazol-5-yl)methyl)carbamoyl)indolin-1-yl)-3-((tert-butoxycarbonyl)amino)-4-oxobutanoate and I-7 using method F: MS (LC/MS) m/z observed 618.94, expected 619.30 [M+H]. Compound was confirmed using LC/MS and moved to next step as it was.

Title compound C15 was prepared from (R)-ethyl 4-((S)-2-(((2H-tetrazol-5-yl)methyl)carbamoyl)indolin-1-yl)-3-((2S,3S)-3-methyl-2-(2-phenylacetamido)pentanamido)-4-oxobutanoate using method D: $^1$H NMR (400 MHz, DMSO-d6) δ 0.66-0.76 (6H, m), 0.96-1.05 (1H, m), 1.32-1.37 (1H, m), 1.60-1.66 (1H, m), 2.57-2.63 (2H, m), 3.13-3.17 (1H, t, J=8 Hz), 3.37-3.40 (1H, d, J=12 Hz), 3.46-3.52 (2H, t, J=12 Hz), 4.16-4.20 (1H, t, J=8 Hz), 4.39-4.42 (1H, d, J=12 Hz), 4.60-4.65 (2H, m), 5.60-5.63 (1H, d, J=12 Hz), 7.00-7.04 (1H, t, J=8 Hz), 7.14-7.23 (6H, m), 8.04-8.08 (1H, t, J=8 Hz), 8.04-8.06 (1H, d, J=8 Hz), 8.80 (1H, bs), 9.02 (1H, bs), MS (LC/MS) m/z observed 590.95, expected 591.27 [M+H] and observed 613.08, expected 613.25 [M+Na].

Example C16

(4R)-4-[(2S,3S)-3-Methyl-2-(2-Phenylacetamido) Pentanamido]-5-Oxo-5-[(2S)-2-[(2H-1,2,3,4-Tetrazol-5-Ylmethyl)Carbamoyl]-2,3-Dihydro-1H-Indol-1-Yl]Pentanoic Acid (R)-tert-Butyl 5-((S)-2-(((2H-tetrazol-5-yl)methyl)carbamoyl)indolin-1-yl)-4-((tert-butoxycarbonyl)amino)-5-oxopentanoate was prepared from I-2 and (R)-5-(tert-butoxy)-2-((tert-butoxycarbonyl)amino)-5-oxopentanoic acid using method C: MS (LC/MS) m/z observed 529.86, expected 530.27 [M+H]. Compound was confirmed using LC/MS and moved to next step as it was.

(R)-Ethyl 5-((S)-2-(((2H-tetrazol-5-yl)methyl)carbamoyl)indolin-1-yl)-4-((2S,3S)-3-methyl-2-(2-phenylacetamido)pentanamido)-5-oxopentanoate was prepared from (R)-tert-butyl 5-((S)-2-(((2H-tetrazol-5-yl)methyl)carbamoyl)indolin-1-yl)-4-((tert-butoxycarbonyl)amino)-5-oxopentanoate and I-7 using method F: MS (LC/MS) m/z observed 633.01, expected 633.32 [M+H]. Compound was confirmed using LC/MS and moved to next step as it was.

Title compound C16 was prepared from (R)-ethyl 5-((S)-2-(((2H-tetrazol-5-yl)methyl)carbamoyl)indolin-1-yl)-4-((2S,3S)-3-methyl-2-(2-phenylacetamido)pentanamido)-5-oxopentanoate using method D: $^1$H NMR (400 MHz, DMSO-d6) δ 0.75-0.82 (6H, m), 1.00-1.05 (1H, m), 1.21-1.27 (1H, m), 1.73-1.83 (2H, m), 2.27-2.33 (1H, m), 3.12-3.20 (1H, t, J=16 Hz), 3.36-3.61 (4H, m), 4.20-4.24 (1H, t, J=8 Hz), 4.32-4.36 (1H, t, J=8 Hz), 4.42-4.48 (1H, dd, J=8, 16 Hz), 4.54-4.60 (1H, dd, J=8, 16 Hz), 4.62-4.68 (1H, dd, J=8, 16 Hz), 5.17-5.20 (1H, d, J=12 Hz) 6.99-7.03 (1H, t, J=8 Hz), 7.12-7.26 (6H, m), 7.99-8.07 (2H, m), 8.80 (1H, bs), 9.02 (1H, bs), MS (LC/MS) m/z observed 604.95, expected 605.28 [M+H] and observed 627.08, expected 627.27 [M+Na].

Example C17

(5S)-5-[(2S,3S)-3-Methyl-2-(2-Phenylacetamido) Pentanamido]-6-Oxo-6-[(2S)-2-[(2H-1,2,3,4-Tetrazol-5-Ylmethyl)Carbamoyl]-2,3-Dihydro-1H-Indol-1-Yl]Hexanoic Acid (S)-tert-Butyl 6-((S)-2-(((2H-tetrazol-5-yl)methyl)carbamoyl)indolin-1-yl)-5-((tert-butoxycarbonyl)amino)-6-oxohexanoate was prepared from I-2 and (S)-6-(tert-butoxy)-2-((tert-butoxycarbonyl)amino)-6-oxohexanoic acid using method C: MS (LC/MS) m/z observed 543.87, expected 544.29 [M+H]. Compound was confirmed using LC/MS and moved to next step as it was.

(S)-Ethyl 6-((S)-2-(((2H-tetrazol-5-yl)methyl)carbamoyl)indolin-1-yl)-5-((2S,3S)-3-methyl-2-(2-phenylacetamido)pentanamido)-6-oxohexanoate was prepared from (S)-tert-butyl 6-((S)-2-(((2H-tetrazol-5-yl)methyl)carbamoyl)indolin-1-yl)-5-((tert-butoxycarbonyl)amino)-6-oxohexanoate and I-7 using method F: MS (LC/MS) m/z observed 647.01, expected 647.33 [M+H]. Compound was confirmed using LC/MS and moved to next step as it was.

Title compound C17 was prepared from (S)-ethyl 6-((S)-2-(((2H-tetrazol-5-yl)methyl)carbamoyl)indolin-1-yl)-5-((2S,3S)-3-methyl-2-(2-phenylacetamido)pentanamido)-6-oxohexanoate using method D: $^1$H NMR (400 MHz, DMSO-d6) δ 0.68-0.83 (6H, m), 0.95-1.08 (1H, m), 1.16-1.25 (1H, m), 1.30-1.40 (1H, m), 1.45-1.80 (4H, m), 2.00-2.25 (2H, m), 3.10-3.55 (4H, m), 4.18 (1H, bs), 4.35 (1H, dd, J=6 Hz, 9 Hz), 4.50 (1H, m), 4.65 (1H, dd, J=6 Hz, 16 Hz), 5.56 (1H, dd, J=3 Hz, 12 Hz), 6.93-7.02 (1H, m), 7.10-7.25 (7H, m), 7.90 (1H, d, J=9 Hz), 8.05 (1H, d, J=8 Hz), 8.52 (1H, d, J=7 Hz), 9.10 (1H, bs), MS (LC/MS) m/z observed 618.98, expected 619.30 [M+H].

Example C18

(2S)-1-[(2S)-6-Amino-2-[(2S,3S)-3-Methyl-2-(2-Phenylacetamido)Pentanamido]Hexanoyl]-N-(2H-1,2,3,4-Tetrazol-5-Ylmethyl)-2,3-Dihydro-1H-Indole-2-Carboxamide (S)-(5-Allyloxycarbonylamino-1-{(S)-2-[(2H-tetrazol-5-ylmethyl)-carbamoyl]-2,3-dihydro-indole-1-carbonyl}-pentyl)-carbamic acid tert-butyl ester was prepared from I-2 and (S)-6-(((allyloxy)carbonyl)amino)-2-((tert-butoxycarbonyl)amino)hexanoate dicyclohexylammonium salt using method C: MS (LC/MS) m/z observed 556.86, expected 557.28 [M+H]. Compound was confirmed using LC/MS and moved to next step as it was.

(S)-1-[6-(1-Allyloxy-vinylamino)-((S)-2-((2S,3S)-3-methyl-2-(2-phenylacetamido)pentanamido)hexanoyl)]-indoline-2-carboxylic acid (2H-tetrazol-5-ylmethyl)-amide was prepared from (S)-(5-allyloxycarbonylamino-1-{(S)-2-[(2H-tetrazol-5-ylmethyl)-carbamoyl]-2,3-dihydro-indole-1-carbonyl}-pentyl)-carbamic acid tert-butyl ester and I-7 using method A: MS (LC/MS) m/z observed 688.04, expected 688.36 [M+H]. Compound was confirmed using LC/MS and moved to next step as it was.

To a stirred solution of (S)-1-[6-(1-allyloxy-vinylamino)-((S)-2-((2S,3S)-3-methyl-2-(2-phenylacetamido)pentanamido)hexanoyl)]-indoline-2-carboxylic acid (2H-tetrazol-5-ylmethyl)-amide (0.145 mmol) and palladium on charcoal (10%, 10 mg) in methanol (2 mL), was added triethylsilane (145 mmol, 10 equivalents) under nitrogen. The reaction mixture was stirred at RT for 1 hr then concentrated to give a residue that was purified by reverse phase column chromatography to give the title compound C18. (1.5 mg): MS (LC/MS) m/z observed 604.24, expected 604.34 [M+H].

Example C19

Tert-Butyl N-[(2S)-1-{2-[(2S,3S)-3-Methyl-2-(2-Phenylacetamido)Pentanamido]Acetyl}-2-[(2H-1,2,3,4-Tetrazol-5-Ylmethyl)Carbamoyl]-2,3-Dihydro-1H-Indol-6-Yl]Carbamate Title compound C19 was prepared from I-12 and (2H-tetrazol-5-yl)methyl-amine using general method L. $^1$H NMR (400 MHz, CD$_3$OD) δ 0.88-0.98 (6H, m), 1.14-1.22 (1H, m), 1.30-1.41 (1H, m), 1.52 (9H, s), 1.87-2.01 (1H, m), 3.12-3.21 (1H, m), 3.59-3.69 (2H, m), 3.84-3.92 (1H, t, J=16 Hz), 4.16-4.24 (1H, t, J=16 Hz), 4.34-4.36 (1H, d, J=8 Hz), 4.51-4.53 (1H, d, J=8 Hz), 4.63-4.72 (2H, m), 5.15-5.17 (1H, d, J=8 Hz), 7.06-7.15 (2H, m), 7.18-7.22 (1H, m), 7.20-7.27 (1H, m), 7.29-7.34 (4H, m), 7.55 (1H, bs), 8.21 (1H, bs), 8.91 (1H, bs) MS (LC/MS) m/z observed 648.13, expected 648.32 [M+H]

Example C20

(2S)-6-Amino-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Title compound C20 was prepared from C19 using general method E. $^1$H NMR (400 MHz, CD$_3$OD) δ 0.76-0.85 (6H, m), 1.05-1.10 (1H, m), 1.30-1.42 (1H, m), 1.72-1.86 (1H, m), 3.13-3.17 (1H, d, J=16 Hz), 3.39-3.47 (2H, m), 3.54-3.71 (3H, m), 4.10-4.15 (1H, dd, J=16, 4 Hz), 4.19-4.26 (1H, m), 4.38-4.41 (1H, dd, J=8, 4 Hz), 4.53-4.69 (2H, m), 5.23-5.26 (1H, d, J=12 Hz), 6.96-6.98 (1H, d, J=8 Hz), 7.21-7.29 (5H, m), 8.01-8.12 (2H, m), 8.27-8.33 (1H, m), 9.17-9.22 (1H, m), 10.01 (1H, bs) MS (LC/MS) m/z observed 548.12, expected 548.32 [M+H]

Example C21

(2S)-6-(Benzylamino)-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide A solution of compound C20 (0.025 g, 0.0385 mmol), DIPEA (0.032 ml, 0.23 mmol) and benzyl bromide (0.015 ml, 0.116 mol) in DCM (4 ml) was sealed in a microwave tube and heated to 70° C. for 10 hr. by microwave irradiation. The reaction mixture was concentrated to dryness and dried well under vacuum to give the crude product, which was purified on preparative HPLC using 0-80% MeOH in water to yield product as an off-white solid 0.0022 g (9%). MS (LC/MS) m/z observed 638.11, expected 638.31 [M+H]. Compound was confirmed using LC/MS and used as directed.

Example C22

3-{[(2S)-1-{2-[(2S,3S)-3-Methyl-2-(2-Phenylacetamido)Pentanamido]Acetyl}-2-[(2H-1,2,3,4-Tetrazol-5-Ylmethyl)Carbamoyl]-2,3-Dihydro-1H-Indol-6-Yl]Carbamoyl}Propanoic Acid Title compound C22 was prepared from C19 and succinic anhydride using method B: $^1$H NMR (400 MHz, DMSO-d6) δ 0.78-0.87 (6H, m), 1.06-1.13 (1H, m), 1.30-1.42 (1H, m), 1.75-1.86 (1H, m), 3.03-3.07 (1H, d, J=16 Hz), 3.44-3.61 (5H, m), 4.09-4.19 (1H, m), 4.23-4.27 (1H, t, J=8 Hz), 4.40-4.44 (1H, t, J=8 Hz), 4.48-4.61 (2H, m), 5.14-5.17 (1H, d, J=12 Hz), 7.09-7.11 (1H, d, J=8 Hz), 7.18-7.22 (1H, m), 7.25-7.31 (4H, m), 7.40-7.44 (1H, t, J=8 Hz), 8.04-8.06 (1H, d, J=8 Hz), 8.12-8.14 (1H, t, J=8 Hz), 8.22 (1H, bs), 8.28-8.32 (1H, t, J=8 Hz), 8.95 (1H, bs), 9.96 (1H, s) 12.10 (1H, bs) MS (LC/MS) m/z observed 648.12, expected 648.28 [M+H]

Example C23

3-{[(S)-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)(Thiophen-3-Yl)Methyl]Carbamoyl}Propanoic Acid (S)-2-((tert-Butoxycarbonyl)amino)-2-(thiophen-3-yl) acetic acid was prepared from (S)-2-amino-2-(thiophen-3-yl)acetic acid using general method K. MS (LC/MS) m/z observed 279.92, expected 280.07 [M+Na]. Compound was confirmed using LC/MS and moved to next step as it was.

(S)-Ethyl 1-(2-((S)-2-((tert-butoxycarbonyl)amino)-2-(thiophen-3-yl)acetamido)acetyl)indoline-2-carboxylate was prepared from I-10 and (R)-2-((tert-butoxycarbonyl)amino)-2-(thiophen-3-yl)acetic acid using general method A. The purification was performed by column chromatography on silica gel using 0% to 50% ethyl acetate in hexanes as the eluent. MS (LC/MS) m/z observed 487.84, expected 488.18 [M+H], observed 510.06, expected 510.18 [M+Na]. Compound was confirmed using LC/MS and moved to next step as it was.

tert-Butyl ((S)-2-((2-((S)-2-(((2H-tetrazol-5-yl)methyl)carbamoyl)indolin-1-yl)-2-oxoethyl)amino)-2-oxo-1-(thiophen-3-yl)ethyl)carbamate was prepared from (S)-ethyl 1-(2-((R)-2-((tert-butoxycarbonyl)amino)-2-(thiophen-3-yl) acetamido)acetyl)indoline-2-carboxylate and (2H-tetrazol-5-yl)methyl-amine using general method L. MS (LC/MS) m/z observed 541.02, expected 541.19 [M+H]. Compound was confirmed using LC/MS and moved to next step as it was.

Title compound C23 was prepared from tert-butyl ((S)-2-((2-((S)-2-(((2H-tetrazol-5-yl)methyl)carbamoyl)indolin-1-yl)-2-oxoethyl)amino)-2-oxo-1-(thiophen-3-yl)ethyl)carbamate and succinic anhydride using method I: $^1$H NMR (400 MHz, DMSO-d6) δ 2.39-2.48 (2H, m), 3.12-3.16 (2H, d, J=16 Hz), 3.58-3.66 (3H, t, J=16 Hz), 4.20-4.24 (1H, d, J=16 Hz), 4.55-4.59 (1H, m), 4.62-4.69 (1H, m), 5.15-5.18 (1H, d, J=12 Hz), 5.64-5.68 (1H, t, J=8 Hz), 7.00-7.04 (1H, t, J=8 Hz), 7.18-7.22 (3H, m), 7.48-7.52 (2H, m), 8.04-8.06 (1H, d, J=8 Hz), 8.53-8.55 (1H, d, J=8 Hz), 8.61-8.64 (1H, m), 9.10 (1H, bs), MS (LC/MS) m/z observed 541.03, expected 541.15 [M+H]

Example C24

3-{[(R)-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)(Thiophen-2-Yl)Methyl]Carbamoyl}Propanoic Acid (R)-2-((tert-Butoxycarbonyl)amino)-2-(thiophen-2-yl) acetic acid was prepared from (R)-2-amino-2-(thiophen-2-yl)acetic acid using general method K. MS (LC/MS) m/z observed 279.92, expected 280.07 [M+Na]. Compound was confirmed using LC/MS and moved to next step as it was.

(S)-Ethyl 1-(2-((R)-2-((tert-butoxycarbonyl)amino)-2-(thiophen-2-yl)acetamido)acetyl)indoline-2-carboxylate was prepared from I-10 and (R)-2-((tert-butoxycarbonyl)amino)-2-(thiophen-2-yl)acetic acid using general method A. The purification was performed on normal phase using 0% to 50% ethyl acetate in hexanes as the eluent. MS (LC/MS) m/z observed 487.89, expected 488.18 [M+H], observed 510.06, expected 510.18 [M+Na]. Compound was confirmed using LC/MS and moved to next step as it was.

tert-Butyl ((S)-2-((2-((S)-2-(((2H-tetrazol-5-yl)methyl)carbamoyl)indolin-1-yl)-2-oxoethyl)amino)-2-oxo-1-(thiophen-2-yl)ethyl)carbamate was prepared from (S)-ethyl 1-(2-((R)-2-((tert-butoxycarbonyl)amino)-2-(thiophen-2-yl) acetamido)acetyl)indoline-2-carboxylate and (2H-tetrazol-5-yl)methyl-amine using general method L. MS (LC/MS) m/z observed 541.04, expected 541.19 [M+H]. Compound was confirmed using LC/MS and moved to next step as it was.

Title compound C24 was prepared from tert-butyl ((S)-2-((2-((S)-2-(((2H-tetrazol-5-yl)methyl)carbamoyl)indolin-1-yl)-2-oxoethyl)amino)-2-oxo-1-(thiophen-2-yl)ethyl)carbamate and succinic anhydride using method I: $^1$H NMR (400 MHz, DMSO-d6) δ 2.41-2.45 (2H, m), 3.10-3.14 (2H, d, J=16 Hz), 3.56-3.64 (3H, t, J=16 Hz), 4.19-4.23 (1H, d, J=16 Hz), 4.52-4.62 (2H, m), 5.14-5.17 (1H, d, J=12 Hz), 5.80-5.84 (1H, t, J=8 Hz), 6.95-6.98 (1H, m), 7.18-7.22 (3H, m), 6.99-7.01 (1H, d, J=8 Hz), 7.13-7.18 (2H, m), 7.20-7.22 (H d, d, J=8 Hz), 7.40-7.42 (1H, d, J=8 Hz), 8.01-8.03 (1H, d, J=8 Hz), 8.62-8.64 (2H, d, J=8 Hz), 9.04 (1H, bs), MS (LC/MS) m/z observed 541.01, expected 541.15 [M+H]

Example C25

4-Oxo-4-[(S)-2-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Piperidin-1-Yl]Butanoic Acid (S)-1-(tert-Butoxycarbonyl)piperidine-2-carboxylic acid was prepared from (S)-piperidine-2-carboxylic acid using general method K. MS (LC/MS) m/z observed 251.99, expected 252.13 [M+Na]. Compound was confirmed using LC/MS and moved to next step as it was.

1-{2-[(1-tert-Butoxycarbonyl-piperidine-(2S)-2-carbonyl)-amino]-acetyl}-(2S)-2,3-dihydro-1H-indole-2-carboxylic acid ethyl ester was prepared from I-10 and (S)-1-(tert-butoxycarbonyl)piperidine-2-carboxylic acid using general method A. The purification was performed by column chromatography on silica gel using 0% to 50% ethyl acetate in hexanes as the eluent. MS (LC/MS) m/z observed 459.96, expected 460.24 [M+H] observed 482.16, expected 482.24 [M+Na]. Compound was confirmed using LC/MS and moved to next step as it was.

(2S)-2-(2-Oxo-2-{(2S)-2-[(2H-tetrazol-5-ylmethyl)-carbamoyl]-2,3-dihydro-indol-1-yl}-ethylcarbamoyl)-piperidine-1-carboxylic acid tert-butyl ester was prepared from 1-{2-[(1-tert-butoxycarbonyl-piperidine-(2S)-2-carbonyl)-amino]-acetyl}-(2S)-2,3-dihydro-1H-indole-2-carboxylic acid ethyl ester and (2H-tetrazol-5-yl)methyl-amine using general method L. MS (LC/MS) m/z observed 513.08, expected 513.25 [M+H]. Compound was confirmed using LC/MS and moved to next step as it was.

Title compound C25 was prepared from (2S)-2-(2-oxo-2-{(2S)-2-[(2H-tetrazol-5-ylmethyl)-carbamoyl]-2,3-dihydro-indol-1-yl}-ethylcarbamoyl)-piperidine-1-carboxylic acid tert-butyl ester and succinic anhydride using method I: $^1$H NMR (400 MHz, DMSO-d6) δ 1.32-1.40 (2H, m), 1.55-1.64 (2H, m), 3.56-3.64 (3H, t, J=16 Hz), 2.19-2.22 (1H, d, J=12 Hz), 2.39-2.47 (2H, m), 2.60-2.64 (2H, t, J=8 Hz), 3.12-3.16 (1H, d, J=16 Hz), 3.79-3.83 (2H, d, J=16 Hz), 4.18-4.26 (1H, m), 4.32-4.35 (1H, d, J=12 Hz), 4.53-4.56 (2H, m), 5.10 (1H, s), 5.16-5.19 (1H, d, J=12 Hz), 6.99-7.03 (1H, t, J=8 Hz), 7.15-7.19 (1H, t, J=8 Hz), 7.22-7.24 (1H, d, J=8 Hz), 7.99-8.04 (2H, m), 9.09 (1H, bs), MS (LC/MS) m/z observed 512.99, expected 513.21 [M+H]

Example C26

(2S)-1-{2-[(2S,3S)-3-Methyl-2-[(Pyrimidin-2-Yl)Amino]Pentanamido]Acetyl}-N-(2H-1,2,3,4-Tetrazol-5-Ylmethyl)-2,3-Dihydro-1H-Indole-2-Carboxamide (2S)-Ethyl 1-(2-((2S,3S)-2-((tert-butoxycarbonyl)amino)-3-methylpentanamido)acetyl)indoline-2-carboxylate was prepared from I-10 and Boc-L-isoleucine using method A. MS (LC/MS) m/z observed 461.98, expected 462.26 [M+H]. Compound was confirmed using LC/MS and moved to next step as it was.

(2S)-1-[2-((2S,3S)-2-Amino-3-methyl-pentanoylamino)-acetyl]-2,3-dihydro-1H-indole-2-carboxylic acid ethyl ester hydrochloride was prepared from (2S)-ethyl 1-(2-((2S,3S)-2-((tert-butoxycarbonyl)amino)-3-methylpentanamido)acetyl)indoline-2-carboxylate using method E. MS (LC/MS) m/z observed 362.08, expected 362.20 [M+H]. Compound was confirmed using LC/MS and moved to next step as it was.

A solution of (2S)-1-[2-((2S,3S)-2-amino-3-methyl-pentanoylamino)-acetyl]-2,3-dihydro-1H-indole-2-carboxylic acid ethyl ester hydrochloride (0.3 g, 0.7537 mmol), DIPEA (0.46 ml, 2.638 mmol) and 2-chloropyrimidine (0.18 g, 1.131 mol) in ACN (9 ml) was sealed in a microwave tube and heated to 130° C. for 16 hrs by microwave irradiation. The reaction mixture was concentrated to dryness and dried well under vacuum to give the crude product, which was purified by column chromatography on silica gel to get the pure product, (2S)-1-{2-[(S)-3-Methyl-(S)-2-(pyrimidin-2-ylamino)-pentanoylamino]-acetyl}-2,3-dihydro-1H-indole-2-carboxylic acid ethyl ester, as off-white solid, 0.07 g (21%). MS (LC/MS) m/z observed 440.10, expected 440.22 [M+H]. Compound was confirmed using LC/MS and moved to next step as is.

Title compound C26 was prepared from (2S)-1-{2-[(S)-3-Methyl-(S)-2-(pyrimidin-2-ylamino)-pentanoylamino]-acetyl}-2,3-dihydro-1H-indole-2-carboxylic acid ethyl ester and (2H-tetrazol-5-yl)methyl-amine using general method L. $^1$H NMR (400 MHz, DMSO-d6) δ 0.82-0.86 (3H, t, J=8 Hz), 0.92-0.94 (3H, d, J=8 Hz), 1.16-1.25 (1H, m), 1.50-1.58 (1H, m), 1.84-1.92 (1H, m), 3.11-3.15 (2H, d, J=16 Hz), 3.52-3.60 (2H, m), 4.15-4.19 (1H, d, J=16 Hz), 4.37-4.41 (1H, t, J=8 Hz), 4.50-4.54 (1H, d, J=16 Hz), 4.62-4.66 (1H, d, J=16 Hz), 5.14-5.17 (1H, d, J=16 Hz), 6.60-6.62 (1 h, t, J=4 Hz), 6.92-6.94 (1H, d, J=8 Hz), 6.98-7.02 (1H, t, J=8 Hz), 7.14-7.18 (1H, t, J=8 Hz), 7.21-7.23 (1H, d, J=8 Hz), 8.00-8.02 (1H, d, J=8 Hz), 8.14 (1H, bs), 8.27-8.29 (2H, d, J=8 Hz), 9.05 (1H, bs), MS (LC/MS) m/z observed 493.14, expected 493.23 [M+H].

Example C27

(2S)-6-Acetamido-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Acetic acid (0.3 g, 4.854 mmol), EDC (1.02 g, 5.339 mmol), HOBt (0.74 g, 4.854 mmol), DIPEA (2.5 ml, 14.560 mmol) and I-11 (1 g, 4.845 mmol) were stirred in anhydrous DCM (100 ml) for 16 hrs. The reaction mixture was concentrated under vacuum to give the crude product, which was purified by column chromatography on silica gel using 0% to 50% ethyl acetate in hexanes as the eluent to give (S)-ethyl 6-acetamidoindoline-2-carboxylate as a pale yellow solid (72%). $^1$H NMR (400 MHz, CDCl$_3$) δ 1.27-1.31 (3H, t, J=8 Hz), 2.12 (3H, s), 3.32-3.37 (2H, m), 4.17-4.23 (2H, q, J=8 Hz), 4.35-4.38 (1H, q, J=4 Hz), 4.51 (1H, s), 6.71-6.73 (1H, d, J=8 Hz), 6.97-6.99 (1H, d, J=8 Hz), 7.05 (1H, s), 7.47 (1H, s), MS (LC/MS) m/z observed 249.07, expected 249.12[M+H].

(S)-Ethyl 6-acetamido-1-(2-((tert-butoxycarbonyl)amino)acetyl)indoline-2-carboxylate was prepared from (S)-ethyl 6-acetamidoindoline-2-carboxylate and Boc-glycine using method C and purified by column chromatography on silica gel using 0% to 80% ethyl acetate in hexanes as the eluent to give (S)-ethyl 6-acetamido-1-(2-((tert-butoxycarbonyl)amino)acetyl)indoline-2-carboxylate, as an off-white solid (62%). MS (LC/MS) m/z observed 405.86, expected 406.19 [M+H], observed 428.10, expected 428.19[M+Na], Compound was confirmed using LC/MS and moved to next step as it was.

(S)-Ethyl 6-acetamido-1-(2-((2S,3S)-3-methyl-2-(2-phenylacetamido)pentanamido)acetyl)indoline-2-carboxylate was prepared from the intermediate (S)-ethyl 6-acetamido-1-(2-((tert-butoxycarbonyl)amino)acetyl)indoline-2-carboxylate and I-7 using method A. MS (LC/MS) m/z observed 537.03, expected 537.26 [M+H]. Compound was confirmed using LC/MS and moved to next step as it was.

Title compound C27 was prepared from (S)-ethyl 6-acetamido-1-(2-((2S,3S)-3-methyl-2-(2-phenylacetamido)pentanamido)acetyl)indoline-2-carboxylate and (2H-tetrazol-5-yl)methyl-amine using general method L. $^1$H NMR (400 MHz, DMSO-d6) δ 0.78-0.86 (6H, m), 1.06-1.13 (1H, m), 1.29-1.44 (1H, m), 1.75-1.86 (1H, m), 2.01 (3H, s), 3.05-3.09 (2H, d, J=16 Hz), 3.43-3.61 (4H, m), 4.09-4.13 (1H, d, J=16 Hz), 4.19-4.28 (1H, m), 4.38-4.44 (1H, m), 4.51-4.59 (2H, m), 5.15-5.18 (1H, d, J=8 Hz), 7.09-7.11 (1H, d, J=8 Hz), 7.18-7.22 (1H, m), 7.27-7.31 (3H, m), 7.40-7.44 (1H, t, J=8 Hz), 8.02-8.04 (1H, d, J=8 Hz), 8.15-8.23 (1H, m), 8.26-8.31 (1H, m), 9.04 (1H, bs), 9.93 (1H, bs), MS (LC/MS) m/z observed 590.15, expected 590.28 [M+H], m/z observed 612.28, expected 612.28 [M+Na].

Example C28

4-Oxo-4-[(2S)-2-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Pyrrolidin-1-Yl]Butanoic Acid 1-{2-[(1-tert-Butoxycarbonyl-pyrrolidine-(2S)-2-carbonyl)-amino]-acetyl}-(2S)-2,3-dihydro-1H-indole-2-carboxylic acid ethyl ester was prepared from I-10 and Boc-L-proline using method A. MS (LC/MS) m/z observed 445.94, expected 446.23 [M+H]. Compound was confirmed using LC/MS and moved to next step as it was.

1-{2-[(1-tert-Butoxycarbonyl-pyrrolidine-(2S)-2-carbonyl)-amino]-acetyl}-(2S)-2,3-dihydro-1H-indole-2-carboxylic acid was prepared from 1-{2-[(1-tert-butoxycarbonyl-pyrrolidine-(2S)-2-carbonyl)-amino]-acetyl}-(2S)-2,3-dihydro-1H-indole-2-carboxylic acid ethyl ester using method D with 2 eq. of LiOH.H$_2$O. MS (LC/MS) m/z observed 417.90, expected 418.20 [M+H]. Compound was confirmed using LC/MS and moved to next step as it was.

(S)-tert-Butyl 2-((2-((S)-2-(((2H-tetrazol-5-yl)methyl)carbamoyl)indolin-1-yl)-2-oxoethyl)carbamoyl)pyrrolidine-1-carboxylate was prepared from 1-{2-[(1-tert-butoxycarbonyl-pyrrolidine-(2S)-2-carbonyl)-amino]-acetyl}-(2S)-2,3-dihydro-1H-indole-2-carboxylic acid and 2H-tetrazol-5-yl)methyl-amine using method A in DMF but without HCl treatment. MS (LC/MS) m/z observed 498.94, expected 499.24 [M+H]. Compound was confirmed using LC/MS and moved to next step as it was.

Title compound C28 was prepared from (S)-tert-butyl 2-((2-((S)-2-(((2H-tetrazol-5-yl)methyl)carbamoyl)indolin-1-yl)-2-oxoethyl)carbamoyl)pyrrolidine-1-carboxylate and succinic anhydride using method I. $^1$H NMR (400 MHz, DMSO-d6) δ 1.86-1.91 (2H, m), 1.95-2.05 (2H, m), 2.40-2.65 (4H, m), 3.11 (1H, m), 3.36 (1H, m), 3.46 (1H, m), 3.63 (1H, m), 4.15 (1H, dd, J=6, 17 Hz), 4.32 (1H, d, J=7 Hz), 4.48 (1H, dd, J=3, 9 Hz), 4.56 (1H, m), 4.65 (1H, m), 5.17 (1H, d, J=11 Hz), 7.01 (1H, t, J=8 Hz), 7.12-7.25 (2H, m), 8.00-8.10 (2H, m), 9.08 (1H, bs), MS (LC/MS) m, observed 499.11, expected 499.21 [M+H]

Example C29

3-{[1-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)Cyclopentyl]Carbamoyl}Propanoic Acid 1-{2-[(1-tert-Butoxycarbonylamino-cyclopentanecarbonyl)-amino]-acetyl}-(2S)-2,3-dihydro-1H-indole-2-carboxylic acid ethyl ester was prepared from I-10 and Boc-L-cycloleucine using method A. MS (LC/MS) m/z observed 459.95, expected 460.24 [M+H]. Compound was confirmed using LC/MS and moved to next step as it was.

1-{2-[(1-tert-Butoxycarbonylamino-cyclopentanecarbonyl)-amino]-acetyl}-(2S)-2,3-dihydro-1H-indole-2-carboxylic acid was prepared from 1-{2-[(1-tert-Butoxycarbonylamino-cyclopentanecarbonyl)-amino]-acetyl}-(2S)-2,3-dihydro-1H-indole-2-carboxylic acid ethyl ester using method D with 2 eq. of LiOH H$_2$O. MS (LC/MS) m/z observed 431.93, expected 432.21 [M+H]. Compound was confirmed using LC/MS and moved to next step as it was.

(2S)-[1-(2-Oxo-2-{2-[(2H-tetrazol-5-ylmethyl)-carbamoyl]-2,3-dihydro-indol-1-yl}-ethylcarbamoyl)-cyclopentyl]-carbamic acid tert-butyl ester was prepared from 1-{2-[(1-tert-butoxycarbonylamino-cyclopentanecarbonyl)-amino]-acetyl}-(2S)-2,3-dihydro-1H-indole-2-carboxylic acid and (2H-tetrazol-5-yl)methyl-amine using method A in DMF but without HCl treatment. MS (LC/MS) m/z observed 512.90, expected 513.26 [M+H]. Compound was confirmed using LC/MS and moved to next step as it was.

Title compound C29 was prepared from (2S)-[1-(2-Oxo-2-{2-[(2H-tetrazol-5-ylmethyl)-carbamoyl]-2,3-dihydro-indol-1-yl}-ethylcarbamoyl)-cyclopentyl]-carbamic acid tert-butyl ester and succinic anhydride using method 1. $^1$H NMR (400 MHz, DMSO-d6) δ 1.55-1.67 (4H, m), 1.83-1.93 (2H, m), 1.98-2.14 (2H, m), 2.34-2.39 (2H, m), 2.41-2.46 (2H, m), 3.11 (1H, m), 3.50-3.63 (2H, m), 4.05 (1H, m), 4.52 (1H, dd, J=7, 16 Hz), 4.68 (1H, dd, J=7, 16 Hz), 5.17 (1H, d, J=11 Hz), 7.01 (1H, t, J=8 Hz), 7.13-7.25 (2H, m), 7.65 (1H, t, J=5 Hz), 8.02 (1H, d, J=8 Hz), 8.12 (1H, bs), 9.10 (1H, bs), MS (LC/MS) m/z observed 513.06, expected 513.22 [M+H]

Example C30

(2S)-7-Acetamido-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Intermediate I-14 (500 mg, 2.427 mmol) and palladium on charcoal (100 mg) were placed in a round bottom flask under nitrogen. Ethanol (10 mL) was then added and hydrogen was bubbled in the reaction mixture for 4 hrs. Then the reaction mixture was filtered over CELITE® and the CELITE® was washed with ethanol (3×15 mL). The filtrate and washings were concentrated to give a brown oil that was further dissolved in DCM (50 mL) and to this was added acetic acid (140 uL, 2.427 mmol), HOBt (372 mg, 2.427 mmol), EDC (512 mg, 2.670 mmol) and DIPEA (845 uL, 4.854 mmol). The reaction was left at RT for 16 hrs and the solvent was evaporated. The product was purified by normal phase column chromatography using 25% to 55% ethyl acetate in hexanes as the eluent to give (S)-ethyl 7-acetamidoindoline-2-carboxylate as an off white solid (103 mg, 17%). $^1$H NMR (400 MHz, CDCl$_3$) δ 1.32 (3H, t, J=7.0 Hz), 2.19 (3H, s), 3.31 (1H, dd, J=8, 16 Hz), 3.45 (1H, dd, J=11, 16 Hz), 4.19-4.30 (2H, qd, J=2, 7 Hz), 4.51 (1H, dd, J=7, 10 Hz), 5.20 (1H, bs), 6.70 (1H, t, J=8 Hz), 6.85 (1H, d, J=8 Hz), 6.96 (1H, d, J=8 Hz), 7.40 (1H, bs), MS (LC/MS) m/z observed 249.07, expected 249.12 [M+H].

(S)-Ethyl 7-acetamido-1-(2-((tert-butoxycarbonyl)amino)acetyl)indoline-2-carboxylate was prepared from (S)-ethyl 7-acetamidoindoline-2-carboxylate and Boc-glycine using method C but purified by normal phase column chromatography using 25% to 55° %/ethyl acetate in hexanes as the eluent. MS (LC/MS) m/z observed 406.09, expected 406.20 [M+H]. Compound was confirmed using LC/MS and moved to next step as it was.

(S)-Ethyl 7-acetamido-1-(2-((2S,3S)-3-methyl-2-(2-phenylacetamido)pentanamido)acetyl)indoline-2-carboxylate was prepared from (S)-ethyl 7-acetamido-1-(2-((tert-butoxycarbonyl)amino)acetyl)indoline-2-carboxylate and I-7 using method A but the product was purified by normal phase column chromatography using 20% to 80% ethyl acetate in hexanes as the eluent. MS (LC/MS) m/z observed 537.08, expected 537.27 [M+H]. Compound was confirmed using LC/MS and moved to next step as it was.

The intermediate ((S)-7-Acetamido-1-(2-((2S,3S)-3-methyl-2-(2-phenylacetamido)pentanamido)acetyl)indoline-2-carboxylic acid) was prepared from (S)-ethyl 7-acetamido-1-(2-((2S,3S)-3-methyl-2-(2-phenylacetamido)pentanamido)acetyl)indoline-2-carboxylate using method D with 2 eq. of LiOH.H$_2$O. MS (LC/MS) m/z observed 509.08, expected 509.24 [M+H]. Compound was confirmed using LC/MS and moved to next step as it was.

Title compound C30 was prepared from (S)-7-acetamido-1-(2-((2S,3S)-3-methyl-2-(2-phenylacetamido)pentanamido)acetyl)indoline-2-carboxylic acid and (2H-tetrazol-5-yl)methyl-amine using method A in DMF but without HCl treatment. $^1$H NMR (400 MHz, CD$_3$OD) δ 0.88-0.92 (3H, t, J=7 Hz), 0.99 (3H, d, J=7 Hz), 1.15 (1H, m), 1.45 (1H, m), 1.92 (1H, m), 2.07 (3H, s), 3.25 (1H, d, J=16 Hz), 3.53-3.70 (3H, m), 4.05 (1H, m), 4.21-4.35 (2H, m), 4.51 (1H, dd, J=6, 12 Hz), 4.80 (1H, m), 5.28 (1H, t, J=9 Hz), 7.12-7.18 (3H, m), 7.23 (1H, m), 7.26-7.34 (4H, m), MS (LC/MS) m/z observed 590.17, expected 590.28 [M+H].

Example C31

Tert-Butyl N-[(2S)-1-{2-[(2S,3S)-3-Methyl-2-(2-Phenylacetamido)Pentanamido]Acetyl}-2-[(2H-1,2,3,4-Tetrazol-5-Ylmethyl)Carbamoyl]-2,3-Dihydro-1H-Indol-5-Yl]Carbamate Intermediate I-13 (1 g, 4.850 mmol) and palladium on charcoal (200 mg) were placed in a round bottom flask under nitrogen. Ethanol (20 mL) was then added and hydrogen was bubbled in the reaction mixture for 4 hrs. Then the reaction mixture was filtered over CELITE® and the CELITE® was washed with ethanol (3×25 mL). The filtrate and washings were concentrated to give a brown oil. This brown oil was the dissolved in toluene (50 mL) and phthalic anhydride (718 mg, 4.85 mmol) was added. The reaction was heated to 80° C. for 7 hrs and the solvent was evaporated. The product was purified by normal phase column chromatography using 5% to 20% ethyl acetate in hexanes as the eluent to give (S)-Ethyl 5-(1,3-dioxoisoindolin-2-yl)indoline-2-carboxylate as an off white solid (750 mg, 46° %). $^1$H NMR (400 MHz, CDCl$_3$) δ 1.31 (3H, t, J=7.0 Hz), 3.38 (1H, dd, J=6, 17 Hz), 3.45 (1H, dd, J=10, 17 Hz), 4.19-4.27 (2H, qd, J=2, 7 Hz), 4.43 (1H, dd, J=7, 10 Hz), 4.58 (1H, bs), 6.78 (1H, d, J=8 Hz), 7.05 (1H, dd, J=2, 8 Hz), 7.08 (1H, bs), 7.76-7.78 (2H, m), 7.91-7.95 (2H, m), MS (LC/MS) m/z observed 337.10, expected 337.12 [M+H].

(S)-Ethyl 1-(2-((tert-butoxycarbonyl)amino)acetyl)-5-(1,3-dioxoisoindolin-2-yl)indoline-2-carboxylate was prepared from (S)-ethyl 5-(1,3-dioxoisoindolin-2-yl)indoline-2-carboxylate and Boc-glycine using method C. MS (LC/MS) m/z observed 493.87, expected 494.19[M+H]. Compound was confirmed using LC/MS and moved to next step as it was.

(S)-Ethyl 5-(1,3-dioxoisoindolin-2-yl)-1-(2-((2S,3S)-3-methyl-2-(2-phenylacetamido)pentanamido)acetyl)indoline-2-carboxylate was prepared from (S)-ethyl 1-(2-((tert-butoxycarbonyl)amino)acetyl)-5-(1,3-dioxoisoindolin-2-yl)indoline-2-carboxylate and I-7 using method A but the product was purified by filtration of the reaction mixture. The solid obtained was the pure compound. MS (LC/MS) m/z observed 625.07, expected 625.27 [M+H]. Compound was confirmed using LC/MS and moved to next step as it was.

(S)-Ethyl 5-(1,3-dioxoisoindolin-2-yl)-1-(2-((2S,3S)-3-methyl-2-(2-phenylacetamido)pentanamido)acetyl)indoline-2-carboxylate (420 mg, 0.672 mmol) was dissolved in a 2:1 mixture DMF/EtOH (90 mL) and hydrazine hydrate 60% solution in water was added (75 uL 1.01 mmol). The reaction was heated to 40° C. for 1 hr and then to 80° C. for 5 hrs. LC/MS showed that the starting material was converted to the desired free amine. The solvents were evaporated and the residue was dissolved in EtOH (25 mL) and lithium hydroxide monohydrate (141 mg, 3.360 mmol) dissolved in water (25 mL) was added. The reaction was left at RT for 4 hrs and then acidified to pH 4 with a saturated solution of citric acid. The mixture was concentrated to dryness and the residue was suspended in water (25 mL) and the solid in suspension was filtered and washed with water (3×10 mL). (S)-5-amino-1-(2-((2S,3S)-3-methyl-2-(2-phenylacetamido)pentanamido)acetyl)indoline-2-carboxylic acid hydrochloride was obtained as a brown solid (325 mg, 96%). MS (LC/MS) m/z observed 466.99, expected 467.23 [M+H]. Compound was confirmed using LC/MS and moved to next step as it was.

(S)-5-Amino-1-(2-((2S,3S)-3-methyl-2-(2-phenylacetamido)pentanamido)acetyl)indoline-2-carboxylic acid hydrochloride (325 mg, 0.646 mmol) was dissolved in dioxane (20 mL) and NaOH (1M, 2 mL, 1.938 mmol) was added, followed by a solution of Boc$_2$O (1.41 g, 6.461 mmol) in dioxane (5 mL). The reaction was left at RT for 16 hrs and then acidified to pH 4 with citric acid (aqueous, saturated solution). The mixture was concentrated and the product was purified on a C18 column using 10-55% MeOH in water to yield (S)-5-((tert-butoxycarbonyl)amino)-1-(2-((2S,3S)-3-methyl-2-(2-phenylacetamido)pentanamido)acetyl)indoline-2-carboxylic acid as an off-white solid (255 mg, 70%). MS (LC/MS) m/z observed 567.10, expected 567.28 [M+H]. Compound was confirmed using LC/MS and moved to next step as it was.

Title compound C31 was prepared from (S)-5-((tert-butoxycarbonyl)amino)-1-(2-((2S,3S)-3-methyl-2-(2-phenylacetamido)pentanamido)acetyl)indoline-2-carboxylic acid and (2H-tetrazol-5-yl)methyl-amine using method A in DMF but without HCl treatment. $^1$H NMR (400 MHz, DMSO-d6) δ 0.65-0.87 (6H, m), 1.10 (1H, m), 1.43 (1H, m), 1.75 (1H, m), 3.00 (1H, d, J=16 Hz), 3.42-3.63 (4H, m), 4.10 (1H, m), 4.25 (1H, m), 4.45-4.67 (2H, m), 5.05 (1H, d, J=1 Hz), 6.35 (1H, d, J=8 Hz), 6.44 (1H, m), 7.23 (1H, m), 7.26-7.32 (4H, m), 7.72 (1H, d, J=9 Hz), 8.00-8.25 (2H, m), 8.95 (1H, bs), MS (LC/MS) m/z observed 648.10, expected 648.33 [M+H].

Example C32

(2S)-5-Amino-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Hydrochloride Title compound C32 was prepared from C31 using method E. $^1$H NMR (400 MHz, DMSO-d6) δ 0.75-0.87 (6H, m), 1.08 (1H, m), 1.40-1.50 (10H, m), 1.74 (1H, m), 3.10 (1H, d, J=16 Hz), 3.42-3.63 (4H, m), 4.10 (1H, m), 4.25 (1H, t, J=11 Hz), 4.40-4.67 (2H, m), 5.13 (1H, d, J=11 Hz), 7.14-7.21 (2H, m), 7.24-7.30 (4H, m), 7.36 (1H, m), 7.88 (1H, d, J=9 Hz), 8.11 (1H, d, J=9 Hz), 8.24 (1H, m), 9.00 (1H, bs), 9.27 (1H, bs), MS (LC/MS) m/z observed 548.05, expected 548.27 [M+H].

Example C33

(2S)-5-(Tert-Butylamino)-1-{2-[(2S,3S)-3-Methyl-2-(2-Phenylacetamido)Pentanamido]Acetyl}-N-(2H-1,2,3,4-Tetrazol-5-Ylmethyl)-2,3-Dihydro-1H-Indole-2-Carboxamide Title compound C32 (25 mg, 0.0428 mmol) was dissolved in DMF (5 mL) in a microwaved vial. Triethylamine (2 mL) and 2-bromo-2-methyl bromide (500 uL) were then added. The reaction was then microwaved at 100° C. for 15 minutes. Additional triethylamine (3 mL) and 2-bromo-2-methyl bromide (1 mL) were added and the reaction was microwaved for an additional 50 minutes at 100° C. Additional triethylamine (2 mL) 2-bromo-2-methyl bromide (1 mL) were added and the reaction was microwaved for an additional 30 minutes at 100° C. The reaction mixture was then filtered to remove salts and the filtrate was concentrated. The product was purified on a C18 column using 10-55% MeOH in water to yield title compound C33 as a brown solid (1.2 mg, 5%). MS (LC/MS) m/z observed 604.20, expected 604.34 [M+H].

Example C34

(2S)—N,N,N-Trimethyl-1-{2-[(2S,3S)-3-Methyl-2-(2-Phenylacetamido)Pentanamido]Acetyl}-2-[(2H-1,2,3,4-Tetrazol-5-Ylmethyl)Carbamoyl]-2,3-Dihydro-1H-Indol-5-Aminium Iodide C32 (25 mg, 0.0428 mmol) was dissolved in DMF (8 mL) in a microwavable vial. Triethylamine (500 uL) and methyl iodide (150 uL) were then added. The reaction was then microwaved at 75° C. for 35 minutes. The reaction mixture was then concentrated and the product was purified on a C18 column using 10-55% MeOH in water to yield title compound C34 as an off-white solid (4 mg, 13° %/). $^1$H NMR (400 MHz, DMSO-d6) δ 0.75-0.87 (6H, m), 1.08 (1H, m), 1.33 (1H, m), 1.74 (1H, m), 2.80-2.86 (9H, m), 3.03 (1H, d, J=16 Hz), 3.42-3.62 (4H, m), 4.10 (1H, m), 4.40 (1H, m), 4.54 (1H, m), 4.63 (1H, m), 5.10 (1H, m), 6.54 (1H, m), 6.64 (1H, bs), 7.20 (1H, m), 7.25-7.32 (4H, m), 7.86 (1H, m), 8.03 (1H, m), 8.09-8.18 (2H, m), 9.07 (1H, bs), MS (LC/MS) m/z observed 590.11, expected 590.32[M].

Example C35

(2S)-5-(Benzylamino)-1-{2-[(2S,3S)-3-Methyl-2-(2-Phenylacetamido)Pentanamido]Acetyl}-N-(2H-1,2,3,4-Tetrazol-5-Ylmethyl-2,3-Dihydro-1H-Indole-2-Carboxamide C32 (36 mg, 0.0616 mmol) was dissolved in DMF (5 mL) in a microwaved vial. Triethylamine (1 mL) and benzyl bromide (8 uL, 0.0678 mmol) were then added. The reaction was then microwaved at 50° C. for 35 minutes. Additional benzyl bromide (15 uL, 0.126 mmol) was added and the reaction was then microwaved at 50° C. for 30 additional minutes. The reaction mixture was then concentrated and the product was purified on a C18 column using 10-55% MeOH in water to yield title compound C35 as an off-white solid (5 mg, 13%). $^1$H NMR (400 MHz, DMSO-d6) δ 0.73-0.85 (6H, m), 1.08 (1H, m), 1.44 (1H, m), 1.75 (1H, m), 2.90 (1H, d, J=16 Hz), 3.42-3.62 (6H, m), 4.08 (1H, m), 4.41 (1H, m), 4.56 (1H, m), 4.68 (1H, m), 5.05 (1H, d, J=11 Hz), 6.35 (1H, m), 6.45 (1H, m), 7.19 (1H, m), 7.21-7.32 (6H, m), 7.33-7.39 (3H, m), 7.78 (1H, m), 8.03 (1H, m), 8.09-8.18 (2H, m), 9.10 (1H, bs), MS (LC/MS) m/z observed 637.99, expected 638.32 [M+H].

Example C36

(2S)-1-{2-[(2S,3S)-2-[(Dimethoxy-1,3,5-Triazin-2-Yl)Amino]-3-Methylpentanamido]Acetyl}-N-(2H-1,2,3,4-Tetrazol-5-Ylmethyl)-2,3-Dihydro-1H-Indole-2-Carboxamide A solution of (2S)-1-[2-((2S,3S)-2-amino-3-methyl-pentanoylamino)-acetyl]-2,3-dihydro-1H-indole-2-carboxylic acid ethyl ester hydrochloride (0.1 gm, 0.1941 mmol) that was prepared as in Example C26, DIPEA (0.085 ml, 0.291 mmol) and 2-chloro-4,6-dimethoxy-1,3,5-triazine (0.051 gm, 0.291 mmol) in ACN (3 ml) was sealed in a microwave tube and heated to 100° C. for 10 min by microwave irradiation. The reaction mixture was concentrated to dryness and dried well under vacuum to give the crude product, which was purified by column chromatography on silica gel to get the pure product (S)-1-(2-((2S,3S)-2-((4,6-dimethoxy-1,3,5-triazin-2-yl)amino)-3-methylpentanamido)acetyl)indoline-2-carboxylic acid ethyl ester as an off-white solid, 0.1 gm (80%). MS (LC/MS) m/z observed 501.15, expected 501.24 [M+H]. Compound was confirmed using LC/MS and moved to next step as it was.

Title compound C36 was prepared from (S)-1-(2-((2S,3S)-2-((4,6-dimethoxy-1,3,5-triazin-2-yl)amino)-3-methyl-pentanamido)acetyl)indoline-2-carboxylic acid ethyl ester and (2H-tetrazol-5-yl)methyl-amine using general method L. $^1$H NMR (400 MHz, DMSO-d6) δ 0.82-0.86 (3H, t, J=8 Hz), 0.90-0.92 (3H, d, J=8 Hz), 1.16-1.24 (1H, m), 1.46-1.53 (1H, m), 1.80-1.87 (1H, m), 3.11-3.15 (2H, d, J=16 Hz), 3.52-3.60 (2H, m), 3.84 (6H, s), 4.16-4.20 (1H, t, J=8 Hz), 4.35-4.42 (1H, m), 4.56-4.62 (1H, d, J=16 Hz), 5.16 (1H, s), 5.14-5.17 (1H, d, J=16 Hz), 6.60-6.62 (1 h, t, J=4 Hz), 6.99-7.03 (1H, t, J=8 Hz), 7.17-7.23 (2H, m), 7.81-7.85 (1H, t, J=8 Hz), 8.02 (1H, s), 8.20 (1H, bs), 8.28 (1H, bs), 9.06 (1H, bs) MS (LC/MS) m/z observed 554.18, expected 554.25 [M+H].

Example C37

(2S)-1-{2-[(2S)-2-[(Dimethoxy-1,3,5-Triazin-2-Yl)Amino]-3-Methylbutanamido]Acetyl}-N-(2H-1,2,3,4-Tetrazol-5-Ylmethyl)-2,3-Dihydro-1H-Indole-2-Carboxamide A solution of (S)-tert-butyl 2-amino-3-methylbutanoate hydrochloride (0.5 g, 2.8 mmol), DIPEA (1.16 ml, 6.7 mmol) and 2-chloro-4,6-dimethoxy-1,3,5-triazine (0.4 g, 1.9 mmol) in ACN (10 ml) was sealed in a microwave tube and heated to 100° C. for 10 min by microwave irradiation. The reaction mixture was concentrated to dryness and dried well under vacuum to give the crude product, which was purified by column chromatography on silica gel to get the pure product (S)-tert-butyl 2-((4,6-dimethoxy-1,3,5-triazin-2-yl)amino)-3-methylbutanoate as an off-white solid, 0.45 g (76%). $^1$H NMR (400 MHz, CDCl$_3$) δ 0.96-1.00 (6H, t, J=8 Hz), 1.45 (9H, s), 2.19-2.27 (1H, m), 3.94 (3H, s), 3.95 (3H, s), 4.58-4.61 (1H, q, J=4H), 5.76-5.78 (1H, d, J=8 Hz). MS (LC/MS) m/z observed 313.06, expected 313.18 [M+H]. Compound was confirmed using LC/MS and moved to next step as it was.

(S)-tert-Butyl 2-((4,6-dimethoxy-1,3,5-triazin-2-yl)amino)-3-methylbutanoate (0.1 g, 0.32 mmol) was stirred in 1:1 mixture of DCM:TFA (4 ml) for 2 hrs at RT. The reaction mixture was concentrated to dryness under vacuum and swapped with DCM (4 ml) three times. Resulting residue was dried well under vacuum and subjected to next reaction as it is. The residue obtained above, I-4 (0.11 g, 0.32 mmol), EDC (0.092 g, 0.48 mmol), HOBt (0.064 g, 0.42 mmol) and DIPEA (0.22 ml, 1.28 mmol) were stirred in anhydrous DCM (5 ml) for 16 hrs. The reaction mixture was concentrated under vacuum to give the crude product which was purified on a C18 column using 10-50% MeOH in water to yield the title compound C37 as an off-white solid (45%). $^1$H NMR (400 MHz, DMSO-d6) δ 0.92-0.98 (6H, m), 2.08-2.06 (1H, m), 1.80-1.87 (1H, m), 2.98-3.11 (2H, m), 3.52-3.58 (2H, m), 3.83 (6H, s), 4.13-4.17 (1H, t, J=8 Hz), 4.32-4.40 (2H, m), 4.47-4.52 (1H, m), 5.13-5.16 (1H, d, J=12 Hz), 6.98-7.02 (1H, t, J=8 Hz), 7.14-7.22 (2H, m), 7.77-7.81 (1H, t, J=8 Hz), 8.03-8.05 (1H, d, J=8 Hz), 8.23 (1H, bs), 8.34 (1H, bs), 8.72 (1H, bs) MS (LC/MS) m/z observed 540.17, expected 540.24 [M+H].

Example C38

3-{[(S)-({2-Oxo-2-[(2S)-2-[(2H-1,2,3,4-Tetrazol-5-Ylmethyl)Carbamoyl]-2,3-Dihydro-1H-Indol-1-Yl]Ethyl}Carbamoyl)(Phenyl)Methyl]Carbamoyl}Propanoic Acid (2S)-2-{[(tert-Butoxy)carbonyl]amino}-2-phenylacetic acid (3.0 g, 12.1 mmol, 92%) was collected as a colorless oil from (S)-phenylglycine (2.0 g, 13.2 mmol) using general method K. $^1$H NMR (400 MHz, CDCl$_3$) δ 7.98 (1H, bs), 7.44 (2H, d, J=7 Hz), 7.34 (3H, m), 5.14 (1H, d, J=7 Hz), 1.23 (9H, s), MS (LC/MS) m/z observed 273.96, expected 274.10 [M+Na]

(2S)-Ethyl 1-{2-[(2S)-2-{[(tert-butoxy)carbonyl]amino}-2-phenylacetamido]acetyl}-2,3-dihydro-1H-indole-2-carboxylate (131 mg, 0.27 mmol, 96%) was collected as an off white solid from the coupling of I-10 (80 mg, 0.28 mmol) with (2S)-2-{[(tert-butoxy)carbonyl]amino}-2-phenylacetic acid (71 mg 0.28 mmol) using general method M. MS (LC/MS) m/z observed 481.88, expected 482.23 [M+H]. Compound was confirmed using LC/MS and moved to next step as it was.

(2S)-1-{2-[(2S)-2-{[(tert-Butoxy)carbonyl]amino}-2-phenylacetamido]acetyl}-2,3-dihydro-1H-indole-2-carboxylic acid (130 mg, 0.28 mmol, 98%) was collected as an off white solid from (2S)-ethyl 1-{2-[(2S)-2-{[(tert-butoxy)carbonyl]amino}-2-phenylacetamido]acetyl}-2,3-dihydro-1H-indole-2-carboxylate (137 mg, 0.285 mmol) using general method D. In this example, the reaction was stopped after 30 min and a gradient of 10-70% MeOH in H$_2$O was used during purification. MS (LC/MS) m/z observed 453.89, expected 454.20 [M+H]. Compound was confirmed using LC/MS and moved to next step as it was.

tert-Butyl N—[(S)-({2-oxo-2-[(2S)-2-[(2H-1,2,3,4-tetrazol-5-ylmethyl)carbamoyl]-2,3-dihydro-1H-indol-1-yl]ethyl}carbamoyl)(phenyl)methyl]carbamate (96 mg, 0.18 mmol, 63%) was collected as an off white solid from (2S)-1-{2-[(2S)-2-{[(tert-butoxy)carbonyl]amino}-2-phenylacetamido]acetyl}-2, 3-dihydro-1H-indole-2-carboxylic acid (130 mg, 0.28 mmol) using general method O. MS (LC/MS) m/z observed 534.91, expected 535.24 [M+H]. Compound was confirmed using LC/MS and moved to next step as it was.

Title compound C38 (41 mg, 0.08 mmol, 43%) was collected as an off white solid from tert-butyl N—[(S)-({2-oxo-2-[(2S)-2-[(2H-1,2,3,4-tetrazol-5-ylmethyl)carbamoyl]-2,3-dihydro-1H-indol-1-yl]ethyl}carbamoyl)(phenyl)methyl]carbamate (96 mg, 0.18 mmol) using general method I. $^1$H NMR (400 MHz, DMSO-d6) δ 9.08 (1H, bs), 8.65 (1H, bs), 8.56 (1H, d, J=8 Hz), 8.05 (1H, d, J=8 Hz), 7.47 (2H, d, J=7 Hz), 7.34 (2H, t, J=7 Hz), 7.28 (1H, d, J=7 Hz), 7.26-7.15 (2H, m), 7.01 (1H, d, J=7 Hz), 5.60 (1H, d, J=6 Hz), 5.17 (1H, d, J=10 Hz), 4.65 (1H, dd, J=16, 5 Hz), 4.53 (1H, dd, J=16, 4 Hz), 4.22 (1H, dd, J=16, 5 Hz), 3.68-3.50 (2H, m), 3.14 (1H, d, J=16 Hz), 2.48-2.39 (4H, m), MS (LC/MS) m/z observed 534.97, expected 535.20 [M+H].

Example C39

(2S)-1-{2-[(2S,3S)-3-Methyl-2-[2-(2H-1,2,3,4-Tetrazol-5-Yl)Acetamido]Pentanamido]Acetyl}-N-(1H-1,2,3-Triazol-4-Ylmethyl)-2,3-Dihydro-1H-Indole-2-Carboxamide (2S)-1-[2-((2S,3S)-2-tert-Butoxycarbonylamino-3-methyl-pentanoylamino)-acetyl]-2,3-dihydro-1H-indole-2-carboxylic acid ethyl ester was prepared from I-10 and Boc-L-isoleucine using method A. MS (LC/MS) m/z observed 461.98, expected 462.26 [M+H]. Compound was confirmed using LC/MS and moved to next step as it was.

(2S)-1-[2-((2S,3S)-2-tert-Butoxycarbonylamino-3-methyl-pentanoylamino)-acetyl]-2,3-dihydro-1H-indole-2-carboxylic acid was prepared from (2S)-1-[2-((2S,3S)-2-tert-butoxycarbonylamino-3-methyl-pentanoylamino)-acetyl]-2,3-dihydro-1H-indole-2-carboxylic acid ethyl ester using method D with 2 eq. of LiOH.H$_2$O. MS (LC/MS) m/z observed 433.96, expected 434.23 [M+H]. Compound was confirmed using LC/MS and moved to next step as it was.

N-[(1S,2S)-2-Methyl-1-({2-oxo-2-[(2S)-2-[(1H-1,2,3-triazol-4-ylmethyl)carbamoyl]-2,3-dihydro-1H-indol-1-yl]ethyl}carbamoyl)butyl]carbamic acid tert-butyl ester was prepared from (2S)-1-[2-((2S,3S)-2-tert-Butoxycarbonylamino-3-methyl-pentanoylamino)-acetyl]-2,3-dihydro-1H-indole-2-carboxylic acid and (2H-1,2,3-triazol-4-yl)methyl-amine) using method A in DMF but without HCl treatment. MS (LC/MS) m/z observed 513.97, expected 514.28 [M+H]. Compound was confirmed using LC/MS and moved to next step as it was.

Title compound C39 was prepared from N-[(1S,2S)-2-methyl-1-({2-oxo-2-[(2S)-2-[(1H-1,2,3-triazol-4-ylmethyl)carbamoyl]-2,3-dihydro-1H-indol-1-yl]ethyl}carbamoyl)butyl]carbamic acid tert-butyl ester and 2-(2H-tetrazol-5-yl)acetic acid using method A but with DMF as solvent for the coupling reaction: $^1$H NMR (400 MHz, DMSO-d6) δ 0.82 (3H, t, J=7.4 Hz), 0.88 (3H, d, J=7 Hz), 1.12 (1H, m), 1.50 (1H, m), 1.78 (1H, m), 3.05 (1H, m), 3.56-3.67 (2H, m), 3.92-4.02 (2H, m), 4.13 (1H, m), 4.31 (1H, t, J=8 Hz), 4.37-4.43 (2H, m), 5.13 (1H, d, J=8 Hz), 7.01 (1H, t, J=8 Hz), 7.14-7.28 (2H, m), 7.70 (1H, s), 8.04 (1H, d, J=8 Hz), 8.34 (1H, bs), 8.47 (1H, d, J=9 Hz), 8.88 (1H, bs), MS (LC/MS) m/z observed 524.62, expected 524.25 [M+H].

Example D1

General Kinetic Enzyme Assay Protocol

A specific 2× assay buffer was prepared for the enzyme to be tested (see Table 2 for final 1× assay buffer compositions). If the assay buffer included DTT, it was added immediately prior to running the assay. A 2× enzyme mix was prepared (see Table 3 for enzyme assay conditions) at 80 uL per well. Compounds were screened at one or two appropriate concentrations (to determine the percent inhibition at those concentrations) and/or a full dose response curve (typically 8 points, to identify the IC$_{50}$) in duplicate, triplicate, or higher replicates as needed. An appropriate control was also assessed in full dose response, in duplicate for each assay/plate. Background control wells consisted of 1× assay buffer, DMSO (5% v/v) and substrate. Positive control wells consisted of enzyme, DMSO (5% v/v) and substrate. Test compounds and control compounds were diluted in DMSO to 40× the final desired concentration. For example, a test compound may be tested in dose response, in serial, tripling dilution condition starting at 20 uM and ending at 9.1 nM (or any appropriate concentration range and dilution scheme). Control compounds were prepared similarly. Diluted compounds were prepared in a dilution plate and transferred to the reaction plate (96-well medium binding plate (Greiner Bio-One FLUOTRAC™)) to allow for the desired final concentrations when added to the enzyme with AB. After mixing, the reaction plate was placed on a shaker (at 300 RPM) for 5 min, followed by incubation (covered) on the bench, for 20 min. Plates were warmed to reaction temperature (see Table 3) for a total incubation time of 30 min. Plates so prepared were ready for addition of substrate and the subsequent reaction.

An appropriate substrate for each assay was prepared in advance at 2× the final desired concentration (see Table 2) in DMSO. The appropriate substrate mix was added to each appropriate well on the reaction plate, and the plate was read immediately in the TECAN plate reader (TECAN INFINITE® M1000 Pro), set to the correct wavelength as needed for each assay (see Table 3) using 25 cycles, kinetic interval of 1 min, number of reads per well of 20 with shaking set to 1 s, double orbital, 2 mm amplitude. For fluorescent assays the gain was set to optimal (50%).

TABLE 2

Assay Buffer Composition.

| Enzyme | Assay Buffer Composition |
| --- | --- |
| Caspase 1, 3, 4, 5, 7, 8*, 9 & 10/a (General caspase assay buffer) | 50 mM HEPES pH 7.2<br>50 mM NaCl<br>0.1% (w/v) CHAPS<br>10 mM EDTA<br>5% (v/v) Glycerol<br>10 mM DTT |
| GzmB & Caspase 8 | 50 mM HEPES pH 7.5<br>10% (w/v) sucrose<br>0.2% (w/v) CHAPS<br>5 mM DTT |

*Can also use GzmB assay buffer for the Caspase-8 assay; Assay buffer components were sourced as follows: HEPES, DTT, Glycerol and sucrose: Sigma-Aldrich, St. Louis, MO, USA, NaCl and EDTA: Fisher Scientific, Pittsburgh, PA, USA, CHAPS: Calbiochem, Billerica, MA, USA.

TABLE 3

Enzyme assay conditions.

| Enzyme | | Substrate | | | Assay | |
| --- | --- | --- | --- | --- | --- | --- |
| Name | Conc. | Name | Conc. (μM) | Ex/Em λ* (nm) | Temp (° C.) | Control Inhibitor |
| hGzmB | 10 nM | Ac-IEPD-AMC | 150 | 380/460 | 30 | Ac-IEPD-CHO |
| Caspase-1 | 6.25 mU/μl | YVAD-AFC | 25 | 400/505 | 37 | Z-VAD-FMK |
| Caspase-3 and Caspase 7 | 6.25 mU/μl | Ac-DEVD-AMC | 20 | 380/460 | 37 | Z-VAD-FMK |
| Caspase-4 and Caspase-5 | 3.125 mU/ul | Ac-WEHD-AFC | 100 | 400/505 | 37 | Z-WEHD-FMK |
| Caspase-8 | 3.125 mU/ul | Ac-IEPD-AMC | 75 | 380/460 | 30 | Ac-IEPD-CHO |
| Caspase-9 | 3.125 mU/ul | LEHD-AFC | 50 | 400/505 | 37 | Q-LEHD-Oph |
| Caspase-10/a | 6.25 mU/μl | Ac-IETD-AMC | 100 | 400/505 | 30 | Ac-AEVD-CHO |

*Ex/Em λ is the excitation and emission wavelengths at which to measure fluorescence. Enzyme and substrate concentrations are the final concentrations in the well. Note that most protocols require preparing 2X enzyme and substrate mixes, as they are diluted 2-fold in the well.

Enzymes were sourced as follows: hGzmB, Froelich Lab, Northshore University Health Systems Research Institute, Evanston, Ill., USA; Caspases, Biovision Inc., Milpitas, Calif., USA. Substrates were sourced as follows: Ac-IEPD-AMC, California Peptide Research Inc., Napa, Calif., USA; YVAD-AFC, Biovision Inc., Milpitas, Calif., USA; Ac-DEVD-AMC, LEHD-AFC, AC-WEHD-AFC and Ac-IETD-AMC, Enzo Life Sciences Inc, Farmingdale, N.Y., USA. Control inhibitors were sourced as follows: Ac-IEPD-CHO, Ac-WEHD-FMK and Q-LEHD-Oph, Biovision Inc., Milpitas, Calif., USA; Z-VAD-FMK, R&D Systems, Minneapolis, Minn., USA; and Ac-AEVD-CHO, Enzo Life Sciences Inc, Farmingdale, N.Y., USA.

Example D2

Human Granzyme B Enzymatic Inhibition Assay

An in vitro fluorogenic detection assay for assessing the $IC_{50}$ and/or percent inhibition at a given concentration of inhibitors against human Granzyme B (hGzmB) enzyme was performed as described in Example D1. When appropriate, percent inhibition data was collected and fitted to generate $IC_{50}$ data using GraphPad Prism 5 (GraphPad Software, La Jolla Calif. USA, www.graphpad.com) and its non-linear regression analysis tools or other equivalent tools.

Select compounds of Examples A1-A57, B1-B7 and C1-C39 exhibited inhibitory activity against hGzmB. Each of the compounds of the invention identified in Table 1 exhibited Granzyme B inhibitory activity.

In certain embodiments, select compounds exhibited $IC_{50} < 50,000$ nM. In other embodiments, select compounds exhibited $IC_{50} < 10,000$ nM. In further embodiments, select compounds exhibited $IC_{50} < 1,000$ nM. In still further embodiments, select compounds exhibited $IC_{50} < 100$ nM. In certain embodiments, select compounds exhibited $IC_{50}$ from 10 nM to 100 nM, preferably from 1 nM to 10 nM, more preferably from 0.1 nM to 1 nM, and even more preferably from 0.01 nM to 0.1 nM.

Example D3

Human Caspase Enzymatic Inhibition Assay

In vitro fluorogenic detection assays for assessing the $IC_{50}$ and/or percent inhibition at a given concentration of inhibitors, against a set of human Caspase enzymes, was performed as described in Example D1. Representative compounds of the invention do not significantly inhibit any caspase enzyme tested at a concentration of 5 μM.

In certain embodiments, the compounds exhibited less than 50% inhibition at 50 μM. In other embodiments, the compounds exhibited greater than 50% inhibition at 50 μM, but less than 10% inhibition at 25 μM.

Example D4

Kinetic Solubility Determination

Kinetic solubility buffer (phosphate buffered saline (PBS, 1×) at pH 7.4) was prepared from PBS (10×) solution, (Fisher Scientific, Pittsburgh, Pa., USA, 10×), by adding PBS (50 mL, 10×) to approximately water (450 mL HPLC grade). The volume of the solution was then adjusted to 500 mL for a total dilution factor of 1:10 and a final PBS concentration of 1×. The pH of the final solution (PBS (1×)) was measured and found to be 7.4.

A DMSO stock solution (typically 10 mM or greater) was used for each compound to be tested. A final DMSO concentration of 2.0% and maximum theoretical compound concentration of typically 200 μM (or greater) was achieved by diluting an aliquot (6 μl) of each stock with kinetic solubility buffer (294 μl, PBS (1×) at pH 7.4) using a liquid handling system (Hamilton STARlet, Hamilton Robotics, Inc., Reno, Nev., USA) and incubated directly in a solubility filter plate (Millipore, Billerica, Mass., USA). Following 24 hour incubation at ambient temperature (20.5-21.7° C.), each sample was vacuum filtered. The filtrate was injected into the chemiluminescent nitrogen detector for quantification (Automated Discovery Workstation, Analiza, Inc., Cleveland, Ohio, USA). Each result was reported both in μM and μg/mL units. Three separate on-board performance indicating standards were assayed in triplicate with each test compound to ensure test results were within the acceptable range.

The equimolar nitrogen response of the detector was calibrated using standards which spanned the dynamic range of the instrument from 0.08 to 4500 μg/ml nitrogen. Each filtrate was quantified with respect to this calibration curve. Each calculated solubility value was corrected for background nitrogen present in the DMSO, and buffer used to prepare each sample. All reported values for samples containing adjacent nitrogen atoms in a ring structure were corrected for the expected non-equimolar response. Each calculated solubility result assumed that each sample was free of nitrogen containing impurities and was stable under the assay conditions. Analyses were performed at Analiza Inc. (Cleveland, Ohio, USA) by published methods (Bhattachar, S. N., et al, *J. Pharma. BioMed Anal.* 41:152-7 2006).

TABLE 4

Kinetic solubility in PBS.

| Code Willoughby 20 | Solubility in aqueous PBS Buffer (1X, pH 7.4) | |
| --- | --- | --- |
|  | uM 4.2-4.9 | ug/mL 2.6-3.0 |
| A1 | 144 | 77 |
| A2 | >150.0 | >80.0 |
| A3 | 139 | 74 |
| A4 | >150 | >80 |
| A6 | >150 | >78 |
| A7 | 124 | 67 |
| A8 | >150 | >88 |
| A10 | >750 | >443 |
| A12 | 594 | 323 |
| A13 | >750 | >386 |
| A14 | 107 | 57 |
| A15 | 565 | 258 |

TABLE 4-continued

Kinetic solubility in PBS.

| Code Willoughby 20 | Solubility in aqueous PBS Buffer (1X, pH 7.4) | |
| --- | --- | --- |
|  | uM 4.2-4.9 | ug/mL 2.6-3.0 |
| A16 | >750 | >385 |
| A17-1 | >750 | >407 |
| A17-2 | >750 | >407 |
| A18 | 679 | 447 |
| A19 | 672 | 391 |
| A20-1 | 535 | 358 |
| A20-2 | 641 | 429 |
| A21-1 | >750 | >425 |
| A21-2 | >750 | >425 |
| A22-1 | >750 | >416 |
| A22-2 | >750 | >416 |
| A23-1 | >750 | >426 |
| A23-2 | 679 | 386 |
| A24 | 719 | 441 |
| A25 | 696 | 462 |
| A26-1 | >750 | >395 |
| A26-2 | 685 | 361 |
| A27 | 53 | 31 |
| A28 | >750 | >393 |
| A30-1 | >750 | >396 |
| A30-2 | >750 | >396 |
| A32 | >750 | >410 |
| A34 | >750 | >443 |
| A43 | 583 | 342 |
| A44 | 724 | 467 |
| A45 | 682 | 359 |
| A46 | >750 | >375 |
| A52 | >750 | >418 |
| A53 | >750 | >407 |
| A54-1 | 451 | 273 |
| A54-2 | >750 | >454 |
| A55 | >750 | >418 |
| A56 | >750 | >407 |
| B1 | 97 | 62 |
| B2 | 12.6 | 8.4 |
| C1 | >150 | >78 |
| C11 | 125 | 68 |
| C12 | 112 | 61 |
| C13 | >750 | >454 |
| C20 | 596 | 348 |
| C22 | >750 | >486 |
| C24 | >750 | >405 |
| C27 | >750 | >442 |
| C32 | >750 | >438 |

Example D5

General Kinetic Enzyme Assay Protocol (384 Well)

A specific 2× assay buffer was prepared for the enzyme to be tested (see Table 5 for final 1× assay buffer compositions). If the assay buffer included DTT, it was added immediately prior to running the assay. A 2× enzyme mix was prepared (see Table 3 for enzyme assay conditions) at 26 uL per well. Compounds were screened at one or two appropriate concentrations (to determine the percent inhibition at those concentrations) and/or a full dose response curve (typically 12 points, to identify the $IC_{50}$) in duplicate, triplicate, or higher replicates as needed. An appropriate control was also assessed in full dose response, in duplicate for each assay/plate. Background control wells consisted of 1× assay buffer and substrate. Positive control wells consisted of enzyme (no DMSO) and substrate. Test compounds and control compounds were diluted in 1× Assay Buffer to 15× the final desired concentration. For example, a test compound may be tested in dose response, in serial, tripling dilution condition starting at 20 uM and ending at 0.1 nM (or any appropriate concentration range and dilution scheme). Control compounds were prepared similarly. Diluted compounds were prepared in a dilution plate and transferred to the reaction plate (384-well medium binding plate (Greiner Bio-One FLUOTRAC™)) to allow for the desired final concentrations when added to the enzyme with AB. After mixing, the reaction plate was placed on a shaker (at 300 RPM) for 5 min, followed by incubation (covered) on the bench, for 20 min. Plates were warmed to reaction temperature (see Table 6) for 5 mins for a total incubation time of 30 min. Plates so prepared were ready for addition of substrate and the subsequent reaction.

An appropriate substrate for each assay was prepared in advance at 2× the final desired concentration (see Table 5) in assay buffer. 30 uL of the appropriate substrate mix was added to each appropriate well on the reaction plate, and the plate was read immediately in the TECAN plate reader (TECAN INFINITE® M1000 Pro), set to the correct wavelength as needed for each assay (see Table 6) using 15 cycles, kinetic interval of 1 min, number of reads per well of 20 with shaking set to 1 s, double orbital, 2 mm amplitude. For fluorescent assays the gain was set to optimal (100% with gain regulation) for all assays except human GzmB which was set to 85 (with the z set at 23000 um).

TABLE 5

Assay Buffer Composition.

| Enzyme | Assay Buffer Composition |
|---|---|
| Caspase 1, 3, 4, 5, 7, 8*, 9 & 10/a (General caspase assay buffer) | 50 mM HEPES pH 7.2<br>50 mM NaCl<br>0.1% (w/v) CHAPS<br>10 mM EDTA<br>5% (v/v) Glycerol<br>10 mM DTT |
| GzmB & Caspase 8 | 50 mM HEPES pH 7.5<br>0.2% (w/v) CHAPS<br>5 mM DTT |
| Cathepsin G | 320 mM Tris-HCL pH 7.4<br>3.2M NaCl |

*Can also use GzmB assay buffer for the Caspase-8 assay; Assay buffer components were sourced as follows: HEPES, DTT, Glycerol and sucrose: Sigma-Aldrich, St. Louis, MO, USA, NaCl and EDTA: Fisher Scientific, Pittsburgh, PA, USA, CHAPS: Calbiochem, Billerica, MA, USA.

TABLE 6

Enzyme assay conditions.

| Enzyme | | Substrate | | | Assay | |
|---|---|---|---|---|---|---|
| Name | Conc. | Name | Conc. (μM) | Ex/Em λ* (nm) | Temp (°C.) | Control Inhibitor |
| hGzmB | 10 nM | Ac-IEPD-AMC | 50 | 380/460 | 30 | V2248 |
| Caspase-1 | 12.5 mU/μL | YVAD-AFC | 5 | 400/505 | 37 | Z-VAD-FMK |
| Caspase-3 and Caspase 7 | 0.8 mU/μL & 1.5 mU/μL | Ac-DEVD-AMC | 40 &5 | 380/460 | 37 | Z-VAD-FMK |
| Caspase-4 and Caspase-5 | 3.125 mU/uL & 1.5 mU/uL | Ac-WEHD-AFC | 40 & 100 | 400/505 | 37 | Z-WEHD-FMK |
| Caspase-8 | 4 mU/uL | Ac-IEPD-AMC | 80 | 380/460 | 37 | Ac-IEPD-CHO |
| Caspase-9 | 2 mU/uL | LEHD-AFC | 50 | 400/505 | 37 | Q-LEHD-Oph |
| Caspase-10/a | 3 mU/μL | Ac-IETD-AMC | 10 | 400/505 | 37 | Ac-AEVD-CHO |
| Cathepsin G | 200 nM | Suc-AAPF-pNA | 200 uM | 410 absorbance | 25 | Cat G inhibitor |
| Human Neutrophil Elastase | 0.125 ug/mL | MeOSuc-AAPF-AFC | 50 | 384/500 | 37 | Sivelestat |

*Ex/Em λ is the excitation and emission wavelengths at which to measure fluorescence. Enzyme and substrate concentrations are the final concentrations in the well. Note that most protocols require preparing 2X enzyme and substrate mixes, as they are diluted 2-fold in the well.

Enzymes were sourced as follows: hGzmB, Froelich Lab, Northshore University Health Systems Research Institute, Evanston, Ill., USA; Caspases and Elastase, Biovision Inc., Milpitas, Calif., USA; Cathepsin G, Athens Research and Technologies, Athens, Ga., USA. Substrates were sourced as follows: Ac-IEPD-AMC, California Peptide Research Inc., Napa, Calif., USA; YVAD-AFC and MeOSuc-AAPF-AFC Biovision Inc., Milpitas, Calif., USA; LEHD-AFC and Suc-AAPF-pNA Millipore, Billerica Mass., USA. Ac-DEVD-AMC, AC-WEHD-AFC and Ac-IETD-AMC, Enzo Life Sciences Inc, Farmingdale, N.Y., USA. Control inhibitors were sourced as follows: Ac-IEPD-CHO, Ac-WEHD-FMK, Q-LEHD-Oph and CatG inhibitor, Biovision Inc., Milpitas, Calif., USA; Z-VAD-FMK, R&D Systems, Minneapolis, Minn., USA; and Ac-AEVD-CHO. Enzo Life Sciences Inc, Farmingdale, N.Y., USA. Sivelestat, Tocris Bioscience, Bristol, UK.

$IC_{50}$ data for representative compounds is set forth in Table 7.

Activity Codes:
A<100 nM;
100 nM<B<1,000 nM;
1,000 nM<C<10,000 nM;
D>10,000 nM

TABLE 7

$IC_{50}$ data for representative compounds.

| Compound | Activity Range |
|---|---|
| A5 | A |
| A13 | A |
| A14 | A |
| A16 | A |
| A17 | A |
| A18 | A |
| A19 | A |
| A20-1 | A |
| A20-2 | A |
| A21-1 | A |
| A21-2 | A |
| A22-1 | A |
| A22-2 | A |
| A23-1 | A |
| A23-2 | A |
| A24 | A |
| A25 | A |
| A26-1 | A |
| A26-2 | A |
| A27 | A |
| A28 | A |
| A30-1 | A |
| A30-2 | A |
| A31 | A |
| A32 | A |
| A33 | A |
| A34 | A |
| A35 | A |
| A36 | A |
| A43 | A |
| A45 | A |
| A46 | A |
| A51 | A |
| A52 | A |
| A53 | A |
| A54-1 | A |
| A54-2 | A |
| A55 | A |
| A56 | A |
| A57-1 | A |
| A57-2 | A |
| C22 | A |
| C39 | A |
| A1 | B |
| A2 | B |

TABLE 7-continued $IC_{50}$ data for representative compounds.

| Compound | Activity Range |
|---|---|
| A3 | B |
| A4 | B |
| A8 | B |
| A9 | B |
| A10 | B |
| A12 | B |
| A15 | B |
| A17-1 | B |
| A17-2 | B |
| A29 | B |
| A37 | B |
| A38 | B |
| A39 | B |
| A40 | B |
| A44 | B |
| A47 | B |
| A49 | B |
| A50 | B |
| B1 | B |
| B7 | B |
| C1 | B |
| C13 | B |
| C16 | B |
| C19 | B |
| C20 | B |
| C24 | B |
| C27 | B |
| C31 | B |
| C32 | B |
| C38 | B |
| A6 | C |
| A7 | C |
| A11 | C |
| A42 | C |
| A48 | C |
| B3 | C |
| B5 | C |
| B6 | C |
| C4 | C |
| C5 | C |
| C6 | C |
| C7 | C |
| C11 | C |
| C14 | C |
| C15 | C |
| C17 | C |
| C23 | C |
| C25 | C |
| I5 | C |
| A41 | D |
| C2 | D |
| C3 | D |
| C8 | D |
| C9 | D |
| C10 | D |
| C12 | D |
| C18 | D |
| C21 | D |
| C26 | D |
| C28 | D |
| C29 | D |
| C30 | D |
| C33 | D |
| C34 | D |
| C35 | D |

Example D6

Human Granzyme B Enzymatic Inhibition Assay

An in vitro fluorogenic detection assay for assessing the $IC_{50}$ and/or percent inhibition at a given concentration of inhibitors against human Granzyme B (hGzmB) enzyme was performed as described in Example D5. When appropriate, percent inhibition data was collected and fitted to generate $IC_{50}$ data using GraphPad Prism 5 (GraphPad Software, La Jolla Calif. USA, www.graphpad.com) and its non-linear regression analysis tools or other equivalent tools.

Select compounds of Examples A1-A57, B1-B7 and $C_1$-$C_{39}$ exhibited inhibitory activity against hGzmB. Each of the compounds of the invention identified in Table 1 exhibited Granzyme B inhibitory activity.

In certain embodiments, select compounds exhibited $IC_{50}$<50,000 nM. In other embodiments, select compounds exhibited $IC_{50}$<10,000 nM. In further embodiments, select compounds exhibited $IC_{50}$<1,000 nM. In still further embodiments, select compounds exhibited $IC_{50}$<100 nM. In certain embodiments, select compounds exhibited $IC_{50}$ from 10 nM to 100 nM, preferably from 1 nM to 10 nM, more preferably from 0.1 nM to 1 nM, and even more preferably from 0.01 nM to 0.1 nM.

Example D7

Human Caspase Enzymatic Inhibition Assay

In vitro fluorogenic detection assays for assessing the $IC_{50}$ and/or percent inhibition at a given concentration of inhibitors, against a set of human Caspase enzymes, was performed as described in Example D5. Representative compounds of the invention do not significantly inhibit any caspase enzyme tested at a concentration of 50 µM.

In certain embodiments, the compounds exhibited less than 50% inhibition at 50 µM. In other embodiments, the compounds exhibited greater than 50% inhibition at 50 µM, but less than 10% inhibition at 25 µM.

Example D8

Inhibition of Fibronectin Cleavage by GzmB

Black, 96 well high-binding assay plates (Griener Bio-one) were treated overnight at 4° C. with 40 uL of 8 ug/mL Hilyte Fluor 488 labeled Fibronectin (Cytoskeleton, Inc). After fibronectin coating, plates were washed 3 times in buffer (20 mM Tris-HCl, pH 7.4, 20 mM NaCl) then once with granzyme B assay buffer (50 mM HEPES, pH 7.5, 0.1% CHAPS). After washing, 50 uL of granzyme B assay buffer was added to each fibronectin-coated well. In a separate non-binding 96 well assay plate 5 uL of 20× inhibitor serial dilution stocks were added to 45 uL of 2.22×GzmB mix to establish inhibition (enzyme/inhibitor mixes were all prepared in granzyme B assay buffer and were incubated first at room temperature for 20 minutes, then at 30° C. for another 10 minutes). After incubation, 50 uL of this 2× enzyme/inhibitor mix was added to the corresponding coated well to initiate fibronectin cleavage (20 nM final granzyme B concentration, 8-point inhibitor dilution series starting at 50 uM). The assay was conducted at 30° C. in the TECAN plate reader (TECAN INFINITE® M1000 Pro), which was programmed to monitor the kinetic fluorescence polarization signal (filter set Ex/Em 470 nm/527 nm) with readings taken every minute, for 1 hour. Proteolytic activity was evaluated as the rate of fluorescence enhancement in the parallel emission over the linear range of the reaction. % Inhibition values were calculated from assay controls and the resulting date is shown in Table 8.

TABLE 8

Inhibition of Fibronectin Cleavage by GzmB Results.

| | Percent Inhibition at Inhibitor Concentration | | |
|---|---|---|---|
| Compound | 50 uM | 5.56 uM | 0.62 uM |
| A13 | 82% | 52% | 11% |
| A27 | 102% | 96% | 57% |
| A28 | 98% | 79% | 45% |

Example D9

Inhibition of Cell Adhesion by GzmB Cleavage of Fibronectin

Black, 96 well high-binding clear-bottom assay plates (Griener Bio-one) were treated overnight at 4° C. with 40 uL of 5 ug/mL Fibronectin (Sigma-Aldrich). After fibronectin coating, wells were washed 3 times in Tris wash buffer (20 mM Tris-HCl, pH 7.4, 20 mM NaCl) then once with granzyme B assay buffer (HEPES, (50 mM, pH 7.5), CHAPS (0.1%)). After washing, 50 uL of granzyme B assay buffer was added to each fibronectin-coated well. In a separate non-binding 96 well assay plate 5 uL of relevant 20× inhibitor dilution stocks were added to 45 uL of 2.22×GzmB mix to establish inhibition (enzyme/inhibitor mixes were all prepared in granzyme B assay buffer and were incubated first at room temperature for 20 minutes, then at 30° C. for another 10 minutes). After incubation, 50 uL of this 2× enzyme/inhibitor mix was added to the corresponding coated well to initiate fibronectin cleavage (20 nM final granzyme B concentration, 3 final inhibitor concentrations—0.1 uM, 10 uM and 100 uM). The assay was conducted at 30° C. in a plate warmer for 2 hours. After incubation, wells were washed 3 times with PBS, and then blocked with 2% BSA in PBS for 1 hour at room temperature. After sufficient blocking, wells were washed an additional 3 times with PBS to remove residual BSA. 3T3 fibroblasts, harvested from sub-confluent conditions, were prepared in serum free DMEM and introduced into the treated wells at 10,000 cells/well. Cells were allowed to adhere for 90 minutes or until appropriate attached phenotype was detected. After attachment, wells were agitated with gentle repeat pipetting 3 times, gently aspirated manually and washed once with PBS. Wells were then fixed with 4% paraformaldehyde in PBS for 1 hr, washed twice with PBS and stained with the nuclear dye DAPI. Microscopic detection and counting of stained nuclei was performed using IMAGE-PRO® Plus software. Cell count was normalized to % Cell Adhesion. The results are shown in Table 9.

TABLE 9

Inhibition of Cell Adhesion by GzmB Results.

| | Percent Cell Adhesion at Inhibitor Concentration | | |
|---|---|---|---|
| Compound | 100 uM | 10 uM | 0.1 uM |
| C16 | 82% | 11% | 9% |

The invention claimed is:

1. A compound having Formula (III):

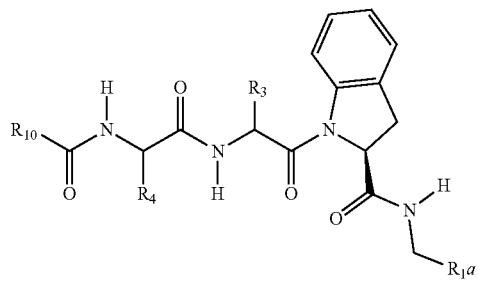

Formula (III)

or a stereoisomer, tautomer, or pharmaceutically acceptable salt thereof, wherein:

$R_{1a}$ is tetrazole or triazole;

$R_3$ is H or C1-C4 alkyl substituted with a carboxylic acid or carboxylate group;

$R_4$ is C3-C6 cycloalkyl or C1-C6 alkyl optionally substituted with hydroxyl or C1-C6 alkoxy; and $R_{10}$ is —$(CH_2)_n$—$CO_2H$, wherein n is 2, 3, 4, 5, or 6, optionally wherein one or more single methylene carbons are substituted with a fluoro, hydroxy, amino, C1-C3 alkyl, or C6-C10 aryl group, optionally wherein one or more single methylene carbons are substituted with two fluoro or C1-C3 alkyl groups, optionally wherein one or more single methylene carbons are substituted with two alkyl groups that taken together with the carbon to which they are attached form a 3, 4, 5, or 6-membered carbocyclic ring, or optionally wherein adjacent carbon atoms from an unsaturated carbon-carbon bond or taken together form a benzene ring; or $R_{10}$ is

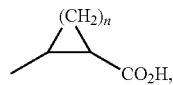

wherein n is 1, 2, 3, or 4, and optionally, for n=3 or 4, wherein adjacent carbon atoms from an unsaturated carbon-carbon bond.

2. A pharmaceutical composition, comprising a compound of claim 1, or a stereoisomer, tautomer, or pharmaceutically acceptable salt thereof, and a pharmaceutically acceptable carrier.

3. A method for inhibiting Granzyme B in a subject, comprising administering an effective amount of a compound of claim 1, or a stereoisomer, tautomer, or pharmaceutically acceptable salt thereof, to a subject in need thereof.

4. A method for treating a disease, disorder, or condition treatable by inhibiting Granzyme B, comprising administering a therapeutically effective amount of a compound of claim 1, or a stereoisomer, tautomer, or pharmaceutically acceptable salt thereof, to a subject in need thereof.

5. The method of claim 4, wherein the disease, disorder, or condition treatable by inhibiting Granzyme B is selected from treating dissection, aneurysm, and atherosclerosis.

6. The method of claim 4, wherein the condition treatable by inhibiting Granzyme B is a wound and administering the compound or composition promotes wound healing.

7. The method of claim 3, wherein administering the compound comprises topical administration, oral administration, or administration by injection.

8. A method for treating cutaneous scleroderma, epidermolysis bullosa, radiation dermatitis, alopecia areata, atopic dermatitis, or discoid lupus erythematosus, comprising administering a therapeutically effective amount of a compound of claim 1, or a stereoisomer, tautomer, or pharmaceutically acceptable salt thereof, to a subject in need thereof.

9. The method of claim 8, wherein administering the compound, stereoisomer, tautomer, or pharmaceutically acceptable salt thereof, comprises topical administration, oral administration, or administration by injection.

* * * * *